(12) United States Patent
Canales et al.

(10) Patent No.: US 8,524,764 B2
(45) Date of Patent: Sep. 3, 2013

(54) **INHIBITORS OF *FLAVIVIRIDAE* VIRUSES**

(75) Inventors: Eda Canales, San Mateo, CA (US); Lee S. Chong, Newark, CA (US); Michael O' Neil Hanrahan Clarke, Redwood City, CA (US); Edward Doerffler, Union City, CA (US); Scott E. Lazerwith, San Francisco, CA (US); Willard Lew, San Mateo, CA (US); Michael Mertzman, Belmont, CA (US); Philip A. Morganelli, Oakland, CA (US); William J. Watkins, Saratoga, CA (US)

(73) Assignee: Gilead Sciences, Inc., Foster City, CA (US)

(*) Notice: Subject to any disclaimer, the term of this patent is extended or adjusted under 35 U.S.C. 154(b) by 99 days.

(21) Appl. No.: 13/006,761

(22) Filed: Jan. 14, 2011

(65) Prior Publication Data

US 2011/0178058 A1 Jul. 21, 2011

Related U.S. Application Data

(60) Provisional application No. 61/295,576, filed on Jan. 15, 2010.

(51) Int. Cl.
*A01N 43/06* (2006.01)
*A61K 31/38* (2006.01)

(52) U.S. Cl.
USPC .......................................... 514/447; 549/69

(58) Field of Classification Search
USPC .......................................... 549/69; 514/447
See application file for complete search history.

(56) References Cited

U.S. PATENT DOCUMENTS

| | | | |
|---|---|---|---|
| 5,861,421 A | 1/1999 | Christensen, IV et al. | |
| 6,881,741 B2 | 4/2005 | Chan Chun Kong et al. | |
| 6,887,877 B2 | 5/2005 | Chan Chun Kong et al. | |
| 7,402,608 B2 | 7/2008 | Chan Chun Kong et al. | |
| 7,521,473 B2 | 4/2009 | Lee et al. | |
| 7,569,600 B2 | 8/2009 | Denis et al. | |
| 2002/0002199 A1 | 1/2002 | Jeppesen et al. | |
| 2003/0229053 A1 | 12/2003 | Chan Chun Kong et al. | |
| 2004/0116509 A1 | 6/2004 | Chan Chun Kong et al. | |
| 2005/0119332 A1 | 6/2005 | Jeppesen et al. | |
| 2006/0142347 A1 | 6/2006 | Chan Chun Kong et al. | |
| 2006/0276533 A1 | 12/2006 | Denis et al. | |
| 2007/0099929 A1 | 5/2007 | Thede et al. | |
| 2008/0299080 A1 | 12/2008 | Chan Chun Kong et al. | |
| 2009/0274655 A1 | 11/2009 | Grimes et al. | |
| 2011/0020278 A1* | 1/2011 | Canales et al. ............... | 424/85.4 |
| 2011/0178129 A1* | 7/2011 | Canales et al. ............... | 514/336 |
| 2012/0156166 A1* | 6/2012 | Cho et al. ..................... | 424/85.4 |

FOREIGN PATENT DOCUMENTS

| | | |
|---|---|---|
| WO | WO-02100846 A1 | 12/2002 |
| WO | WO-02100851 A2 | 12/2002 |
| WO | WO-2004/052885 | 6/2004 |
| WO | WO-2005/095386 A1 | 10/2005 |
| WO | WO-2006/072347 A2 | 7/2006 |
| WO | WO 2006072348 A2 * | 7/2006 |
| WO | WO-2007/093365 A2 | 8/2007 |
| WO | WO-2008058393 A1 | 5/2008 |
| WO | WO 2010/065668 | 6/2010 |
| WO | WO-2011/011303 | 1/2011 |
| WO | WO 2011/031669 | 3/2011 |
| WO | WO 2011/068715 | 6/2011 |
| WO | WO-2011/088345 | 7/2011 |
| WO | WO-2012/006055 | 1/2012 |
| WO | WO 2012006055 A2 * | 1/2012 |

OTHER PUBLICATIONS

Boyer, N. et al. (2000) "Pathogenesis, diagnosis and management of hepatitis C," *Journal of Hepatology* 32 (suppl 1):98-112.
Calisher, C. et al. (1989) "Antigenic Relationships between *Flaviviruses* as Determined by Cross-neutralization Tests with Polyclonal Antisera," *J.gen. Virol.* 70:37-43.
Di Besceglie, A. et al. (1999) "Some 1.8 percent of the U.S. adult population are infected with the hepatitis C virus, most without knowing it" *Scientific American* October pp. 80-85.
Domingo, E. et al. (1985) "The quasispecies (extremely heterogeneous) nature of viral RNA genome populations: biological relevance—a review" *Gene* 40:1-8.
Dymock, B. et al. (2000) " Novel approaches to the treatment of hepatitis C virus infection," *Antiviral Chemistry & Chemotherapy* 11(2):79-86.
Fukumoto, T. et al. (1996) "Viral Dynamics of Hepatitis C Early After Orthotopic Liver Transplantation: Evidence for Rapid Turnover of Serum Virions," *Hepatology* 24:1351-1354.
Gordon, C. et al. (2005) "Control of Hepatitis C: A Medicinal Chemistry Perspective," *Journal of Medicinal Chemistry* 48(1):1-20.
Herlihy, K. et al. (2008) "Development of Intergenotypic Chimeric Replicons to Determine the Broad-Spectrum Antiviral Activities of Hepatitis C Virus Polymerase Inhibitors," *Antimicrobial Agents and Chemotherapy* 52(10):3523-3534.

(Continued)

*Primary Examiner* — James O Wilson
*Assistant Examiner* — Alexander R Pagano
(74) *Attorney, Agent, or Firm* — Kilpatrick Townsend & Stockton LLP

(57) ABSTRACT

Provided are compounds of Formula I:

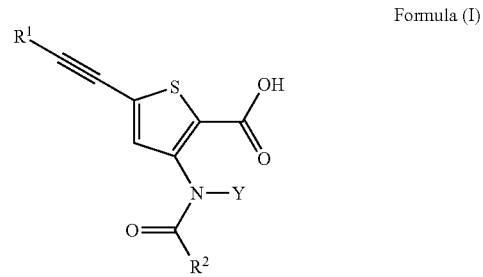

Formula (I)

and pharmaceutically acceptable salts and esters thereof. The compounds, compositions, and methods provided are useful for the treatment of Flaviviridae virus infections, particularly hepatitis C infections.

20 Claims, No Drawings

(56) References Cited

OTHER PUBLICATIONS

Maradpour, D. et al. (2007) "Replication of Hepatitis C Virus," *Nature Reviews/Microbiolory* 596):453-463.

Martell, M. et al. (1992) "Hepatitis C Virus (HCV) Circulates as a Population of Different but Closely Related Genomes: Quasispecies Nature of HCV Genome Distribution," *Journal of Virology* 66(5):3225-3229.

Moennig, V. et al. (1992) "The Pestiviruses," *Advances in Virus Research* 41:53-98.

Neumann, A. (1998) "Hepatitis C Viral Dynamics in Vivo and the Antiviral Efficacy of Interferon-α Therapy," *SCIENCE* 282:103-107.

Schul, W. (2007) "A Dengue Fever Viremia Model in Mice Shows Reduction in Viral Replication and Suppression of the Inflammatory Response after Treatment with Antiviral Drugs," *J. Infectious Disease* 195:665-674.

Scott, L. et al. (2002) "Interferon-α-2b Plus Ribavirin," *Drugs* 62:507-556.

International Search Report and Written Opinion for International App. No. PCT/US2011/021279, International filing date Jan. 14, 2011, mailed on May 2, 2011.

International Search Report and Written Opinion for International App. No. PCT/US2010/042394, International filing date Jul. 19, 2010, mailed on Sep. 29, 2010.

International Search Report and Written Opinion for International App. No. PCT/US2011/021335, International filing date Jan. 14, 2011, mailed on Feb. 22, 2011.

Office Action for U.S. Appl. No. 12/838,684, mailed Aug. 2, 2012.

Notice of Allowance for U.S. Appl. No. 13/392,467, mailed Sep. 21, 2012.

Office Action for U.S. Appl. No. 13/007,150, mailed Oct. 3, 2012.

U.S. Appl. No. 13/549,130, filed Jul. 13, 2012, Watkins et al.

U.S. Appl. No. 13/801,011, filed Mar. 13, 2013, Watkins et al.

U.S. Appl. No. 13/801,039, filed Mar. 13, 2013, Evans et al.

U.S. Appl. No. 13/800,991, filed Mar. 13, 2013, Hashash et al.

International Search Report and Written Opinion for PCT/US2010/047983 mailed Nov. 15, 2010.

International Search Report and Written Opinion for PCT/US2012/046741 mailed Aug. 22, 2012.

Office Communications for U.S. Appl. No. 13/392,467.

Office Communications for U.S. Appl. No. 12/838,684.

Office Communications for U.S. Appl. No. 13/007,150.

\* cited by examiner

INHIBITORS OF *FLAVIVIRIDAE* VIRUSES

This application is filed under 35 U.S.C. 111(a) claiming the benefit under 35 U.S.C. 119(e) of U.S. provisional application 61/295,576 filed Jan. 15, 2010 which is herein incorporated by reference in its entirety for all purposes.

FIELD OF THE INVENTION

The present application includes novel inhibitors of Flaviviridae viruses, compositions containing such compounds, therapeutic methods that include the administration of such compounds.

BACKGROUND OF THE INVENTION

Viruses comprising the Flaviviridae family include at least three distinguishable genera including pestiviruses, flaviviruses, and hepaciviruses (Calisher, et al., *J. Gen. Virol.*, 1993, 70, 37-43). While pestiviruses cause many economically important animal diseases such as bovine viral diarrhea virus (BVDV), classical swine fever virus (CSFV, hog cholera) and border disease of sheep (BDV), their importance in human disease is less well characterized (Moennig, V., et al., Adv. Vir. Res. 1992, 48, 53-98). Flaviviruses are responsible for important human diseases such as dengue fever and yellow fever while hepaciviruses cause hepatitis C virus infections in humans. Other important viral infections caused by the Flaviviridae family include West Nile virus (WNV) Japanese encephalitis virus (JEV), tick-borne encephalitis virus, Junjin virus, Murray Valley encephalitis, St Louis enchaplitis, Omsk hemorrhagic fever virus and Zika virus.

The hepatitis C virus (HCV) is the leading cause of chronic liver disease worldwide (Boyer, N. et al. J Hepatol. 32:98-112, 2000) so a significant focus of current antiviral research is directed toward the development of improved methods of treatment of chronic HCV infections in humans (Di Besceglie, A. M. and Bacon, B. R., Scientific American, October: 80-85, (1999); Gordon, C. P., et al., *J. Med. Chem.* 2005, 48, 1-20; Maradpour, D.; et al., *Nat. Rev. Micro.* 2007, 5(6), 453-463). A number of HCV treatments are reviewed by Bymock et al. in Antiviral Chemistry & Chemotherapy, 11:2; 79-95 (2000). Virologic cures of patients with chronic HCV infection are difficult to achieve because of the prodigious amount of daily virus production in chronically infected patients and the high spontaneous mutability of HCV virus (Neumann, et al., *Science* 1998, 282, 103-7; Fukimoto, et al., *Hepatology,* 1996, 24, 1351-4; Domingo, et al., *Gene,* 1985, 40, 1-8; Martell, et al., *J. Virol.* 1992, 66, 3225-9.

Currently, there are primarily two antiviral compounds, ribavirin, a nucleoside analog, and interferon-alpha (α) (IFN), that are used for the treatment of chronic HCV infections in humans. Ribavirin alone is not effective in reducing viral RNA levels, has significant toxicity, and is known to induce anemia. The combination of IFN and ribavirin has been reported to be effective in the management of chronic hepatitis C (Scott, L. J., et al. *Drugs* 2002, 62, 507-556) but less than half the patients given this treatment show a persistent benefit.

Combined, infections from the Flaviviridae virus family cause significant mortality, morbidity and economic losses throughout the world. Alkynyl substituted thiophenes with anti-Flaviviridae virus activity have been disclosed by Chan, et al., WO 2008058393; Wunberg, et al., WO 2006072347; and Chan, et al., WO 2002100851; but none of these are currently clinically approved antiviral therapeutics. Therefore, there remains a need to develop effective treatments for Flaviviridae virus infections.

SUMMARY OF THE INVENTION

Provided are compounds of Formula I:

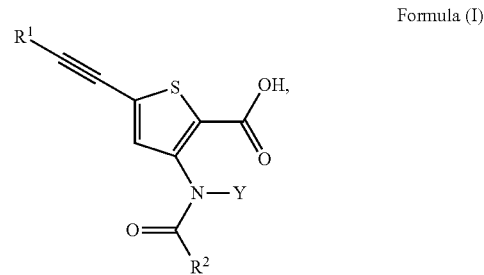

Formula (I)

or a pharmaceutically acceptable salt or ester thereof, wherein:

$R^1$ is selected from the group consisting of optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, optionally substituted 3-18 membered heterocyclylalkyl and optionally substituted $C_{6-18}$ arylalkyl, wherein, each substituted $R^1$ is substituted with one or more $Q^1$;

each $Q^1$ is independently selected from the group consisting of halogen, oxo, oxide, —$NO_2$, —N(=O), —$SR^{10}$, —$S(O)R^{10}$, —$S(O)_2R^{10}$, —$S(O)_2NR^{10}R^{11}$, —$NR^{10}C(O)R^{11}$, —$NR^{10}C(O)NR^{11}R^{12}$, —$NR^{10}S(O)R^{11}$, —$NR^{10}S(O)_2R^{11}$, —$OP(O)R^{11}R^{12}$, —$P(O)R^{11}R^{12}$, —$P(O)OR^{11}R^{12}$, —$P(O)(OR^{11})OR^{12}$, —$C(O)NR^{11}R^{12}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{6-12}$ arylalkyl, optionally substituted $C_{6-12}$ aryl, optionally substituted 3-14 membered heteroaryl, optionally substituted $C_{1-6}$ alkyloxy, optionally substituted $C_{2-6}$ alkenyloxy, optionally substituted $C_{2-6}$ alkynyloxy, optionally substituted $C_{3-6}$ cycloalkyloxy, optionally substituted $C_{6-12}$ aryloxy, optionally substituted 3-14 membered heteroaryloxy, optionally substituted 4-12 membered heterocyclyloxy, optionally substituted —$C(O)C_{1-6}$ alkyl, optionally substituted —$C(O)C_{2-6}$ alkenyl, optionally substituted —$C(O)C_{2-6}$ alkynyl, optionally substituted —$C(O)C_{3-6}$ cycloalkyl, optionally substituted —$C(O)C_{6-12}$ aryl, optionally substituted —C(O)-3-14 membered heteroaryl, optionally substituted —$C(O)C_{6-12}$ arylalkyl, optionally substituted-3-10 membered heterocyclyl, —OH, —$NR^{11}R^{12}$, —$C(O)OR^{10}$, —CN, —$N_3$, —$C(=NR^{13})NR^{11}R^{12}$, —$C(=NR^{13})OR^{10}$, —$NR^{10}C(=NR^{13})NR^{11}R^{12}$, —$NR^{11}C(O)OR^{10}$, and —$OC(O)NR^{11}R^{12}$;

each $R^{10}$, $R^{11}$, and $R^{12}$, independently, is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, and optionally substituted $C_{6-18}$ arylalkyl;

or $R^{11}$ and $R^{12}$ taken together with the atoms to which they are attached form a 3 to 10 membered heterocyclyl;

each $R^{13}$, independently, is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, optionally substituted $C_{6-18}$ arylalkyl, —CN, —C(O)$R^{14}$, —CHO and —S(O)$_2R^{14}$;

each $R^{14}$, independently, is optionally substituted $C_{1-12}$ alkyl;

wherein, each substituted $Q^1$, substituted $R^{10}$, substituted $R^{11}$, substituted $R^{12}$, substituted $R^{13}$, or substituted $R^{14}$ is independently substituted with one or more $Q^6$;

$R^2$ is selected from the group consisting of optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, and optionally substituted $C_{6-18}$ arylalkyl;

wherein, each substituted $R^2$ is substituted with one or more $Q^2$;

each $Q^2$, independently, is selected from the group consisting of halogen, oxo, oxide, —NO$_2$, —N(═O), —SR$^{20}$, —S(O)R$^{20}$, —S(O)$_2$R$^{20}$, —S(O)$_2$NR$^{20}$R$^{21}$, —NR$^{20}$C(O)R$^{21}$, —NR$^{20}$C(O)NR$^{21}$R$^{22}$, —NR$^{20}$S(O)R$^{21}$, —NR$^{20}$S(O)$_2$R$^{21}$, —OP(O)R$^{21}$R$^{22}$, —P(O)R$^{21}$R$^{22}$, —P(O)OR$^{21}$R$^{22}$, OR$^{21}$)OR$^{22}$, —C(O)NR$^{21}$R$^{22}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{6-12}$ arylalkyl, optionally substituted $C_{6-12}$ aryl, optionally substituted 3-14 membered heteroaryl, optionally substituted $C_{1-6}$ alkyloxy, optionally substituted $C_{2-6}$ alkenyloxy, optionally substituted $C_{2-6}$ alkynyloxy, optionally substituted $C_{3-6}$ cycloalkyloxy, optionally substituted $C_{6-12}$ aryloxy, optionally substituted 3-14 membered heteroaryloxy, optionally substituted 4-12 membered heterocyclyloxy, optionally substituted —C(O)$C_{1-6}$ alkyl, optionally substituted —C(O)$C_{2-6}$ alkenyl, optionally substituted —C(O)$C_{2-6}$ alkynyl, optionally substituted —C(O)$C_{3-6}$ cycloalkyl, optionally substituted —C(O)$C_{6-12}$ aryl, optionally substituted —C(O)-3-14 membered heteroaryl, optionally substituted —C(O)$C_{6-12}$ arylalkyl, optionally substituted 3-10 membered heterocyclyl, —OH, —NR$^{21}$R$^{22}$, —C(O)OR$^{20}$, —CN, —N$_3$, —C(═NR$^{23}$)NR$^{21}$R$^{22}$, —C(═NR$^{23}$)OR$^{20}$, —NR$^{20}$C(═NR$^{23}$)NR$^{21}$R$^{22}$, —NR$^{21}$C(O)OR$^{20}$, and —OC(O)NR$^{21}$R$^{22}$;

each $R^{20}$, $R^{21}$, and $R^{22}$, independently, is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, and optionally substituted $C_{6-18}$ arylalkyl;

or $R^{21}$ and $R^{22}$ taken together with the atoms to which they are attached form a 3 to 10 membered heterocyclyl;

each $R^{23}$, independently, is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, optionally substituted $C_{6-18}$ arylalkyl, —CN, —C(O)R$^{24}$, —CHO and —S(O)$_2$R$^{24}$;

each $R^{24}$ individually is optionally substituted $C_{1-12}$ alkyl;

wherein, each substituted $Q^2$, substituted $R^{20}$, substituted $R^{21}$, substituted $R^{22}$, substituted $R^{23}$, or substituted $R^{24}$ is independently substituted with one or more $Q^6$;

Y is —$R^3$-L-Het, —N($R^4$)($R^5$) or —$R^6$═NOR$^7$;

$R^3$ is selected from the group consisting of optionally substituted $C_{1-12}$ alkylene, $C_{2-12}$ alkenylene, substituted $C_{2-12}$ alkenylene, $C_{2-12}$ alkynylene, substituted $C_{2-12}$ alkynylene, $C_{3-12}$ cycloalkylene, substituted $C_{3-12}$ cycloalkylene, $C_{3-12}$ cycloalkylalkylene, substituted $C_{3-12}$ cycloalkylalkylene, optionally substituted $C_{6-14}$ arylene, optionally substituted 3-14 membered heteroarylene, optionally substituted 3-12 membered heterocyclylene, optionally substituted 3-18 membered heteroarylalkylene, and optionally substituted $C_{6-18}$ arylalkylene;

wherein each substituted $R^3$ is substituted with one or more $Q^3$;

each $Q^3$, independently, is selected from the group consisting of halogen, oxo, oxide, —NO$_2$, —N(═O), —SR$^{30}$, —S(O)R$^{30}$, —S(O)$_2$R$^{30}$, —S(O)$_2$NR$^{30}$R$^{31}$, —NR$^{30}$C(O)R$^{31}$, —NR$^{30}$C(O)NR$^{31}$R$^{32}$, —NR$^{30}$S(O)R$^{31}$, —NR$^{30}$S(O)$_2$R$^{31}$, —OP(O)R$^{31}$R$^{32}$, —P(O)R$^{31}$R$^{32}$, —P(O)OR$^{31}$R$^{32}$, —P(O)(OR$^{31}$)OR$^{32}$, —C(O)NR$^{31}$R$^{32}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{6-12}$ arylalkyl, optionally substituted $C_{6-12}$ aryl, optionally substituted 3-14 membered heteroaryl, optionally substituted $C_{1-6}$ alkyloxy, optionally substituted $C_{2-6}$ alkenyloxy, optionally substituted $C_{2-6}$ alkynyloxy, optionally substituted $C_{3-6}$ cycloalkyloxy, optionally substituted $C_{6-12}$ aryloxy, optionally substituted 3-14 membered heteroaryloxy, optionally substituted 4-12 membered heterocyclyloxy, optionally substituted —C(O)$C_{1-6}$ alkyl, optionally substituted —C(O)$C_{2-6}$ alkenyl, optionally substituted —C(O)$C_{2-6}$ alkynyl, optionally substituted —C(O)$C_{3-6}$ cycloalkyl, optionally substituted —C(O)$C_{6-12}$ aryl, optionally substituted —C(O)-3-14 membered heteroaryl, optionally substituted —C(O)$C_{6-12}$ arylalkyl, optionally substituted 3-10 membered heterocyclyl, —OH, —NR$^{31}$R$^{32}$, —C(O)OR$^{30}$, —CN, —N$_3$, —C(═NR$^{33}$)NR$^{31}$R$^{32}$, —C(═NR$^{33}$)OR$^{30}$, —NR$^{30}$C(═NR$^{33}$)NR$^{31}$R$^{32}$, —NR$^{31}$C(O)OR$^{30}$, and —OC(O)NR$^{31}$R$^{32}$;

each $R^{30}$, $R^{31}$, and $R^{32}$, independently is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, and optionally substituted $C_{6-18}$ arylalkyl;

or $R^{31}$ and $R^{32}$ taken together with the atoms to which they are attached form a 3 to 10 membered heterocyclyl;

each $R^{33}$ independently is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, optionally substituted $C_{6-18}$ arylalkyl, —CN, —C(O)R$^{34}$, —CHO and —S(O)$_2$R$^{34}$;

each $R^{34}$ individually is optionally substituted $C_{1-12}$ alkyl;

wherein, each substituted $Q^3$, substituted $R^{30}$, substituted $R^{31}$, substituted $R^{32}$, substituted $R^{33}$, or substituted $R^{34}$ is independently substituted with one or more $Q^6$;

L is selected from the group consisting of —OC(O)N(R$^4$)—, —N(R$^4$)C(O)O—, —N(R$^4$)S(O)$_2$—, —N(R$^4$)C(O)—, —C(O)—, —C(O)O—, —OC(O)—, —N(R$^4$)N(R$^4$)C(O)O—, and —N(R$^4$)N(R$^4$)—;

Het is an optionally substituted 3-12 membered heterocyclyl or optionally substituted 3-14 membered heteroaryl;

wherein, each substituted Het is substituted with one or more $Q^4$;

each $Q^4$, independently, is selected from the group consisting of halogen, oxo, oxide, —NO$_2$, —N(=O), —SR$^{40}$, —S(O)R$^{40}$, —S(O)$_2$R$^{40}$, —S(O)$_2$NR$^{40}$R$^{41}$, —NR$^{40}$C(O)R$^{41}$, —NR$^{40}$C(O)NR$^{41}$R$^{42}$, —NR$^{40}$S(O)R$^{41}$, —NR$^{40}$S(O)$_2$R$^{41}$, —OP(O)R$^{41}$R$^{42}$, —P(O)R$^{41}$R$^{42}$, —P(O)OR$^{41}$R$^{42}$, —P(O)(OR$^{41}$)OR$^{42}$, —C(O)NR$^{41}$R$^{42}$, optionally substituted C$_{1-6}$ alkyl, optionally substituted C$_{2-6}$ alkenyl, optionally substituted C$_{2-6}$ alkynyl, optionally substituted C$_{3-6}$ cycloalkyl, optionally substituted C$_{6-12}$ arylalkyl, optionally substituted C$_{6-12}$ aryl, optionally substituted 3-14 membered heteroaryl, optionally substituted C$_{1-6}$ alkyloxy, optionally substituted C$_{2-6}$ alkenyloxy, optionally substituted C$_{2-6}$ alkynyloxy, optionally substituted C$_{3-6}$ cycloalkyloxy, optionally substituted C$_{6-12}$ aryloxy, optionally substituted 3-14 membered heteroaryloxy, optionally substituted 4-12 membered heterocyclyloxy, optionally substituted —C(O)C$_{1-6}$ alkyl, optionally substituted —C(O)C$_{2-6}$ alkenyl, optionally substituted —C(O)C$_{2-6}$ alkynyl, optionally substituted —C(O)C$_{3-6}$ cycloalkyl, optionally substituted —C(O)C$_{6-12}$ aryl, optionally substituted —C(O)-3-14 membered heteroaryl, optionally substituted —C(O)C$_{6-12}$ arylalkyl, optionally substituted 3-10 membered heterocyclyl, —OH, —NR$^{41}$R$^{42}$, —C(O)OR$^{40}$, —CN, —N$_3$, —C(=NR$^{43}$)NR$^{41}$R$^{42}$, —C(=NR$^{43}$)OR$^{40}$, —NR$^{40}$C(=NR$^{43}$)NR$^{41}$R$^{42}$, —NR$^{41}$C(O)OR$^{40}$, and —OC(O)NR$^{41}$R$^{42}$;

each R$^{40}$, R$^{41}$, and R$^{42}$, independently is selected from the group consisting of H, optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{6-14}$ aryl, optionally substituted 3-14 membered heteroaryl, optionally substituted 3-12 membered heterocyclyl, optionally substituted 3-18 membered heteroarylalkyl, and optionally substituted C$_{6-18}$ arylalkyl;

or R$^{41}$ and R$^{42}$ taken together with the atoms to which they are attached form a 3 to 10 membered heterocyclyl;

each R$^{43}$, independently, is selected from the group consisting of H, optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{6-14}$ aryl, optionally substituted 3-14 membered heteroaryl, optionally substituted 3-12 membered heterocyclyl, optionally substituted 3-18 membered heteroarylalkyl, optionally substituted C$_{6-18}$ arylalkyl, —ON, —C(O)R$^{44}$, —CHO and —S(O)$_2$R$^{44}$;

each R$^{44}$ individually is optionally substituted C$_{1-12}$ alkyl;

wherein, each substituted $Q^4$, substituted R$^{40}$, substituted R$^{41}$, substituted R$^{42}$, substituted R$^{43}$, or substituted R$^{44}$ is independently substituted with one or more $Q^5$;

each $Q^5$, individually, is selected from the group consisting of halogen, oxo, oxide, —NO$_2$, —N(=O), —SR$^{50}$, —S(O)R$^{50}$, —S(O)$_2$R$^{50}$, —S(O)$_2$NR$^{50}$R$^{51}$, —NR$^{50}$C(O)R$^{51}$, —NR$^{50}$C(O)NR$^{51}$R$^{52}$, —NR$^{50}$S(O)R$^{51}$, —NR$^{50}$S(O)$_2$R$^{51}$, —OP(O)R$^{51}$R$^{52}$, —P(O)R$^{51}$R$^{52}$, —P(O)OR$^{51}$R$^{52}$, —P(O)(OR$^{51}$)OR$^{52}$, —C(O)NR$^{51}$R$^{52}$, optionally substituted C$_{1-6}$ alkyl, optionally substituted C$_{2-6}$ alkenyl, optionally substituted C$_{2-6}$ alkynyl, optionally substituted C$_{3-6}$ cycloalkyl, optionally substituted C$_{6-12}$ arylalkyl, optionally substituted C$_{6-12}$ aryl, optionally substituted 3-14 membered heteroaryl, optionally substituted C$_{1-6}$ alkyloxy, optionally substituted C$_{2-6}$ alkenyloxy, optionally substituted C$_{2-6}$ alkynyloxy, optionally substituted C$_{3-6}$ cycloalkyloxy, optionally substituted C$_{6-12}$ aryloxy, optionally substituted 3-14 membered heteroaryloxy, optionally substituted 4-12 membered heterocyclyloxy, optionally substituted —C(O)C$_{1-6}$ alkyl, optionally substituted —C(O)C$_{2-6}$ alkenyl, optionally substituted —C(O)C$_{2-6}$ alkynyl, optionally substituted —C(O)C$_{3-6}$ cycloalkyl, optionally substituted —C(O)C$_{6-12}$ aryl, optionally substituted —C(O)-3-14 membered heteroaryl, optionally substituted —C(O)C$_{6-12}$ arylalkyl, optionally substituted 3-10 membered heterocyclyl, —OH, —NR$^{51}$R$^{52}$, —C(O)OR$^{50}$, —CN, —N$_3$, —C(=NR$^{53}$)NR$^{51}$R$^{52}$, —C(=NR$^{53}$)OR$^{50}$, —NR$^{50}$C(=NR$^{53}$)NR$^{51}$R$^{52}$, —NR$^{51}$C(O)OR$^{50}$, and —OC(O)NR$^{51}$R$^{52}$;

each R$^{50}$, R$^{51}$, and R$^{52}$, independently is selected from the group consisting of H, optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{6-14}$ aryl, optionally substituted 3-14 membered heteroaryl, optionally substituted 3-12 membered heterocyclyl, optionally substituted 3-18 membered heteroarylalkyl, and optionally substituted C$_{6-18}$ arylalkyl;

or R$^{51}$ and R$^{52}$ taken together with the atoms to which they are attached form a 3 to 10 membered heterocyclyl;

each R$^{53}$, independently, is selected from the group consisting of H, optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{6-14}$ aryl, optionally substituted 3-14 membered heteroaryl, optionally substituted 3-12 membered heterocyclyl, optionally substituted 3-18 membered heteroarylalkyl, optionally substituted C$_{6-18}$ arylalkyl, —CN, —C(O)R$^{54}$, —CHO and —S(O)$_2$R$^{54}$;

each R$^{54}$, independently, is optionally substituted C$_{1-12}$ alkyl;

wherein, each substituted $Q^5$, substituted R$^{50}$, substituted R$^{51}$, substituted R$^{52}$, substituted R$^{53}$, or substituted R$^{54}$ is independently substituted with one or more $Q^6$;

each $Q^6$, independently, is selected from the group consisting of halogen, oxo, oxide, —NO$_2$, —N(=O), —SR$^{60}$, —S(O)R$^{60}$, —S(O)$_2$R$^{60}$, —S(O)$_2$NR$^{60}$R$^{61}$, —NR$^{60}$C(O)R$^{61}$, —NR$^{60}$C(O)NR$^{61}$R$^{62}$, —NR$^{60}$S(O)R$^{61}$, —NR$^{60}$S(O)$_2$R$^{61}$, —OP(O)R$^{61}$R$^{62}$, —P(O)R$^{61}$R$^{62}$, —P(O)OR$^{61}$R$^{62}$, —P(O)(OR$^{61}$)OR$^{62}$, —C(O)NR$^{61}$R$^{62}$, C$_{1-6}$ alkyl, C$_{2-6}$ alkenyl, C$_{2-6}$ alkynyl, C$_{3-6}$ cycloalkyl, C$_{6-12}$ arylalkyl, C$_{6-12}$ aryl, 3-14 membered heteroaryl, C$_{1-6}$ alkyloxy, C$_{2-6}$ alkenyloxy, C$_{2-6}$ alkynyloxy, C$_{3-6}$ cycloalkyloxy, C$_{6-12}$ aryloxy, 3-14 membered heteroaryloxy, 4-12 membered heterocyclyloxy, —C(O)C$_{1-6}$ alkyl, —C(O)C$_{2-6}$ alkenyl, —C(O)C$_{2-6}$ alkynyl, —C(O)C$_{3-6}$ cycloalkyl, —C(O)C$_{1-6}$ haloalkyl, —C(O)C$_{6-12}$ aryl, —C(O)-3-14 membered heteroaryl, —C(O)C$_{6-12}$ arylalkyl, 3-10 membered heterocyclyl, —OH, —NR$^{61}$R$^{62}$, —C(O)OR$^{60}$, —CN, —N$_3$, —C(=NR$^{63}$)NR$^{61}$R$^{62}$, —C(=NR$^{63}$)OR$^{60}$, —NR$^{60}$C(=NR$^{63}$)NR$^{61}$R$^{62}$, —NR$^{61}$C(O)OR$^{60}$, and —OC(O)NR$^{61}$R$^{62}$;

each R$^{60}$, R$^{61}$, and R$^{62}$, independently, is selected from the group consisting of H, C$_{1-12}$ alkyl, C$_{2-12}$ alkenyl, C$_{2-12}$ alkynyl, C$_{3-12}$ cycloalkyl, C$_{1-12}$ haloalkyl, C$_{6-14}$ aryl, 3-14 membered heteroaryl, 3-12 membered heterocyclyl, 3-18 membered heteroarylalkyl, and C$_{6-18}$ arylalkyl;

or R$^{61}$ and R$^{62}$ taken together with the atoms to which they are attached form a 3 to 10 membered heterocyclyl;

each $R^{63}$ independently is selected from the group consisting of H, $C_{1-12}$ alkyl, $C_{2-12}$ alkenyl, $C_{2-12}$ alkynyl, $C_{3-12}$ cycloalkyl, $C_{6-14}$ aryl, 3-14 membered heteroaryl, 3-12 membered heterocyclyl, 3-18 membered heteroarylalkyl, $C_{6-18}$ arylalkyl, —CN, —C(O)$R^{64}$, —CHO and —S(O)$_2R^{64}$;

each $R^{64}$ individually is $C_{1-12}$ alkyl;

each $R^4$ is independently H, $C_1$-$C_{12}$ alkyl, $C_3$-$C_{12}$ cycloalkyl, 3-14 membered heteroaryl or 3-12 membered heterocyclyl wherein each $C_1$-$C_{12}$ alkyl, $C_3$-$C_{12}$ cycloalkyl, 3-14 membered heteroaryl or 3-12 membered heterocyclyl is optionally substituted with one or more $Q^1$;

each $R^5$ is independently $C_1$-$C_{12}$ alkyl, $C_3$-$C_{12}$ cycloalkyl, 3-14 membered heteroaryl or 3-12 membered heterocyclyl wherein each $C_1$-$C_{12}$ alkyl, $C_3$-$C_{12}$ cycloalkyl, 3-14 membered heteroaryl or 3-12 membered heterocyclyl is optionally substituted with one or more $Q^1$;

$R^6$ is $C_1$-$C_{12}$ alkylyne, $C_3$-$C_{12}$ cycloalkylyne, or 3-12 membered heterocyclylyne wherein each $C_1$-$C_{12}$ alkylyne, $C_3$-$C_{12}$ cycloalkylyne, or 3-12 membered heterocyclylyne is optionally substituted with one or more $Q^1$; and $R^7$ is selected from the group consisting of optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, optionally substituted 3-18 membered heterocyclylalkyl and optionally substituted $C_{6-18}$ arylalkyl;

wherein, each substituted $R^7$ is substituted with one or more $Q^2$.

In another embodiment, a method for treating Flaviviridae viral infections is provided comprising administering an effective amount of a compound of Formula I to a patient in need thereof. The compound of Formula I is administered to a human subject in need thereof, such as a human being who is infected with viruses of the Flaviviridae family. In another embodiment, the compound of Formula I is administered to a human subject in need thereof, such as a human being who is infected with a HCV virus. In one embodiment, the treatment results in the reduction of one or more of the in viral loads or clearance of RNA in the patient.

In another embodiment, provided is a method of treating and/or preventing a disease caused by a viral infection wherein the viral infection is caused by a virus selected from the group consisting of dengue virus, yellow fever virus, West Nile virus, Japanese encephalitis virus, tick-borne encephalitis virus, Junjin virus, Murray Valley encephalitis virus, St Louis encephalitis virus, Omsk hemorrhagic fever virus, bovine viral disarrhea virus, Zika virus and Hepatitis C virus; by administering to a subject in need thereof a therapeutically effective amount of a compound of Formula I, or a pharmaceutically acceptable salt thereof.

In another embodiment, provided is the use of a compound of Formula I for the manufacture of a medicament for the treatment of Flaviviridae viral infections. In another aspect of this embodiment, the Flaviviridae viral infection is an HCV infection.

In another embodiment, provided is a compound of Formula I for use in treating a Flaviviridae viral infection. In another aspect of this embodiment, the Flaviviridae viral infection is an acute or chronic HCV infection. In another aspect of this embodiment, the treatment results in the reduction of one or more of the viral loads or clearance of RNA in the patient. In another aspect of this embodiment, the treatment results in the reduction of the HCV viral load or clearance of HCV viral RNA in the patient.

In another embodiment, provided is a method for treating or preventing HCV comprising administering an effective amount of a compound of Formula Ito a patient in need thereof. In another embodiment, provided is the use of a compound of the present invention for the manufacture of a medicament for the treatment or prevention of HCV.

In another embodiment, provided is a pharmaceutical composition comprising a compound of Formula I and one or more pharmaceutically acceptable carriers or excipients. The pharmaceutical composition of Formula I may further comprise one or more additional therapeutic agents. The one or more additional therapeutic agent may be, without limitation, selected from: interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophilin inhibitors, HCV IRES inhibitors, pharmacokinetic enhancers, and other drugs for treating HCV, or mixtures thereof.

In another embodiment, provided is a method for the treatment or prevention of the symptoms or effects of an HCV infection in an infected animal which comprises administering to, i.e. treating, said animal with a pharmaceutical combination composition or formulation comprising an effective amount of a Formula I compound, and a second compound having anti-HCV properties.

In another embodiment, provided are compounds of Formula I and pharmaceutically acceptable salts thereof and all racemates, enantiomers, diastereomers, tautomers, polymorphs, pseudopolymorphs and amorphous forms thereof.

In another embodiment, provided are processes and novel intermediates disclosed herein which are useful for preparing Formula I compounds.

In other embodiments, novel methods for synthesis, analysis, separation, isolation, purification, characterization, and testing of the compounds of Formula I are provided.

The present invention includes combinations of aspects and embodiments, as well as preferences, as herein described throughout the present specification.

DETAILED DESCRIPTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims.

All documents referenced herein are each incorporated by reference in their entirety for all purposes.

In one embodiment of Formula I, $R^1$ is optionally substituted $C_{1-12}$ alkyl, optionally substituted $C_{2-12}$ alkenyl, optionally substituted $C_{2-12}$ alkynyl, or optionally substituted $C_{3-12}$ cycloalkyl. In another aspect of this embodiment, $R^1$ is optionally substituted $C_1$-$C_{12}$ alkyl. In another aspect of this embodiment, $R^1$ is optionally substituted $C_3$-$C_7$ secondary or tertiary alkyl. In another aspect of this embodiment, $R^1$ is prop-2-yl (isopropyl) or 2-methylprop-2-yl (t-butyl).

In another embodiment of Formula I, $R^2$ is optionally substituted $C_{1-12}$ alkyl, optionally substituted $C_{2-12}$ alkenyl, optionally substituted $C_{2-12}$ alkynyl, optionally substituted $C_{3-12}$ cycloalkyl, or optionally substituted $C_{6-18}$ arylalkyl. In another aspect of this embodiment, $R^2$ is optionally substituted $C_{3-12}$ cycloalkyl. In another aspect of this embodiment, $R^2$ is optionally substituted methylcyclohexyl or optionally substituted methylcyclohexenyl. In another aspect of this embodiment, $R^2$ is optionally substituted 4-methylcyclohexyl. In another aspect of this embodiment, $R^2$ is optionally substituted 4-methylcyclohexenyl. In a preferred aspect of this embodiment, $R^2$ is

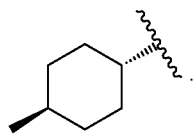 [SMILES: *[C@H]1CC[C@H](C)CC1]

In another preferred aspect of this embodiment, $R^2$ is

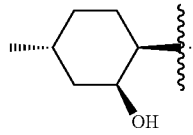 [SMILES: *[C@@H]1CC[C@@H](C)C[C@@H]1O]

In another preferred aspect of this embodiment, $R^2$ is

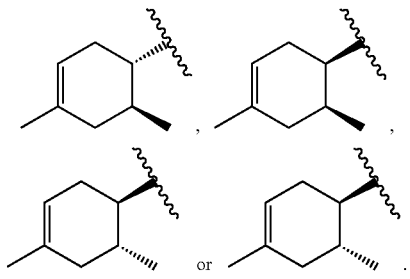

In another preferred aspect of this embodiment, $R^2$ is

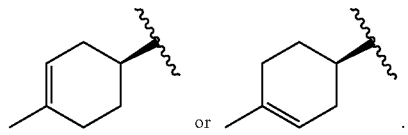

In another embodiment of Formula I, Y is —$R^3$-L-Het. In another embodiment of Formula I, Y is —$N(R^4)(R^5)$. In another embodiment of Formula I, Y is —$R^6$=$NOR^7$.

In another embodiment of Formula I, Y is —$R^3$-L-Het, $R^1$ is optionally substituted $C_1$-$C_{12}$ alkyl, and $R^2$ is optionally substituted $C_{3-12}$ cycloalkyl. In another aspect of this embodiment, $R^3$ is optionally substituted $C_{1-12}$ alkylene, $C_{2-12}$ alkenylene, substituted $C_{2-12}$ alkenylene, $C_{2-12}$ alkynylene, substituted $C_{2-12}$ alkynylene, $C_{3-12}$ cycloalkylene, substituted $C_{3-12}$ cycloalkylene, $C_{3-12}$ cycloalkylalkylene, substituted $C_{3-12}$ cycloalkylalkylene, optionally substituted $C_{6-14}$ arylene, optionally substituted 3-14 membered heteroarylene, optionally substituted 3-12 membered heterocyclylene, optionally substituted 3-18 membered heteroarylalkylene, or optionally substituted $C_{6-18}$ arylalkylene. In another aspect of this embodiment, $R^3$ is optionally substituted $C_{1-12}$ alkylene, $C_{3-12}$ cycloalkylene, substituted $C_{3-12}$ cycloalkylene, $C_{3-12}$ cycloalkylalkylene, substituted $C_{3-12}$ cycloalkylalkylene, optionally substituted $C_{6-14}$ arylene, or optionally substituted 3-12 membered heterocyclylene. In another aspect of this embodiment, L is —OC(O)N($R^4$)—, —N($R^4$)C(O)O—, —N($R^4$)S(O)$_2$—, —N($R^4$)C(O)—, —C(O)—, —C(O)O—, —OC(O)—, —N($R^4$)N($R^4$)C(O)O—, or —N($R^4$)N($R^4$)—. In another aspect of this embodiment, L is —OC(O)N($R^4$)—. In another aspect of this embodiment, L is —N($R^4$)C(O)O—. In another aspect of this embodiment, L is —N($R^4$)S(O)$_2$—. In another aspect of this embodiment, L is —N($R^4$)C(O)—. In another aspect of this embodiment, L is —C(O)—. In another aspect of this embodiment, L is —C(O)O—. In another aspect of this embodiment, L is —OC(O)—. In another aspect of this embodiment, L is —N($R^4$)N($R^4$)C(O)O—. In another aspect of this embodiment, L is —N($R^4$)N($R^4$)—.

In another embodiment of Formula I, Y is —$R^3$-L-Het, $R^1$ is optionally substituted $C_1$-$C_{12}$ alkyl, $R^2$ is optionally substituted $C_{3-12}$ cycloalkyl and $R^3$ is optionally substituted $C_{1-12}$ alkylene, $C_{3-12}$ cycloalkylene, substituted $C_{3-12}$ cycloalkylene, $C_{3-12}$ cycloalkylalkylene, substituted $C_{3-12}$ cycloalkylalkylene, optionally substituted $C_{6-14}$ arylene, or optionally substituted 3-12 membered heterocyclylene. In another aspect of this embodiment, $R^3$ is optionally substituted $C_{1-6}$ alkylene. In another aspect of this embodiment, $R^3$ is $C_{4-6}$ cycloalkylene or substituted $C_{4-6}$ cycloalkylene. In another aspect of this embodiment, $R^3$ is an optionally substituted 5-6 membered heterocyclylene. In another aspect of this embodiment, L is —OC(O)N($R^4$)—, —N($R^4$)C(O)O—, —N($R^4$)S(O)$_2$—, —N($R^4$)C(O)—, —C(O)—, —C(O)O—, —OC(O)—, —N($R^4$)N($R^4$)C(O)O—, or —N($R^4$)N($R^4$)—. In another aspect of this embodiment, L is —OC(O)N($R^4$)—. In another aspect of this embodiment, L is —N($R^4$)C(O)O—. In another aspect of this embodiment, —N($R^4$)S(O)$_2$—. In another aspect of this embodiment, L is —N($R^4$)C(O)—. In another aspect of this embodiment, L is —C(O)—. In another aspect of this embodiment, L is —C(O)O—. In another aspect of this embodiment, L is —OC(O)—. In another aspect of this embodiment, L is —N($R^4$)N($R^4$)C(O)O—. In another aspect of this embodiment, L is —N($R^4$)N($R^4$)—. In another aspect of this embodiment, Het is an optionally substituted 3-12 membered heterocyclyl or optionally substituted 3-14 membered heteroaryl wherein said optionally substituted 3-12 membered heterocyclyl or optionally substituted 3-14 membered heteroaryl comprises one to four heteroatoms selected from O, S, or N. In another aspect of this embodiment, Het is an optionally substituted 3-12 membered heterocyclyl comprising one or two heteroatoms selected from O, S, or N. In another aspect of this embodiment, Het is an optionally substituted 5-10 membered heteroaryl comprising one to four heteroatoms selected from O, S, or N.

In another embodiment of Formula I, Y is —$N(R^4)(R^5)$, $R^1$ is optionally substituted $C_1$-$C_{12}$ alkyl, and $R^2$ is optionally substituted $C_{3-12}$ cycloalkyl. In another aspect of this embodiment, $R^4$ is independently H or $1$-$C_{1-2}$ alkyl wherein $1$-$C_{1-2}$ alkyl is optionally substituted with one or more $Q^1$. In another aspect of this embodiment, $R^4$ is H or optionally substituted $C_1$-$C_6$ alkyl. In another aspect of this embodiment, $R^5$ is $C_1$-$C_{12}$ alkyl, $C_3$-$C_{12}$ cycloalkyl, 3-14 membered heteroaryl or 3-12 membered heterocyclyl wherein each $C_1$-$C_{12}$ alkyl, $C_3$-$C_{12}$ cycloalkyl, 3-14 membered heteroaryl or 3-12 membered heterocyclyl is optionally substituted with one or more $Q^1$. In another aspect of this embodiment, $R^5$ is $C_1$-$C_6$ alkyl, $C_6$-$C_6$ cycloalkyl, 5-10 membered heteroaryl or 4-10 membered heterocyclyl wherein each $C_1$-$C_6$ alkyl, $C_5$-$C_6$ cycloalkyl, 5-10 membered heteroaryl or 4-10 membered heterocyclyl is optionally substituted with one or more $Q^1$.

In another embodiment of Formula I, Y is —R$^6$=NOR$^7$, R$^1$ is optionally substituted C$_1$-C$_{12}$ alkyl, and R$^2$ is optionally substituted C$_{3-12}$ cycloalkyl. In another aspect of this embodiment, R$^6$ is C$_1$-C$_{12}$ alkylyne, C$_3$-C$_{12}$ cycloalkylyne, or 3-12 membered heterocyclylyne wherein each C$_1$-C$_{12}$ alkylyne, C$_3$-C$_{12}$ cycloalkylyne, or 3-12 membered heterocyclylyne is optionally substituted with one or more Q$^1$. In another aspect of this embodiment, R$^6$ is C$_5$-C$_6$ cycloalkylyne or 4-6 membered heterocyclylyne wherein each C$_5$-C$_6$ cycloalkylyne or 4-6 membered heterocyclylyne is optionally substituted with one or more Q. In another aspect of this embodiment, R$^6$ is cyclohexylyne. In another aspect of this embodiment, R$^7$ is optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{6-14}$ aryl, optionally substituted 3-14 membered heteroaryl, optionally substituted 3-12 membered heterocyclyl, optionally substituted 3-18 membered heteroarylalkyl, optionally substituted 3-18 membered heterocyclylalkyl or optionally substituted C$_{6-18}$ arylalkyl; wherein, when R$^7$ is substituted, R$^7$ is substituted with one or more Q$^2$. In another aspect of this embodiment, R$^7$ is optionally substituted C$_1$-C$_6$ alkyl. In another aspect of this embodiment, R$^7$ is optionally substituted C$_7$-C$_{11}$ arylalkyl. In another aspect of this embodiment, R$^7$ is optionally substituted 6-11 membered heteroarylalkyl. In another aspect of this embodiment, R$^7$ is optionally substituted 6-11 membered heterocyclylalkyl.

In another embodiment of Formula I, R$^1$ is optionally substituted C$_3$-C$_7$ secondary or tertiary alkyl and R$^2$ is optionally substituted methylcyclohexyl or optionally substituted methylcyclohexenyl. In another aspect of this embodiment, R$^1$ is prop-2-yl (isopropyl) or 2-methylprop-2-yl (t-butyl). In another aspect of this embodiment, R$^2$ is optionally substituted 4-methylcyclohexyl. In a preferred aspect of this embodiment, R$^2$ is

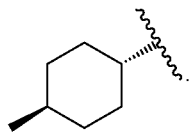 [SMILES: *[C@H]1CC[C@H](C)CC1]

In another preferred aspect of this embodiment, R$^2$ is

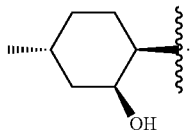 [SMILES: *[C@@H]1CC[C@@H](C)C[C@@H]1O]

In another preferred aspect of this embodiment, R$^2$ is

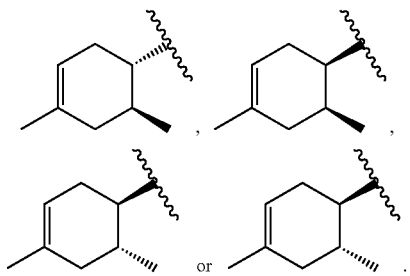

In another preferred aspect of this embodiment, R$^2$ is

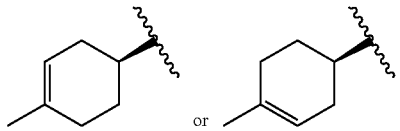

In another embodiment of Formula I, Y is —R$^3$-L-Het, R$^1$ is optionally substituted C$_3$-C$_7$ secondary or tertiary alkyl and R$^2$ is optionally substituted methylcyclohexyl or optionally substituted methylcyclohexenyl. In another aspect of this embodiment, R$^3$ is optionally substituted C$_{1-6}$ alkylene. In another aspect of this embodiment, R$^3$ is C$_{4-6}$ cycloalkylene or substituted C$_{4-6}$ cycloalkylene. In another aspect of this embodiment, R$^3$ is an optionally substituted 5-6 membered heterocyclylene. In another aspect of this embodiment, L is —OC(O)N(R$^4$)—, —N(R$^4$)C(O)O—, —N(R$^4$)S(O)$_2$—, —N(R$^4$)C(O)—, —C(O)—, —C(O)O—, —OC(O)—, —N(R$^4$)N(R$^4$)C(O)O—, or —N(R$^4$)N(R$^4$)—. In another aspect of this embodiment, L is —OC(O)N(R$^4$)—. In another aspect of this embodiment, L is —N(R$^4$)C(O)O—. In another aspect of this embodiment, L is —N(R$^4$)S(O)$_2$—. In another aspect of this embodiment, L is —N(R$^4$)C(O)—. In another aspect of this embodiment, L is —C(O)—. In another aspect of this embodiment, —C(O)O—. In another aspect of this embodiment, L is —OC(O)—. In another aspect of this embodiment, L is —N(R$^4$)N(R$^4$)C(O)O—. In another aspect of this embodiment, L is —N(R$^4$)N(R$^4$)—. In another aspect of this embodiment, Het is an optionally substituted 3-12 membered heterocyclyl or optionally substituted 3-14 membered heteroaryl wherein said optionally substituted 3-12 membered heterocyclyl or optionally substituted 3-14 membered heteroaryl comprises one to four heteroatoms selected from O, S, or N. In another aspect of this embodiment, Het is an optionally substituted 3-12 membered heterocyclyl comprising one or two heteroatoms selected from O, S, or N. In aspect of this embodiment, Het is an optionally substituted 5-10 membered heteroaryl comprising one to four heteroatoms selected from O, S, or N.

In another embodiment of Formula I, Y is —R$^3$—N(R$^4$)C(O)O-Het, R$^1$ is optionally substituted C$_3$-C$_7$ secondary or tertiary alkyl and R$^2$ is optionally substituted methylcyclohexyl or optionally substituted methylcyclohexenyl. In another aspect of this embodiment, R$^3$ is optionally substituted C$_{1-6}$ alkylene. In another aspect of this embodiment, R$^3$ is C$_{4-6}$ cycloalkylene or substituted C$_{4-6}$ cycloalkylene. In another aspect of this embodiment, Het is an optionally substituted 3-12 membered heterocyclyl or optionally substituted 3-14 membered heteroaryl wherein said optionally substituted 3-12 membered heterocyclyl or optionally substituted 3-14 membered heteroaryl comprises one to four heteroatoms selected from O, S, or N. In another aspect of this embodiment, Het is an optionally substituted 3-12 membered heterocyclyl comprising one or two heteroatoms selected from O, S, or N. In aspect of this embodiment, Het is an optionally substituted 5-10 membered heteroaryl comprising one to four heteroatoms selected from O, S, or N.

In another embodiment of Formula I, Y is —R$^3$—C(O)O-Het, R$^1$ is optionally substituted C$_3$-C$_7$ secondary or tertiary alkyl, R$^2$ is optionally substituted methylcyclohexyl or optionally substituted methylcyclohexenyl and R$^3$ is an optionally substituted 5-6 membered heterocyclylene. In another aspect of this embodiment, Het is an optionally substituted 3-12 membered heterocyclyl or optionally substituted 3-14 membered heteroaryl wherein said optionally substituted 3-12 membered heterocyclyl or optionally substituted 3-14 membered heteroaryl comprises one to four heteroatoms selected from O, S, or N. In another aspect of this embodiment, Het is an optionally substituted 3-12 membered heterocyclyl comprising one or two heteroatoms selected from O, S, or N. In aspect of this embodiment, Het is an optionally substituted 5-10 membered heteroaryl comprising one to four heteroatoms selected from O, S, or N. In another aspect of this embodiment —$R^3$—C(O)O-Het is:

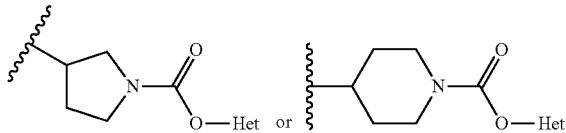

wherein the pyrrolidinyl or piperidinyl ring is optionally substituted.

In another embodiment of Formula I, Y is —N($R^4$)($R^5$), $R^1$ is optionally substituted $C_3$-$C_7$ secondary or tertiary alkyl and $R^2$ is optionally substituted methylcyclohexyl or optionally substituted methylcyclohexenyl. In another aspect of this embodiment, $R^4$ is H or optionally substituted $C_1$-$C_6$ alkyl. In another aspect of this embodiment, $R^5$ is $C_1$-$C_{12}$ alkyl, $C_3$-$C_{12}$ cycloalkyl, 3-14 membered heteroaryl or 3-12 membered heterocyclyl wherein each $C_1$-$C_{12}$ alkyl, $C_3$-$C_{12}$ cycloalkyl, 3-14 membered heteroaryl or 3-12 membered heterocyclyl is optionally substituted with one or more $Q^1$. In another aspect of this embodiment, $R^5$ is $C_1$-$C_6$ alkyl, $C_5$-$C_6$ cycloalkyl, 5-10 membered heteroaryl or 4-10 membered heterocyclyl wherein each $C_1$-$C_6$ alkyl, $C_5$-$C_6$ cycloalkyl, 5-10 membered heteroaryl or 4-10 membered heterocyclyl is optionally substituted with one or more $Q^1$.

In another embodiment of Formula I, Y is —$R^6$=$NOR^7$, $R^1$ is optionally substituted $C_3$-$C_7$ secondary or tertiary alkyl and $R^2$ is optionally substituted methylcyclohexyl or optionally substituted methylcyclohexenyl. In another aspect of this embodiment, $R^6$ is $C_5$-$C_6$ cycloalkylyne, or 4-6 membered heterocyclylyne wherein each $C_5$-$C_6$ cycloalkylyne or 4-6 membered heterocyclylyne is optionally substituted with one or more $Q^1$. In another aspect of this embodiment, $R^6$ is cyclohexylyne. In another aspect of this embodiment, $R^7$ is optionally substituted $C_1$-$C_6$ alkyl. In another aspect of this embodiment, $R^7$ is optionally substituted $C_7$-$C_{11}$ arylalkyl. In another aspect of this embodiment, $R^7$ is optionally substituted 6-11 membered heteroarylalkyl. In another aspect of this embodiment, $R^7$ is optionally substituted 6-11 membered heterocyclylalkyl.

In another embodiment, compounds of Formula I comprise compounds of Formula II:

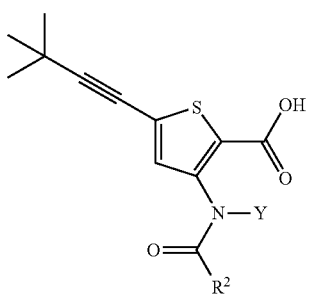

Formula II or pharmaceutically acceptable salts and esters thereof, wherein:
$R^2$ is optionally substituted 4-methylcyclohexyl or optionally substituted methylcyclohexenyl and the remaining variables are defined as for Formula I.

In one embodiment of Formula II, $R^2$ is:

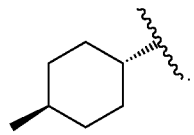 [SMILES: *[C@H]1CC[C@H](C)CC1]

In one embodiment of Formula II, $R^2$ is:

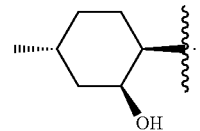

In another embodiment, $R^2$ is

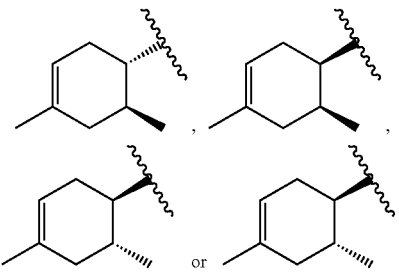

In another embodiment, $R^2$ is

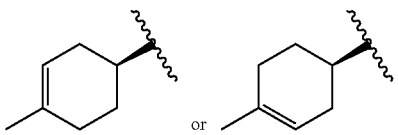

In one embodiment of Formula II, Y is —$R^3$-L-Het. In another aspect of this embodiment, $R^3$ is optionally substituted $C_{1-6}$ alkylene. In another aspect of this embodiment, $R^3$ is $C_{4-6}$ cycloalkylene or substituted $C_{4-6}$ cycloalkylene. In another aspect of this embodiment, $R^3$ is an optionally substituted 5-6 membered heterocyclylene. In another aspect of this embodiment, L is —OC(O)N($R^4$)—, N($R^4$)C(O)O—, —N($R^4$)S(O)$_2$—, —N($R^4$)C(O)—, —C(O)—, —C(O)O—, —OC(O)—, —N($R^4$)N($R^4$)C(O)O—, or —N($R^4$)N($R^4$)—. In another aspect of this embodiment, L is —OC(O)N($R^4$)—. In another aspect of this embodiment, L is —N($R^4$)C(O)O—. In another aspect of this embodiment, L is —N($R^4$)S(O)$_2$—. In another aspect of this embodiment, L is —N($R^4$)C(O)—. In another aspect of this embodiment, —C(O)—. In another aspect of this embodiment, —C(O)O—. In another aspect of this embodiment, L is —OC(O)—. In another aspect of this embodiment, L is —N($R^4$)N($R^4$)C(O)O—. In another aspect of this embodiment, L is —N($R^4$)N($R^4$)—. In another aspect of this embodiment, Het is an optionally substituted 3-12 membered heterocyclyl or optionally substituted 3-14 membered heteroaryl wherein said optionally substituted 3-12 membered heterocyclyl or optionally substituted 3-14 membered heteroaryl comprises one to four heteroatoms selected from O, S, or N. In another aspect of this embodiment, Het is an optionally substituted 3-12 membered heterocyclyl comprising one or two heteroatoms selected from O, S, or N. In another aspect of this embodiment, Het is an optionally substituted 5-10 membered heteroaryl comprising one to four heteroatoms selected from O, S, or N. In another aspect of this embodiment, $R^2$ is:

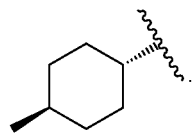 [SMILES: *[C@H]1CC[C@H](C)CC1]

In another aspect of this embodiment, $R^2$ is:

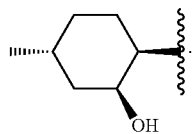 [SMILES: *[C@@H]1CC[C@@H](C)C[C@@H]1O]

In another preferred aspect of this embodiment, $R^2$ is

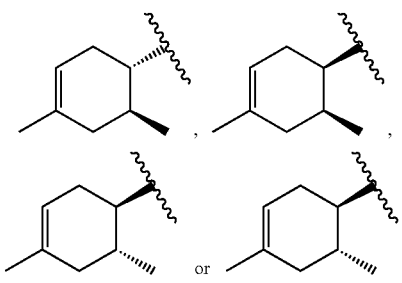

In another preferred aspect of this embodiment, $R^2$ is

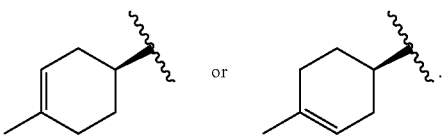

In another embodiment of Formula II, Y is —$R^3$-L-Het wherein Het is an optionally substituted 3-12 membered heterocyclyl or optionally substituted 3-14 membered heteroaryl wherein said optionally substituted 3-12 membered heterocyclyl or optionally substituted 3-14 membered heteroaryl comprises one to four heteroatoms selected from O, S, or N. In another aspect of this embodiment, Het is optionally substituted pyridinyl. In another aspect of this embodiment, Het is optionally substituted pyridazinyl. In another aspect of this embodiment, Het is optionally substituted tetrahydro-2H-pyranyl. In another aspect of this embodiment, Het is optionally substituted piperidinyl. In another aspect of this embodiment, Het is optionally substituted pyrrolidinyl. In another aspect of this embodiment, Het is optionally substituted tetrahydrothiophenyl. In another aspect of this embodiment, Het is optionally substituted pyrazinyl. In another aspect of this embodiment, Het is optionally substituted 1H-tetrazolyl. In another aspect of this embodiment, Het is optionally substituted azetidinyl. In another aspect of this embodiment, Het is optionally substituted tetrahydrofuranyl. In another aspect of this embodiment, Het is optionally substituted tetrahydro-2H-furo[2,3-b]furanyl. In another aspect of this embodiment, Het is optionally substituted thiazoyl. In another aspect of this embodiment, Het is optionally substituted 1H-imidazolyl. In another aspect of this embodiment, Het is optionally substituted 4H-1,2,4-triazolyl. In another aspect of this embodiment, Het is optionally substituted 1H-pyrazolyl. In another aspect of this embodiment, Het is optionally substituted 1,3,4-thiadiazolyl. In another aspect of this embodiment, Het is optionally substituted quinolinyl. In another aspect of this embodiment, Het is optionally substituted [1,2,4]triazolo[4,3-a]pyridinyl. In another aspect of this embodiment, Het is optionally substituted thiophenyl. In another aspect of this embodiment, Het is optionally substituted 1,2,4-thiadiazolyl. In another aspect of this embodiment, Het is optionally substituted pyrimidinyl. In another aspect of this embodiment, Het is optionally substituted 1H-1,2,3-triazolyl. In another aspect of this embodiment, Het is optionally substituted 1,3,4-oxadiazolyl. In another aspect of this embodiment, Het is optionally substituted imidazo[1,2-b]pyridazinyl. In another aspect of this embodiment, $R^2$ is:

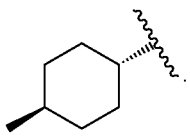 [SMILES: *[C@H]1CC[C@H](C)CC1]

In another aspect of this embodiment, $R^2$ is:

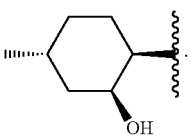 [SMILES: *[C@@H]1CC[C@@H](C)C[C@@H]1O]

In another preferred aspect of this embodiment, $R^2$ is

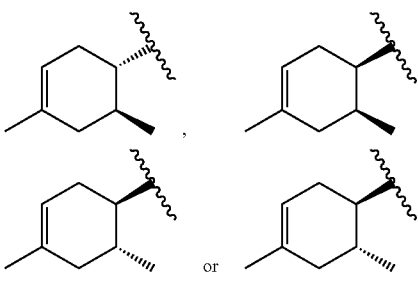

In another preferred aspect of this embodiment, $R^2$ is

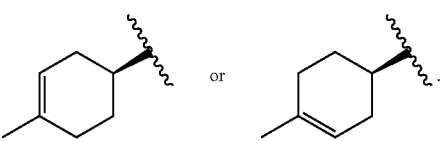

In another embodiment of Formula II, Y is —R³—N(R⁴)C(O)O-Het. In another aspect of this embodiment, R³ is optionally substituted C$_{1-6}$ alkylene. In another aspect of this embodiment, R³ is C$_{4-6}$ cycloalkylene or substituted C$_{4-6}$ cycloalkylene. In another aspect of this embodiment, Het is an optionally substituted 3-12 membered heterocyclyl or optionally substituted 3-14 membered heteroaryl wherein said optionally substituted 3-12 membered heterocyclyl or optionally substituted 3-14 membered heteroaryl comprises one to four heteroatoms selected from O, S, or N. In another aspect of this embodiment, Het is an optionally substituted 3-12 membered heterocyclyl comprising one or two heteroatoms selected from O, S, or N. In aspect of this embodiment, Het is an optionally substituted 5-10 membered heteroaryl comprising one to four heteroatoms selected from O, S, or N. In another aspect of this embodiment, Het is optionally substituted pyridinyl. In another aspect of this embodiment, Het is optionally substituted pyridazinyl. In another aspect of this embodiment, Het is optionally substituted tetrahydro-2H-pyranyl. In another aspect of this embodiment, Het is optionally substituted piperidinyl. In another aspect of this embodiment, Het is optionally substituted pyrrolidinyl. In another aspect of this embodiment, Het is optionally substituted tetrahydrothiophenyl. In another aspect of this embodiment, Het is optionally substituted pyrazinyl. In another aspect of this embodiment, Het is optionally substituted 1H-tetrazolyl. In another aspect of this embodiment, Het is optionally substituted azetidinyl. In another aspect of this embodiment, Het is optionally substituted tetrahydrofuranyl. In another aspect of this embodiment, Het is optionally substituted tetrahydro-2H-furo[2,3-b]furanyl. In another aspect of this embodiment, Het is optionally substituted thiazoyl. In another aspect of this embodiment, Het is optionally substituted 1H-imidazolyl. In another aspect of this embodiment, Het is optionally substituted 4H-1,2,4-triazolyl. In another aspect of this embodiment, Het is optionally substituted 1H-pyrazolyl. In another aspect of this embodiment, Het is optionally substituted 1,3,4-thiadiazolyl. In another aspect of this embodiment, Het is optionally substituted quinolinyl. In another aspect of this embodiment, Het is optionally substituted [1,2,4]triazolo[4,3-a]pyridinyl. In another aspect of this embodiment, Het is optionally substituted thiophenyl. In another aspect of this embodiment, Het is optionally substituted 1,2,4-thiadiazolyl. In another aspect of this embodiment, Het is optionally substituted pyrimidinyl. In another aspect of this embodiment, Het is optionally substituted 1H-1,2,3-triazolyl. In another aspect of this embodiment, Het is optionally substituted 1,3,4-oxadiazolyl. In another aspect of this embodiment, Het is optionally substituted imidazo[1,2-b]pyridazinyl. In another aspect of this embodiment, R² is:

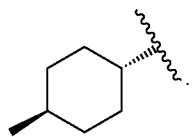

In another aspect of this embodiment, R² is:

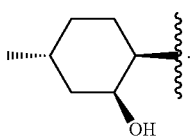

In another preferred aspect of this embodiment, R² is

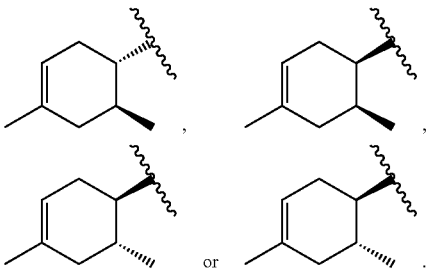

In another preferred aspect of this embodiment, R² is

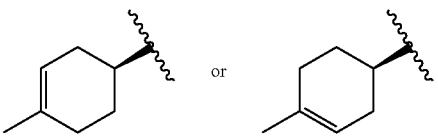

In another embodiment of Formula II, Y is —R³—C(O)O-Het and R³ is an optionally substituted 5-6 membered heterocyclylene. In another aspect of this embodiment, Het is an optionally substituted 3-12 membered heterocyclyl or optionally substituted 3-14 membered heteroaryl wherein said optionally substituted 3-12 membered heterocyclyl or optionally substituted 3-14 membered heteroaryl comprises one to four heteroatoms selected from O, S, or N. In another aspect of this embodiment, Het is an optionally substituted 3-12 membered heterocyclyl comprising one or two heteroatoms selected from O, S, or N. In aspect of this embodiment, Het is an optionally substituted 5-10 membered heteroaryl comprising one to four heteroatoms selected from O, S, or N. In another aspect of this embodiment, Het is optionally substituted pyridinyl. In another aspect of this embodiment, Het is optionally substituted pyridazinyl. In another aspect of this embodiment, Het is optionally substituted tetrahydro-2H-pyranyl. In another aspect of this embodiment, Het is optionally substituted piperidinyl. In another aspect of this embodiment, Het is optionally substituted pyrrolidinyl. In another aspect of this embodiment, Het is optionally substituted tetrahydrothiophenyl. In another aspect of this embodiment, Het is optionally substituted pyrazinyl. In another aspect of this embodiment, Het is optionally substituted 1H-tetrazolyl. In another aspect of this embodiment, Het is optionally substituted azetidinyl. In another aspect of this embodiment, Het is optionally substituted tetrahydrofuranyl. In another aspect of this embodiment, Het is optionally substituted tetrahydro-2H-furo[2,3-b]furanyl. In another aspect of this embodiment, Het is optionally substituted thiazoyl. In another aspect of this embodiment, Het is optionally substituted 1H-imidazolyl. In another aspect of this embodiment, Het is optionally substituted 4H-1,2,4-triazolyl. In another aspect of this embodiment, Het is optionally substituted 1H-pyrazolyl. In another aspect of this embodiment, Het is optionally substituted 1,3,4-thiadiazolyl. In another aspect of this embodiment, Het is optionally substituted quinolinyl. In another aspect of this embodiment, Het is optionally substituted [1,2,4]triazolo[4,3-a]pyridinyl. In another aspect of this embodiment, Het is optionally substituted thiophenyl. In another aspect of this embodiment, Het is optionally substituted 1,2,4-thiadiazolyl. In another aspect of this embodiment, Het is optionally substituted pyrimidinyl. In another aspect of this embodiment, Het is optionally substituted 1H-1,2,3-triazolyl. In another aspect of this embodiment, Het is optionally substituted 1,3,4-oxadiazolyl. In another aspect of this embodiment, Het is optionally substituted imidazo[1,2-b]pyridazinyl. In another aspect of this embodiment —$R^3$—C(O)O-Het is:

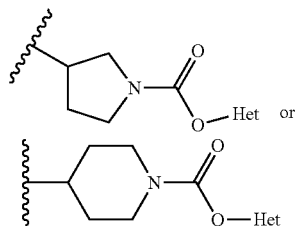

wherein the pyrrolidinyl or piperidinyl ring is optionally substituted. In another aspect of this embodiment, $R^2$ is:

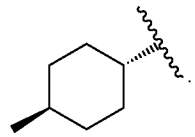 [SMILES: *[C@H]1CC[C@H](C)CC1]

In another aspect of this embodiment, $R^2$ is:

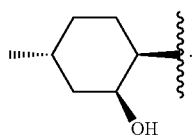 [SMILES: *[C@@H]1CC[C@@H](C)C[C@@H]1O]

In another preferred aspect of this embodiment, $R^2$ is

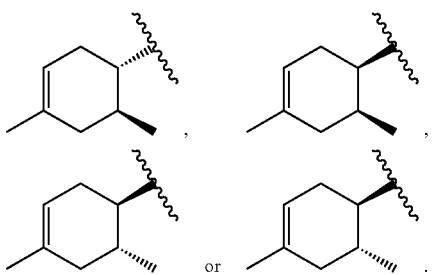

In another preferred aspect of this embodiment, $R^2$ is

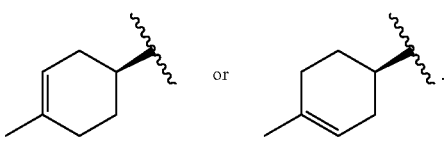

In another embodiment of Formula II, Y is —N($R^4$)($R^5$). In another aspect of this embodiment, $R^4$ is H or optionally substituted $C_1$-$C_6$ alkyl. In another aspect of this embodiment, $R^5$ is $C_1$-$C_6$ alkyl, $C_5$-$C_6$ cycloalkyl, 5-10 membered heteroaryl or 4-10 membered heterocyclyl wherein each $C_1$-$C_6$ alkyl, $C_5$-$C_6$ cycloalkyl, 5-10 membered heteroaryl or 4-10 membered heterocyclyl is optionally substituted with one or more $Q^1$. In another aspect of this embodiment, $R^4$ is optionally substituted $C_1$-$C_6$ alkyl and $R^5$ is $C_1$-$C_6$ alkyl, $C_5$-$C_6$ cycloalkyl, 5-10 membered heteroaryl or 4-10 membered heterocyclyl wherein each $C_1$-$C_6$ alkyl, $C_5$-$C_6$ cycloalkyl, 5-10 membered heteroaryl or 4-10 membered heterocyclyl is optionally substituted with one or more $Q^1$. In another aspect of this embodiment, $R^2$ is:

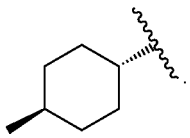 [SMILES: *[C@H]1CC[C@H](C)CC1]

In another aspect of this embodiment, $R^2$ is:

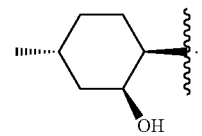 [SMILES: *[C@@H]1CC[C@@H](C)C[C@@H]1O]

In another preferred aspect of this embodiment, $R^2$ is

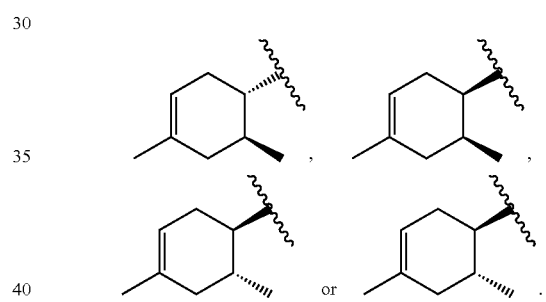

In another preferred aspect of this embodiment, $R^2$ is

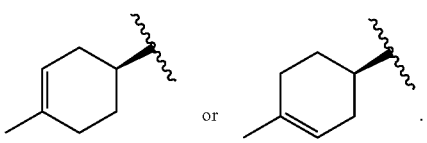

In another embodiment of Formula II, Y is —$R^6$=$NOR^7$. In another aspect of this embodiment, $R^6$ is $C_5$-$C_6$ cycloalkylyne, or 4-6 membered heterocyclylyne wherein each $C_5$-$C_6$ cycloalkylyne or 4-6 membered heterocyclylyne is optionally substituted with one or more $Q^1$. In another aspect of this embodiment, $R^6$ is cyclohexylyne. In another aspect of this embodiment, $R^7$ is optionally substituted $C_1$-$C_6$ alkyl. In another aspect of this embodiment, $R^7$ is optionally substituted $C_7$-$C_{11}$ arylalkyl. In another aspect of this embodiment, $R^7$ is optionally substituted 6-11 membered heteroarylalkyl. In another aspect of this embodiment, $R^7$ is optionally substituted 6-11 membered heterocyclylalkyl. In another aspect of this embodiment, $R^6$ is cyclohexylyne and $R^7$ is optionally substituted $C_1$-$C_6$ alkyl. In another aspect of this embodiment, $R^6$ is cyclohexylyne and $R^7$ is optionally substituted $C_7$-$C_{11}$ arylalkyl. In another aspect of this embodiment, $R^6$ is cyclohexylyne and $R^7$ is optionally substituted 6-11 membered heteroarylalkyl. In another aspect of this embodiment, $R^6$ is cyclohexylyne and $R^7$ is optionally substituted 6-11 membered heterocyclylalkyl. In another aspect of this embodiment, $R^2$ is:

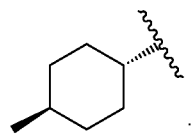 [SMILES: *[C@H]1CC[C@H](C)CC1]

In another aspect of this embodiment, $R^2$ is:

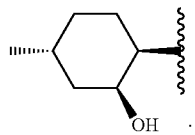 [SMILES: *[C@@H]1CC[C@@H](C)C[C@@H]1O]

In another preferred aspect of this embodiment, $R^2$ is

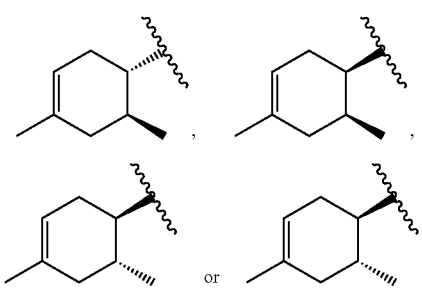

In another preferred aspect of this embodiment, $R^2$ is

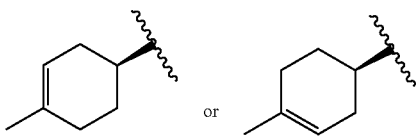

In another embodiment, the compound of Formula I or Formula II is

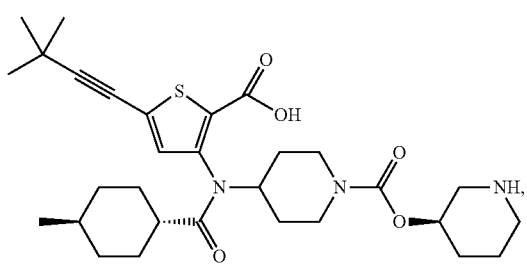

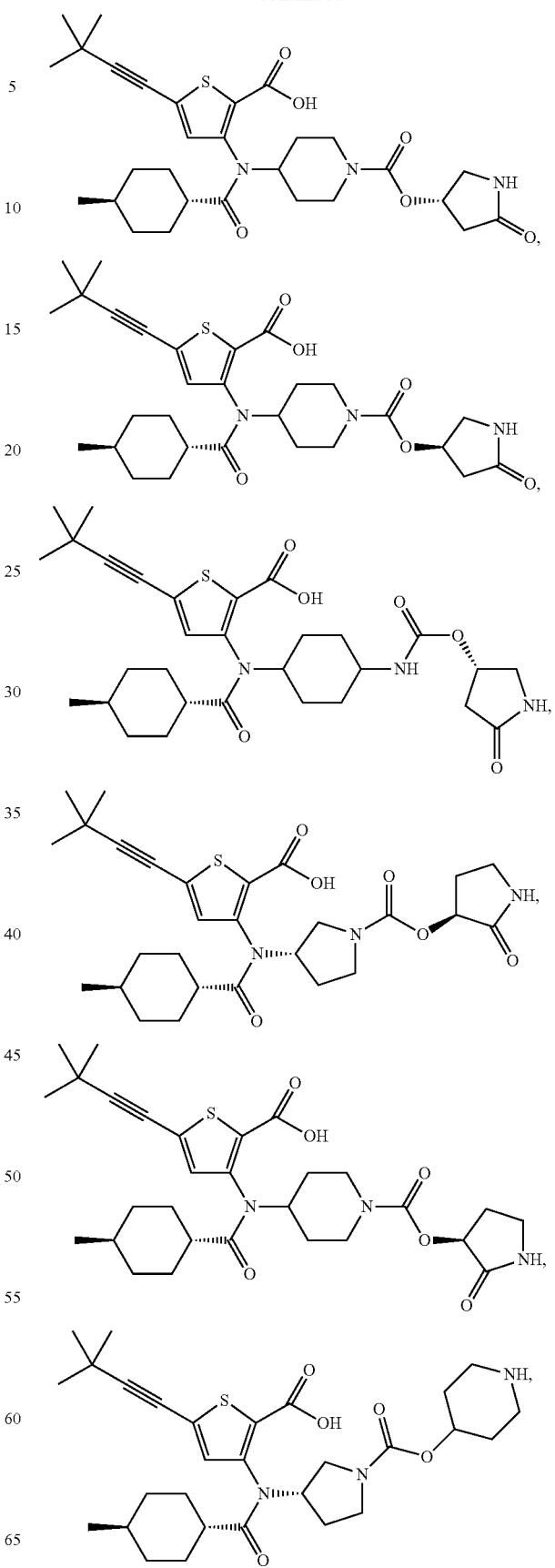

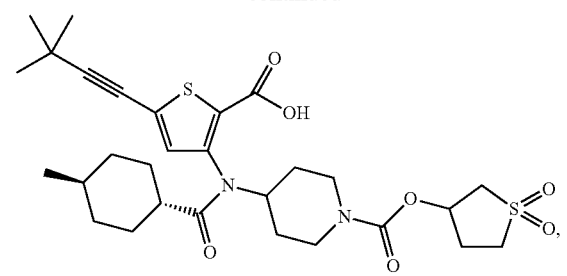
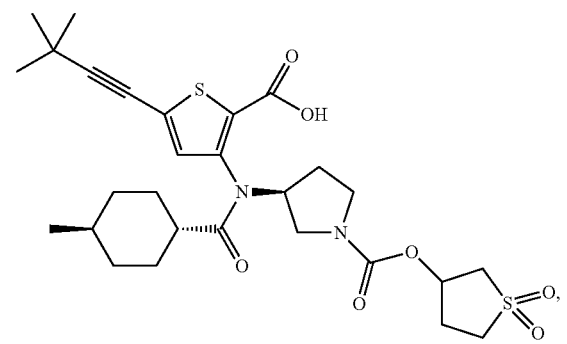
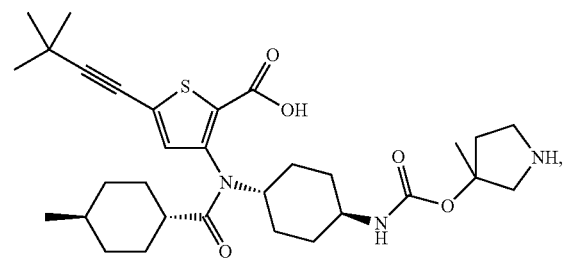
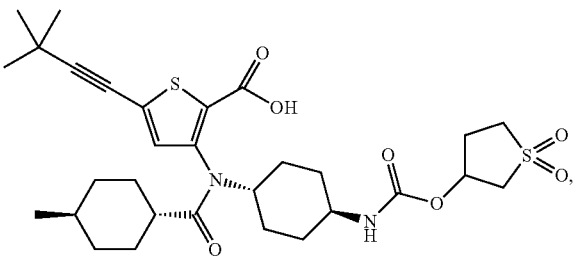
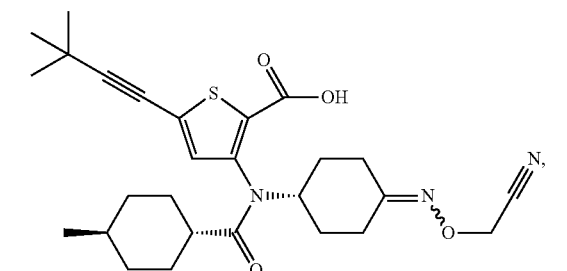
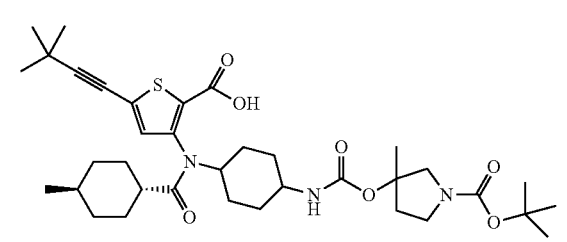
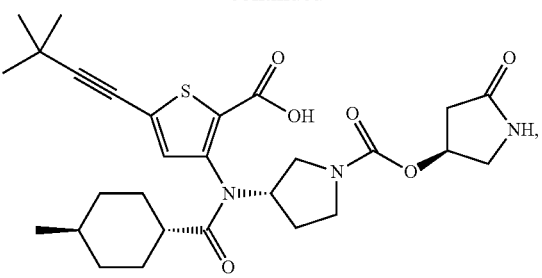
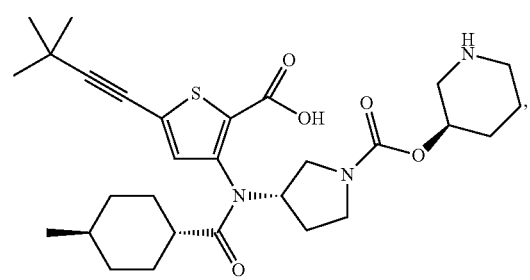
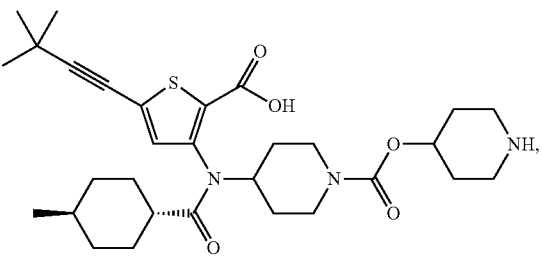
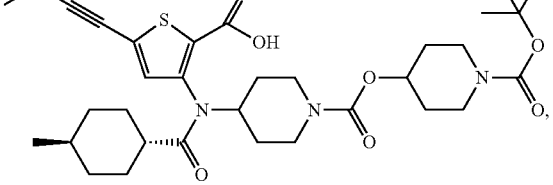
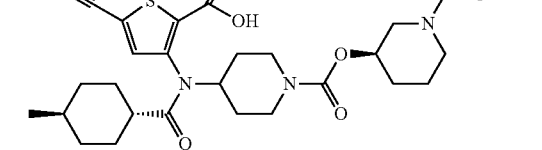
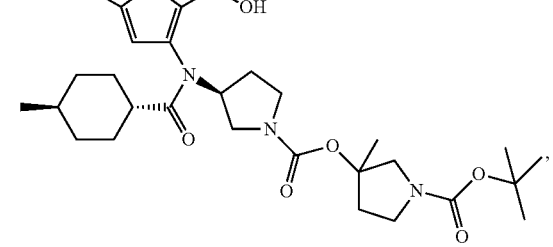

25
-continued
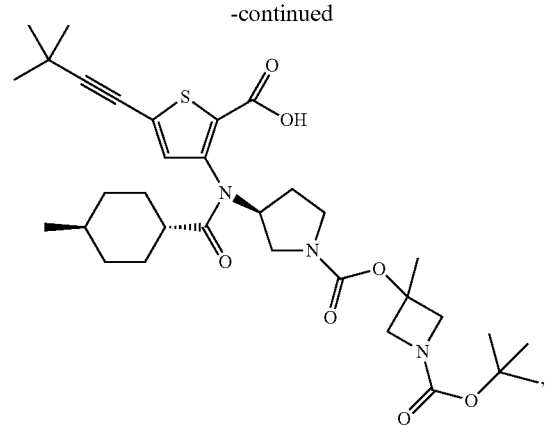
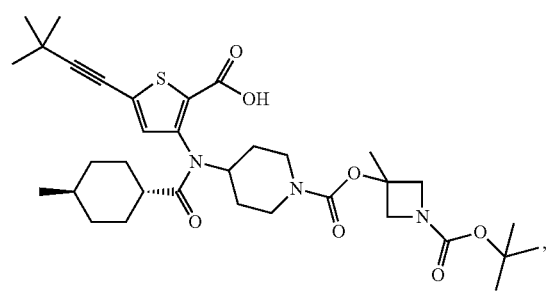
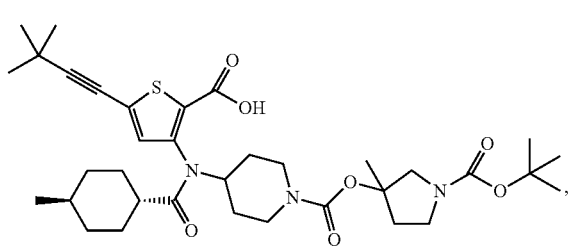
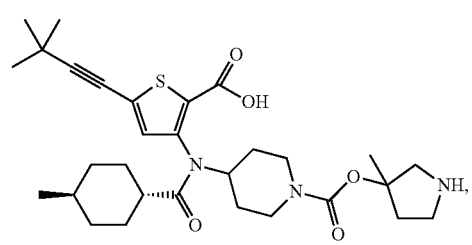
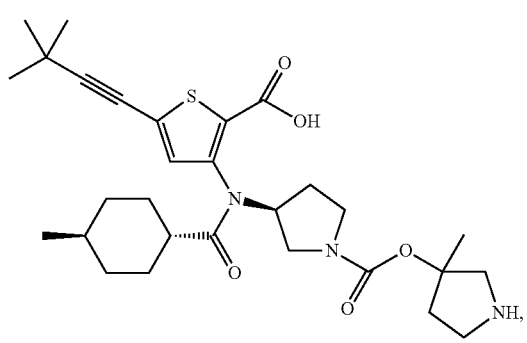
26
-continued
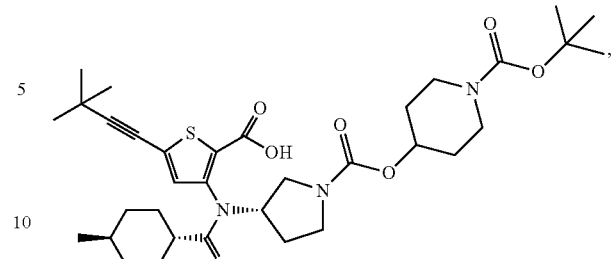
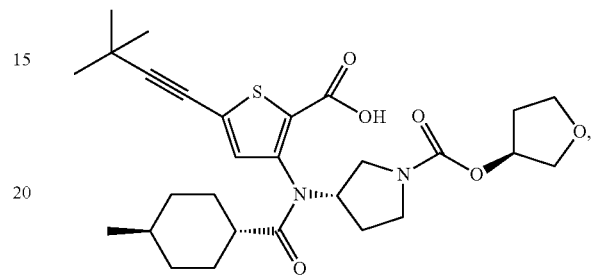
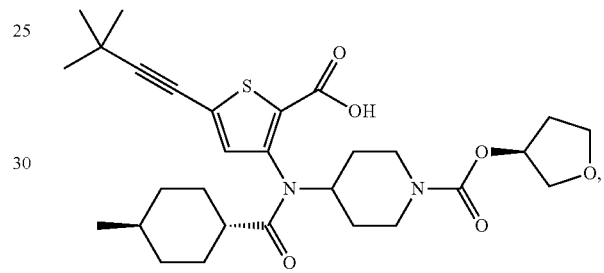
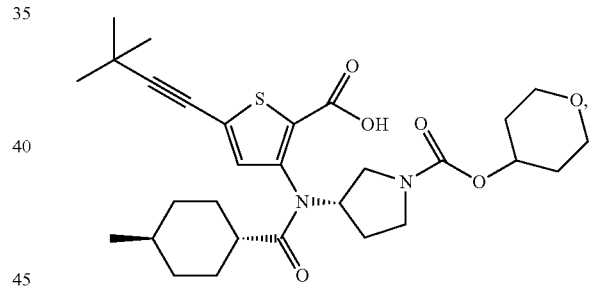
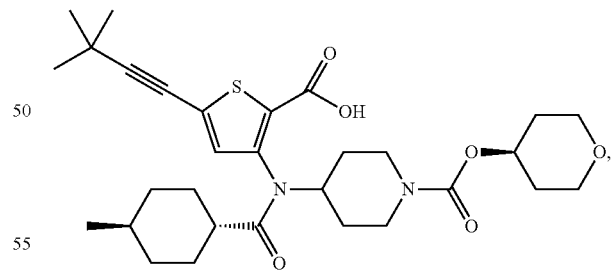
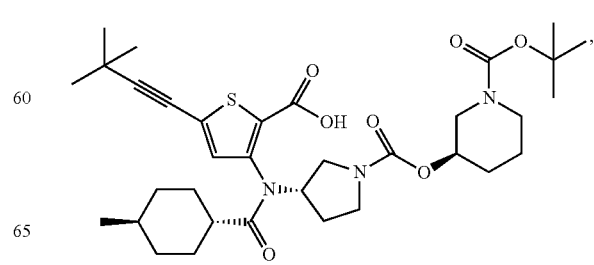

27
-continued
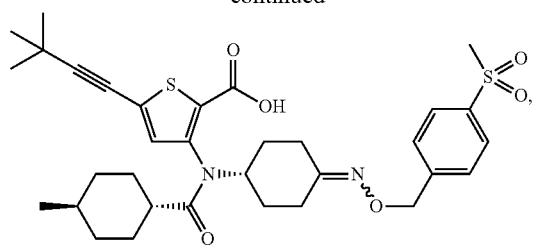
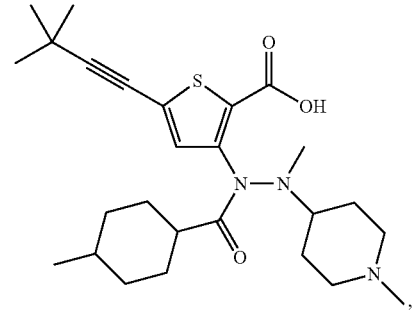
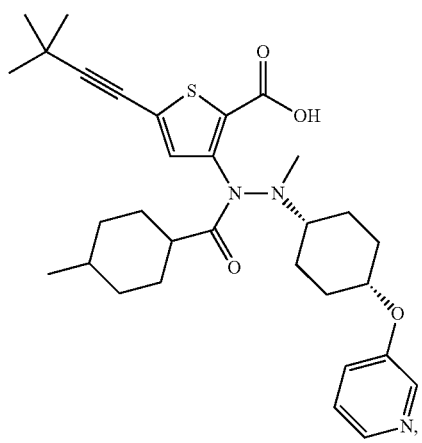
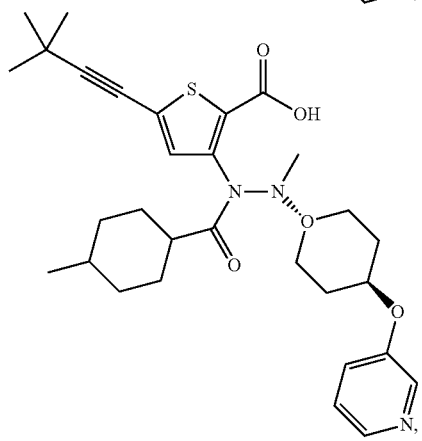
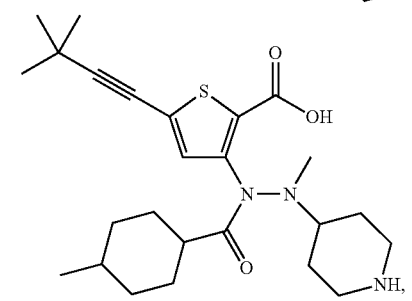
28
-continued
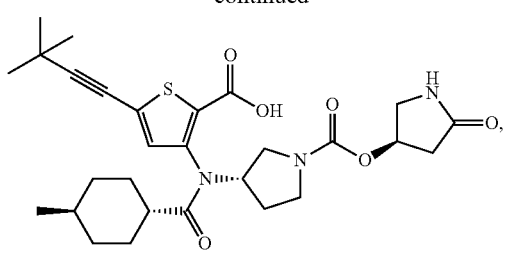
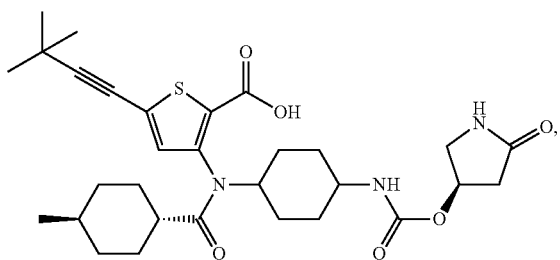
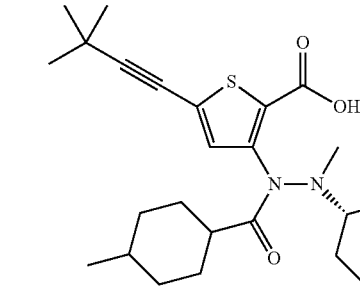
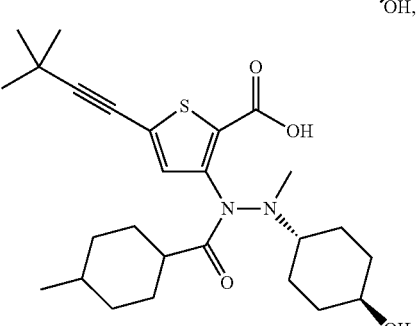
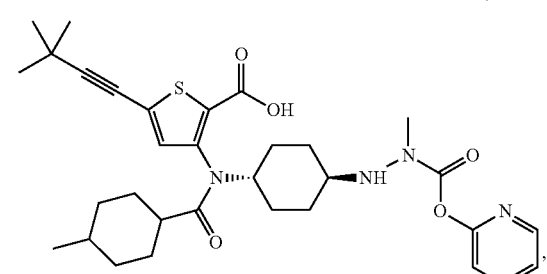
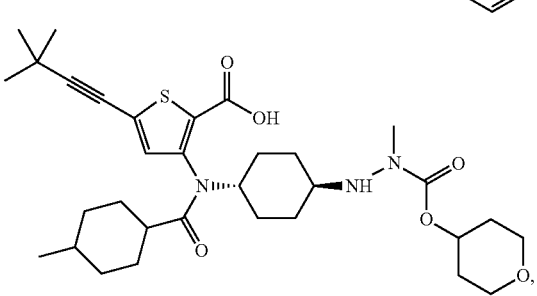

-continued
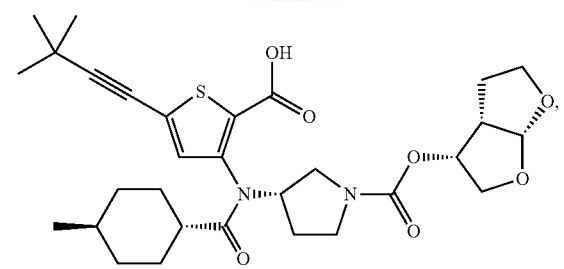
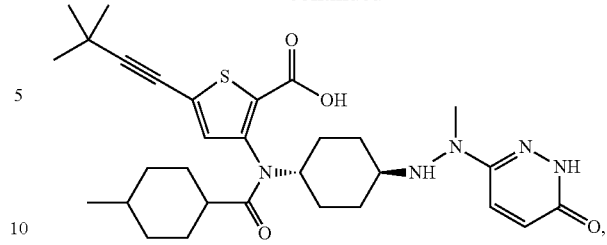
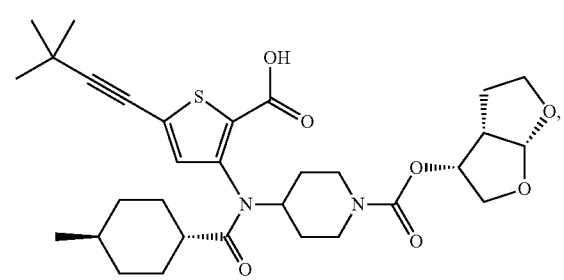
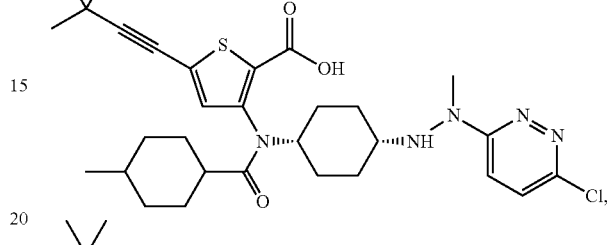
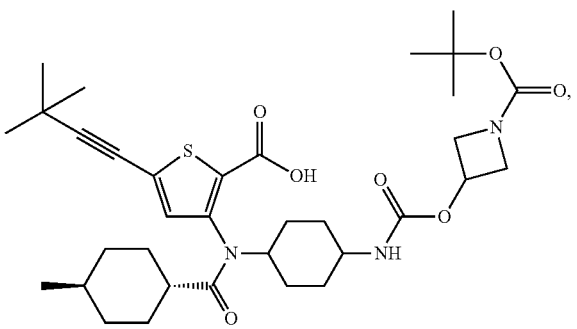
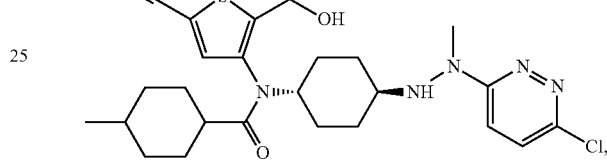
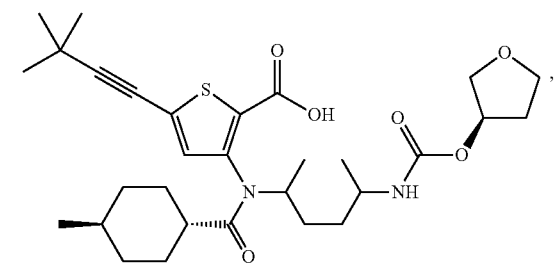
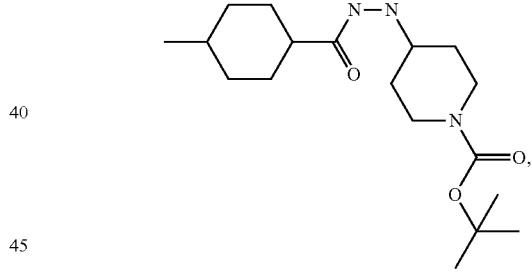
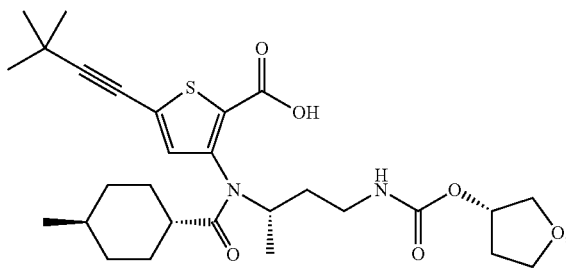
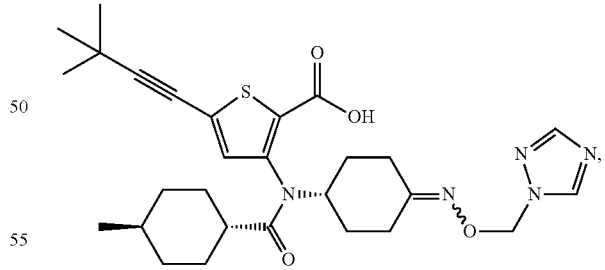
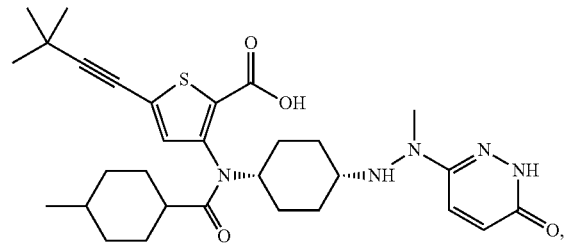
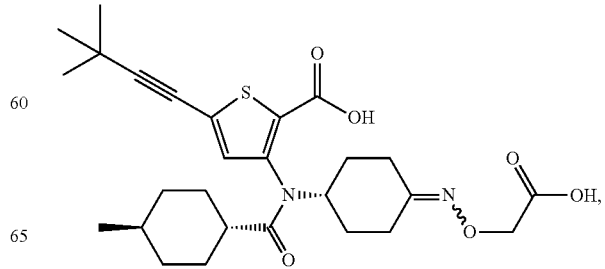

31
-continued
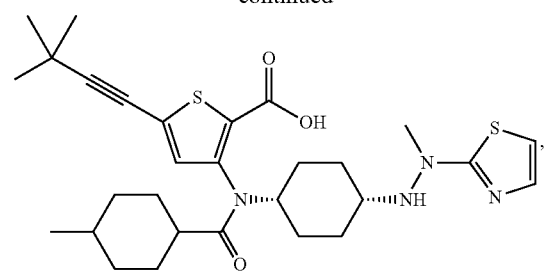
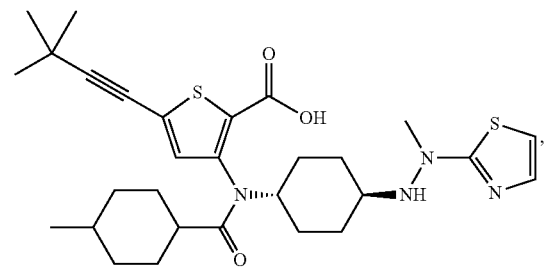
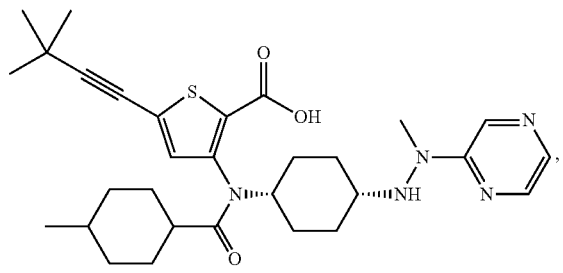
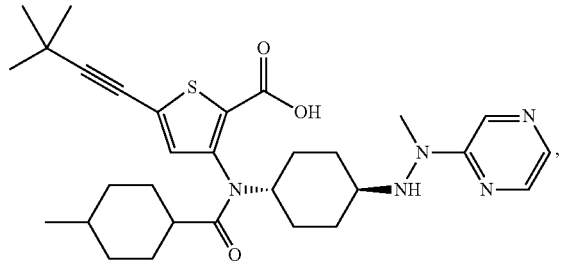
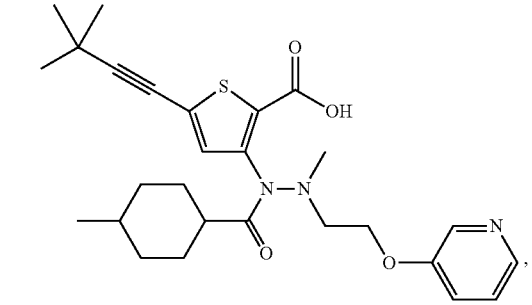
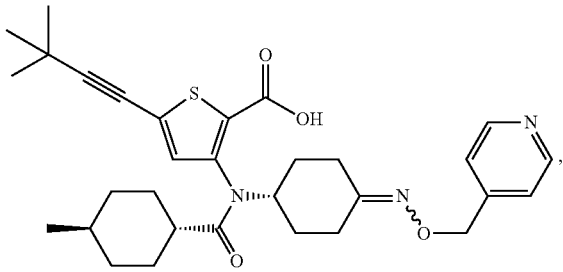
32
-continued
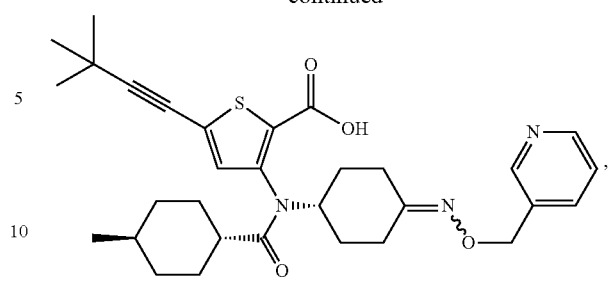
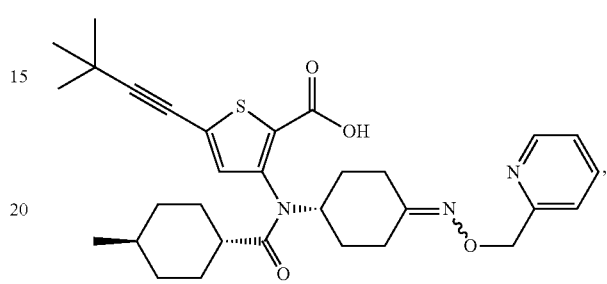
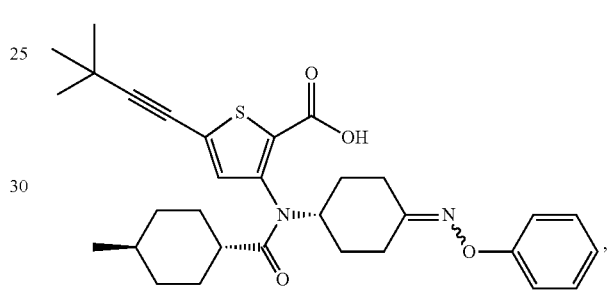
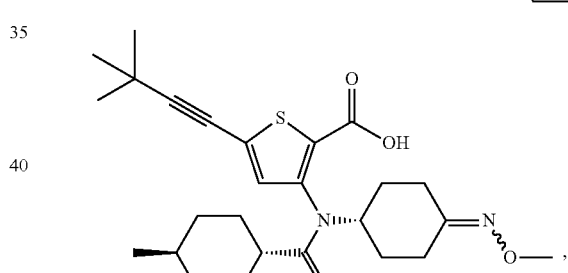
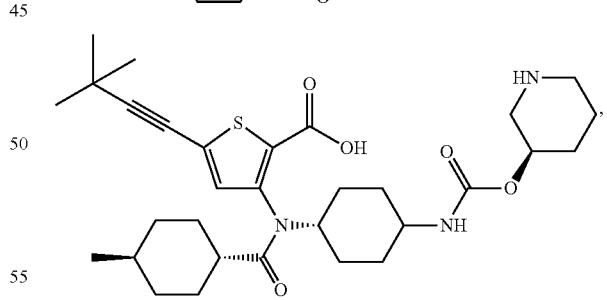
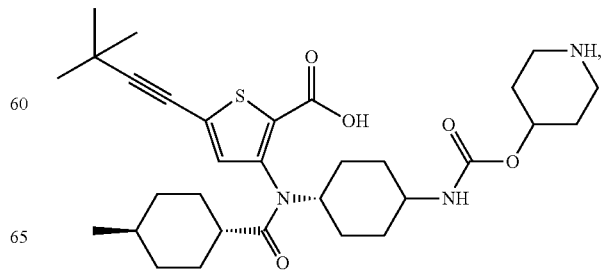

33
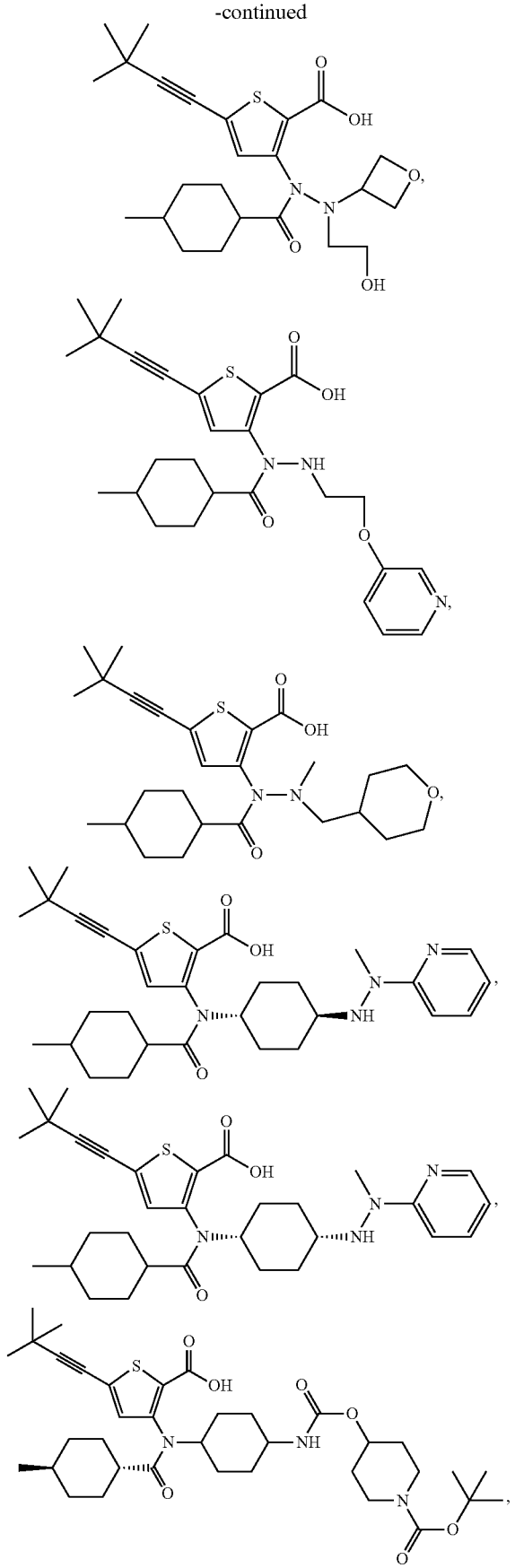
34
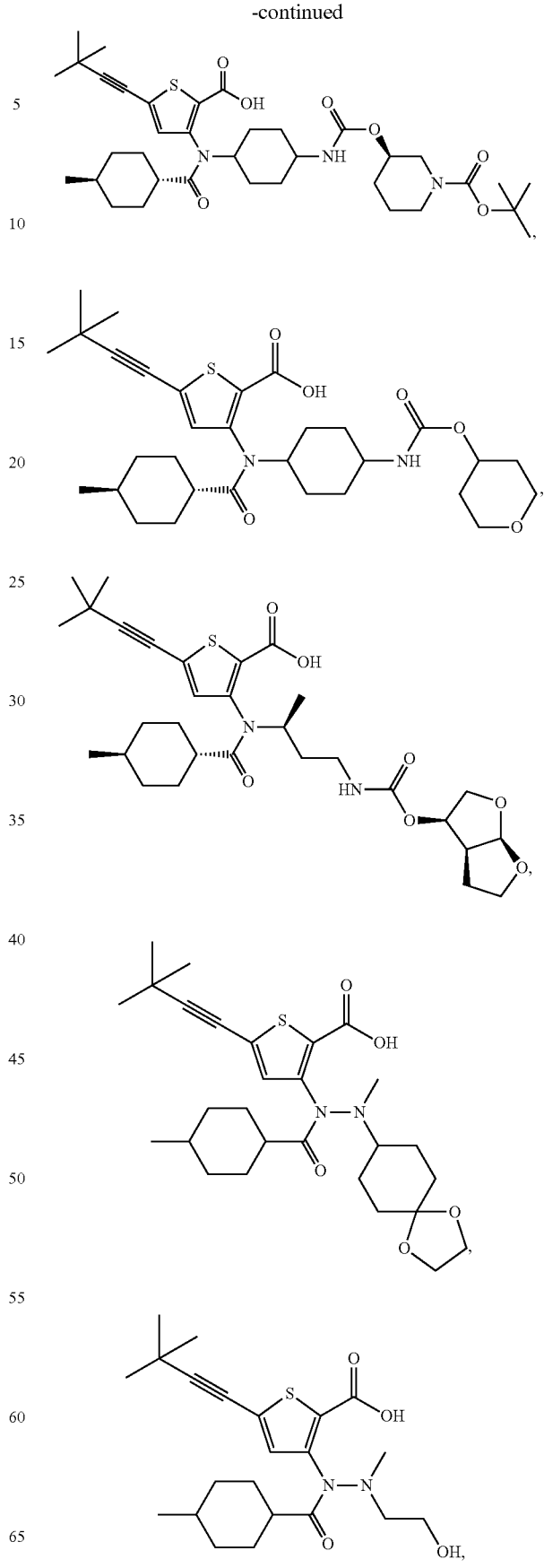

35
-continued
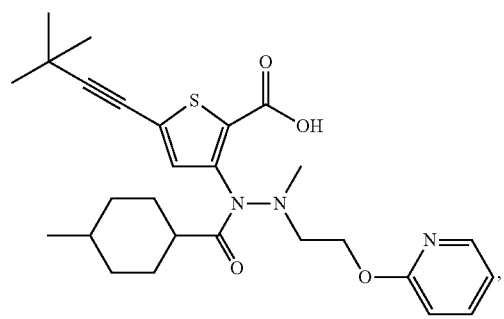
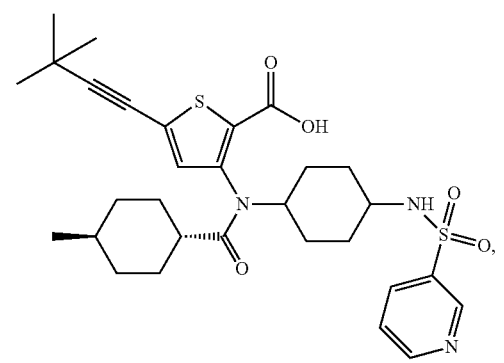
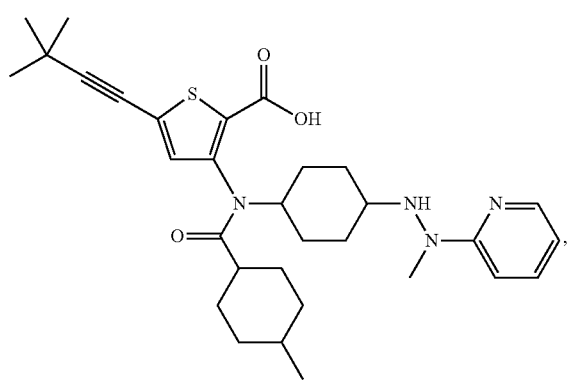
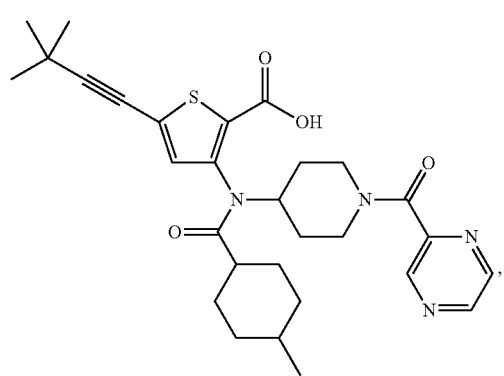
36
-continued
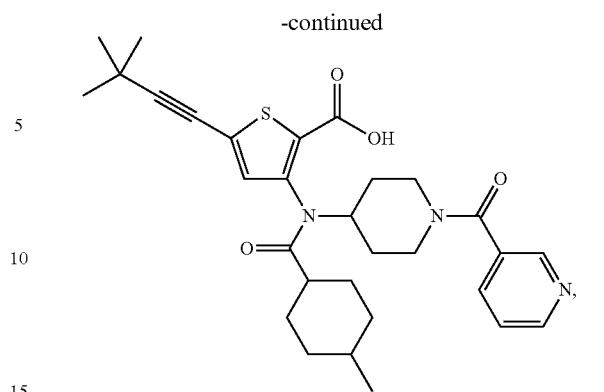
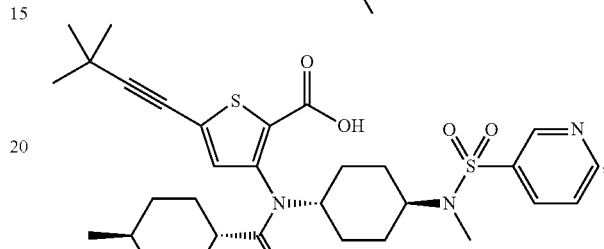
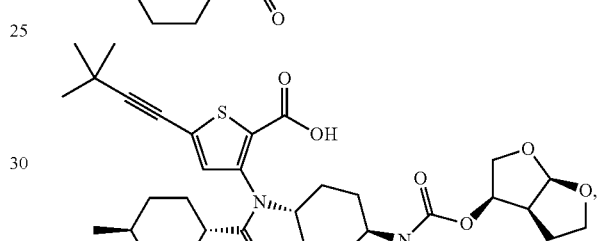
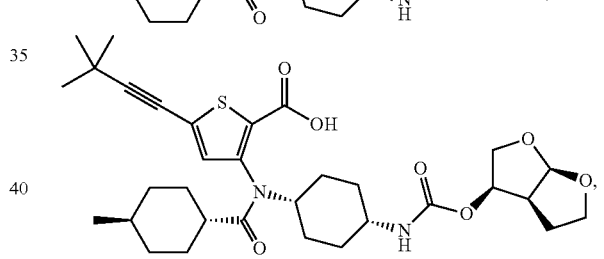
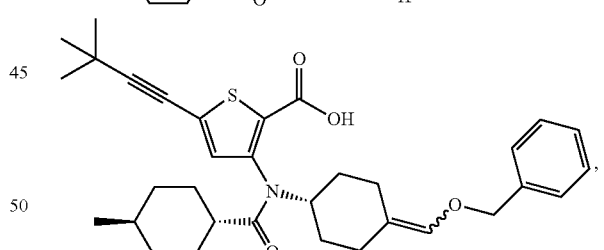
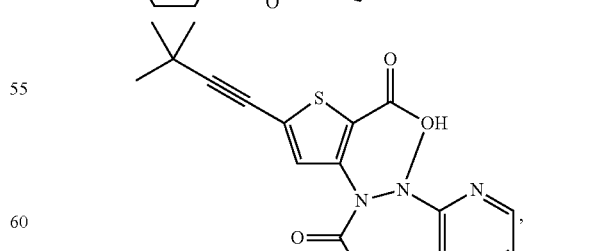
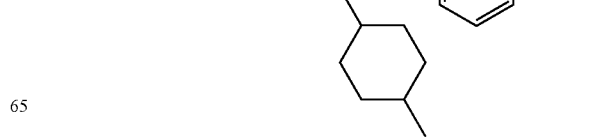

-continued

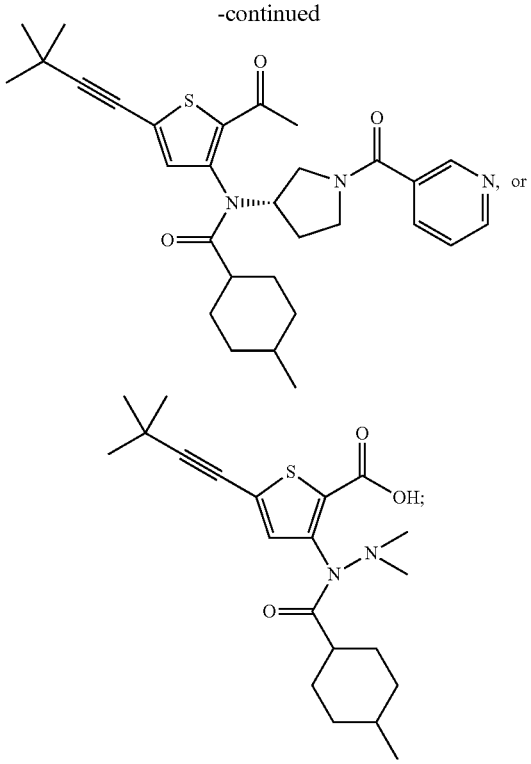

or a pharmaceutically acceptable salt or ester thereof.

Definitions

Unless stated otherwise, the following terms and phrases as used herein are intended to have the following meanings. The fact that a particular term or phrase is not specifically defined should not be correlated to indefiniteness or lacking clarity, but rather terms herein are used within their ordinary meaning. When trade names are used herein, applicants intend to independently include the tradename product and the active pharmaceutical ingredient(s) of the tradename product.

The term "treating", and grammatical equivalents thereof, when used in the context of treating a disease, means slowing or stopping the progression of a disease, or ameliorating at least one symptom of a disease, more preferably ameliorating more than one symptom of a disease. For example, treatment of a hepatitis C virus infection can include reducing the HCV viral load in an HCV, infected human being, and/or reducing the severity of jaundice present in an HCV infected human being.

"Alkyl" is hydrocarbon containing normal, secondary, tertiary or cyclic carbon atoms. For example, an alkyl group can have 1 to 20 carbon atoms (i.e, $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —OtBu), and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like.

"Alkenyl" is a hydrocarbon containing normal, secondary, tertiary, or cyclic carbon atoms with at least one site of unsaturation, i.e. a carbon-carbon, sp2 double bond. For example, an alkenyl group can have 2 to 20 carbon atoms (i.e., $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of suitable alkenyl groups include, but are not limited to, vinyl (—CH=$CH_2$), allyl (—$CH_2CH$=$CH_2$), cyclopentenyl (—$C_5H_7$), and 5-hexenyl (—$CH_2CH_2CH_2CH_2CH$=$CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkyne,), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

"Alkylene" refers to a saturated, branched or straight chain radical or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1-ethylene (—$CH(CH_3)$—), 1,2-ethylene (—$CH_2CH_2$—), 1,1-propylene (—$CH(CH_2CH_3)$—), 1,2-propylene (—$CH_2CH(CH_3)$—), 1,3-propylene (—$CH_2CH_2CH_2$—), 1,4-butylene (—$CH_2CH_2CH_2CH_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH=CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—CH$_2$C≡C—), and 4-pentynyl (—CH$_2$CH$_2$CH$_2$C≡C—).

"Alkylyne" refers to a saturated, branched or straight chain radical having two radical centers derived by the removal of three hydrogen atoms from two carbon atoms of a parent alkane. For example, an alkylyne group can have 2 to 20 carbon atoms, 2 to 10 carbon atoms, or 2 to 6 carbon atoms. Typical alkylyne radicals include, but are not limited to, 1,2-ethylyne (—CH$_2$CH=), 1,2-propylyne (—CH$_2$C(CH$_3$)=), 1,3-propylyne (—CH$_2$CH$_2$CH=), 1,4-butylyne (—CH$_2$CH$_2$CH$_2$CH=), and the like.

"Aryl" means a monovalent aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl, and the like.

"Arylene" refers to an aryl as defined above having two monovalent radical centers derived by the removal of two hydrogen atoms from the same or two different carbon atoms of a parent aryl. Typical arylene radicals include, but are not limited to, phenylene.

"Arylalkyl" refers to an acyclic alkyl radical in which one of the hydrogen atoms bonded to a carbon atom, typically a terminal or sp3 carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 20 carbon atoms, e.g., the alkyl moiety is 1 to 6 carbon atoms and the aryl moiety is 6 to 14 carbon atoms.

"Cycloalkyl" refers to a saturated or partially unsaturated ring having 3 to 7 carbon atoms as a monocycle, 7 to 12 carbon atoms as a bicycle, and up to about 20 carbon atoms as a polycycle. Monocyclic cycloalkyl groups have 3 to 6 ring atoms, still more typically 5 or 6 ring atoms. Bicyclic cycloalkyl groups have 7 to 12 ring atoms, e.g., arranged as a bicyclo (4,5), (5,5), (5,6) or (6,6) system, or 9 or 10 ring atoms arranged as a bicyclo (5,6) or (6,6) system. Cycloalkyl groups include hydrocarbon mono-, bi-, and poly-cyclic rings, whether fused, bridged, or spiro. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, bicyclo[3.1.0]hex-6-yl and the like.

"Cycloalkylene" refers to a cycloalkyl as defined above having two monovalent radical centers derived by the removal of two hydrogen atoms from the same or two different carbon atoms of a parent cycloalkyl. Typical cycloalkylene radicals include, but are not limited to, cyclopropylene, cyclobutylene, cyclopentylene and cyclohexylene.

"Cycloalkylyne" refers to a cycloalkyl as defined above having two radical centers derived by the removal of three hydrogen atoms from two carbon atoms of a parent cycloalkyl. Two of the hydrogen atoms are removed from the same carbon atom and one hydrogen atom is removed from an alternative carbon atom of the ring. Non-limiting examples of cycloalkylyne radicals include:

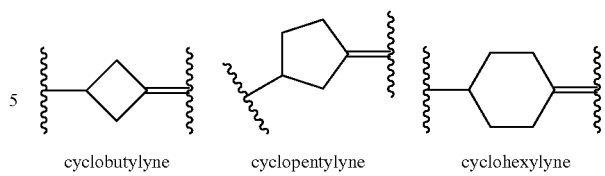

cyclobutylyne  cyclopentylyne  cyclohexylyne

"Halogen" refers to F, Cl, Br, or I.

As used herein the term "haloalkyl" refers to an alkyl group, as defined herein, that is substituted with at least one halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include such substituents as perfluoroalkyl groups such as —CF$_3$.

As used herein, the term "haloalkoxy" refers to a group —OR$^a$, where R$^a$ is a haloalkyl group as herein defined. As non-limiting examples, haloalkoxy groups include —O(CH$_2$)F, —O(CH)F$_2$, and —OCF$_3$.

"Heterocycle" or "heterocyclyl" refers to a saturated or partially saturated cyclic group having from 1 to 14 carbon atoms and from 1 to 6 heteroatoms selected from N, S, P, or O, and includes single ring and multiple ring systems including, fused, bridged, and Spiro ring systems. "Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and J. Am. Chem. Soc. (1960) 82:5566. In one embodiment, the carbon, nitrogen, phosphorous, or sulfur atom(s) of the heterocyclic group may be oxidized to provide for C(=O), N-oxide, phosphinane oxide, sulfinyl, or sulfonyl moieties.

As one example, substituted heterocyclyls include, for example, heterocyclic rings substituted with any of the substituents disclosed herein including oxo groups. A non-limiting example of a carbonyl substituted heterocyclyl is:

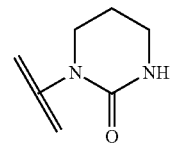

Examples of heterocycles include by way of example and not limitation dihydroypyridyl, tetrahydropyridyl (piperidyl), tetrahydrothiophenyl, sulfur oxidized tetrahydrothiophenyl, piperidinyl, 4-piperidonyl, pyrrolidinyl, azetidinyl, 2-pyrrolidonyl, tetrahydrofuranyl, decahydroquinolinyl, octahydroisoquinolinyl, pyranyl, morpholinyl, and bis-tetrahydrofuranyl:

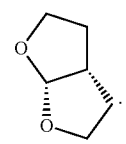

"Heterocyclene" or "heterocyclylene" refers to a "heterocycle" or "heterocyclyl" as defined above having two monovalent radical centers derived by the removal of two hydrogen atoms from the same or two different carbon atoms of a parent heterocycle, the removal of two hydrogen atoms from two nitrogen atoms of a parent heterocycle, or the removal of a hydrogen atom from a nitrogen and the removal of a hydrogen atom from a carbon atom of a parent heterocycle. Non-limiting examples of heterocyclene or heterocyclylenes are:

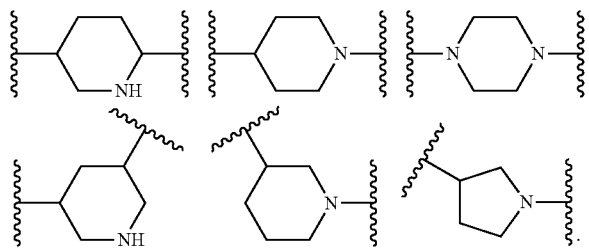

"Heterocyclelyne" or "heterocyclylyne" refers to a "heterocycle" or "heterocyclyl" as defined above having two radical centers derived by the removal of three hydrogen atoms from two carbon atoms of a parent heterocycle or the removal of a hydrogen atom from a nitrogen atom and the removal of two hydrogen atoms from the same carbon atom of a parent heterocycle. Non-limiting examples of heterocyclelyne or "heterocyclylyne radicals include:

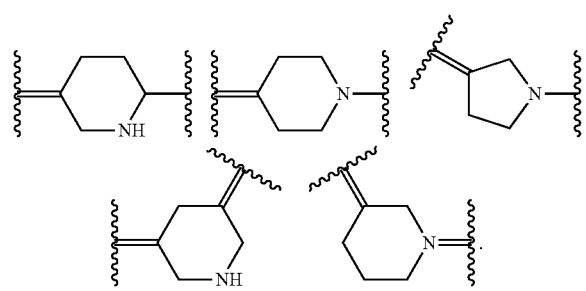

"Heteroaryl" refers to a monovalent aromatic heterocyclyl having at least one heteroatom in the ring. Thus, "heteroaryl" refers to an aromatic group of from 1 to 14 carbon atoms and 1 to 6 heteroatoms selected from oxygen, nitrogen, sulfur, or phosphorous. For multiple ring systems, by way of example, the term "heteroaryl" includes fused, bridged, and spiro ring systems having aromatic and non-aromatic rings. In one embodiment, the carbon, nitrogen, or sulfur ring atom(s) of the heteroaryl group may be oxidized to provide for C(=O), N-oxide, sulfinyl, or sulfonyl moieties.

Examples of heteroaryls include by way of example and not limitation pyridyl, thiazolyl, pyrimidinyl, furanyl, thienyl, pyrrolyl, pyrazolyl, imidazolyl, tetrazolyl, benzofuranyl, thianaphthalenyl, indolyl, quinolinyl, isoquinolinyl, benzimidazolyl, tetrahydroquinolinyl, tetrahydroisoquinolinyl, 6H-1,2,5-thiadiazinyl, 2H,6H-1,5,2-dithiazinyl, thienyl, thianthrenyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl. "Heterocyclylene" refers to a heterocyclyl, as defined herein, derived by replacing a hydrogen atom from a carbon atom or heteroatom of a heterocyclyl, with an open valence. Similarly, "heteroarylene" refers to an aromatic heterocyclylene.

"Heterocyclylalkyl" refers to an acyclic alkyl radical in which one of the hydrogen atoms bonded to a carbon atom, typically a terminal or sp3 carbon atom, is replaced with a heterocyclyl radical (i.e., a heterocyclyl-alkylene-moiety). Typical heterocyclyl alkyl groups include, but are not limited to heterocyclyl-CH$_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclylalkyl group comprises 2 to 20 carbon atoms and 1-6 heteroatoms, e.g., the alkyl portion of the heterocyclylalkyl group comprises 1 to 6 carbon atoms and the heterocyclyl moiety comprises 1 to 14 carbon atoms. Examples of heterocyclylalkyls include by way of example and not limitation 5-membered sulfur, oxygen, phosphorus, and/or nitrogen containing heterocycles such as pyrrolidiylmethyl, 2-tetrahydrofuranylyletham-1-yl, and the like, 6-membered sulfur, oxygen, and/or nitrogen containing heterocycles such as piperidinylmethyl, morpholinylmethyl, piperidinylethyl, teterahydropyranylethyl, and the like.

"Heteroarylalkyl" refers to an alkyl group, as defined herein, in which a hydrogen atom has been replaced with a heteroaryl group as defined herein. Non-limiting examples of heteroaryl alkyl include —CH$_2$-pyridinyl, —CH$_2$-pyrrolyl, —CH$_2$-oxazolyl, —CH$_2$-indolyl, —CH$_2$-isoindolyl, —CH$_2$-purinyl, —CH$_2$-furanyl, —CH$_2$-thienyl, —CH$_2$-benzofuranyl, —CH$_2$-benzothiophenyl, —CH$_2$-carbazolyl, —CH$_2$-imidazolyl, —CH$_2$-thiazolyl, —CH$_2$-isoxazolyl, —CH$_2$-pyrazolyl, —CH$_2$-isothiazolyl, —CH$_2$-quinolyl, —CH$_2$-isoquinolyl, —CH$_2$-pyridazyl, —CH$_2$-pyrimidyl, —CH$_2$-pyrazyl, —CH(CH$_3$)-pyridinyl, —CH(CH$_3$)-pyrrolyl, —CH(CH$_3$)-oxazolyl, —CH(CH$_3$)-indolyl, —CH(CH$_3$)-isoindolyl, —CH(CH$_3$)-purinyl, —CH(CH$_3$)-furanyl, —CH(CH$_3$)-thienyl, —CH(CH$_3$)-benzofuranyl, —CH(CH$_3$)-benzothiophenyl, —CH(CH$_3$)— carbazolyl, —CH(CH$_3$)-imidazolyl, —CH(CH$_3$)-thiazolyl, —CH(CH$_3$)-isoxazolyl, —CH(CH$_3$)-pyrazolyl, —CH(CH$_3$)-isothiazolyl, —CH(CH$_3$)-quinolyl, —CH(CH$_3$)-isoquinolyl, —CH(CH$_3$)-pyridazyl, —CH(CH$_3$)-pyrimidyl, —CH(CH$_3$)-pyrazyl, and the like.

The term "heterocyclyloxy" represents a heterocyclyl group attached to the adjacent atom by an oxygen.

When there is a sulfur atom present, the sulfur atom can be at different oxidation levels, namely, S, SO, SO$_2$, or SO$_3$. All such oxidation levels are within the scope of the present invention.

When there is a phosphorous atom present, the phosphorous atom can be at different oxidation levels, namely, POR$^a$R$^b$R$^c$, PO$_2$R$^a$R$^b$, or PO$_3$R$^a$R$^b$, where R$^a$, R$^b$, and R$^c$ each independently is chosen from H, C$_{1-12}$ alkyl, C$_{2-12}$ alkenyl, C$_{2-12}$ alkynyl, C$_{6-14}$ aryl, 3-12 membered heterocycle, 3-18 membered heteroarylalkyl, C$_{6-18}$ arylalkyl; or two taken together (with or without oxygens) form a 5 to 10 membered heterocycle. All such oxidation levels are within the scope of the present invention The term "optionally substituted" in reference to a particular moiety of the compound of the Formulae of the invention, for example an "optionally substituted aryl group", refers to a moiety having none, one, or more substituents.

The term "substituted" in reference to alkyl, alkylene, aryl, arylalkyl, alkoxy, heterocyclyl, heteroaryl, carbocyclyl, etc., for example, "substituted alkyl", "substituted alkylene", "substituted aryl", "substituted arylalkyl", "substituted heterocyclyl", and "substituted carbocyclyl" means alkyl, alkylene, aryl, arylalkyl, heterocyclyl, carbocyclyl respectively, in which one or more hydrogen atoms are each independently replaced with a non-hydrogen substituent. Divalent groups may also be similarly substituted. Unless otherwise indicated, typical substituents include, but are not limited to, —X, —$R^b$, —$O^-$, —$OR^b$, —$SR^b$, —$S^-$, —$NR^b{}_2$, —$N^+R^b{}_3$, =$NR^b$, —$CX_3$, —CN, —OCN, —SCN, —N=C=O, —NCS, —NO, —$NO_2$, =$N_2$, —$N_3$, —NHC(=O)$R^b$, —OC(=O)$R^b$, —NHC(=O)$NR^b{}_2$, —S(=O)$_2$—, —S(=O)$_2$OH, —S(=O)$_2R^b$, —OS(=O)$_2OR^b$, —S(=O)$_2NR^b{}_2$, —S(=O)$R^b$, —OP(=O)($OR^b$)$_2$, —P(=O)($OR^b$)$_2$, —P(=O)($O^-$)$_2$, —P(=O)(OH)$_2$, —P(O)($OR^b$)($O^-$), —C(=O)$R^b$, —C(=O)X, —C(S)$R^b$, —C(O)$OR^b$, —C(O)$O^-$, —C(S)$OR^b$, —C(O)$SR^b$, —C(S)$SR^b$, —C(O)$NR^b{}_2$, —C(S)$NR^b{}_2$, —C(=$NR^b$)$NR^b{}_2$, where each X is independently a halogen: F, Cl, Br, or I; and each $R^b$ is independently H, alkyl, aryl, arylalkyl, a heterocycle, or a protecting group or prodrug moiety. Alkylene, alkenylene, and alkynylene groups may also be similarly substituted. Unless otherwise indicated, when the term "substituted" is used in conjunction with groups such as arylalkyl, which have two or more moieties capable of substitution, the substituents can be attached to the aryl moiety, the alkyl moiety, or both.

Those skilled in the art will recognize that when moieties such as "alkyl", "aryl", "heterocyclyl", etc. are substituted with one or more substituents, they could alternatively be referred to as "alkylene", "arylene", "heterocyclylene", etc. moieties (i.e., indicating that at least one of the hydrogen atoms of the parent "alkyl", "aryl", "heterocyclyl" moieties has been replaced with the indicated substituent(s)). When moieties such as "alkyl", "aryl", "heterocyclyl", etc. are referred to herein as "substituted" or are shown diagrammatically to be substituted (or optionally substituted, e.g., when the number of substituents ranges from zero to a positive integer), then the terms "alkyl", "aryl", "heterocyclyl", etc. are understood to be interchangeable with "alkylene", "arylene", "heterocyclylene", etc.

As will be appreciated by those skilled in the art, the compounds of the present invention may exist in solvated or hydrated form. The scope of the present invention includes such forms. Again, as will be appreciated by those skilled in the art, the compounds may be capable of esterification. The scope of the present invention includes esters and other physiologically functional derivatives. The scope of the present invention includes prodrug forms of the compound herein described.

"Ester" means any ester of a compound in which any of the —COOH functions of the molecule is replaced by a —C(O)OR function, or in which any of the —OH functions of the molecule are replaced with a —OC(O)R function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound. Example of prodrugs include ester moieties, quaternary ammonium moieties, glycol moieties, and the like.

One skilled in the art will recognize that substituents and other moieties of the compounds of Formula I should be selected in order to provide a compound which is sufficiently stable to provide a pharmaceutically useful compound which can be formulated into an acceptably stable pharmaceutical composition. Compounds of Formula I which have such stability are contemplated as falling within the scope of the present invention.

As will be appreciated by those skilled in the art, the compounds of the present invention may contain one or more chiral centers. The scope of the present invention includes such forms. Again, as will be appreciated by those skilled in the art, the compound is capable of esterification. The scope of the present invention includes esters and other physiologically functional derivatives. In addition, the scope of the present invention includes prodrug forms of the compound herein described.

A compound of Formula I-II and its pharmaceutically acceptable salts may exist as different polymorphs or pseudopolymorphs. As used herein, crystalline polymorphism means the ability of a crystalline compound to exist in different crystal structures. Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I-II and their pharmaceutically acceptable salts.

A compound of Formula I-II and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I-II and their pharmaceutically acceptable salts.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by the formulae of the present invention, as well as any wholly or partially equilibrated mixtures thereof. The present invention also includes the individual isomers of the compounds represented by the formulas above as mixtures with isomers thereof in which one or more chiral centers are inverted.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to stereoisomers of a compound which are non-superimposable mirror images of one another.

"Atropisomers" refer to stereoisomers of a compound resulting from hindered rotation about single bonds where the steric strain barrier to rotation is high enough to allow for the isolation of the individual conformer. Atropisomers display axial chirality. Atropisomers may be equilibrated thermally and the interconversion barrier may be measured kinetically. Atropisomerism may occur apart from the presence of other forms of chiral isomerism. Thus, as illustrated, the depicted nitrogen atom is planar and compounds of Formula I are capable of existing as atropisomers:

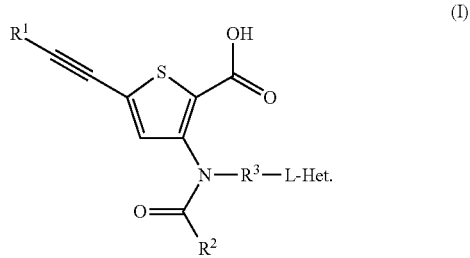

(I)

In one embodiment of the present invention, the compounds exist in a conformeric form of Formula Ia:

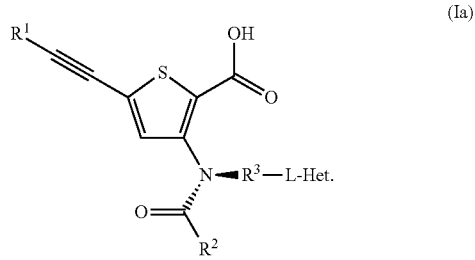

(Ia)

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York.

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The present invention includes a salt or solvate of the compounds herein described, including combinations thereof such as a solvate of a salt. The compounds of the present invention may exist in solvated, for example hydrated, as well as unsolvated forms, and the present invention encompasses all such forms.

Typically, but not absolutely, the salts of the present invention are pharmaceutically acceptable salts. Salts encompassed within the term "pharmaceutically acceptable salts" refer to non-toxic salts of the compounds of this invention.

Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates.

The modifier "about" used in connection with a quantity is inclusive of the stated value and has the meaning dictated by the context (e.g., includes the degree of error associated with measurement of the particular quantity).

Whenever a compound described herein is substituted with more than one of the same designated group, e.g., "R" or "$R^1$", then it will be understood that the groups may be the same or different, i.e., each group is independently selected. Wavy lines,

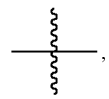

indicate the site of covalent bond attachments to the adjoining substructures, groups, moieties, or atoms.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Selected substituents comprising the compounds of Formula I-II may be present to a recursive degree. In this context, "recursive substituent" means that a substituent may recite another instance of itself. The multiple recitations may be direct or indirect through a sequence of other substituents. Because of the recursive nature of such substituents, theoretically, a large number of compounds may be present in any given embodiment. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis. Recursive substituents may be an intended aspect of the invention. One of ordinary skill in the art of medicinal chemistry understands the versatility of such substituents. To the degree that recursive substituents are present in an embodiment of the invention, they may recite another instance of themselves, 0, 1, 2, 3, or 4 times.

The compounds of Formula I-II also include molecules that incorporate isotopes of the atoms specified in the particular molecules. Non-limiting examples of these isotopes include D, T, $^{14}C$, $^{13}C$, $^{18}O$ and $^{15}N$.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene and Peter G. M. Wuts (John Wiley & Sons, Inc., New York, 1999, ISBN 0-471-16019-9) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-Forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $^3H$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti-infective activity of their own.

The definitions and substituents for various genus and sub-genus of the present compounds are described and illustrated herein. It should be understood by one skilled in the art that any combination of the definitions and substituents described above should not result in an inoperable species or compound. "Inoperable species or compounds" means compound structures that violates relevant scientific principles (such as, for example, a carbon atom connecting to more than four covalent bonds) or compounds too unstable to permit isolation and formulation into pharmaceutically acceptable dosage forms.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations of the invention, both for veterinary and for human use, comprise at least one active ingredient, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 µm (including particle sizes in a range between 0.1 and 500 µm in increments such as 0.5 µm, 1 µm, 30 µm, 35 µm, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

The effective dose of an active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. The effective dose can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

In yet another embodiment, the present application discloses pharmaceutical compositions comprising a compound of Formula I or a pharmaceutically acceptable salt thereof, and a pharmaceutically acceptable carrier or excipient.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy, Including HCV Combination Therapy

In another embodiment, the compounds of the present invention may be combined with one or more active agent. Non-limiting examples of suitable combinations include combinations of one or more compounds of the present invention with one or more interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV.

More specifically, one or more compounds of the present invention may be combined with one or more compounds selected from the group consisting of 1) interferons, e.g., pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), and belerofon, 2) ribavirin and its analogs, e.g., ribavirin (Rebetol, Copegus), and taribavirin (Viramidine), 3) HCV NS3 protease inhibitors, e.g., boceprevir (SCH-503034, SCH-7), telaprevir (VX-950), VX-813, TMC-435 (TMC435350), ABT-450, BI-201335, BI-1230, MK-7009, SCH-900518, VBY-376, VX-500, GS-9256, GS-9451, BMS-790052, BMS-605339, PHX-1766, AS-101, YH-5258, YH5530, YH5531, and ITMN-191 (R-7227), 4) alpha-glucosidase 1 inhibitors, e.g., celgosivir (MX-3253), Miglitol, and UT-231B, 5) hepatoprotectants, e.g., emericasan (IDN-6556), ME-3738, GS-9450 (LB-84451), silibilin, and MitoQ, 6) nucleoside or nucleotide inhibitors of HCV NS5B polymerase, e.g., R1626, R7128 (R4048), IDX184, IDX-102, PSI-7851, BCX-4678, valopicitabine (NM-283), and MK-0608, 7) non-nucleoside inhibitors of HCV NS5B polymerase, e.g., filibuvir (PF-868554), ABT-333, ABT-072, BI-207127, VCH-759, VCH-916, JTK-652, MK-3281, VBY-708, VCH-222, A848837, ANA-598, GL60667, GL59728, A-63890, A-48773, A-48547, BC-2329, VCH-796 (nesbuvir), GSK625433, BILN-1941, XTL-2125, and GS-9190, 8) HCV NS5A inhibitors, e.g., AZD-2836 (A-831), AZD-7295 (A-689), and BMS-790052, 9) TLR-7 agonists, e.g., imiquimod, 852A, GS-9524, ANA-773, ANA-975, AZD-8848 (DSP-3025), PF-04878691, and SM-360320, 10) cyclophillin inhibitors, e.g., DEBIO-025, SCY-635, and NIM811, 11) HCV IRES inhibitors, e.g., MCI-067, 12) pharmacokinetic enhancers, e.g., BAS-100, SPI-452, PF-4194477, TMC-41629, GS-9350, GS-9585, and roxythromycin, 13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, FK-788, and VX-497 (merimepodib);

14) mevalonate decarboxylase antagonists, e.g., statins, HMGCoA synthase inhibitors (e.g., hymeglusin), squalene synthesis inhibitors (e.g., zaragozic acid);

15) angiotensin II receptor antagonists, e.g., losartan, irbesartan, olmesartan, candesartan, valsartan, telmisartan, eprosartan;

16) angiotensin-converting enzyme inhibitors, e.g., captopril, zofenopril, enalapril, ramipril, quinapril, perindopril, lisinopril, benazepril, fosinopril;

17) other anti-fibrotic agents, e.g., amiloride and 18) endothelin antagonists, e.g. bosentan and ambrisentan.

In yet another embodiment, the present application discloses pharmaceutical compositions comprising a compound of the present invention, or a pharmaceutically acceptable salt thereof, in combination with at least one additional active agent, and a pharmaceutically acceptable carrier or excipient. In yet another embodiment, the present application provides a combination pharmaceutical agent with two or more therapeutic agents in a unitary dosage form. Thus, it is also possible to combine any compound of the invention with one or more other active agents in a unitary dosage form.

The combination therapy may be administered as a simultaneous or sequential regimen. When administered sequentially, the combination may be administered in two or more administrations.

Co-administration of a compound of the invention with one or more other active agents generally refers to simultaneous or sequential administration of a compound of the invention and one or more other active agents, such that therapeutically effective amounts of the compound of the invention and one or more other active agents are both present in the body of the patient.

Co-administration includes administration of unit dosages of the compounds of the invention before or after administration of unit dosages of one or more other active agents, for example, administration of the compounds of the invention within seconds, minutes, or hours of the administration of one or more other active agents. For example, a unit dose of a compound of the invention can be administered first, followed within seconds or minutes by administration of a unit dose of one or more other active agents. Alternatively, a unit dose of one or more other active agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active agents. In other cases, it may be desirable to administer a unit dose of one or more other active agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

As will be appreciated by those skilled in the art, when treating a viral infection such as HCV, such treatment may be characterized in a variety of ways and measured by a variety of endpoints. The scope of the present invention is intended to encompass all such characterizations.

SYNTHETIC EXAMPLES

Certain abbreviations and acronyms are used in describing the experimental details. Although most of these would be understood by one skilled in the art, Table 1 contains a list of many of these abbreviations and acronyms.

TABLE 1

List of abbreviations and acronyms.

| Abbreviation | Meaning |
|---|---|
| Ac | acetyl |
| ACN | acetonitrile |
| AIBN | 2,2'-azobis(2-methylpropionitrile) |
| BINAP | 2,2'-bis(diphenylphosphino)-1,1'-binaphthyl |
| Bn | benzyl |
| BnBr | benzylbromide |
| BSA | bis(trimethylsilyl)acetamide |
| BzCl | benzoyl chloride |
| CDI | carbonyl diimidazole |
| DABCO | 1,4-diazabicyclo[2.2.2]octane |
| dba | dibenzylideneacetone |
| DBN | 1,5-diazabicyclo[4.3.0]non-5-ene |
| DDQ | 2,3-dichloro-5,6-dicyano-1,4-benzoquinone |
| DBU | 1,5-diazabicyclo[5.4.0]undec-5-ene |
| DCA | dichloroacetamide |
| DCC | dicyclohexylcarbodiimide |
| DCE | 1,2-dichloroethane |
| DCM | dichloromethane |
| deg | degrees |
| DIAD | di-isopropylazodicarboxylate |
| DIEA | N,N-di-isopropylethylamine |
| DMAP | 4-dimethylaminopyridine |
| DME | 1,2-dimethoxyethane |
| DMTCl | dimethoxytrityl chloride |
| DMSO | dimethylsulfoxide |
| DMTr | 4,4'-dimethoxytrityl |
| DMF | dimethylformamide |
| EtOAc | ethyl acetate |
| ES, ESI | electrospray ionization |
| HMDS | hexamethyldisilazane |
| HPLC | high pressure liquid chromatography |
| LC | liquid chromatography |
| LDA | lithium diisopropylamide |
| LRMS | low resolution mass spectrum |

TABLE 1-continued

List of abbreviations and acronyms.

| Abbreviation | Meaning |
|---|---|
| MCPBA | meta-chloroperbenzoic acid |
| MeCN | acetonitrile |
| MeOH | methanol |
| MMTC | mono methoxytrityl chloride |
| m/z or m/e | mass to charge ratio |
| MH$^+$ | mass plus 1 |
| MH$^-$ | mass minus 1 |
| MsOH | methanesulfonic acid |
| MS or ms | mass spectrum |
| NBS | N-bromosuccinimide |
| NMP | N-methylpyrrolidine |
| Ph | phenyl |
| rt or r.t. | room temperature |
| TBAF | tetrabutylammonium fluoride |
| TES | triethylsilyl |
| THF | tetrahydrofuran |
| THP | tetrahydropyran |
| TMSCl | chlorotrimethylsilane |
| TMSBr | bromotrimethylsilane |
| TMSI | iodotrimethylsilane |
| TMSOTf | (trimethylsilyl)trifluoromethylsulfonate |
| TEA | triethylamine |
| TBA | tributylamine |
| TBAP | tributylammonium pyrophosphate |
| TBSCl | t-butyldimethylsilyl chloride |
| TEAB | triethylammonium bicarbonate |
| TFA | trifluoroacetic acid |
| TLC or tlc | thin layer chromatography |
| Tr | triphenylmethyl |
| Tol | 4-methylbenzoyl |
| Turbo Grignard | 1:1 mixture of isopropylmagnesium chloride and lithium chloride |
| xantphos | 4,5-bis(diphenylphosphino)-9,9-dimethylxanthene |
| δ | parts per million down field from tetramethylsilane |

General Schemes

The compounds of this invention may be synthesized by several routes with key bond-forming steps as indicated in Schemes A-C, in which the carboxylate substituent R indicates either a protecting group such as an alkyl ester (where necessary), or the free acid itself. Alkyl ester protecting groups are conveniently removed by saponification with an alkali metal hydroxide in a protic solvent such as water or an alcohol, and may be facilitated by use of ethereal solvent mixtures and/or heating. Alternatively they may be removed by dealkylation through heating with an alkali metal halide in an aprotic solvent. As will be appreciated, substituents on Het may be modified subsequent to other bond-forming steps by, for example, N-oxidation with a typical oxidant such as metachloroperbenzoic acid in a solvent such as dichloromethane, O-dealkylation through treatment with a reagent such as boron tribromide in a solvent such as dichloromethane, or hydrolysis.

Scheme A

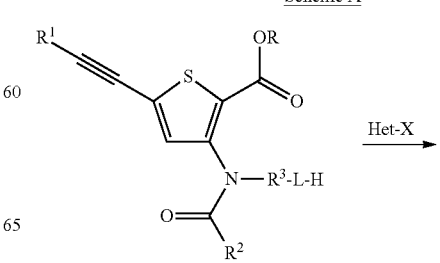

-continued

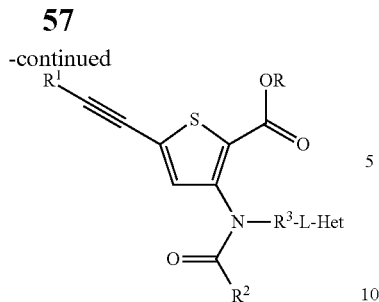

The bond between L and Het may be formed by displacement of X on Het, where X is a leaving group such as a halide, sulfinate, sulfonate or phosphate moiety. The reaction is conveniently performed by deprotonation of L-H with a base such as sodium hydride or potassium hexamethyldisilazide, or is facilitated by the presence of a tertiary amine; it can be carried out in a variety of solvents such as THF, dioxane, dichloromethane, NMP, DMF or DMSO and may be accelerated by heating.

Scheme B

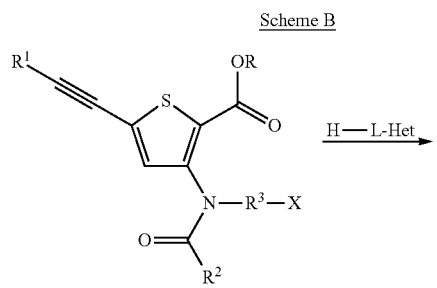

-continued

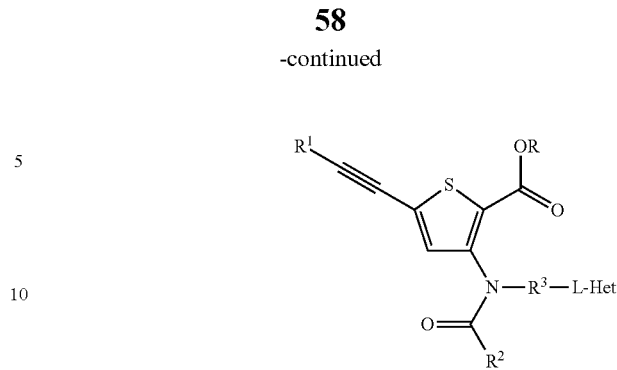

The bond between $R^3$ and L may be formed by nucleophilic displacement of a leaving group X on $R^3$. The leaving group may vary widely and includes, but is not limited to, halide, carboxylate, sulfinate, sulfonate or phosphate moieties, and it may be generated from the corresponding alcohol in situ through treatment with reagents such as dialkyl azodicarboxylates. The reaction may also be facilitated by deprotonation of Het-L-H with a base such as sodium hydride or potassium hexamethyldisilazide, or is facilitated by the presence of a tertiary amine; it can be carried out in a variety of solvents such as THF, dioxane, dichloromethane, NMP, DMF or DMSO and may be accelerated by heating.

Scheme C

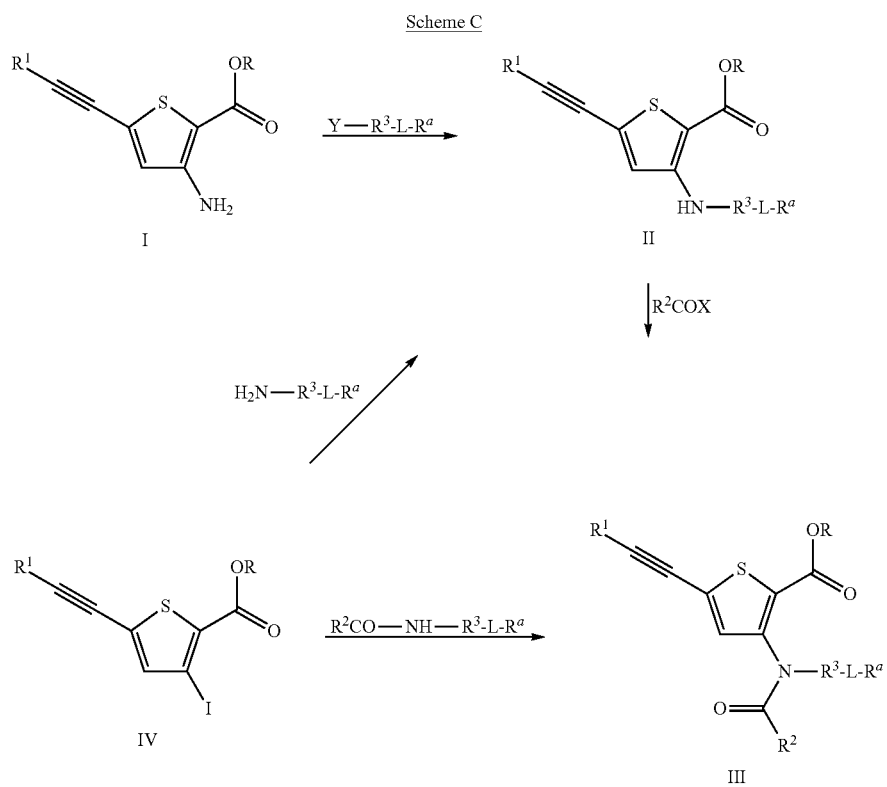

The starting material in Scheme A may be synthesized as depicted in Scheme C. Substituted 3-aminothiophenes II may be generated by reductive amination of Y—R³-L-R (where Y indicates an aldehyde or ketone and R and R^a depict optional protecting groups), or by direct alkylation (where Y indicates a leaving group such as a halide, sulfinate, sulfonate or phosphate moiety) of the 3-aminothiophene I (see patent application WO2008/58393). In the latter case the alkylation may be facilitated by deprotonation of the amine with a base such as sodium hydride or potassium hexamethyldisilazide, and can be carried out in a variety of solvents such as THF, dioxane, dichloromethane, NMP, DMF or DMSO and may be accelerated by heating. In cases where R³ is aromatic, the reaction may be catalyzed by Pd (*J. Org. Chem.*, 2000, 65, 1158-1174). Alternatively II may be generated by coupling of an amine with a 3-iodothiophene IV catalyzed by Pd (*J. Org. Chem.*, 2000, 65, 1158-1174). The amine II is converted to the amide III by acylation with a carboxylic acid derivative such as an acyl chloride or anhydride in the presence of a base such as pyridine or a tertiary amine in an inert solvent such as dichloromethane. Alternatively IV may be converted to III directly by amidation catalyzed by Cu (*J. Am. Chem. Soc.*, 2002, 124, 7421-7428).

The starting material for Scheme B may be generated in an analogous fashion, with the leaving group X being generated in a final step by standard methods from the precursor alcohol.

The synthesis of iodothiophene IV is illustrated below for the case where R¹=tBu, and other variants may be synthesized in analogous fashion:

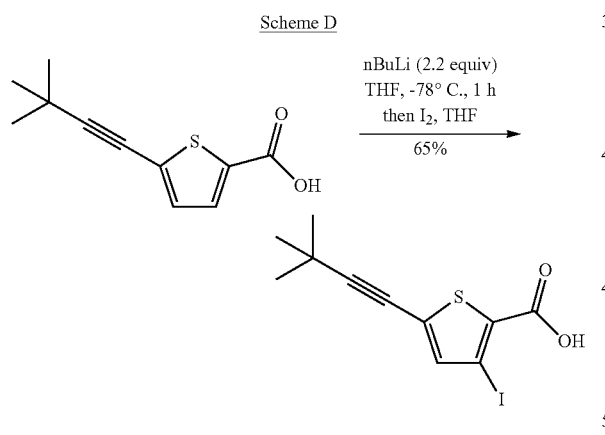

To a solution of 5-(3,3-Dimethyl-but-1-ynyl)-thiophene-2-carboxylic acid (6.2 g, 30 mmol; see U.S. Pat. No. 5,861,421) in THF (100 mL) was added a solution of nBuLi (2.0 M in pentane, 33 mL, 66 mmol) via an addition funnel at −78° C. After addition, the reaction was stirred at −78° C. for 1 h. A solution of I₂ (7.7 g, 30 mmol) in THF (100 mL) was added slowly (ca. 15 min) to the flask. After a further 10 mins, the reaction was quenched with 1 N HCl (50 mL) and warmed to room temperature. The volatiles were removed in vacuo and the residue was dissolved in ether (500 mL). The organic solution was washed with 1 M Na₂S₂O₃ (100 mL×2), brine (100 mL) and dried over Na₂SO₄. After concentrated in vacuo, the residue was purified by silica gel chromatography (EtOAc/hexanes) to give 5-(3,3-Dimethyl-but-1-ynyl)-3-iodo-thiophene-2-carboxylic acid (5.9 g, 65%) as a white solid.

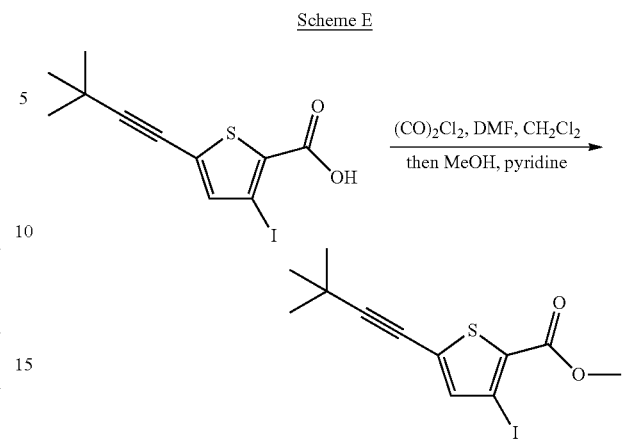

To a solution of 5-(3,3-Dimethyl-but-1-ynyl)-3-iodo-thiophene-2-carboxylic acid (1.0 g, 3.0 mmol) and DMF (20 μL) in dry dichloromethane (10 mL) was added oxalyl chloride (508 μL, 6.0 mmol) at room temperature. After stirring at room temperature for 90 min, the reaction was concentrated in vacuo to remove volatiles. The residue was dissolved in pyridine (5 mL) and methanol (5 mL) and stirred for 2 h. The volatiles were removed in vacuo and the residue was participated between ether (150 mL) and saturated NH₄Cl solution (50 mL). The organic layer was washed with saturated NH₄Cl solution (50 mL) and dried over Na₂SO₄. After concentration in vacuo, the residue was purified by silica gel chromatography (EtOAc/hexanes) to give the desired product (835 mg, 80%).

Experimentals

Example 31

Compound 31—Synthesis of 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester

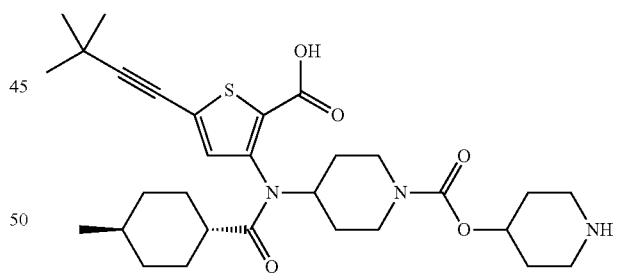

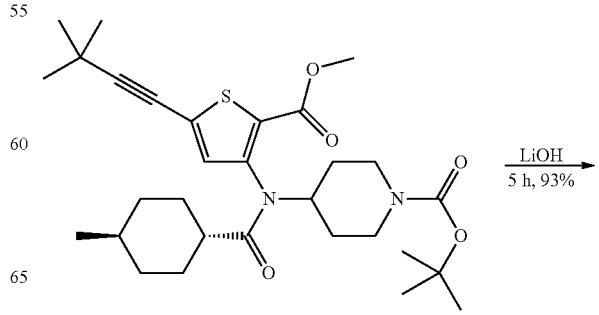

-continued

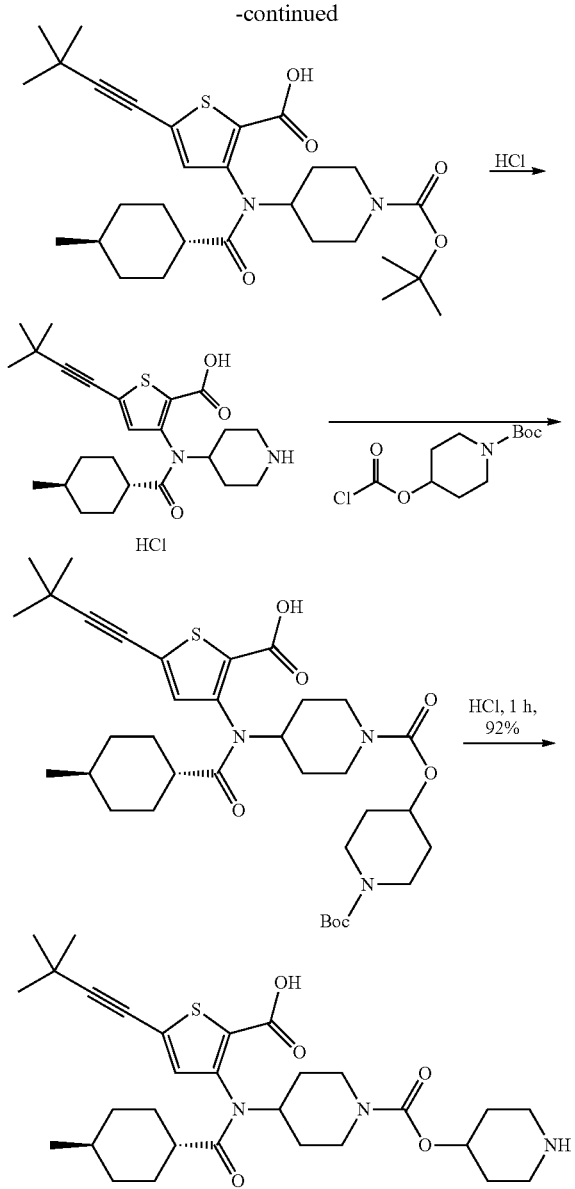

4-[[5-(3,3-dimethyl-but-1-ynyl)-2-methoxycarbonyl-thiophen-3-yl]-(4-trans-methyl-cyclohexanecarbonyl)-amino]-piperidine-1-carboxylic acid tert-butyl ester (1.5 g, 2.73 mmol) was dissolved in ACN (10 mL). To the solution was added a solution of lithium hydroxide (253 mg, 11.01 mmol) in water (10 mL). The reaction was stirred at room temperature for 6 hours. The reaction was complete as determined by LC/MS. The pH was adjusted to 5 with 1N HCl in water. The product was extracted with ethyl acetate (3×10 mL). The combined organics were dried with sodium sulfate, filtered and were concentrated under reduced pressure and 4-[[2-carboxy-5-(3,3-dimethyl-but-1-ynyl)-thiophen-3-yl]-(4-trans-methyl-cyclohexanecarbonyl)-amino]-piperidine-1-carboxylic acid tert-butyl ester (1.35 g, 93%) was recovered as a white solid.

4-[[2-carboxy-5-(3,3-dimethyl-but-1-ynyl)-thiophen-3-yl]-(4-trans-methyl-cyclohexanecarbonyl)-amino]-piperidine-1-carboxylic acid tert-butyl ester (1.35 g, 2.53 mmol) was dissolved in 4N HCl in dioxane (6 mL, 24 mmol). The reaction was stirred at room temperature for 0.5 hours and found to be complete as determined by LC/MS. The reaction was concentrated under reduced pressure.

The HCl salt of 5-(3,3-dimethyl-but-1-ynyl)-3-[(4-trans-methyl-cyclohexanecarbonyl)-piperidin-4-yl-amino]-thiophene-2-carboxylic acid (100 mg, 0.2 mmol) was suspended in ACN (1 mL) and a saturated aqueous solution of NaHCO$_3$ (1 mL). After 15 minutes, 4-hydroxy-piperidine-1-carboxylic acid tert-butyl ester chloroformate (1.0 mmol) was added as a solution in THF (1 mL). The reaction was stirred at room temperature for 1 hour. The reaction was found to be complete by LC/MS. Boc protected 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester was purified by HPLC to afford a white solid (76 mg, 53%).

LC/MS (m/z): 658 [M+1], 558 [M−99]

Retention time: 2.64 min

LC: Thermo Finnigan PDA Detector

MS: Thermo Scientific LCQ Fleet

Column: Phenomenex Gemini-nx 3u C18 110A 30×3 mm

Solvents: Acetonitrile with 0.1% trifluoroacetic acid, Water with 0.1% trifluoroacetic acid Gradient: 0 min-3.1 min 2%-100% ACN, 3.1 min-3.75 min 100% ACN Boc protected 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester (35 mg, 0.05 mmol) was dissolved in 4N HCl in dioxane (2 mL, 8.0 mmol). The reaction was stirred at room temperature for 1 hour. The reaction was complete as determined by LC/MS. The reaction was concentrated under reduced pressure. The HCl salt of 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester (31 mg, 94%) was found as a white solid.

LC/MS (m/z): 558 [M+1]

Retention time: 2.14 min

Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN.

Synthesis of 4-Hydroxy-piperidine-1-carboxylic acid tert-butyl ester chloroformate

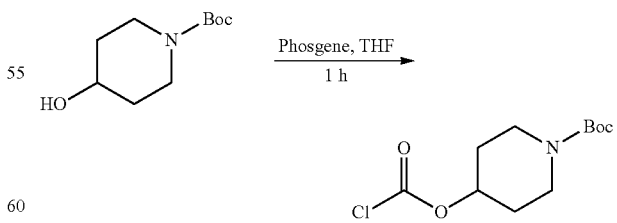

To a solution of 4-hydroxy-piperidine-1-carboxylic acid tert-butyl ester (201 mg, 1.0 mmol) in THF (2 mL) was added a 20% solution of phosgene in toluene (358 μL, 1.7 mmol). The reaction was stirred at room temperature for 1 hour. The reaction was concentrated under reduced pressure.

Method B

Example 32

Compound 32—Synthesis of 5-(3,3-dimethyl-but-1-ynyl)-3-{(4-trans-methyl-cyclohexanecarbonyl)-[4-(tetrahydro-pyran-4-yloxycarbonylamino)-cyclohexyl]-amino}-thiophene-2-carboxylic acid

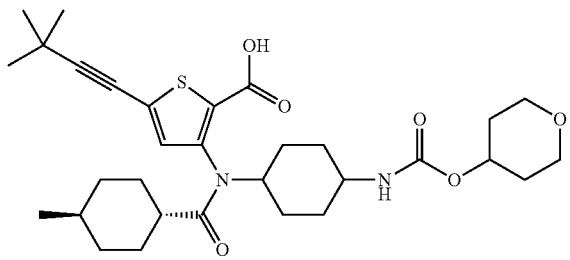

32

Scheme 7

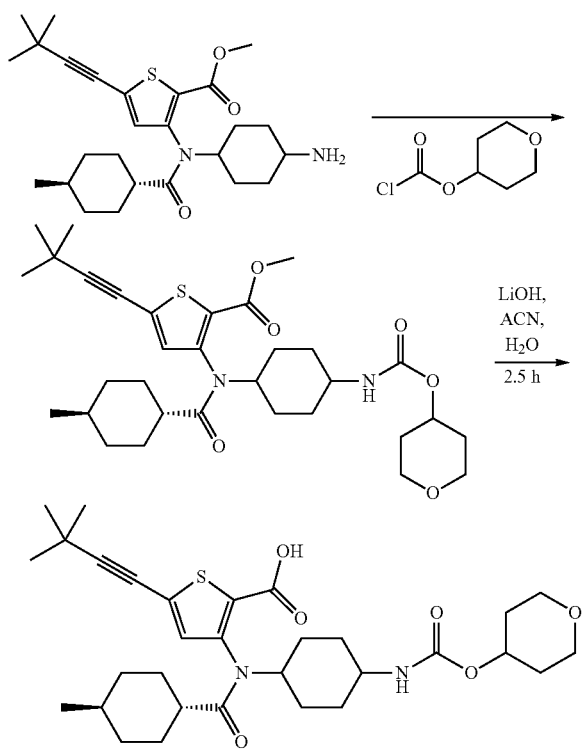

5-(3,3-dimethyl-but-1-ynyl)-3-[(4-trans-methyl-cyclohexanecarbonyl)-(4-oxo-cyclohexyl)-amino]-thiophene-2-carboxylic acid methyl ester (5.00 g, 10.93 mmol) and ammonium acetate (8.42 g, 109.30 mmol) were dissolved in MeOH (100 mL) under an atmosphere of nitrogen. To the reaction was added 4 Å molecular sieves, powdered (500 mg). After 30 min, sodium triacetoxyborohydride (3.46 g, 16.40 mmol) was added in 4 portions. The reaction was stirred for 18 h until found complete by LC/MS. The reaction was filtered through a pad of celite followed by a MeOH wash and was concentrated. 3-[(4-amino-cyclohexyl)-(4-trans-methyl-cyclohexanecarbonyl)-amino]-5-(3,3-dimethyl-but-1-ynyl)-thiophene-2-carboxylic acid methyl ester (3.35 g, 67%) was purified by HPLC to afford a white solid.

3-[(4-amino-cyclohexyl)-(4-trans-methyl-cyclohexanecarbonyl)-amino]-5-(3,3-dimethyl-but-1-ynyl)-thiophene-2-carboxylic acid methyl ester (100 mg, 0.22 mmol) was suspended in ACN (1 mL) and a saturated aqueous solution of NaHCO$_3$ (1 mL). After 15 minutes, tetrahydro-pyran-4-ol chloroformate (0.65 mmol) as prepared in a similar fashion to 4-hydroxy-piperidine-1-carboxylic acid tert-butyl ester chloroformate except that tetrahydro-pyran-4-ol was used instead of hydroxy-piperidine-1-carboxylic acid tert-butyl ester was added as a solution in THF (1 mL). The reaction was stirred at room temperature for 1.5 hours. The reaction was complete by LC/MS. 5-(3,3-dimethyl-but-1-ynyl)-3-{(4-trans-methyl-cyclohexanecarbonyl)-[4-(tetrahydro-pyran-4-yloxycarbonylamino)-cyclohexyl]-amino}-thiophene-2-carboxylic acid methyl ester was extracted with EtOAc (3×5 mL). The combined organics were dried with sodium sulfate, filtered and were concentrated under reduced pressure.

5-(3,3-dimethyl-but-1-ynyl)-3-{(4-trans-methyl-cyclohexanecarbonyl)-[4-(tetrahydro-pyran-4-yloxycarbonylamino)-cyclohexyl]-amino}-thiophene-2-carboxylic acid methyl ester was dissolved in ACN (1 mL). To the reaction was added a solution of lithium hydroxide (25 mg, 1.1 mmol) in water (1 mL). The reaction was stirred at room temperature for 2.5 hours. The reaction was complete by LC/MS. 5-(3,3-dimethyl-but-1-ynyl)-3-{(4-trans-methyl-cyclohexanecarbonyl)-[4-(tetrahydro-pyran-4-yloxycarbonylamino)-cyclohexyl]-amino}-thiophene-2-carboxylic acid (50 mg, 40% over 2 steps) was purified by HPLC to afford a white solid.

LC/MS (m/z): 448 [M−124]

Retention time: 2.46 min

Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN.

Example 33

Compound 33—Synthesis of 3-(S)-[[2-carboxy-5-(3,3-dimethyl-but-1-ynyl)-thiophen-3-yl]-(4-trans-methyl-cyclohexanecarbonyl)-amino]-pyrrolidine-1-carboxylic acid 5-oxo-pyrrolidin-3-(S)-yl ester

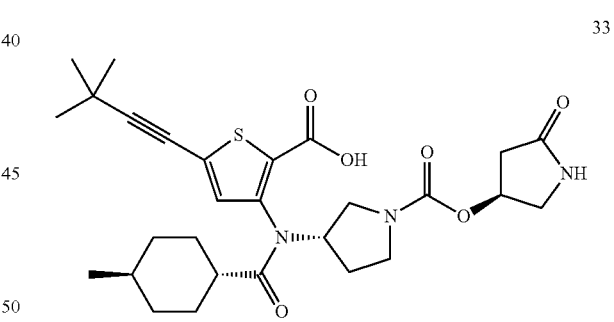

33

3-(S)-[[2-carboxy-5-(3,3-dimethyl-but-1-ynyl)-thiophen-3-yl]-(4-trans-methyl-cyclohexanecarbonyl)-amino]-pyrrolidine-1-carboxylic acid 5-oxo-pyrrolidin-3-(S)-yl ester was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester using method A except that the HCl salt of 5-(3,3-dimethyl-but-1-ynyl)-3-[(4-trans-methyl-cyclohexanecarbonyl)-pyrrolidin-3-(S)-yl-amino]-thiophene-2-carboxylic acid was used instead of the HCl salt of 5-(3,3-dimethyl-but-1-ynyl)-3-[(4-trans-methyl-cyclohexanecarbonyl)-piperidin-4-yl-amino]-thiophene-2-carboxylic acid and 4-(S)-hydroxy-pyrrolidin-2-one was used instead of 4-hydroxy-piperidine-1-carboxylic acid tert-butyl ester.

LC/MS (m/z): 544 [M+1]

Retention time: 1.98 min

LC: Thermo Finnigan PDA Detector
MS: Thermo Scientific LCQ Fleet
Column: Phenomenex Gemini-nx 3u C18 110A 30×3 mm
Solvents: Acetonitrile with 0.1% trifluoroacetic acid, Water with 0.1% trifluoroacetic acid
Gradient: 0 min-3.1 min 2%-100% ACN, 3.1 min-3.75 min 100% ACN 5-(3,3-Dimethyl-but-1-ynyl)-3-[(4-trans-methyl-cyclohexanecarbonyl)-pyrrolidin-3-(S)-yl-amino]-thiophene-2-carboxylic acid was synthesized as follows a) Synthesis of 5-(3,3-dimethyl-but-1-ynyl)-3-iodo-thiophene-2-carboxylic acid methyl ester

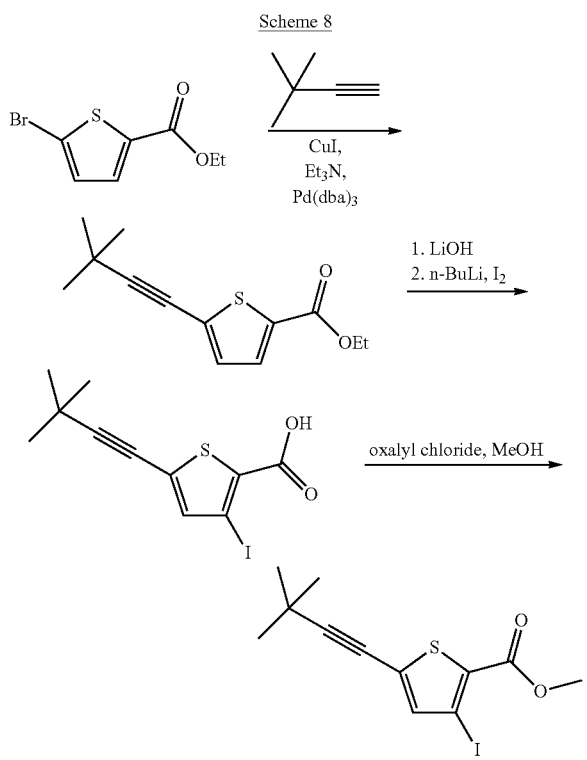

A mixture of 5-Bromo-thiophene-2-carboxylic acid ethyl ester (7 g, 30 mmol), copper iodide (1.2 g, 6 mmol), triethylamine (20 mL) in DMF (100 mL) was degassed in a 350 mL pressure bottle. Then tris(dibenzylideneacetone)dipalladium (0) (2.1 g, 3 mmol) and 3,3-dimethyl-but-1-yne (18.3 mL, 150 mmol) were added and heated at 80 degree for 3 hours. The reaction mixture was filtered on celite and washed with ethyl acetate. The solution was diluted with water and extracted twice with ethyl acetate. The organic phases were combined and washed with water. After drying and concentration, the crude residue was purified by flash chromatography to yield 6.9 g (95%) of 5-(3,3-Dimethyl-but-1-ynyl)-thiophene-2-carboxylic acid ethyl ester as a yellow oil.

A solution of 5-(3,3-dimethyl-but-1-ynyl)-thiophene-2-carboxylic acid ethyl ester (6.9 g) in THF (100 mL) was added LiOH (1.5N, 100 mL). The mixture was stirred at room temperature for 4 hours. Acidified reaction with HCl to pH=2, then remove volatiles under vacuo. The resulting beige color solid was collected by filtration, washed with water then dried overnight to give 6.2 g of product which was used without further purification.

To a solution of 5-(3,3-Dimethyl-but-1-ynyl)-thiophene-2-carboxylic acid (6.2 g, 30 mmol; see U.S. Pat. No. 5,861,421) in THF (100 mL) was added a solution of nBuLi (2.0 M in pentane, 33 mL, 66 mmol) via an addition funnel at −78° C. After addition, the reaction was stirred at −78° C. for 1 h. A solution of $I_2$ (7.7 g, 30 mmol) in THF (100 mL) was added slowly (ca. 15 min) to the flask. After a further 10 mins, the reaction was quenched with 1 N HCl (50 mL) and warmed to room temperature. The volatiles were removed in vacuo and the residue was dissolved in ether (500 mL). The organic solution was washed with 1 M $Na_2S_2O_3$ (100 mL×2), brine (100 mL) and dried over $Na_2SO_4$. After concentrated in vacuo, the residue was purified by silica gel chromatography (EtOAc/hexanes) to give 5-(3,3-Dimethyl-but-1-ynyl)-3-iodo-thiophene-2-carboxylic acid (5.9 g, 65%) as a white solid.

To a solution of 5-(3,3-dimethyl-but-1-ynyl)-3-iodo-thiophene-2-carboxylic acid (1.0 g, 3.0 mmol) and DMF (20 μL) in dry dichloromethane (10 mL) was added oxalyl chloride (508 μL, 6.0 mmol) at room temperature. After stirring at room temperature for 90 min, the reaction was concentrated in vacuo to remove volatiles. The residue was dissolved in pyridine (5 mL) and methanol (5 mL) and stirred for 2 h. The volatiles were removed in vacuo and the residue was participated between ether (150 mL) and saturated $NH_4Cl$ solution (50 mL). The organic layer was washed with saturated $NH_4Cl$ solution (50 mL) and dried over $Na_2SO_4$. After concentration in vacuo, the residue was purified by silica gel chromatography (EtOAc/hexanes) to give the desired product (835 mg, 80%).

b) Synthesis of 5-(3,3-dimethyl-but-1-ynyl)-3-[(4-methyl-cyclohexanecarbonyl)-pyrrolidin-3S-yl-amino]-thiophene-2-carboxylic acid methyl ester

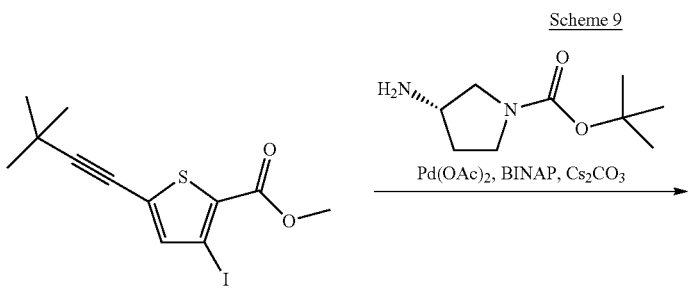

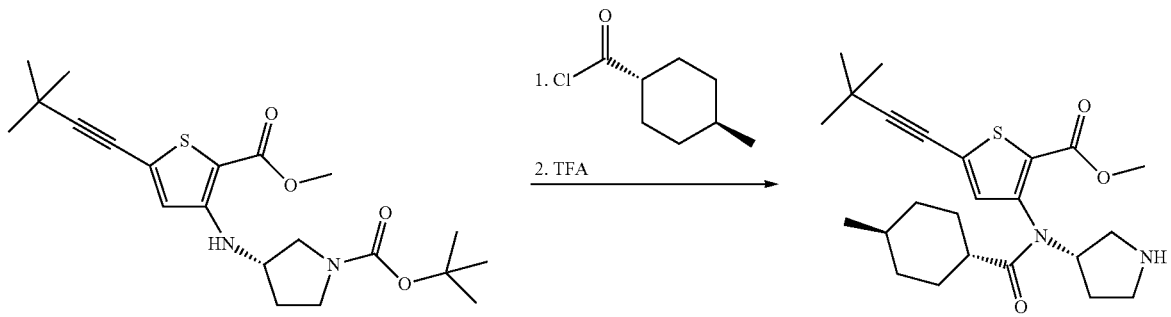

A mixture of 5-(3,3-dimethyl-but-1-ynyl)-3-iodo-thiophene-2-carboxylic acid methyl ester (0.5 g, 1.5 mmol), palladium acetate (0.015 g, 0.32 mmol), BINAP (0.009 g, 0.15 mmol), cesium carbonate (1.2 g, 4.5 mmol) and (3S)-Amino-pyrrolidine-1-carboxylic acid tert-butyl ester (0.252 g, 1.01 mmol) in toluene (8 mL) was heated to 110° C. for 8 h. The reaction was diluted with ethyl acetate filtered through a Celite pad and purified by silica gel chromatography to give 3-[5-(3,3-dimethyl-but-1-ynyl)-2-methoxycarbonyl-thiophen-3S-ylamino]-pyrrolidine-1-carboxylic acid tert-butyl ester in 70% yield.

To a cooled (0° C.) THF (3 mL) solution of 3-[5-(3,3-dimethyl-but-1-ynyl)-2-methoxycarbonyl-thiophen-3S-ylamino]-pyrrolidine-1-carboxylic acid tert-butyl ester (1.0 mmol) was first added KHMDS (1.0 mmol, 0.5 M in toluene), followed by neat trans-4-methyl-cyclohexanecarbonyl chloride (0.2 mL, 1.24 mmol). The reaction was warmed slowly to room temperature and quenched with saturated ammonium chloride solution. The reaction mixture was diluted with EtOAc, washed with water, brine, dried over sodium sulfate, filtrated and concentrated. The crude was then diluted with EtOAc (10 mL), treated with 4M HCl in dioxane (0.5 mL) and heated to 50° C. for 30 min. The reaction mixture was cooled to room temperature concentrated and purified by silica gel column chromatography to give the title compound in 70% yield.

5-(3,3-Dimethyl-but-1-ynyl)-3-[(4-methyl-cyclohexanecarbonyl)-pyrrolidin-3S-yl-amino]-thiophene-2-carboxylic acid methyl ester (0.3 g, 0.7 mmol) in a 3:2:1 mixture of THF:MeOH:water (5 mL) was treated with lithium hydroxide monohydrate (0.69 g, 1.65 mmol) and heated to 60° C. for 1 hour. The organic volatiles were evaporated under reduced pressure and the crude material was purified by reverse-phase HPLC to afford 5-(3,3-dimethyl-but-1-ynyl)-3-[(4-trans-methyl-cyclohexanecarbonyl)-pyrrolidin-3-(S)-yl-amino]-thiophene-2-carboxylic acid in 60% yield.

Example 34

Compound 34—Synthesis of 3-(S)-[[2-carboxy-5-(3,3-dimethyl-but-1-ynyl)-thiophen-3-yl]-(4-trans-methyl-cyclohexanecarbonyl)-amino]-pyrrolidine-1-carboxylic acid 5-oxo-pyrrolidin-3-(R)-yl ester

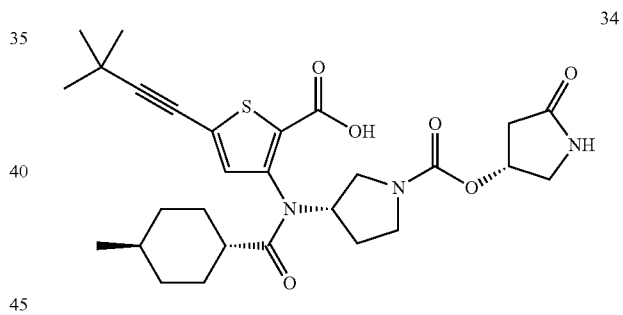

34

3-(S)-[[2-Carboxy-5-(3,3-dimethyl-but-1-ynyl)-thiophen-3-yl]-(4-trans-methyl-cyclohexanecarbonyl)-amino]-pyrrolidine-1-carboxylic acid 5-oxo-pyrrolidin-3-(R)-yl ester was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester using method A except that the HCl salt of 5-(3,3-dimethyl-but-1-ynyl)-3-[(4-trans-methyl-cyclohexanecarbonyl)-pyrrolidin-3-(S)-yl-amino]-thiophene-2-carboxylic acid was used instead of the HCl salt of 5-(3,3-dimethyl-but-1-ynyl)-3-[(4-trans-methyl-cyclohexanecarbonyl)-piperidin-4-yl-amino]-thiophene-2-carboxylic acid and 4-(R)-hydroxy-pyrrolidin-2-one was used instead of 4-hydroxy-piperidine-1-carboxylic acid tert-butyl ester.

LC/MS (m/z): 544 [M+1]

Retention time: 2.18 min

Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN.

Example 35

Compound 35—Synthesis of 3-(S)-[[2-Carboxy-5-(3,3-dimethyl-but-1-ynyl)-thiophen-3-yl]-(4-methyl-cyclohexanecarbonyl)-amino]-pyrrolidine-1-carboxylic acid hexahydro-furo[2,3-b]furan-3-(R)-yl ester

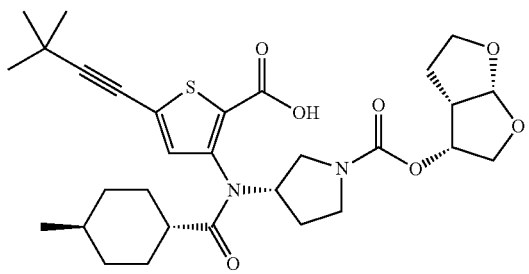

35

3-(S)-[[2-Carboxy-5-(3,3-dimethyl-but-1-ynyl)-thiophen-3-yl]-(4-methyl-cyclohexanecarbonyl)-amino]-pyrrolidine-1-carboxylic acid hexahydro-furo[2,3-b]furan-3-(R)-yl ester was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester using method A except that the HCl salt of 5-(3,3-dimethyl-but-1-ynyl)-3-[(4-trans-methyl-cyclohexanecarbonyl)-pyrrolidin-3-(S)-yl-amino]-thiophene-2-carboxylic acid was used instead of the HCl salt of 5-(3,3-dimethyl-but-1-ynyl)-3-[(4-trans-methyl-cyclohexanecarbonyl)-piperidin-4-yl-amino]-thiophene-2-carboxylic acid and 4-nitro-benzoic acid hexahydro-furo[2,3-b]furan-3-(R)-yl ester was used in place of the chloroformate of 4-hydroxy-piperidine-1-carboxylic acid tert-butyl ester.

LC/MS (m/z): 572.92 [M+1], 595.15 [M+Na$^+$]
Retention time: 2.48 min
Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN.

Example 36

Compound 36—Synthesis of 4-[[2-carboxy-5-(3,3-dimethyl-but-1-ynyl)-thiophen-3-yl]-(4-methyl-cyclohexanecarbonyl)-amino]-piperidine-1-carboxylic acid hexahydro-furo[2,3-b]furan-3-(R)-yl ester

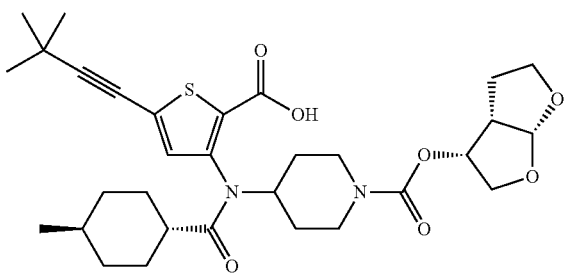

36

4-[[2-carboxy-5-(3,3-dimethyl-but-1-ynyl)-thiophen-3-yl]-(4-methyl-cyclohexanecarbonyl)-amino]-piperidine-1-carboxylic acid hexahydro-furo[2,3-b]furan-3-(R)-yl ester was prepared in a similar fashion to 5-(3,3-dimethyl-but-1-ynyl)-3-{(4-trans-methyl-cyclohexanecarbonyl)-[4-(tetrahydro-pyran-4-yloxycarbonylamino)-cyclohexyl]-amino}-thiophene-2-carboxylic acid using method B, except the HCl salt of 5-(3,3-dimethyl-but-1-ynyl)-3-[(4-methyl-cyclohexanecarbonyl)-piperidin-4-yl-amino]-thiophene-2-carboxylic acid methyl ester was used instead of 3-[(4-amino-cyclohexyl)-(4-trans-methyl-cyclohexanecarbonyl)-amino]-5-(3,3-dimethyl-but-1-ynyl)-thiophene-2-carboxylic acid methyl ester, and 4-nitro-benzoic acid hexahydro-furo[2,3-b]furan-3-(R)-yl ester was used in place of the chloroformate of tetrahydro-pyran-4-ol.

LC/MS (m/z): 587.01 [M+1], 609.20 [M+Na$^+$]
Retention time: 2.40 min
Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN.

Example 37

Compound 37—Synthesis of 3-(R)-{3-(S)-[[2-carboxy-5-(3,3-dimethyl-but-1-ynyl)-thiophen-3-yl]-(4-trans-methyl-cyclohexanecarbonyl)-amino]-pyrrolidine-1-carbonyloxy}-piperidine-1-carboxylic acid tert-butyl ester

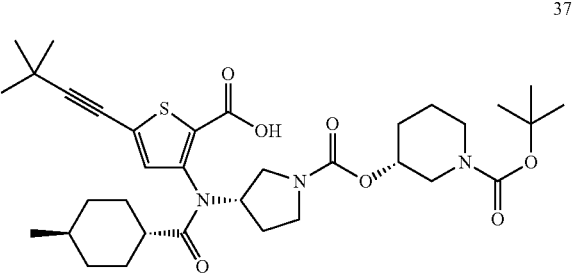 [SMILES: CC(C)(C)C#Cc1cc(N(C(=O)[C@H]2CC[C@H](C)CC2)[C@H]2CCN(C(=O)O[C@@H]3CCCN(C(=O)OC(C)(C)C)C3)C2)c(C(=O)O)s1]

37

3-(R)-{3-(S)-[[2-carboxy-5-(3,3-dimethyl-but-1-ynyl)-thiophen-3-yl]-(4-trans-methyl-cyclohexanecarbonyl)-amino]-pyrrolidine-1-carbonyloxy}-piperidine-1-carboxylic acid tert-butyl ester was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester using method A except that the HCl salt of 5-(3,3-dimethyl-but-1-ynyl)-3-[(4-trans-methyl-cyclohexanecarbonyl)-pyrrolidin-3-(S)-yl-amino]-thiophene-2-carboxylic acid was used instead of the HCl salt of 5-(3,3-dimethyl-but-1-ynyl)-3-[(4-trans-methyl-cyclohexanecarbonyl)-piperidin-4-yl-amino]-thiophene-2-carboxylic acid and 3-(R)-hydroxy-piperidine-1-carboxylic acid tert-butyl ester was used instead of 4-hydroxy-piperidine-1-carboxylic acid tert-butyl ester.

LC/MS (m/z): 545 [M−98]
Retention time: 2.26 min
LC: Thermo Finnigan PDA Detector
MS: Thermo Scientific LCQ Fleet
Column: Phenomenex Gemini-nx 3u C18 110A 30×3 mm
Solvents: Acetonitrile with 0.1% trifluoroacetic acid, Water with 0.1% trifluoroacetic acid
Gradient: 0 min-3.1 min 2%-100% ACN, 3.1 min-3.75 min 100% ACN

Example 38

Compound 38—Synthesis of 3-(S)-[[2-carboxy-5-(3,3-dimethyl-but-1-ynyl)-thiophen-3-yl]-(4-trans-methyl-cyclohexanecarbonyl)-amino]-pyrrolidine-1-carboxylic acid piperidin-3-(R)-yl ester

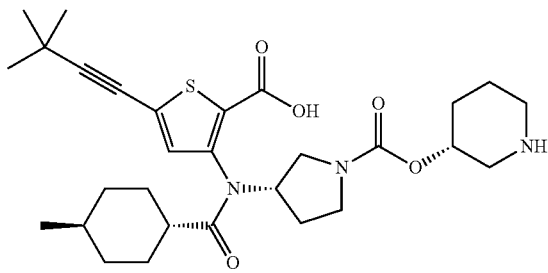

3-(S)-[[2-carboxy-5-(3,3-dimethyl-but-1-ynyl)-thiophen-3-yl]-(4-trans-methyl-cyclohexanecarbonyl)-amino]-pyrrolidine-1-carboxylic acid piperidin-3-(R)-yl ester was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester using method A except that the HCl salt of 5-(3,3-dimethyl-but-1-ynyl)-3-[(4-trans-methyl-cyclohexanecarbonyl)-pyrrolidin-3-(S)-yl-amino]-thiophene-2-carboxylic acid was used instead of the HCl salt of 5-(3,3-dimethyl-but-1-ynyl)-3-[(4-trans-methyl-cyclohexanecarbonyl)-piperidin-4-yl-amino]-thiophene-2-carboxylic acid and 3-(R)-hydroxy-piperidine-1-carboxylic acid tert-butyl ester was used instead of 4-hydroxy-piperidine-1-carboxylic acid tert-butyl ester.

LC/MS (m/z): 544 [M+1]
Retention time: 2.18 min
Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN.

Example 39

Compound 39—Synthesis of 4-{3-(S)-[[2-carboxy-5-(3,3-dimethyl-but-1-ynyl)-thiophen-3-yl]-(4-trans-methyl-cyclohexanecarbonyl)-amino]-pyrrolidine-1-carbonyloxy}-piperidine-1-carboxylic acid tert-butyl ester

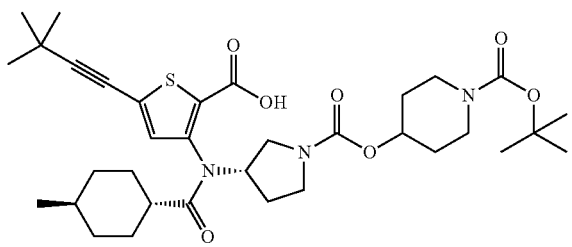

4-{3-(S)-[[2-carboxy-5-(3,3-dimethyl-but-1-ynyl)-thiophen-3-yl]-(4-trans-methyl-cyclohexanecarbonyl)-amino]-pyrrolidine-1-carbonyloxyl}-piperidine-1-carboxylic acid tert-butyl ester was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester using method A except that the HCl salt of 5-(3,3-dimethyl-but-1-ynyl)-3-[(4-trans-methyl-cyclohexanecarbonyl)-pyrrolidin-3-(S)-yl-amino]-thiophene-2-carboxylic acid was used instead of the HCl salt of 5-(3,3-dimethyl-but-1-ynyl)-3-[(4-trans-methyl-cyclohexanecarbonyl)-piperidin-4-yl-amino]-thiophene-2-carboxylic acid.

LC/MS (m/z): 644 [M+1], 544 [M−99]
Retention time: 2.56 min
LC: Thermo Finnigan PDA Detector
MS: Thermo Scientific LCQ Fleet
Column: Phenomenex Gemini-nx 3u C18 110A 30×3 mm
Solvents: Acetonitrile with 0.1% trifluoroacetic acid, Water with 0.1% trifluoroacetic acid
Gradient: 0 min-3.1 min 2%-100% ACN, 3.1 min-3.75 min 100% ACN

Example 40

Compound 40—Synthesis of 3-(S)-[[2-carboxy-5-(3,3-dimethyl-but-1-ynyl)-thiophen-3-yl]-(4-trans-methyl-cyclohexanecarbonyl)-amino]-pyrrolidine-1-carboxylic acid piperidin-4-yl ester

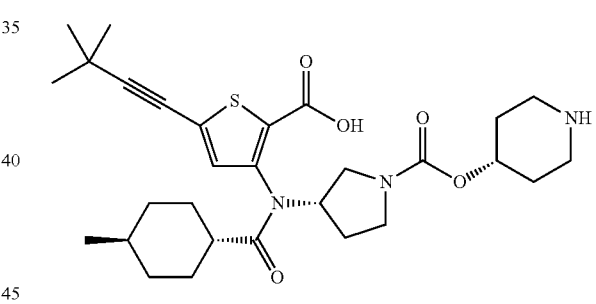

3-(S)-[[2-carboxy-5-(3,3-dimethyl-but-1-ynyl)-thiophen-3-yl]-(4-trans-methyl-cyclohexanecarbonyl)-amino]-pyrrolidine-1-carboxylic acid piperidin-4-yl ester was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester using method A except that the HCl salt of 5-(3,3-dimethyl-but-1-ynyl)-3-[(4-trans-methyl-cyclohexanecarbonyl)-pyrrolidin-3-(S)-yl-amino]-thiophene-2-carboxylic acid was used instead of the HCl salt of 5-(3,3-dimethyl-but-1-ynyl)-3-[(4-trans-methyl-cyclohexanecarbonyl)-piperidin-4-yl-amino]-thiophene-2-carboxylic acid.

LC/MS (m/z): 544 [M+1]
Retention time: 2.09 min
Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN.

Example 41

Compound 41—Synthesis of 3-(S)-[[2-carboxy-5-(3, 3-dimethyl-but-1-ynyl)-thiophen-3-yl]-(4-trans-methyl-cyclohexanecarbonyl)-amino]-pyrrolidine-1-carboxylic acid tetrahydro-pyran-4-yl ester

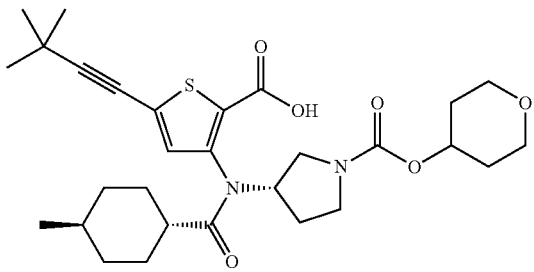

41

3-(S)-[[2-carboxy-5-(3,3-dimethyl-but-1-ynyl)-thiophen-3-yl]-(4-trans-methyl-cyclohexanecarbonyl)-amino]-pyrrolidine-1-carboxylic acid tetrahydro-pyran-4-yl ester was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester using method A except that the HCl salt of 5-(3,3-dimethyl-but-1-ynyl)-3-[(4-trans-methyl-cyclohexanecarbonyl)-pyrrolidin-3-(S)-yl-amino]-thiophene-2-carboxylic acid was used instead of the HCl salt of 5-(3,3-dimethyl-but-1-ynyl)-3-[(4-trans-methyl-cyclohexanecarbonyl)-piperidin-4-yl-amino]-thiophene-2-carboxylic acid and tetrahydro-pyran-4-ol was used instead of 4-hydroxy-piperidine-1-carboxylic acid tert-butyl ester.

LC/MS (m/z): 544 [M]
Retention time: 2.57 min
LC: Thermo Finnigan PDA Detector
MS: Thermo Scientific LCQ Fleet
Column: Phenomenex Gemini-nx 3u C18 110A 30×3 mm
Solvents: Acetonitrile with 0.1% trifluoroacetic acid, Water with 0.1% trifluoroacetic acid
Gradient: 0 min-3.1 min 2%-100% ACN, 3.1 min-3.75 min 100% CAN

Example 42

Compound 42—Synthesis of 3-(S)-[[2-carboxy-5-(3, 3-dimethyl-but-1-ynyl)-thiophen-3-yl]-(4-trans-methyl-cyclohexanecarbonyl)-amino]-pyrrolidine-1-carboxylic acid tetrahydro-furan-3-(R)-yl ester

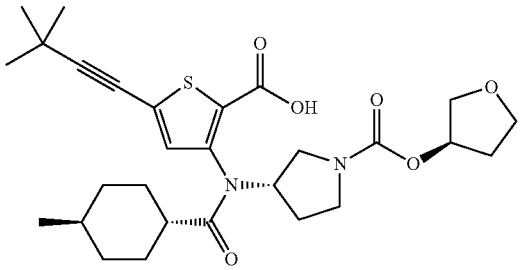

42

3-(S)-[[2-carboxy-5-(3,3-dimethyl-but-1-ynyl)-thiophen-3-yl]-(4-trans-methyl-cyclohexanecarbonyl)-amino]-pyrrolidine-1-carboxylic acid tetrahydro-furan-3-(R)-yl ester was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester using method A except that the HCl salt of 5-(3,3-dimethyl-but-1-ynyl)-3-[(4-trans-methyl-cyclohexanecarbonyl)-pyrrolidin-3-(S)-yl-amino]-thiophene-2-carboxylic acid was used instead of the HCl salt of 5-(3,3-dimethyl-but-1-ynyl)-3-[(4-trans-methyl-cyclohexanecarbonyl)-piperidin-4-yl-amino]-thiophene-2-carboxylic acid and tetrahydro-furan-3-(R)-ol was used instead of 4-hydroxy-piperidine-1-carboxylic acid tert-butyl ester.

LC/MS (m/z): 531 [M+1]
Retention time: 2.21 min
LC: Thermo Finnigan PDA Detector
MS: Thermo Scientific LCQ Fleet
Column: Phenomenex Gemini-nx 3u C18 110A 30×3 mm
Solvents: Acetonitrile with 0.1% trifluoroacetic acid, Water with 0.1% trifluoroacetic acid
Gradient: 0 min-3.1 min 2%-100% ACN, 3.1 min-3.75 min 100% ACN

Example 43

Compound 43—Synthesis of 3-(S)-[[2-carboxy-5-(3, 3-dimethyl-but-1-ynyl)-thiophen-3-yl]-(4-trans-methyl-cyclohexanecarbonyl)-amino]-pyrrolidine-1-carboxylic acid 2-oxo-pyrrolidin-3-(R)-yl ester

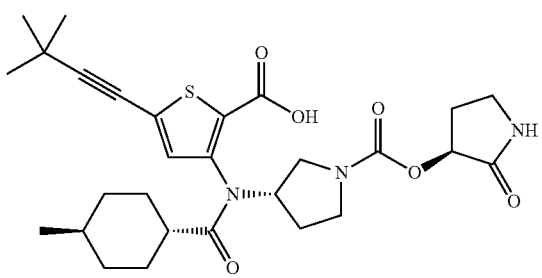

43

3-(S)-[[2-Carboxy-5-(3,3-dimethyl-but-1-ynyl)-thiophen-3-yl]-(4-trans-methyl-cyclohexanecarbonyl)-amino]-pyrrolidine-1-carboxylic acid 2-oxo-pyrrolidin-3-(R)-yl ester was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester using method A except that the HCl salt of 5-(3,3-dimethyl-but-1-ynyl)-3-[(4-trans-methyl-cyclohexanecarbonyl)-pyrrolidin-3-(S)-yl-amino]-thiophene-2-carboxylic acid was used instead of the HCl salt of 5-(3,3-dimethyl-but-1-ynyl)-3-[(4-trans-methyl-cyclohexanecarbonyl)-piperidin-4-yl-amino]-thiophene-2-carboxylic acid and 3-(R)-hydroxy-pyrrolidin-2-one was used instead of 4-hydroxy-piperidine-1-carboxylic acid tert-butyl ester.

LC/MS (m/z): 562 [M+19]
Retention time: 2.18 min
Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN.

Example 44

Compound 44—Synthesis of 4-{4-[[2-carboxy-5-(3,3-dimethyl-but-1-ynyl)-thiophen-3-yl]-(4-trans-methyl-cyclohexanecarbonyl)-amino]-cyclohexylcarbamoyloxy}-piperidine-1-carboxylic acid tert-butyl ester

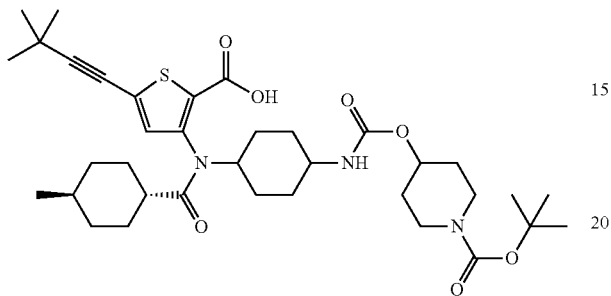

44

4-{4-[[2-Carboxy-5-(3,3-dimethyl-but-1-ynyl)-thiophen-3-yl]-(4-trans-methyl-cyclohexanecarbonyl)-amino]-cyclohexylcarbamoyloxy}-piperidine-1-carboxylic acid tert-butyl ester was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester using method A except that the HCl salt of 3-[(4-amino-cyclohexyl)-(4-trans-methyl-cyclohexanecarbonyl)-amino]-5-(3,3-dimethyl-but-1-ynyl)-thiophene-2-carboxylic acid was used instead of the HCl salt of 5-(3,3-dimethyl-but-1-ynyl)-3-[(4-trans-methyl-cyclohexanecarbonyl)-piperidin-4-yl-amino]-thiophene-2-carboxylic acid.

LC/MS (m/z): 670 [M−1]
Retention time: 2.54 min
Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN.

Example 45

Compound 45—Synthesis of 5-(3,3-dimethyl-but-1-ynyl)-3-{(4-trans-methyl-cyclohexanecarbonyl)-[4-(piperidin-4-yloxycarbonylamino)-cyclohexyl]-amino}-thiophene-2-carboxylic acid

45

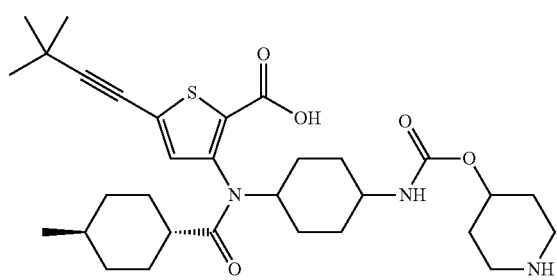

5-(3,3-Dimethyl-but-1-ynyl)-3-{(4-trans-methyl-cyclohexanecarbonyl)-[4-(piperidin-4-yloxycarbonylamino)-cyclohexyl]-amino}-thiophene-2-carboxylic acid was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester using method A except that the HCl salt of 3-[(4-amino-cyclohexyl)-(4-trans-methyl-cyclohexanecarbonyl)-amino]-5-(3,3-dimethyl-but-1-ynyl)-thiophene-2-carboxylic acid was used instead of the HCl salt of 5-(3,3-dimethyl-but-1-ynyl)-3-[(4-trans-methyl-cyclohexanecarbonyl)-piperidin-4-yl-amino]-thiophene-2-carboxylic acid.

LC/MS (m/z): 572 [M+1]
Retention time: 2.07 min
Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN.

Example 46

Compound 46—Synthesis of 3-(R)-{-4-[[2-carboxy-5-(3,3-dimethyl-but-1-ynyl)-thiophen-3-yl]-(4-trans-methyl-cyclohexanecarbonyl)-amino]-cyclohexylcarbamoyloxy}-piperidine-1-carboxylic acid tert-butyl ester

46

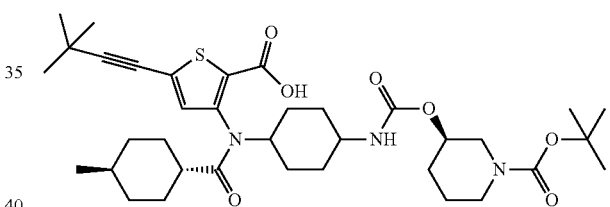

3-(R)-{4-[[2-carboxy-5-(3,3-dimethyl-but-1-ynyl)-thiophen-3-yl]-(4-trans-methyl-cyclohexanecarbonyl)-amino]-cyclohexylcarbamoyloxy}-piperidine-1-carboxylic acid tert-butyl ester was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester using method A except that the HCl salt of 3-[(4-amino-cyclohexyl)-(4-trans-methyl-cyclohexanecarbonyl)-amino]-5-(3,3-dimethyl-but-1-ynyl)-thiophene-2-carboxylic acid was used instead of the HCl salt of 5-(3,3-dimethyl-but-1-ynyl)-3-[(4-trans-methyl-cyclohexanecarbonyl)-piperidin-4-yl-amino]-thiophene-2-carboxylic acid and 3-(R)-hydroxy-piperidine-1-carboxylic acid tert-butyl ester was used instead of 4-hydroxy-piperidine-1-carboxylic acid tert-butyl ester.

LC/MS (m/z): 670 [M−1]
Retention time: 2.58 min
Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN.

Example 47

Compound 47—Synthesis of 5-(3,3-dimethyl-but-1-ynyl)-3-{(4-trans-methyl-cyclohexanecarbonyl)-[4-(piperidin-3-(R)-yloxycarbonylamino)-cyclohexyl]-amino}-thiophene-2-carboxylic acid

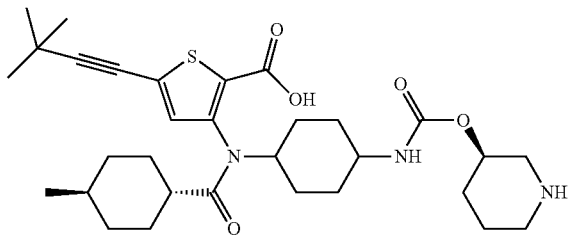

47

5-(3,3-dimethyl-but-1-ynyl)-3-{(4-trans-methyl-cyclohexanecarbonyl)-[4-(piperidin-3-(R)-yloxycarbonylamino)-cyclohexyl]-amino}-thiophene-2-carboxylic acid was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester using method A except that the HCl salt of 3-[(4-amino-cyclohexyl)-(4-trans-methyl-cyclohexanecarbonyl)-amino]-5-(3,3-dimethyl-but-1-ynyl)-thiophene-2-carboxylic acid was used instead of the HCl salt of 5-(3,3-dimethyl-but-1-ynyl)-3-[(4-trans-methyl-cyclohexanecarbonyl)-piperidin-4-yl-amino]-thiophene-2-carboxylic acid and 3-(R)-hydroxy-piperidine-1-carboxylic acid tert-butyl ester was used instead of 4-hydroxy-piperidine-1-carboxylic acid tert-butyl ester.

LC/MS (m/z): 572 [M+1]

Retention time: 2.11 min

Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN.

Example 48

Compound 48—Synthesis of 5-(3,3-dimethyl-but-1-ynyl)-3-{(4-trans-methyl-cyclohexanecarbonyl)-[4-(tetrahydro-furan-3-(R)-yloxycarbonylamino)-cyclohexyl]-amino}-thiophene-2-carboxylic acid

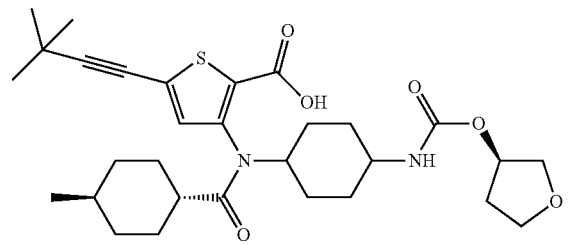

48

5-(3,3-Dimethyl-but-1-ynyl)-3-{(4-trans-methyl-cyclohexanecarbonyl)-[4-(tetrahydro-furan-3-(R)-yloxycarbonylamino)-cyclohexyl]-amino}-thiophene-2-carboxylic acid was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester using method A except that the HCl salt of 3-[(4-amino-cyclohexyl)-(4-trans-methyl-cyclohexanecarbonyl)-amino]-5-(3,3-dimethyl-but-1-ynyl)-thiophene-2-carboxylic acid was used instead of the HCl salt of 5-(3,3-dimethyl-but-1-ynyl)-3-[(4-trans-methyl-cyclohexanecarbonyl)-piperidin-4-yl-amino]-thiophene-2-carboxylic acid and tetrahydro-furan-3-(R)-ol was used instead of 4-hydroxy-piperidine-1-carboxylic acid tert-butyl ester.

LC/MS (m/z): 434 [M−124]

Retention time: 2.42 min

Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN.

Example 49

Compound 49—Synthesis of 5-(3,3-dimethyl-but-1-ynyl)-3-{(4-trans-methyl-cyclohexanecarbonyl)-[4-(5-oxo-pyrrolidin-3-(S)-yloxycarbonylamino)-cyclohexyl]-amino}-thiophene-2-carboxylic acid

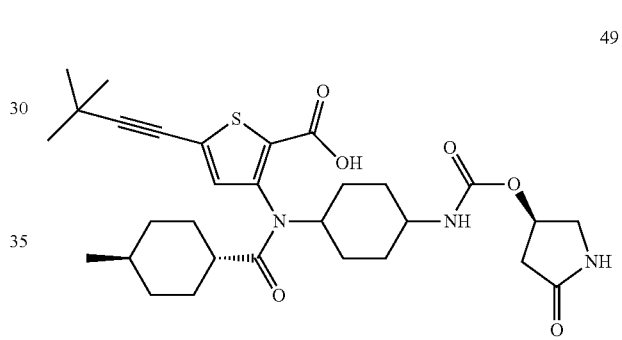

49

5-(3,3-Dimethyl-but-1-ynyl)-3-{(4-trans-methyl-cyclohexanecarbonyl)-[4-(5-oxo-pyrrolidin-3-(S)-yloxycarbonylamino)-cyclohexyl]-amino}-thiophene-2-carboxylic acid was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester using method A except that the HCl salt of 3-[(4-amino-cyclohexyl)-(4-trans-methyl-cyclohexanecarbonyl)-amino]-5-(3,3-dimethyl-but-1-ynyl)-thiophene-2-carboxylic acid was used instead of the HCl salt of 5-(3,3-dimethyl-but-1-ynyl)-3-[(4-trans-methyl-cyclohexanecarbonyl)-piperidin-4-yl-amino]-thiophene-2-carboxylic acid and 4-(S)-hydroxy-pyrrolidin-2-one was used instead of 4-hydroxy-piperidine-1-carboxylic acid tert-butyl ester.

LC/MS (m/z): 572 [M+1]

Retention time: 2.08 min

LC: Thermo Finnigan PDA Detector

MS: Thermo Scientific LCQ Fleet

Column: Phenomenex Gemini-nx 3u C18 110A 30×3 mm

Solvents: Acetonitrile with 0.1% trifluoroacetic acid, Water with 0.1% trifluoroacetic acid Gradient: 0 min-3.1 min 2%-100% ACN, 3.1 min-3.75 min 100% ACN

Example 50

Compound 50—Synthesis of 5-(3,3-dimethyl-but-1-ynyl)-3-{(4-trans-methyl-cyclohexanecarbonyl)-[4-(2-oxo-pyrrolidin-3-(R)-yloxycarbonylamino)-cyclohexyl]-amino}-thiophene-2-carboxylic acid

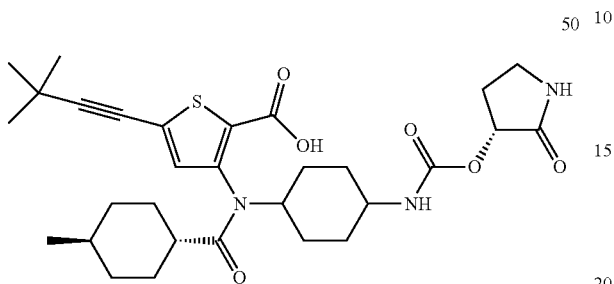

50

5-(3,3-Dimethyl-but-1-ynyl)-3-{(4-trans-methyl-cyclohexanecarbonyl)-[4-(2-oxo-pyrrolidin-3-(R)-yloxycarbonylamino)-cyclohexyl]-amino}-thiophene-2-carboxylic acid was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester using method A except that the HCl salt of 3-[(4-amino-cyclohexyl)-(4-trans-methyl-cyclohexanecarbonyl)-amino]-5-(3,3-dimethyl-but-1-ynyl)-thiophene-2-carboxylic acid was used instead of the HCl salt of 5-(3,3-dimethyl-but-1-ynyl)-3-[(4-trans-methyl-cyclohexanecarbonyl)-piperidin-4-yl-amino]-thiophene-2-carboxylic acid and 3-(R)-hydroxy-pyrrolidin-2-one was used instead of 4-hydroxy-piperidine-1-carboxylic acid tert-butyl ester.

LC/MS (m/z): 447 [M−124]
Retention time: 2.52 min
Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN.

Example 51

Compound 51—Synthesis of Boc protected 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-3-(R)-yl ester

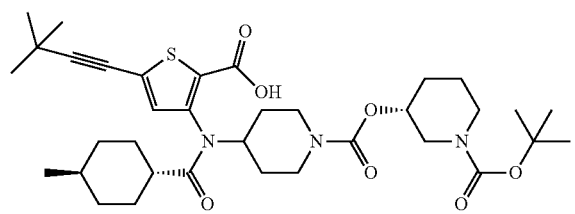

51

Boc protected 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-3-(R)-yl ester was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester using method A except that 3-(R)-hydroxy-piperidine-1-carboxylic acid tert-butyl ester was used instead of 4-hydroxy-piperidine-1-carboxylic acid tert-butyl ester.

LC/MS (m/z): 558 [M−99]
Retention time: 2.64 min
Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN.

Example 52

Compound 52—Synthesis of 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-3-(R)-yl ester

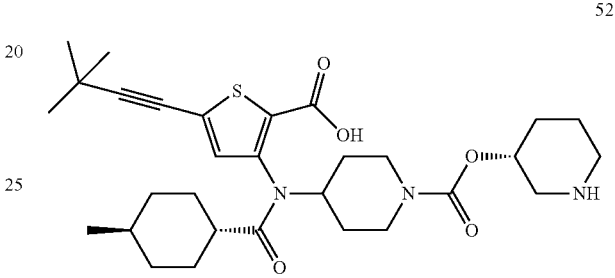

52

4-[[2-Carboxy-5-(3,3-dimethyl-but-1-ynyl)-thiophen-3-yl]-(4-trans-methyl-cyclohexanecarbonyl)-amino]-piperidine-1-carboxylic acid piperidin-3-(R)-yl ester was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester using method A except that 3-(R)-hydroxy-piperidine-1-carboxylic acid tert-butyl ester was used instead of 4-hydroxy-piperidine-1-carboxylic acid tert-butyl ester.

LC/MS (m/z): 558 [M+1]
Retention time: 2.15 min
Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN.

Example 53

Compound 53—Synthesis of 4-[[2-carboxy-5-(3,3-dimethyl-but-1-ynyl)-thiophen-3-yl]-(4-trans-methyl-cyclohexanecarbonyl)-amino]-piperidine-1-carboxylic acid tetrahydro-furan-3-(R)-yl ester

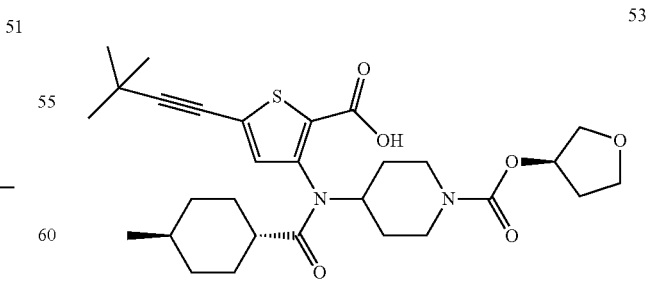

53

4-[[2-Carboxy-5-(3,3-dimethyl-but-1-ynyl)-thiophen-3-yl]-(4-trans-methyl-cyclohexanecarbonyl)-amino]-piperidine-1-carboxylic acid tetrahydro-furan-3-(R)-yl ester was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl except that tetrahydro-furan-3-(R)-ol was used instead of 4-hydroxy-piperidine-1-carboxylic acid tert-butyl ester.

LC/MS (m/z): 545 [M+1]
Retention time: 2.28 min
LC: Thermo Finnigan PDA Detector
MS: Thermo Scientific LCQ Fleet
Column: Phenomenex Gemini-nx 3u C18 110A 30×3 mm
Solvents: Acetonitrile with 0.1% trifluoroacetic acid, Water with 0.1% trifluoroacetic acid
Gradient: 0 min-3.1 min 2%-100% ACN, 3.1 min-3.75 min 100% ACN Example 54

Compound 54—Synthesis of 4-[[2-carboxy-5-(3,3-dimethyl-but-1-ynyl)-thiophen-3-yl]-(4-trans-methyl-cyclohexanecarbonyl)-amino]-piperidine-1-carboxylic acid tetrahydro-pyran-4-yl ester

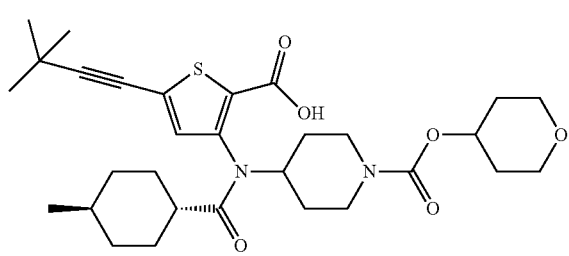

54

4-[[2-Carboxy-5-(3,3-dimethyl-but-1-ynyl)-thiophen-3-yl]-(4-trans-methyl-cyclohexanecarbonyl)-amino]-piperidine-1-carboxylic acid tetrahydro-pyran-4-yl ester was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl except that tetrahydro-pyran-4-ol was used instead of 4-hydroxy-piperidine-1-carboxylic acid tert-butyl ester.

LC/MS (m/z): 559 [M+1]
Retention time: 2.35 min
Gradient: 0 min-3.1 min 2%-100% ACN, 3.1 min-3.75 min 100% ACN Example 55

Compound 55—Synthesis of 4-[[2-carboxy-5-(3,3-dimethyl-but-1-ynyl)-thiophen-3-yl]-(4-trans-methyl-cyclohexanecarbonyl)-amino]-piperidine-1-carboxylic acid 5-oxo-pyrrolidin-3-(R)-yl ester

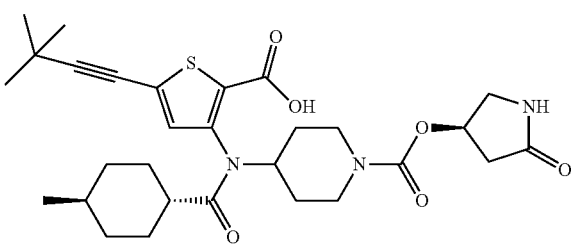

55

4-[[2-Carboxy-5-(3,3-dimethyl-but-1-ynyl)-thiophen-3-yl]-(4-trans-methyl-cyclohexanecarbonyl)-amino]-piperidine-1-carboxylic acid 5-oxo-pyrrolidin-3-(R)-yl ester was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl except that 4-(R)-hydroxy-pyrrolidin-2-one was used instead of 4-hydroxy-piperidine-1-carboxylic acid tert-butyl ester.

LC/MS (m/z): 433 [M−124]
Retention time: 2.54 min
Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN.

Example 56

Compound 56—Synthesis of 4-[[2-carboxy-5-(3,3-dimethyl-but-1-ynyl)-thiophen-3-yl]-(4-trans-methyl-cyclohexanecarbonyl)-amino]-piperidine-1-carboxylic acid 5-oxo-pyrrolidin-3-(S)-yl ester

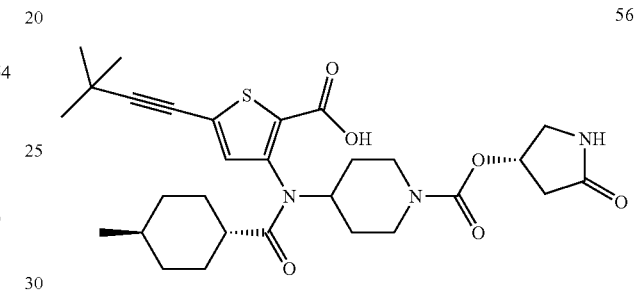

56

4-[[2-Carboxy-5-(3,3-dimethyl-but-1-ynyl)-thiophen-3-yl]-(4-trans-methyl-cyclohexanecarbonyl)-amino]-piperidine-1-carboxylic acid 5-oxo-pyrrolidin-3-(R)-yl ester was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl except that 4-(S)-hydroxy-pyrrolidin-2-one was used instead of 4-hydroxy-piperidine-1-carboxylic acid tert-butyl ester.

LC/MS (m/z): 433 [M−124]
Retention time: 2.54 min
Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN Example 57

Compound 57—Synthesis of 4-[[2-carboxy-5-(3,3-dimethyl-but-1-ynyl)-thiophen-3-yl]-(4-methyl-cyclohexanecarbonyl)-amino]-piperidine-1-carboxylic acid 2-oxo-pyrrolidin-3-(S)-yl ester

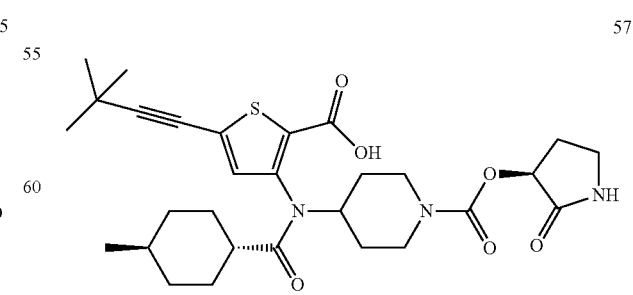

57

4-[[2-Carboxy-5-(3,3-dimethyl-but-1-ynyl)-thiophen-3-yl]-(4-methyl-cyclohexanecarbonyl)-amino]-piperidine-1- carboxylic acid 2-oxo-pyrrolidin-3-(S)-yl ester was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl except that 3-(S)-Hydroxy-pyrrolidin-2-one was used instead of 4-hydroxy-piperidine-1-carboxylic acid tert-butyl ester.

LC/MS (m/z): 576 [M+19]
Retention time: 2.16 min
LC: Thermo Electron Surveyor HPLC
MS: Finnigan LCQ Advantage MAX Mass Spectrometer
Column: Phenomenex Polar RP 30 mm×4.6 mm
Solvents: Acetonitrile with 0.1% formic acid, Water with 0.1% formic acid Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN Method D Example 64

Compound 64—Synthesis of 5-(3,3-Dimethyl-but-1-ynyl)-3-[[3-(hexahydro-furo[2,3-b]furan-3-yloxycarbonylamino)-1-(S)-methyl-propyl]-(trans-4-methyl-cyclohexanecarbonyl)-amino]-thiophene-2-carboxylic acid

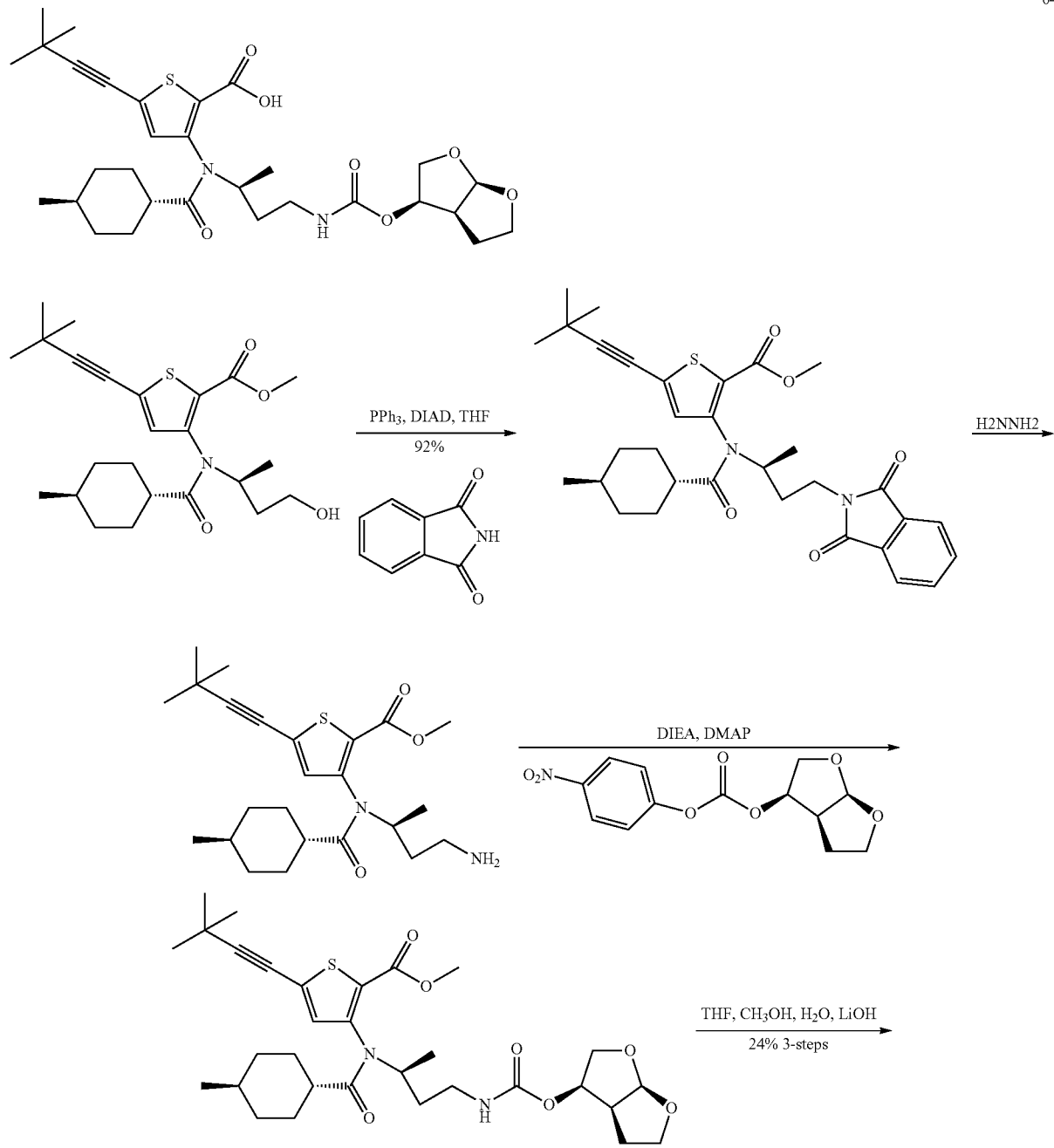

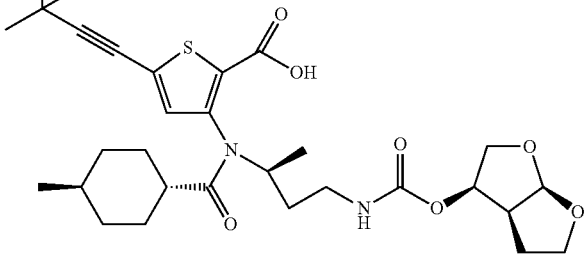

A mixture of 5-(3,3-dimethyl-but-1-ynyl)-3-[(3-hydroxy-1-(S)-methyl-propyl)-(trans-4-methyl-cyclohexanecarbonyl)-amino]-thiophene-2-carboxylic acid TFA salt (1.40 g, 3.23 mmol) in THF (30 mL) was cooled to 0° C. and triphenylphosphine (2.53 g, 9.69 mmol) was added followed by phthalimide (0.713 g, 4.84 mmol). The reaction was stirred until homogenious then DIAD (1.06 mL, 5.49 mmol) was added. After warming to rt., the reaction was determined to be complete by LC/MS in 1 h. The reaction was quenched with $CH_3OH$ (1.0 mL) and the solvent removed under reduced pressure. 5-(3,3-Dimethyl-but-1-ynyl)-3-[[3-(1,3-dioxo-1,3-dihydro-isoindole-2-yl)-1-(S)-methyl propyl]-(trans-4-methyl-cyclohexylcarbonyl)-amino]-thiophene-2-carboxylic acid methyl ester (1.67 g, 92%) was isolated by silica gel chromatography as an off-white solid.

A mixture of 5-(3,3-dimethyl-but-1-ynyl)-3-[[3-(1,3-dioxo-1,3-dihydro-isoindole-2-yl)-1-(S)-methyl propyl]-(trans-4-methyl-cyclohexylcarbonyl)-amino]-thiophene-2-carboxylic acid methyl ester (168 mg, 0.30 mmol) in $CH_3OH$ (2 mL) and hydrazine (15 µL, 0.45 mmol) was placed in a preheated 80° C. oil bath and stirred for 2 h. The reaction was determined to be complete by LC/MS. Solvent was removed under reduced pressure and the crude material was coevaporated with toluene. 3-[[3-Amino-1-(S)-methyl-propyl)-(trans-4-methyl-cyclohexanecarbonyl)-amino]-5-(3,3-dimethyl-but-1-ynyl)-thiophene-2-carboxylic acid methyl ester was used as is for the next step without purification.

A mixture of crude 3-[[3-Amino-1-(S)-methyl-propyl)-(trans-4-methyl-cyclohexanecarbonyl)-amino]-5-(3,3-dimethyl-but-1-ynyl)-thiophene-2-carboxylic acid methyl ester in ACN (3.0 mL) was treated with carbonic acid hexahydro-furo[2,3-b]furan-3-yl ester 4-nitro-phenyl ester (0.11 g, 0.375 mmol) followed by diisopropylethyl amine (0.1 mL, 0.625 mmol) and DMAP (cat). The reaction was stirred for 1 h and quenched with $CH_3OH$ (1 mL). Solvent was removed under reduced pressure and the crude material was partitioned between EtOAc, and ½ sat $NaHCO_{3(aq)}$. The organics were dried over $Na_2SO_4$, solids filtered and solvent removed under reduced pressure. 5-(3,3-Dimethyl-but-1-ynyl)-3-[[3-(hexahydro-furo[2,3-b]furan-3-yloxycarbonylamino)-1-(S)-methyl-propyl]-(trans-4-methyl-cyclohexanecarbonyl)-amino]-thiophene-2-carboxylic acid methyl ester was isolated by reverse phase HPLC and carried forward wet to the next reaction.

A mixture of 5-(3,3-Dimethyl-but-1-ynyl)-3-[[3-(hexahydro-furo[2,3-b]furan-3-yloxycarbonylamino)-1-(S)-methyl-propyl]-(trans-4-methyl-cyclohexanecarbonyl)-amino]-thiophene-2-carboxylic acid methyl ester in THF (2 mL) and $CH_3OH$ (1 mL) was treated with dissolve $LiOH.H_2O$ (0.1 g, 2.38 mmol) in $H_2O$ (2 mL). The reaction was determined to be complete after 5 h. The pH was adjusted to 2 with $2N HCl_{(aq)}$. After diluting with $CH_3OH$ (3 mL), 5-(3,3-Dimethyl-but-1-ynyl)-3-[[3-(hexahydro-furo[2,3-b]furan-3-yloxycarbonylamino)-1-(S)-methyl-propyl]-(trans-4-methyl-cyclohexanecarbonyl)-amino]-thiophene-2-carboxylic acid TFA salt (0.41 g, 24% 3-steps) was isolated by reverse phase HPLC as a white solid.

LC/MS=597.20 ($M^+$+Na)

Retention time: 3.76 min

Gradient: 0 min-0.2 min 5% ACN, 0.2 min-3.95 min 5%-100% ACN, 3.95 min-5.20 min 100% ACN, 5.20 min-5.5 min 100%-5% ACN, 5.5 min-6 min 5% ACN.

Example 65

Compound 65—Synthesis of 5-(3,3-dimethyl-but-1-ynyl)-3-[[trans-4-methyl-cyclohexanecarbonyl)-[1-(S)-methyl-3-(tetrahydrofuran-3-yloxycarbonylamino)-propyl]-amino]-thiophene-2-carboxylic acid

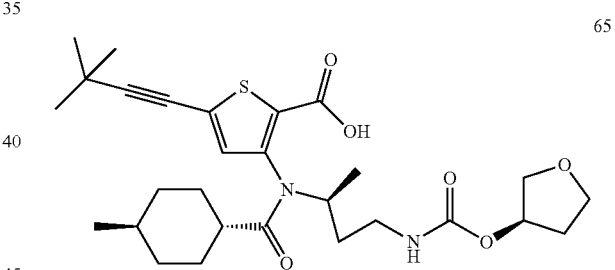

65

A solution of 3-[[3-Amino-1-(S)-methyl-propyl)-(trans-4-methyl-cyclohexanecarbonyl)-amino]-5-(3,3-dimethyl-but-1-ynyl)-thiophene-2-carboxylic acid methyl ester (0.08 g, 0.146 mmol) in $CH_3CN$ (1.5 mL) was prepared. 3-(R)-Hydroxy-tetrahydrofuranyl-chloroformate (0.132 g, 0.88 mmol), which was prepared in a manner similar to method G, was added followed by diisopropylethyl amine (0.25 mL, 1.50 mmol) and DMAP (cat). After stirring at rt for 30 min., the reaction was determined to be complete by LC/MS. The reaction was quenched with $H_2O$ (1 mL) and the organics removed under reduced pressure and 5-(3,3-dimethyl-but-1-ynyl)-3-[[trans-4-methyl-cyclohexanecarbonyl)-[1-(S)-methyl-3-(tetrahydrofuran-3-yloxycarbonylamino)-propyl]-amino]-thiophene-2-carboxylic acid methyl ester was carried forward without purification.

A mixture of 5-(3,3-dimethyl-but-1-ynyl)-3-[[trans-4-methyl-cyclohexanecarbonyl)-[1-(S)-methyl-3-(tetrahydrofuran-3-yloxycarbonylamino)-propyl]-amino]-thiophene-2-carboxylic acid methyl ester in THF (2 mL) and $CH_3OH$ (1 mL) was treated with dissolve $LiOH.H_2O$ (0.1 g, 2.38 mmol) in $H_2O$ (2 mL). The reaction was determined to be complete after 1 h. The pH was adjusted to 2 with 2NHCl$_{(aq)}$, the reaction diluted with CH$_3$OH (3 mL) and 5-(3,3-dimethyl-but-1-ynyl)-3-[[trans-4-methyl-cyclohexanecarbonyl]-[1-(S)-methyl-3-(tetrahydrofuran-3-yloxycarbonylamino)-propyl]-amino]-thiophene-2-carboxylic acid TFA salt (0.046 g, 47%) was isolated by reverse phase HPLC as a white solid.

LC/MS=555.24 (M+Na$^+$)

Retention time: 3.65 min

Gradient: 0 min-0.2 min 5% ACN, 0.2 min-3.95 min 5%-100% ACN, 3.95 min-5.20 min 100% ACN, 5.20 min-5.5 min 100%-5% ACN, 5.5 min-6 min 5% ACN.

Method E

Example 66

Compound 66—5-(3,3-Dimethyl-but-ynyl)-3-[[4-(hexahydro-furo[2,3-b]furan-3-yloxycarbonylamino)-cyclohexyl]-(trans-4-methyl-cyclohexanecarbonyl)-amino]-thiophene-2-carboxylic acid A solution of 3-[(4-amino-cyclohexyl)-(trans-4-methylcyclohexanecarbonyl)-amino]-5-(3,3-dimethyl-but-1ynyl) thiophene-2-carboxylic acid methyl ester (0.40 g, 0.873 mmol) in ACN (5.0 mL) was cooled to 0° C. and carbonic acid hexahydro-furo[2,3-b]furan-3-yl ester 4-nitro-phenyl ester (0.295 g, 1.0 mmol) was added, followed by DIEA (391 µL, 2.18 mmol) and DMAP (cat). The reaction mixture was warmed to rt, and stirred for 1 h. The solvent was removed under reduced pressure and the crude reaction mixture was partitioned between EtOAc and 2N K$_2$CO$_{3(aq)}$. The layers were separated and the organics washed repeatedly with 2N K$_2$CO$_{3(aq)}$. Both epimers of 5-(3,3-Dimethyl-but-ynyl)-3-[[4-(hexahydro-furo[2,3-b]furan-3-yloxycarbonylamino)-cyclohexyl]-(trans-4-methyl-cyclohexanecarbonyl)-amino]-thiophene-2-carboxylic acid methyl ester were isolated by reverse phase HPLC and carried forward wet into the next reaction.

To each of the wet fractions of 5-(3,3-Dimethyl-but-ynyl)-3-[[4-(hexahydro-furo[2,3-b]furan-3-yloxycarbonylamino)-cyclohexyl]-(trans-4-methyl-cyclohexanecarbonyl)-amino]-

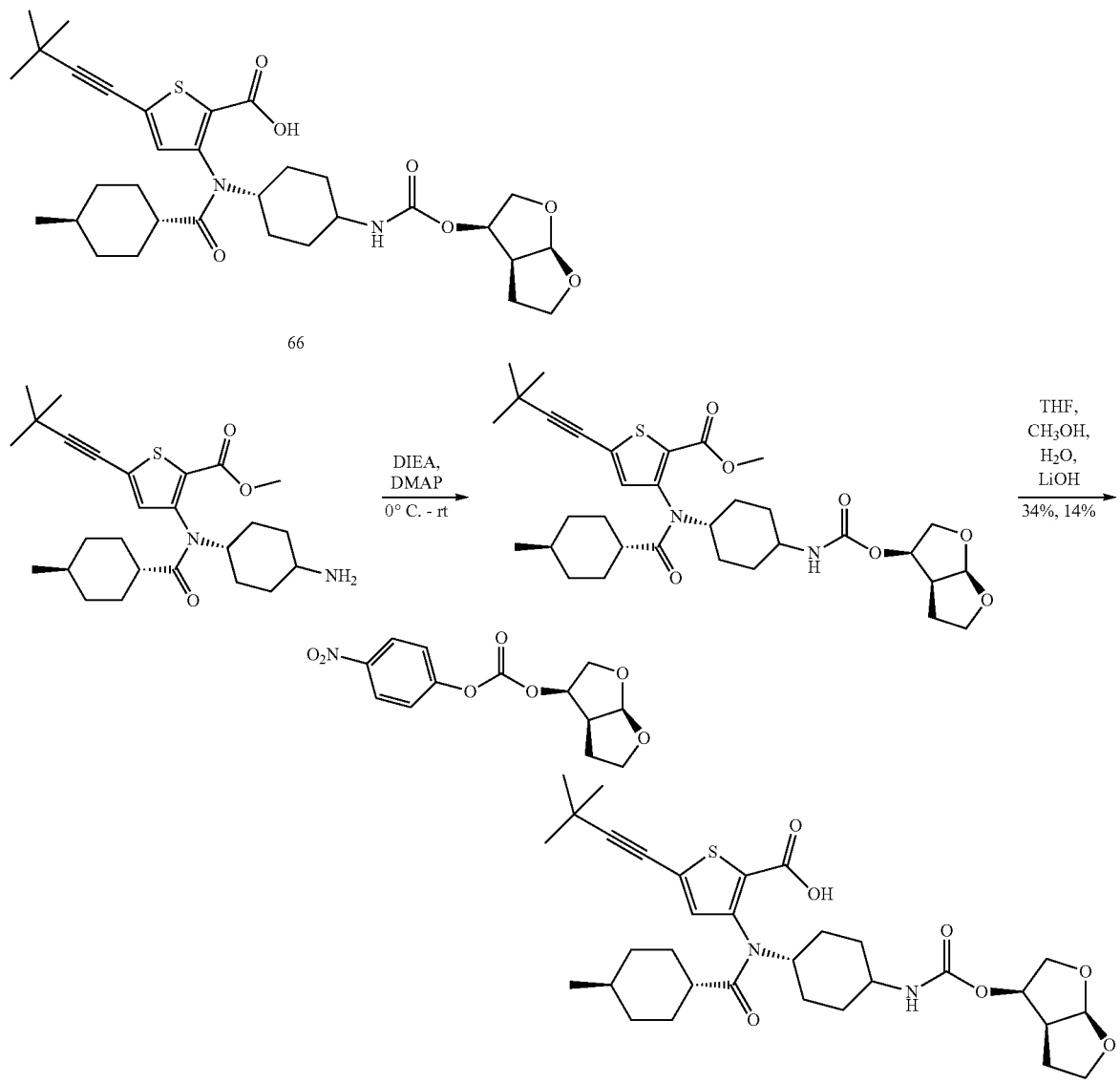

thiophene-2-carboxylic acid methyl ester were added THF (0.5 mL), CH₃OH (0.2 mL), and LiOH (0.021 g, 0.5 mmol). The reactions were allowed to stir at rt for 2 h. The reactions were determined to be complete by LC/MS. The reactions were quenched with 2N HCl$_{(aq)}$ to pH=ca. 2. Both epimers of 5-(3,3-Dimethyl-but-ynyl)-3-[[4-(hexahydro-furo[2,3-b]furan-3-yloxycarbonylamino)-cyclohexyl]-(trans-4-methyl-cyclohexanecarbonyl)-amino]-thiophene-2-carboxylic acid TFA salt (fast eluting: 89 mg, 34%, slow eluting 34 mg, 14%) were isolated by reverse phase HPLC as an off-white solid.

LC/MS=623.20 (M⁺+Na)

Retention time: 3.76 min

Gradient: 0 min-0.2 min 5% ACN, 0.2 min-3.95 min 5%-100% ACN, 3.95 min-5.20 min 100% ACN, 5.20 min-5.5 min 100%-5% ACN, 5.5 min-6 min 5% ACN.

Method F

Example 67

Compound 67—3-(S)-{3-[[2-Carboxy-5-(3,3-dimethyl-but-1-ynyl)-thiophene-3-yl](trans-4-methyl-cyclohexanecarbonyl)-amino]-pyrrolidine-1-carbonyloxy}-3-methyl-pyrrolidine-1-carboxylic acid tert-butyl ester

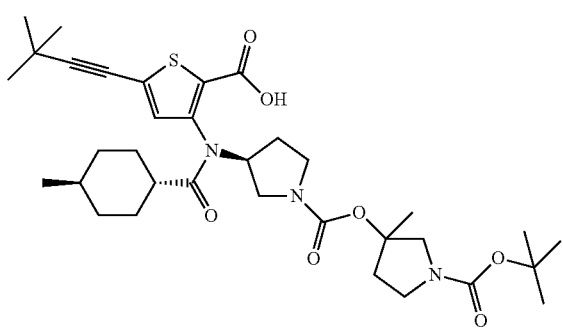

67

Example 68

Compound 68—3-(S)-[[2-Carboxy-5-(3,3-dimethyl-but-1-ynyl)-thiophen-3-yl]-(trans-4-methylcyclohexanecarbonyl)-amino]-pyrrolidine-1-carbocylic-acid-3-methyl-pyrrolidin-3-yl-ester

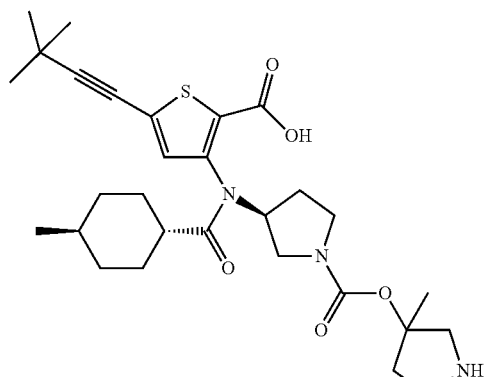

68

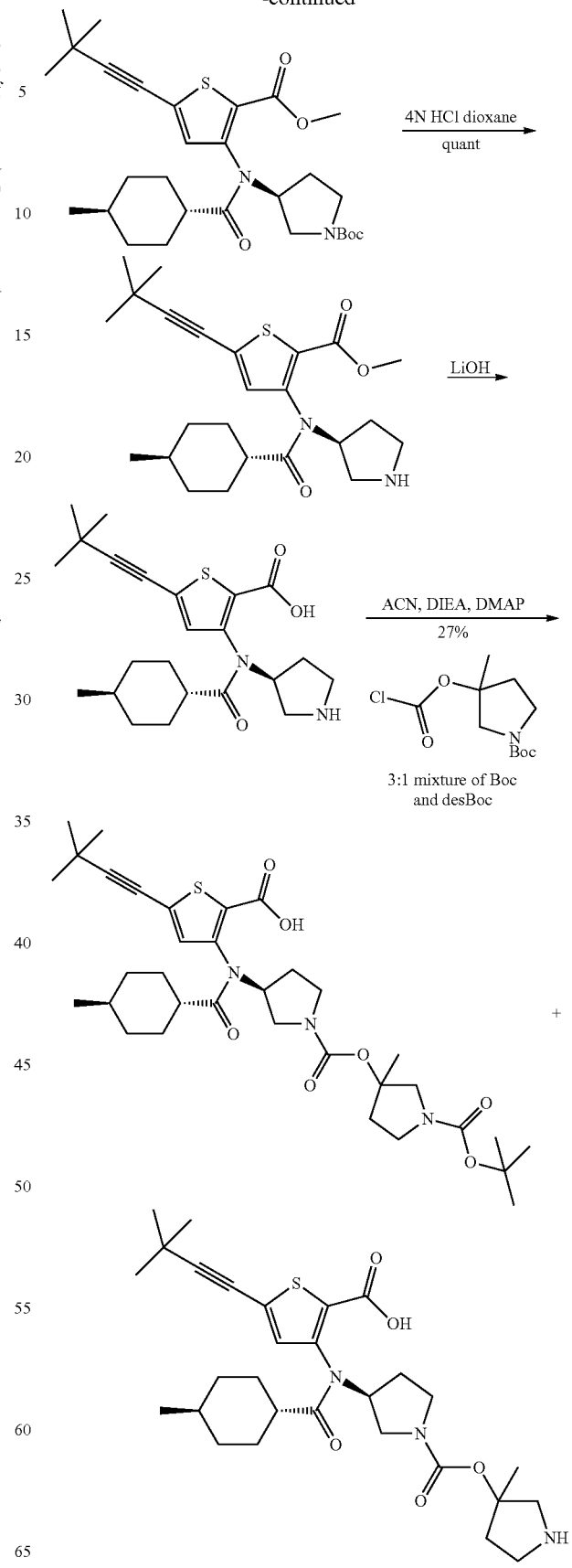

3-(S)-[[5-(3,3-Dimethyl-but-1-ynyl)-2-methoxycarbonyl-thiophene-3-(S)-yl]-(trans-4-methyl-cyclohexanecarbonyl)-amino]-pyrrolidine-1-carboxylic acid tert-butyl ester (3.10 g, 5.85 mmol) was taken up in CH$_2$Cl$_2$ (50 mL) and 4N HCl in dioxane (25 mL, 100 mmol) was added in one portion. The reaction was stirred for 2 h and was determined to be complete by LC/MS. Solvents were removed under reduced pressure and the crude reaction mixture was co-evaporated with 3×25 mL toluene. 5-(3,3-dimethyl-but-1-ynyl)-3-[[trans-4-methyl-cyclohexanecarbonyl)-pyrrolidin-3-(S)-yl-amino]-thiophene-carboxylic acid methyl ester was carried forward crude into the next step.

A mixture of 5-(3,3-dimethyl-but-1-ynyl)-3-[[trans-4-methyl-cyclohexanecarbonyl)-pyrrolidin-3-(S)-yl-amino]-thiophene-carboxylic acid methyl ester in THF (25 mL) and CH$_3$OH (10 mL) was treated with LiOH.H$_2$O (1.43 g, 34.2 mmol) in H$_2$O (10 mL). The reaction was determined to be complete by LC/MS after 2 h. The pH was adjusted to 2 with 2N HCl$_{(aq)}$ and the solvents were removed under reduced pressure. Co-evaporation with CH$_3$OH, then EtOAc, and finally toluene removed all H$_2$O. 5-(3,3-Dimethyl-but-1-ynyl)-3-[[trans-4-methyl-cyclohexanecarbonyl)-pyrrolidin-3-(S)-yl-amino]-thiophene-carboxylic acid was carried forward crude with LiCl salt into the next step.

5-(3,3-Dimethyl-but-1-ynyl)-3-[[trans-4-methyl-cyclohexanecarbonyl)-pyrrolidin-3-(S)-yl-amino]-thiophene-carboxylic acid (150 mg) was taken up in ACN (2.0 mL). The heterogeneous solution was allowed to stir for 5 min, then DIEA (250 μL, 2.3 mmol) and DMAP (cat) was added sequentially to the solution. The reaction was allowed to stir for 5 min then 3-chlorocarbonyloxy-3-methyl-pyrrolidine-1-carboxylic acid tert-butyl ester (≈200 mg) prepared in a manner similar to method G was added in one portion. The reaction was stirred at rt for 15 min and determined to be complete by LC/MS. Solvent was removed under reduced pressure. The reaction mixture was partitioned between EtOAc and 2N HCl$_{(aq)}$. The organics were dried over Na$_2$SO$_4$, solids filtered and solvent removed under reduced pressure. 3-{3-[[2-Carboxy-5-(3,3-dimethyl-but-1-ynyl)-thiophene-3-yl]-(trans-4-methyl-cyclohexanecarbonyl)-3-(S)-amino]-pyrrolidine-1-carbonyloxy}-3-methyl-pyrrolidine-1-carboxylic acid tert-butyl ester TFA salt (35 mg, 20%) and 3-{3-[[2-Carboxy-5-(3,3-dimethyl-but-1-ynyl)-thiophene-3-yl]-(trans-4-methyl-cyclohexanecarbonyl)-3-(S)-amino]-pyrrolidine-1-carbonyloxy}-3-methyl-pyrrolidine-1-carboxylic acid TFA salt (11 mg, 7%) were isolated by reverse phase HPLC as white solids. 3-{3-[[2-Carboxy-5-(3,3-dimethyl-but-1-ynyl)-thiophene-3-yl]-(trans-4-methyl-cyclohexanecarbonyl)-3-(S)-amino]-pyrrolidine-1-carbonyloxy}-3-methyl-pyrrolidine-1-carboxylic acid tert-butyl ester TFA salt LC/MS=544.14 (M$^+$–Boc)
Retention time: 4.02 min
Gradient: 0 min-0.2 min 5% ACN, 0.2 min-3.95 min 5%-100% ACN, 3.95 min-5.20 min 100% ACN, 5.20 min-5.5 min 100%-5% ACN, 5.5 min-6 min 5% ACN.

3-{3-[[2-Carboxy-5-(3,3-dimethyl-but-1-ynyl)-thiophene-3-yl]-(trans-4-methyl-cyclohexanecarbonyl)-3-(S)-amino]-pyrrolidine-1-carbonyloxy}-3-methyl-pyrrolidine-1-carboxylic acid TFA salt LC/MS=544.10 (M$^+$+1)
Retention time: 3.36 min
Gradient: 0 min-0.2 min 5% ACN, 0.2 min-3.95 min 5%-100% ACN, 3.95 min-5.20 min 100% ACN, 5.20 min-5.5 min 100%-5% ACN, 5.5 min-6 min 5% ACN.

Method G

3-Chlorocarbonyloxy-3-methyl-pyrrolidine-1-carboxylic acid tert-butyl ester

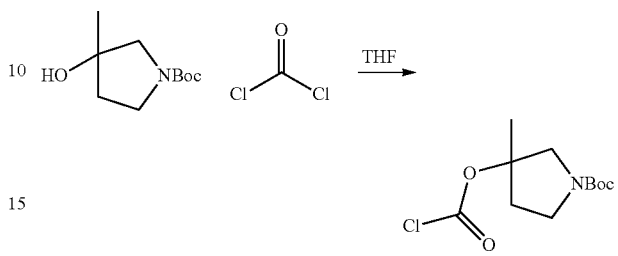

A solution of 3-hydroxy-3-methylpyrrolidine-carboxylic acid tert-butyl ester (200 mg, 1.00 mmol) in THF (4 mL) was slowly treated with phosgene 20% in toluene (0.954 mL). After stirring at rt for 16 h, solvents were removed under reduced pressure and co-evaporate with CH$_2$Cl$_2$. The crude 3-chlorocarbonyloxy-3-methylpyrrolidine-carboxylic acid tert-butyl ester was used directly in the next step.

Example 69

Compound 69—Synthesis of 3-[[2-carboxy-5-(3,3-dimethyl-but-1-ynyl)-thiophen-3-yl]-(trans-4-methyl-cyclohexanecarbonyl)-3-(S)-amino]-pyrrolidine-1-carboxylic acid 1-tert-butoxycarbonyl-3-methyl-azetidin-3-yl ester

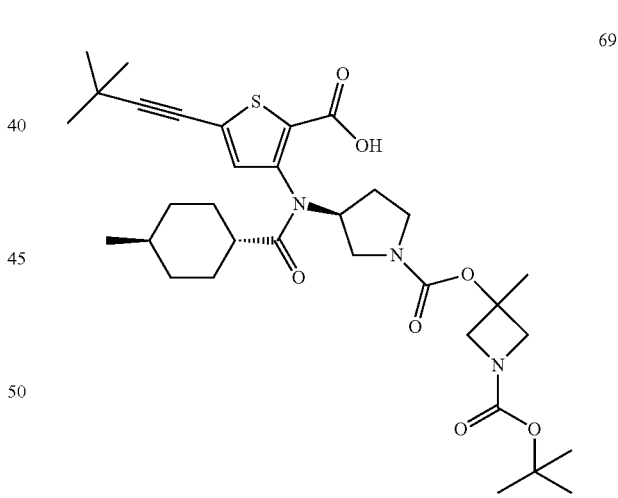

5-(3,3-Dimethyl-but-1-ynyl)-3-[[trans-4-methyl-cyclohexanecarbonyl)-pyrrolidin-3-(S)-yl-amino]-thiophene-carboxylic acid (150 mg) was taken up in ACN (2.0 mL). The heterogeneous solution was allowed to stir for 5 min, and then DIEA (250 μL, 2.3 mmol) and DMAP (cat) were added sequentially. The reaction was allowed to stir for 5 min then 3-chlorocarbonyloxy-3-methyl-azetidine-1-carboxylic acid tert-butyl ester (≈200 mg) which was prepared in a similar manner to Method G was added in one portion. The reaction was stirred at rt for 15 min and determined to be complete by LC/MS. Solvent was removed under reduced pressure. The reaction mixture was partitioned between EtOAc and 2N HCl$_{(aq)}$. The organics were dried over Na$_2$SO$_4$, solids filtered and solvent removed under reduced pressure. 3-[[2-Carboxy-5-(3,3-dimethyl-but-1-ynyl)-thiophene-3-yl]-(trans-4-methyl-cyclohexanecarbonyl)-3-(S)-amino]-pyrrolidine-1-carboxylic acid 1-tert-butoxycarbonyl-3-methyl-azetidin-3-yl ester TFA salt (46 mg, 26%)

LC/MS=630 (M$^+$+1)

Retention time: 3.89 min

Gradient: 0 min-0.2 min 5% ACN, 0.2 min-3.95 min 5%-100% ACN, 3.95 min-5.20 min 100% ACN, 5.20 min-5.5 min 100%-5% ACN, 5.5 min-6 min 5% ACN.

Example 70

Compound 70—Synthesis of 3-[[2-carboxy-5-(3,3-dimethyl-but-1-ynyl)-thiophene-3-yl]-(trans-4-methylcyclohexanecarbonyl)-3-(S)-amino]-pyrrolidine-1-carboxylic acid 1,1-dioxo-tetrahydro-1λ$^6$-thiophene-3-yl ester

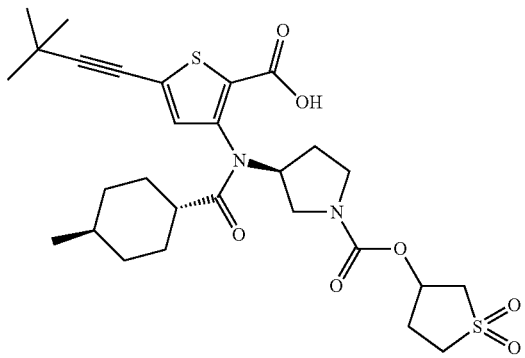

70

5-(3,3-Dimethyl-but-1-ynyl)-3-[[trans-4-methyl-cyclohexanecarbonyl)-pyrrolidin-3-(S)-amino]-thiophene-carboxylic acid (200 mg) was taken up in ACN (4.0 mL). The heterogeneous solution was allowed to stir for 5 min, and then DIEA (500 µL, 4.6 mmol) and DMAP (cat) were added sequentially. The reaction was allowed to stir for 5 min then 3-chlorocarbonyloxy-1,1-dioxo-tetrahydro-1λ$^6$-thiophene (≈200 mg), which was prepared in a similar manner to method G, was added in one portion. The reaction was stirred at rt for 15 min and determined to be complete by LC/MS. Solvent was removed under reduced pressure. The reaction mixture was partitioned between EtOAc and 2N HCl$_{(aq)}$. The organics were dried over Na$_2$SO$_4$, solids filtered and solvent removed under reduced pressure. 3-[[2-Carboxy-5-(3,3-dimethyl-but-1-ynyl)-thiophene-3-yl]-(trans-4-methylcyclohexanecarbonyl)-3-(S)-amino]-pyrrolidine-1-carboxylic acid 1,1-dioxo-tetrahydro-1λ$^6$-thiophene-3-yl ester TFA salt (37 mg, 19%)

LC/MS=454.97 (M$^+$-methylcyclohexylcarbonyl)

Retention time: 3.56 min

Gradient: 0 min-0.2 min 5% ACN, 0.2 min-3.95 min 5%-100% ACN, 3.95 min-5.20 min 100% ACN, 5.20 min-5.5 min 100%-5% ACN, 5.5 min-6 min 5% ACN.

Example 71

Compound 71—4-[[2-Carboxy-5-(3,3-dimethyl-but-1-ynyl)-thiophen-3-yl]-(trans-4-methyl-cyclohexanecarbonyl)-amino]-piperidine-1-carboxylic acid 1-tert-butoxycarbonyl-3-methyl-pyrrolidin-3-yl ester

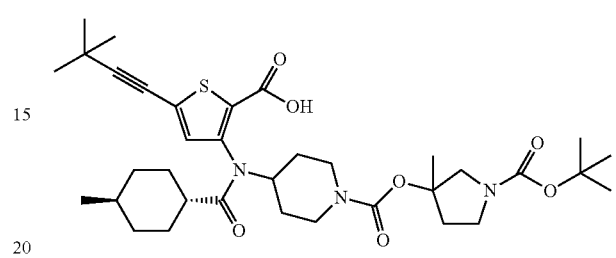

71

And

Example 72

Compound 72—4-[[2-Carboxy-5-(3,3-dimethyl-but-1-ynyl)-thiophen-3-yl]-(trans-4-methyl-cyclohexanecarbonyl)-amino]-piperidine-1-carboxylic acid 3-methyl-pyrrolidin-3-yl ester

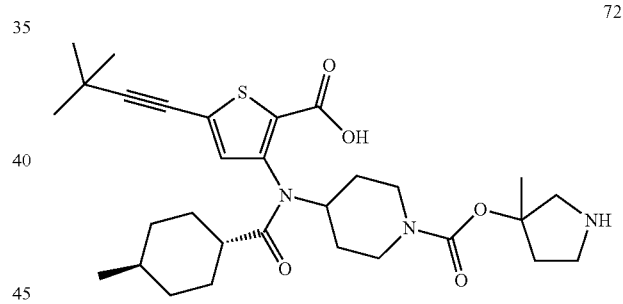

72

5-(3,3-Dimethyl-but-1-ynyl)-3-[(trans-4-methyl-cyclohexanecarbonyl)-piperidin-4-yl-amino]-thiophene-2-carboxylic acid (150 mg) was taken up in ACN (2.0 mL). The heterogeneous solution was allowed to stir for 5 min, and then DIEA (250 µL, 2.3 mmol) and DMAP (cat) were added sequentially. The reaction was allowed to stir for 5 min then 3-chlorocarbonyloxy-3-methylpyrrolidine-carboxylic acid tert-butyl ester (≈200 mg), which was prepared in a similar manner to method G, was added in one portion. The reaction was stirred at rt for 15 min and determined to be complete by LC/MS. Solvent was removed under reduced pressure. The reaction mixture was partitioned between EtOAc and 2N HCl$_{(aq)}$. The organics were dried over Na$_2$SO$_4$, solids filtered and solvent removed under reduced pressure. 4-[[2-Carboxy-5-(3,3-dimethyl-but-1-ynyl)-thiophen-3-yl]-(trans-4-methyl-cyclohexanecarbonyl)-amino]-piperidine-1-carboxylic acid 1-tert-butoxycarbonyl-3-methyl-pyrrolidin-3-yl ester TFA salt (26 mg, 18%) and 4-[[2-Carboxy-5-(3,3-dimethyl-but-1-ynyl)-thiophen-3-yl]-(trans-4-methyl-cyclohexanecarbonyl)-amino]-piperidine-1-carboxylic acid 3-methylpyrrolidin-3-yl ester TFA salt (8 mg, 6%) were isolated by reverse phase HPLC as white solids.

4-[[2-Carboxy-5-(3,3-dimethyl-but-1-ynyl)-thiophen-3-yl]-(trans-4-methyl-cyclohexanecarbonyl)-amino]-piperidine-1-carboxylic acid 1-tert-butoxycarbonyl-3-methyl-pyrrolidin-3-yl ester LC/MS=558.19 (M+−Boc)

Retention time: 4.03 min

Gradient: 0 min-0.2 min 5% ACN, 0.2 min-3.95 min 5%-100% ACN, 3.95 min-5.20 min 100% ACN, 5.20 min-5.5 min 100%-5% ACN, 5.5 min-6 min 5% ACN.

4-[[2-Carboxy-5-(3,3-dimethyl-but-1-ynyl)-thiophen-3-yl]-(trans-4-methyl-cyclohexanecarbonyl)-amino]-piperidine-1-carboxylic acid 3-methyl-pyrrolidin-3-yl ester

LC/MS=558.09 (M++1)

Retention time: 3.40 min

Gradient: 0 min-0.2 min 5% ACN, 0.2 min-3.95 min 5%-100% ACN, 3.95 min-5.20 min 100% ACN, 5.20 min-5.5 min 100%-5% ACN, 5.5 min-6 min 5% ACN Example 73

Compound 73—Synthesis of 4-[[2-carboxy-5-(3,3-dimethyl-but-1-ynyl)-thiophen-3-yl]-(trans-4-methyl-cyclohexanecarbonyl)-amino]-piperidine-1-carboxylic acid 1-tert-butoxycarbonyl-3-methyl-azetidin-3-yl ester

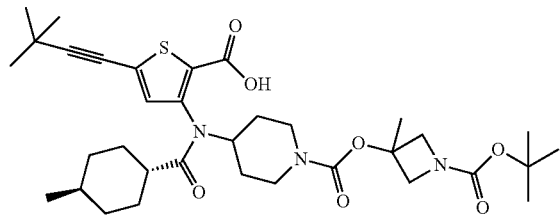

73

5-(3,3-Dimethyl-but-1-ynyl)-3-[(4-methyl-cyclohexanecarbonyl)-piperidin-4-yl-amino]-thiophene-2-carboxylic acid (150 mg) was taken up in ACN (2.0 mL). The heterogeneous solution was allowed to stir for 5 min, and then DIEA (250 µL, 2.3 mmol) and DMAP (cat) were added sequentially. The reaction was allowed to stir for 5 min then 3-chlorocarbonyloxy-3-methylpyrrolidine-carboxylic acid tert-butyl ester (≈200 mg), which was prepared in a similar manner to method G, was added in one portion. The reaction was stirred at rt for 15 min and determined to be complete by LC/MS. Solvent was removed under reduced pressure. The reaction mixture was partitioned between EtOAc and 2N HCl$_{(aq)}$. The organics were dried over Na$_2$SO$_4$, solids filtered and solvent removed under reduced pressure. 4-[[2-Carboxy-5-(3,3-dimethyl-but-1-ynyl)-thiophen-3-yl]-(trans-4-methyl-cyclohexanecarbonyl)-amino]-piperidine-1-carboxylic acid 1-tert-butoxycarbonyl-3-methyl-azetidin-3-yl ester TFA salt (38 mg, 22%) was isolated by reverse phase HPLC as a white solid.

LC/MS=544.20 (M+−Boc)

Retention time: 4.01 min

Gradient: 0 min-0.2 min 5% ACN, 0.2 min-3.95 min 5%-100% ACN, 3.95 min-5.20 min 100% ACN, 5.20 min-5.5 min 100%-5% ACN, 5.5 min-6 min 5% ACN.

Example 74

Compound 74—Synthesis of 4-[[2-carboxy-5-(3,3-dimethyl-but-1-ynyl)-thiophen-3-yl]-(trans-4-methyl-cyclohexanecarbonyl)-amino]-piperidine-1-carboxylic acid 1,1-dioxo-tetrahydro-1λ$^6$-thiophen-3-yl ester

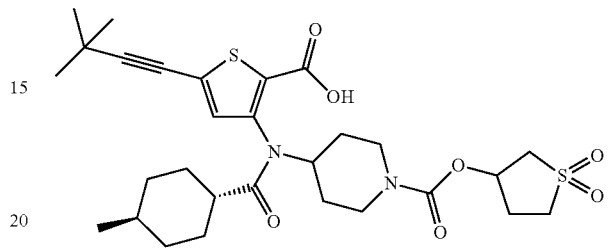

74

5-(3,3-Dimethyl-but-1-ynyl)-3-[(trans-4-methyl-cyclohexanecarbonyl)-piperidin-4-yl-amino]-thiophene-2-carboxylic acid (200 mg) was taken up in ACN (4.0 mL). The heterogeneous solution was allowed to stir for 5 min, then DIEA (350 µL, 2.3 mmol) and DMAP (cat) were added. The reaction was allowed to stir for 5 min then 3-chlorocarbonyloxy-1,1-dioxo-tetrahydro-1λ$^6$-thiophene (≈200 mg), which was prepared in a similar fashion as method G, was added in one portion. The reaction was stirred at rt for 15 min and determined to be complete by LC/MS. Solvent was removed under reduced pressure. The reaction mixture was partitioned between EtOAc and 2N HCl$_{(aq)}$. The organics were dried over Na$_2$SO$_4$, solids filtered and solvent removed under reduced pressure. 4-[[2-Carboxy-5-(3,3-dimethyl-but-1-ynyl)-thiophen-3-yl]-(trans-4-methyl-cyclohexanecarbonyl)-amino]-piperidine-1-carboxylic acid 1,1-dioxo-tetrahydro-1λ$^6$-thiophen-3-yl ester TFA salt (2.0 mg, 1%) was isolated by reverse phase HPLC as a white solid.

LC/MS=469.10 (M+−methylcyclohexycarbonyl)

Retention time: 3.70 min

Gradient: 0 min-0.2 min 5% ACN, 0.2 min-3.95 min 5%-100% ACN, 3.95 min-5.20 min 100% ACN, 5.20 min-5.5 min 100%-5% ACN, 5.5 min-6 min 5% ACN.

Example 75

Compound 75—Synthesis of 3-{4-[[2-carboxy-5-(3,3-dimethyl-but-1-ynyl)-thiophen-3-yl]-(trans-4-methyl-cyclohexanecarbonyl)-cyclohexylcarbamoyloxy}-3-methyl-pyrrolidine-1-carboxylic acid tert-butyl ester

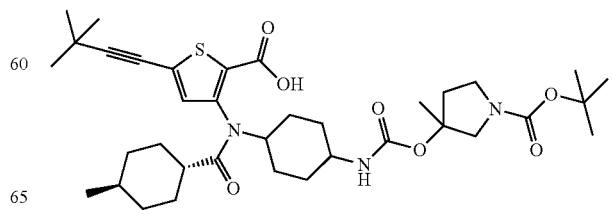

75

3-[4-Amino-cyclohexyl)-(trans-4-methyl-cyclohexanecarbonyl)-amino]-5-(3,3-dimethyl-but-1-ynyl)-thiophene-2-carboxylic acid (150 mg) was taken up in ACN (2.5 mL). The heterogeneous solution was allowed to stir for 5 min, then DIEA (250 µL, 2.3 mmol) and DMAP (cat) were added sequentially. The reaction was allowed to stir for 5 min then 3-chlorocarbonyloxy-3-methylpyrrolidine-carboxylic acid tert-butyl ester (≈200 mg), which was prepared in a manner similar to method G, was added in one portion. The reaction was stirred at rt for 15 min and determined to be complete by LC/MS. Solvent was removed under reduced pressure. The reaction mixture was partitioned between EtOAc and 2N HCl$_{(aq)}$. The organics were dried over Na$_2$SO$_4$, solids filtered and solvent removed under reduced pressure. 3-{4-[[2-Carboxy-5-(3,3-dimethyl-but-1-ynyl)-thiophen-3-yl]-(trans-4-methyl-cyclohexanecarbonyl)-cyclohexylcarbamoyloxy}-3-methyl-pyrrolidine-1-carboxylic acid tert-butyl ester TFA salt (84 mg, 47%) was isolated by reverse phase HPLC as a white solid.

LC/MS=572.21 (M$^+$—Boc)

Retention time: 4.03 min

Gradient: 0 min-0.2 min 5% ACN, 0.2 min-3.95 min 5%-100% ACN, 3.95 min-5.20 min 100% ACN, 5.20 min-5.5 min 100%-5% ACN, 5.5 min-6 min 5% ACN.

Example 76

Compound 76—5-(3,3-Dimethyl-but-1-ynyl)-3-{(trans-4-cyclohexanecarbonyl)-[4-(3-methyl-pyrrolidin-3-yloxycarbonylamino)-cyclohexyl]-amino}-thiophene-2-carboxylic acid

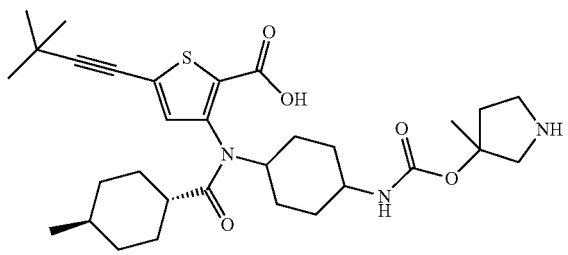

76

A mixture of 3-{4-[[2-Carboxy-5-(3,3-dimethyl-but-1-ynyl)-thiophen-3-yl]-(trans-4-methyl-cyclohexanecarbonyl)-cyclohexylcarbamoyloxy}-3-methyl-pyrrolidine-1-carboxylic acid tert-butyl ester TFA salt (50 mg) in CH$_2$Cl$_2$ (2.0 mL) and 4N HCl in dioxane (0.5 mL) was stirred at rt for 2 h. The reaction was determined to be complete by LC/MS. Solvents were removed under reduced pressure. 5-(3,3-Dimethyl-but-1-ynyl)-3-{(trans-4-cyclohexanecarbonyl)-[4-(3-methyl-pyrrolidin-3-yloxycarbonylamino)-cyclohexyl]-amino}-thiophene-2-carboxylic acid TFA salt (32 mg, 73%) was isolated by reverse phase HPLC as a white solid.

LC/MS=572.19 (M$^+$+1)

Retention time: 3.17/3.24 min

Gradient: 0 min-0.2 min 5% ACN, 0.2 min-3.95 min 5%-100% ACN, 3.95 min-5.20 min 100% ACN, 5.20 min-5.5 min 100%-5% ACN, 5.5 min-6 min 5% ACN.

Example 77

Compound 77—Synthesis of 5-(3,3-dimethyl-but-1-ynyl)-3-[[4-(1,1-dioxo-tetrahydro-1λ$^6$-thiophen-3-yloxycarbonylamino)-cyclohexyl]-(trans-4-methyl-cyclohexanecarbonyl)-amino]-thiophene-2-carboxylic acid

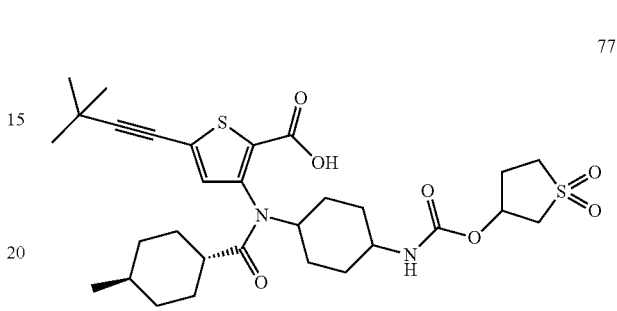

77

3-[4-Amino-cyclohexyl)-(trans-4-methyl-cyclohexanecarbonyl)-amino]-5-(3,3-dimethyl-but-1-ynyl)-thiophene-2-carboxylic acid (200 mg) was taken up in ACN (4.0 mL). The heterogeneous solution was allowed to stir for 5 min, then DIEA (500 µL, 4.6 mmol) and DMAP (cat) were added sequentially. The reaction was allowed to stir for 5 min then 3-chlorocarbonyloxy-1,1-dioxo-tetrahydro-1λ$^6$-thiophene (≈200 mg), which was prepared in a similar manner to method G, was added in one portion. The reaction was stirred at rt for 15 min and determined to be complete by LC/MS. Solvent was removed under reduced pressure. The reaction mixture was partitioned between EtOAc and 2N HCl$_{(aq)}$. The organics were dried over Na$_2$SO$_4$, solids filtered and solvent removed under reduced pressure. 5-(3,3-Dimethyl-but-1-ynyl)-3-[[4-(1,1-dioxo-tetrahydro-1λ$^6$-thiophen-3-yloxycarbonylamino)-cyclohexyl]-(trans-4-methylcyclohexanecarbonyl)-amino]-thiophene-2-carboxylic acid TFA salt (36 mg, 19%)

LC/MS=606.86 (M$^+$+1)

Retention time: 3.61 min

Gradient: 0 min-0.2 min 5% ACN, 0.2 min-3.95 min 5%-100% ACN, 3.95 min-5.20 min 100% ACN, 5.20 min-5.5 min 100%-5% ACN, 5.5 min-6 min 5% ACN.

Example 79

Compound 79—Synthesis of 5-(3,3-Dimethyl-but-1-ynyl)-3-{(4-methyl-cyclohexanecarbonyl)-[4-(N'-methyl-N'-pyridin-2-yl-hydrazino)-cyclohexyl]-amino}-thiophene-2-carboxylic acid

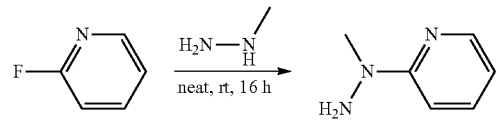

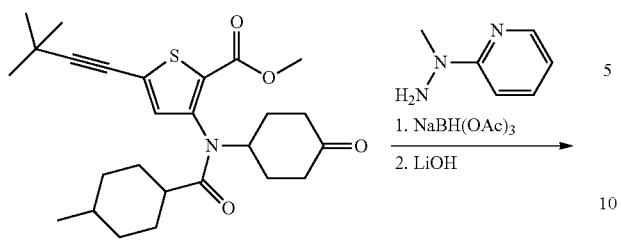

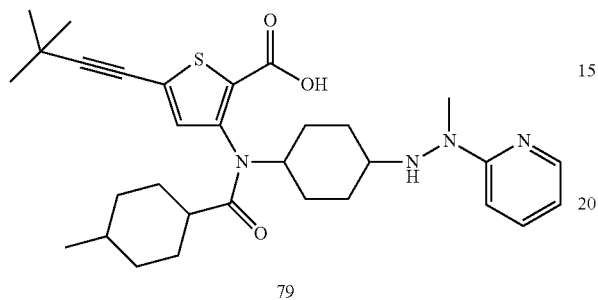

79

Example 80

Compound 80—Synthesis of 5-(3,3-Dimethyl-but-1-ynyl)-3-{(4-methyl-cyclohexanecarbonyl)-[4-(N'-methyl-N'-pyrazin-2-yl-hydrazino)-cyclohexyl]-amino}-thiophene-2-carboxylic acid

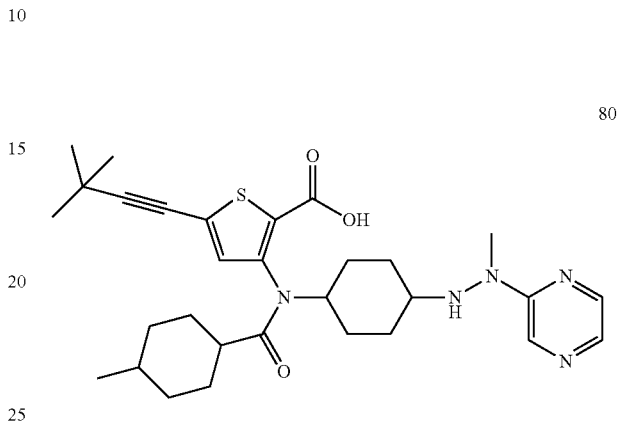

80

2-Bromopyridine (5 mL, 52.4 mmol) and methylhydrazine (20 mL, 360 mmol) were mixed together in a flask fitted with a water-condenser. After a few minutes a vigorous exothermic reaction occurred with refluxing of the methylhydrazine. When the reaction had subsided, the mixture was left for 16 hours, and the excess methylhydrazine was removed under reduced pressure. The cooled residue was stirred with aqueous sodium hydroxide solution (30 ml of 20%), and the resulting solution was extracted with ether (3×100 ml). The combined extracts were dried ($K_2CO_3$) and purified by silica gel chromatography 0-3% $EtOH/CH_2Cl_2$ to give 4.8 g of N-Methyl-N-pyridin-2-yl-hydrazine.

A mixture of 5-(3,3-Dimethyl-but-1-ynyl)-3-[(4-methyl-cyclohexanecarbonyl)-(4-oxo-cyclohexyl)-amino]-thiophene-2-carboxylic acid methyl ester (412 mg, 0.90 mmol) and N-Methyl-N-pyridin-2-yl-hydrazine (222 mg, 1.8 mmol) in DCE (6 mL) was treated with AcOH (200 μL, 3.0 mmol) followed by $NaBH(OAc)_3$ (300 mg, 4.08 mmol) in two or three portions. After 30 min, $NaHCO_3$ (saturated aqueous solution, 4-8 mL) was added to the mixture, followed by brine (20 mL), and the crude product was extracted with ethyl acetate (2×20 mL). The combined organic layers were concentrated and the crude material was dissolved in a 3:2:1 mixture of THF:MeOH:water (20 mL), treated with lithium hydroxide (4.5 mmol, 188 mg) and heated to 60 deg C. for 2 hours. The residue was purified by HPLC (Gemini column, 35% acetonitrile:water, 2 min, 35-50% acetonitrile:water, 2 min, 50-100% acetonitrile: water 13 min, both solvents containing 0.1% trifluoroacetic acid). This resulted in 189 mg (37% yield) of the title compound as its trans isomer (TFA salt): MS (m/z): 551.3 [M–H]$^+$; HPLC retention time: 3.39 min (2-98% acetonitrile:water with 0.05% trifluoroacetic acid) and 71 mg (14% yield) of the title compound as its cis isomer (TFA salt): MS (m/z): 551.3 [M–H]$^+$; HPLC retention time: 3.52 min (2-98% acetonitrile:water with 0.05% trifluoroacetic acid).

2-Chloropyrazine (1 g, 8.3 mmol) and methylhydrazine (1.31 mL, 25 mmol) were mixed together in a flask fitted with a water condenser. After a few minutes an exotherm was observed. After 16 h the excess methylhydrazine was removed under reduced pressure. The cooled residue was stirred with aqueous sodium hydroxide solution (20 ml of 20%), and the resulting solution was extracted with ether (6×100 ml). The combined extracts were dried ($K_2CO_3$) and concentrated to give a light orange solid 370 mg of N-Methyl-N-pyrazin-2-yl-hydrazine.

A mixture of 5-(3,3-Dimethyl-but-1-ynyl)-3-[(4-methyl-cyclohexanecarbonyl)-(4-oxo-cyclohexyl)-amino]-thiophene-2-carboxylic acid methyl ester (100 mg, 0.22 mmol) and N-Methyl-N-pyrazin-2-yl-hydrazine (41 mg, 0.33 mmol) in DCE (2 mL) was treated with AcOH (100 μL, 1.5 mmol) followed by $NaBH(OAc)_3$ (120 mg, 0.5 mmol) in two portions. After 5 h, $NaHCO_3$ (saturated aqueous solution, 2 mL) was added to the mixture, followed by brine (20 mL), and the crude product was extracted with ethyl acetate (2×20 mL). The combined organic layers were concentrated and the crude material was dissolved in a 3:2:1 mixture of THF:MeOH: water (20 mL), treated with lithium hydroxide (1.1 mmol, 46 mg) and heated to 60 deg C. for 1 hours. The residue was purified by HPLC (Gemini column, 35% acetonitrile:water, 2 min, 35-50% acetonitrile:water, 2 min, 50-100% acetonitrile: water 13 min, both solvents containing 0.1% trifluoroacetic acid). This resulted in 11 mg of the title compound as its trans isomer (TFA salt): MS (m/z): 552.2 [M–H]$^+$; HPLC retention time: 26.05 min (Phenomenex Luna C18, 2-98% acetonitrile: water with 0.1% trifluoroacetic acid, 30 min gradient) and 7 mg of the title compound as its cis isomer (TFA salt): MS (m/z): 552.2 [M–H]$^+$; HPLC retention time: 24.38 min (Phenomenex Luna C18, 2-98% acetonitrile:water with 0.1% trifluoroacetic acid, 30 min gradient).

Example 81

Compound 81—Synthesis of 5-(3,3-Dimethyl-but-1-ynyl)-3-{(4-methyl-cyclohexanecarbonyl)-[4-(N'-methyl-N'-thiazol-2-yl-hydrazino)-cyclohexyl]-amino}-thiophene-2-carboxylic acid

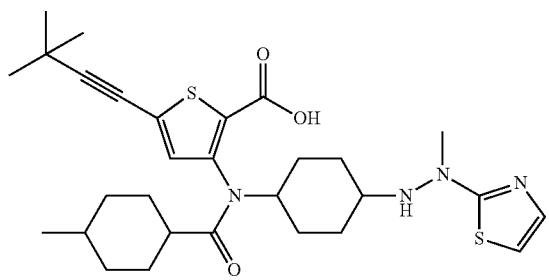

81

2-Chlorothiazole (0.9 g, 7.52 mmol) was placed in a flask fitted with a water condenser and methylhydrazine (1.31 mL, 25 mmol) was added dropwise. An immediate exotherm was observed and methylhydrazine began to reflux. When the reaction had subsided, the mixture was left for 16 hours, and the excess methylhydrazine was removed under reduced pressure. The cooled residue was stirred with aqueous sodium hydroxide solution (20 ml of 20%), and the resulting solution was extracted with ether (6×100 ml). The combined extracts were dried ($K_2CO_3$) and concentrated to give 485 mg of N-Methyl-N-thiazol-2-yl-hydrazine.

A mixture of 5-(3,3-Dimethyl-but-1-ynyl)-3-[(4-methyl-cyclohexanecarbonyl)-(4-oxo-cyclohexyl)-amino]-thiophene-2-carboxylic acid methyl ester (200 mg, 0.44 mmol) and N-Methyl-N-thiazol-2-yl-hydrazine (112 mg, 0.87 mmol) in DCE (4 mL) was treated with AcOH (200 µL, 3.0 mmol) followed by $NaBH(OAc)_3$ (120 mg, 0.57 mmol) in two portions. After 5 h, $NaHCO_3$ (saturated aqueous solution, 3 mL) was added to the mixture, followed by brine (20 mL), and the crude product was extracted with ethyl acetate (2×20 mL). The combined organic layers were concentrated and the crude material was dissolved in a 3:2:1 mixture of THF:MeOH:water (20 mL), treated with lithium hydroxide (2.2 mmol, 92 mg) and heated to 60 deg C. for 1 hours. The residue was purified by HPLC (Gemini column, 35% acetonitrile:water, 2 min, 35-50% acetonitrile:water, 2 min, 50-100% acetonitrile:water 13 min, both solvents containing 0.1% trifluoroacetic acid). This resulted in 36 mg of the title compound as its trans isomer (TFA salt): MS (m/z): 557.2 $[M-H]^+$; HPLC retention time: 3.43 min (2-98% acetonitrile:water with 0.05% trifluoroacetic acid) and 8 mg of the title compound as its cis isomer (TFA salt): MS (m/z): 557.2 $[M-H]^+$; HPLC retention time: 3.41 min (2-98% acetonitrile:water with 0.05% trifluoroacetic acid).

Example 82

Compound 82—Synthesis of 5-(3,3-Dimethyl-but-1-ynyl)-3-[{4-[N'-(6-hydroxy-pyridazin-3-yl)-N'-methyl-hydrazino]-cyclohexyl}-(4-methyl-cyclohexanecarbonyl)-amino]-thiophene-2-carboxylic acid

Example 83

Compound 83—[{4-[N'-(6-Chloro-pyridazin-3-yl)-N'-methyl-hydrazino]-cyclohexyl}-(4-methyl-cyclohexanecarbonyl)-amino]-5-(3,3-dimethyl-but-1-ynyl)-thiophene-2-carboxylic acid

82

83

3,6-Dichloro-pyridazine (1 g, 6/5 mmol) was placed in a flask fitted with a water condenser and methylhydrazine (1.31 mL, 25 mmol) was added dropwise. An immediate exotherm was observed and methylhydrazine begins to reflux. When the reaction had subsided, the mixture was left for 16 hours, and the excess methylhydrazine was removed under reduced pressure. The cooled residue was stirred with aqueous sodium hydroxide solution (20 ml of 20%), and the resulting solution was extracted with ether (6×100 ml). The combined extracts were dried ($K_2CO_3$) and concentrated to give 427 mg of N-(6-Chloro-pyridazin-3-yl)-N-methyl-hydrazine.

A mixture of 5-(3,3-Dimethyl-but-1-ynyl)-3-[(4-methyl-cyclohexanecarbonyl)-(4-oxo-cyclohexyl)-amino]-thiophene-2-carboxylic acid methyl ester (500 mg, 1.09 mmol) and N-(6-Chloro-pyridazin-3-yl)-N-methyl-hydrazine (260 mg, 1.64 mmol) in DCE (8 mL) was treated with AcOH (0.5 mL, 8.4 mmol) followed by $NaBH(OAc)_3$ (347 mg, 1.64 mmol) in two portions. After 5 h, $NaHCO_3$ (saturated aqueous solution, 10 mL) was added to the mixture, followed by brine (20 mL), and the crude product was extracted with ethyl acetate (2×50 mL). The combined organic layers were concentrated and the crude material was dissolved in 4 mL of acetic acid, treated with NaOAc (893 mg, 10.9 mmol) and heated in a sealed tube at 100 deg C. for 16 h. Upon cooling the mixture was diluted with ethyl acetate and neutralized with $NaHCO_3$ (saturated aqueous solution). The combined organic layers were concentrated and the crude material was dissolved in a 3:2:1 mixture of THF:MeOH:

water (20 mL), treated with lithium hydroxide (5.45 mmol, 228 mg) and heated to 60 deg C. for 1 hour.

The crude material was purified by HPLC (Gemini column, 35% acetonitrile:water, 2 min, 35-50% acetonitrile:water, 2 min, 50-100% acetonitrile: water 13 min, both solvents containing 0.1% trifluoroacetic acid). This resulted in 16 mg of 3-[{[4-[N'-(6-Chloro-pyridazin-3-yl)-N'-methyl-hydrazino]-cyclohexyl}-(4-methyl-cyclohexanecarbonyl)-amino]-5-(3,3-dimethyl-but-1-ynyl)-thiophene-2-carboxylic acid as the trans isomer (TFA salt): MS (m/z): 587.2 [M−H]$^+$; HPLC retention time: 26.39 min (Phenomenex Luna C18, 2-98% acetonitrile:water with 0.1% trifluoroacetic acid, 30 min gradient); 4 mg of 3-[{4-[N'-(6-Chloro-pyridazin-3-yl)-N'-methyl-hydrazino]-cyclohexyl}-(4-methyl-cyclohexanecarbonyl)-amino]-5-(3,3-dimethyl-but-1-ynyl)-thiophene-2-carboxylic acid as the cis isomer (TFA salt): MS (m/z): 587.2 [M−H]$^+$; HPLC retention time: 24.03 min (Phenomenex Luna C18, 2-98% acetonitrile:water with 0.1% trifluoroacetic acid, 30 min gradient); 44 mg of 5-(3,3-Dimethyl-but-1-ynyl)-3-[{4-[N'-(6-hydroxy-pyridazin-3-yl)-N'-methyl-hydrazino]-cyclohexyl}-(4-methyl-cyclohexanecarbonyl)-amino]-thiophene-2-carboxylic acid as its trans isomer (TFA salt): MS (m/z): 569.4 [M−H]$^+$; HPLC retention time: 26.15 min (Phenomenex Luna C18, 2-98% acetonitrile:water with 0.1% trifluoroacetic acid, 30 min gradient), and 71 mg of 5-(3,3-Dimethyl-but-1-ynyl)-3-[{4-[N'-(6-hydroxy-pyridazin-3-yl)-N'-methyl-hydrazino]-cyclohexyl}-(4-methyl-cyclohexanecarbonyl)-amino]-thiophene-2-carboxylic acid as its cis isomer (TFA salt): MS (m/z): 569.4 [M−H]$^+$; HPLC retention time: 24.67 min (Phenomenex Luna C18, 2-98% acetonitrile:water with 0.1% trifluoroacetic acid, 30 min gradient).

Hydroxylamine Synthesis

Hydroxylamine 1: Synthesis of O-pyridin-2-ylmethylhydroxylamine dihydrochloride

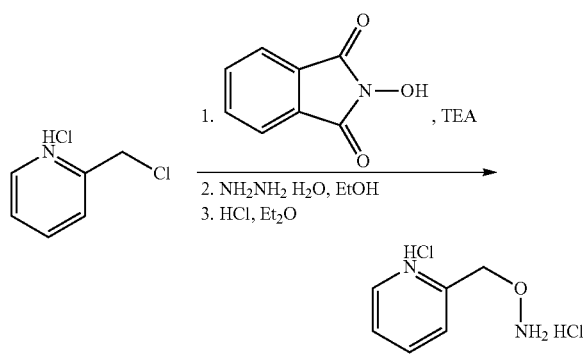

2-Chloromethylpyridine hydrochloride (514 mg, 3.13 mmol), N-hydroxyphthalimide (515 mg, 3.18 mmol), and triethylamine (1.3 mL, 9.3 mmol) were mixed in acetonitrile (5 mL) and stirred at 80° C. for 2.5 hours. The reaction mixture was diluted with ethyl acetate and washed sequentially with 1N NaOH$_{(aq)}$, water, and brine. The organic phase was dried over MgSO$_4$, filtered, and concentrated. The residue was recrystallized from ethyl acetate and hexanes to provide N-(pyridine-2-ylmethoxy)phthalimide (364 mg, 1.44 mmol).

Hydrazine monohydrate (53 μL, 1.5 mmol) was added to a solution of N-(pyridine-2-ylmethoxy)phthalimide (356 mg, 1.41 mmol) in ethanol (2 mL) and stirred at 80° C. for one hour in a sealed tube. The reaction mixture was diluted with ethyl acetate, adsorbed onto silica gel, and purified by SGC (0-20% [8:1 EtOH:NH$_4$OH$_{(aq)}$]/DCM). After concentration of fractions the residue was taken up in diethyl ether and treated with 4N HCl$_{(Et2O)}$ to provide O-pyridin-2-ylmethyl-hydroxylamine dihydrochloride (152 mg, 0.77 mmol) as a white solid.

Using the same procedure as described for O-pyridin-2-ylmethylhydroxylamine dihydrochloride, the hydroylamines shown below were synthesized.

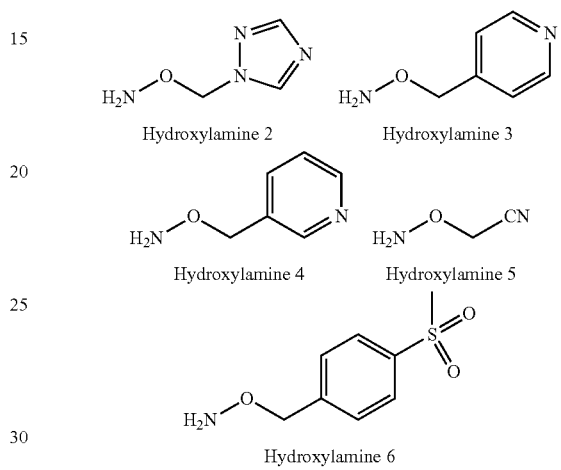

Example 112

Compound 112—Synthesis of 5-(3,3-Dimethyl-but-1-ynyl)-3-{(4-trans-methyl-cyclohexanecarbonyl)-[4-(pyridin-2-ylmethoxyimino)-cyclohexyl]-amino}-thiophene-2-carboxylic acid

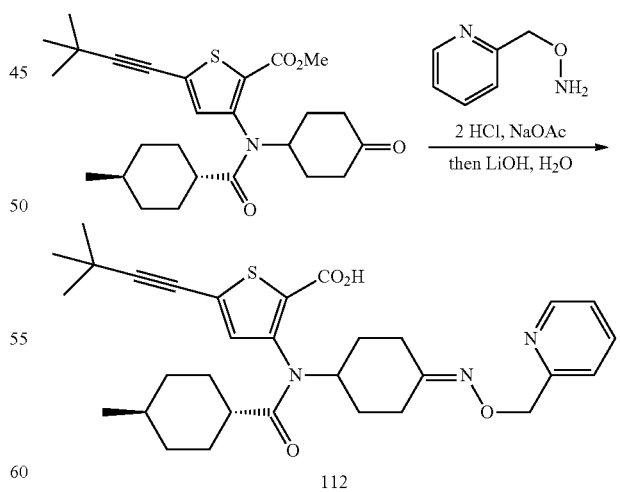

5-(3,3-dimethyl-but-1-ynyl)-3-[(trans-4-methyl-cyclohexanecarbonyl)-(4-oxo-cyclohexyl)-amino]-thiophene-2-carboxylic acid methyl ester (264 mg, 0.58 mmol), O-pyridin-2-ylmethylhydroxylamine dihydrochloride (142 mg, 0.72 mmol), and sodium acetate (177 mg, 2.2 mmol) were mixed in 2:1 MeOH:DCM (3 mL) and stirred at 50° C. for 1 hour. Lithium hydroxide monohydrate (240 mg, 5.7 mmol) and water (1 mL) were then added and the reaction mixture continued to stir at 50° C. for 2 hours. The reaction mixture was then partitioned between ethyl acetate and 5% citric acid$_{(aq)}$. The aqueous phase was neutralized with 4N NaOH$_{(aq)}$ and thrice extracted with ethyl acetate. The combined organic phases were washed with brine, dried over MgSO$_4$, filtered, and concentrated. The residue was purified by HPLC (Gemini column; 25% acetonitrile:water, 2 min; 25-100% acetonitrile:water, 16 min; 100% acetonitrile, 3 min; both solvents containing 0.1% trifluoroacetic acid). This resulted in 234 mg (19% yield over 2 steps) of the title compound as a white powder (TFA salt): MS (m/z): 550.2 [M+H]$^+$; HPLC retention time: 3.55 min (2-98% acetonitrile:water with 0.05% trifluoroacetic acid).

Example 113

Compound 113—3-(N-(4-Benzyloxyimino)cyclohexyl)-4-methylcyclohexanecarboxamido)-5-(3,3-dimethylbut-1-ynyl)thiophene-2-carboxylic acid

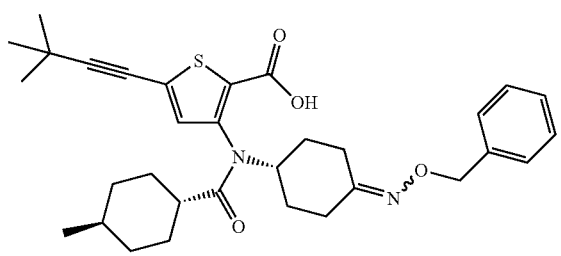

113

Prepared in the same manner as Example 112 using O-benzylhydroxylamine. MS (m/z): 549.1 [M+H]$^+$; HPLC retention time: 5.23 min.

Example 114

Compound 114—3-(N-(4-((1H-1,2,4-Triazol-1-yl)methoxyimino)cyclohexyl)-4-methylcyclohexanecarboxamido)-5-(3,3-dimethylbut-1-ynyl)thiophene-2-carboxylic acid

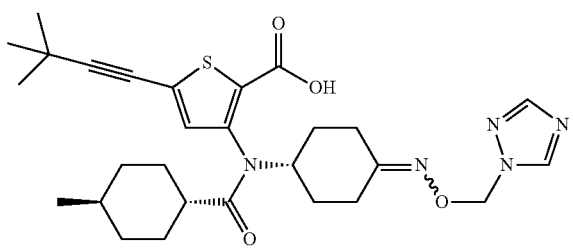

114

Prepared in the same manner as Example 112 using hydroxylamine 2. MS (m/z): 540.1 [M+H]$^+$; HPLC retention time: 4.29 min.

Example 115

Compound 115—3-(N-(4-(Carboxymethoxyimino)cyclohexyl)-4-methylcyclohexanecarboxamido)-5-(3,3-dimethylbut-1-ynyl)thiophene-2-carboxylic acid

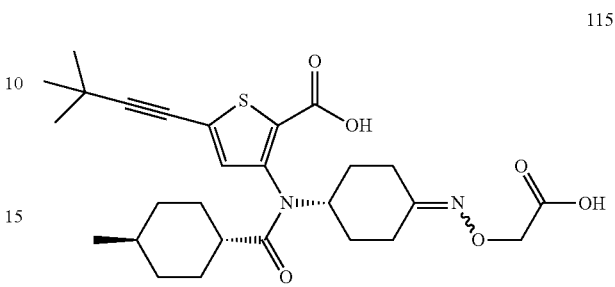

115

Prepared in the same manner as Example 112 using hydroxylamine 5. MS (m/z): 517.0 [M+H]$^+$; HPLC retention time: 4.28 min.

Example 116

Compound 116—3-(N-(4-(Cyanomethoxyimino)cyclohexyl)-4-methylcyclohexanecarboxamido)-5-(3,3-dimethylbut-1-ynyl)thiophene-2-carboxylic acid

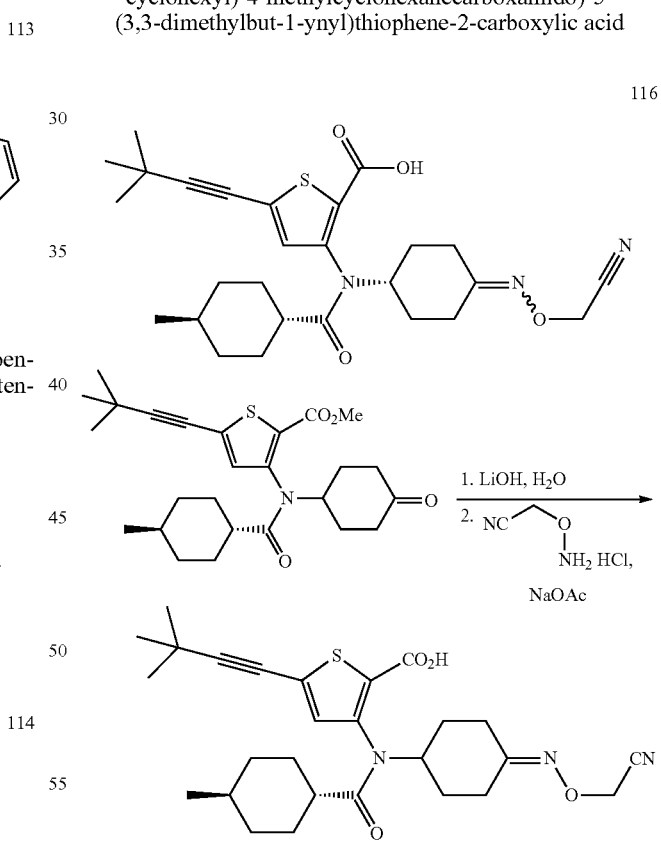

116

5-(3,3-Dimethyl-but-1-ynyl)-3-[(trans-4-methyl-cyclohexanecarbonyl)-(4-oxo-cyclohexyl)-amino]-thiophene-2-carboxylic acid methyl ester (519 mg, 1.13 mmol) was dissolved in a mixture of 3:2:1 THF:MeOH:H$_2$O (25 mL). Lithium hydroxide (5 mL, 1.0N aqueous solution) was added and the reaction mixture was stirred at 60° C. for 1 hour. The reaction mixture was then partitioned between ethyl acetate and water. The aqueous phase was neutralized with 5% citric acid$_{(aq)}$, and thrice extracted with ethyl acetate. The combined organic phases were washed with brine, dried over MgSO₄, filtered, and concentrated to afford 505 mg of 5-(3,3-dimethyl-but-1-ynyl)-3-[(trans-4-methyl-cyclohexanecarbonyl)-(4-oxo-cyclohexyl)-amino]-thiophene-2-carboxylic acid which was carried on without further purification.

5-(3,3-Dimethyl-but-1-ynyl)-3-[(trans-4-methyl-cyclohexanecarbonyl)-(4-oxo-cyclohexyl)-amino]-thiophene-2-carboxylic acid (505 mg, 1.02 mmol), O-cyanomethylhydroxylamine hydrochloride (174 mg, 1.32 mmol), and sodium acetate (212 mg, 2.6 mmol) were mixed in 2:1 MeOH:DCM (7.5 mL) and stirred at 50° C. for 1 hour. The reaction mixture was then partitioned between ethyl acetate and water. The aqueous phase was thrice extracted with ethyl acetate and the combined organic layers were washed with brine, dried over MgSO₄, filtered, and concentrated. The residue was purified by HPLC (Gemini column; 25% acetonitrile:water, 2 min; 25-100% acetonitrile:water, 16 min; 100% acetonitrile, 3 min; both solvents containing 0.1% trifluoroacetic acid). This resulted in 159 mg (28% yield over 2 steps) of the title compound as a white powder: MS (m/z): 495.7 [M−H]⁻; HPLC retention time: 4.68 min (2-98% acetonitrile:water with 0.05% trifluoroacetic acid).

Example 117

Compound 117—5-(3,3-Dimethylbut-1-ynyl)-3-(4-methyl-N-(4-(pyridin-4-ylmethoxyimino)cyclohexyl)cyclohexanecarboxamido)thiophene-2-carboxylic acid

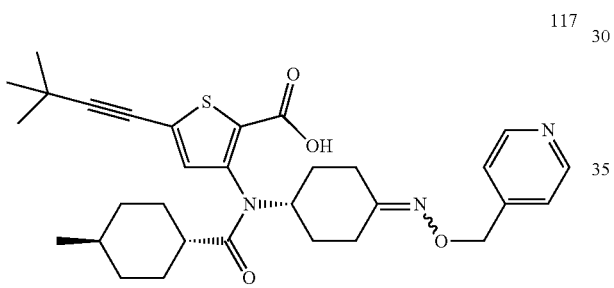

Prepared in the same manner as Example 112 using hydroxylamine 3. MS (m/z): 550.1 [M+H]⁺; HPLC retention time: 3.46 min.

Example 118

Compound 118—5-(3,3-Dimethylbut-1-ynyl)-3-(4-methyl-N-(4-(pyridin-3-ylmethoxyimino)cyclohexyl)cyclohexanecarboxamido)thiophene-2-carboxylic acid

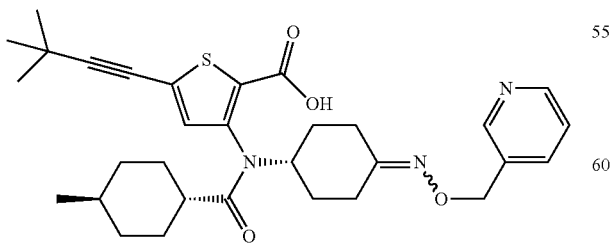

Prepared in the same manner as Example 112 using hydroxylamine 4. MS (m/z): 550.1 [M+H]⁺; HPLC retention time: 3.47 min.

Example 119

Compound 119—5-(3,3-Dimethylbut-1-ynyl)-3-(4-methyl-N-(4-(phenoxyimino)cyclohexyl)cyclohexanecarboxamido)thiophene-2-carboxylic acid

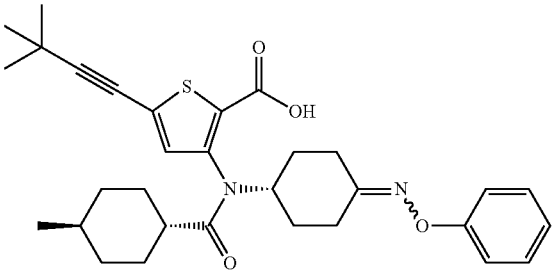

Prepared in the same manner as Example 112 using O-phenylhydroxylamine. MS (m/z): 535.0 [M+H]⁺; HPLC retention time: 5.38 min.

Example 120

Compound 120—5-(3,3-Dimethylbut-1-ynyl)-3-(N-(4-(methoxyimino)cyclohexyl)-4-methylcyclohexanecarboxamido)thiophene-2-carboxylic acid

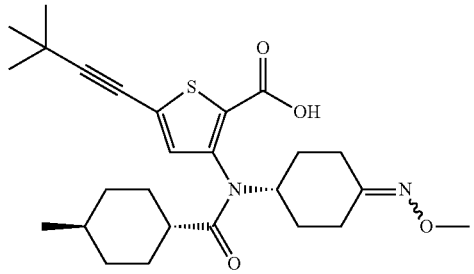

Prepared in the same manner as Example 112 using O-methylhydroxylamine. MS (m/z): 473.0 [M+H]⁺; HPLC retention time: 4.79 min.

Example 121

Compound 121—3-(N-(4-(4-(Methylsulfonyl)benzyloxyimino)cyclohexyl)-4-methylcyclohexanecarboxamido)-5-(3,3-dimethylbut-1-ynyl)thiophene-2-carboxylic acid

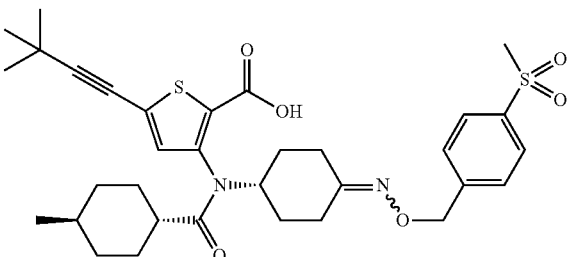

Prepared in the same manner as Example 112 using hydroxylamine 6. MS (m/z): 627.0 [M+H]⁺; HPLC retention time: 4.75 min.

Example 122

Compound 122—Synthesis of 5-(3,3-dimethyl-but-1-ynyl)-3-[(N'-(1,4-dioxa-spiro[4.5]dec-8-yl)-N'-methyl-N-(4-methyl-cyclohexanecarbonyl)-hydrazino]-thiophene-2-carboxylic acid

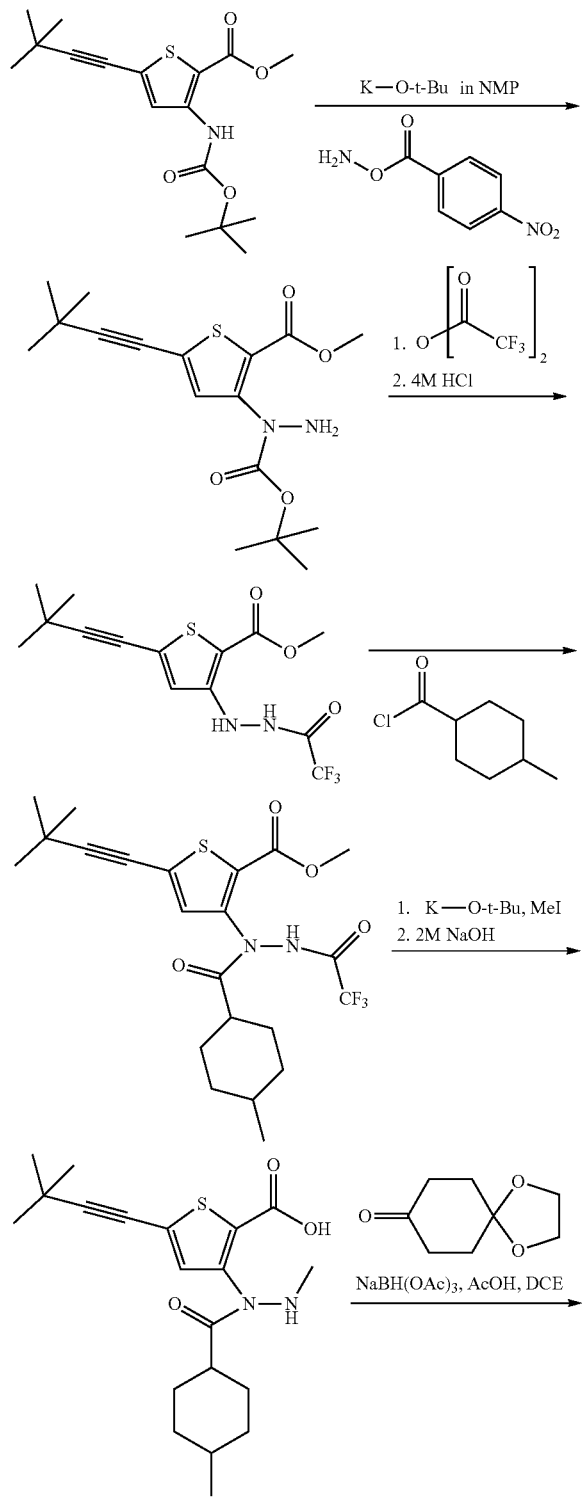

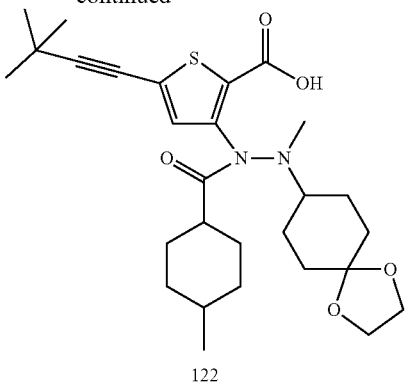

122

To a solution of 3-tert-butoxycarbonylamino-5-(3,3-dimethyl-but-1-ynyl)-thiophene-2-carboxylic acid methyl ester (4.3 g, 12.8 mmol) in NMP (64 mL) was added K-OtBu (1.6 g, 14.1 mmol). After 10 min a solution of O-4-nitrobenzoyl-hydroxylamine (3.0 g, 16.6 mmol) in NMP (16 mL) was added dropwise and the reaction was allowed to stir for 16 h. The reaction was quenched with LiCl solution (5% in water, 50 mL) and diluted with EtOAc (50 mL). The crude product was washed 3×50 mL with 5% LiCl solution, dried over $Na_2SO_4$, and purified by silica gel chromatography 0-30% EtOAc/hexanes to give 3-(N-tert-butoxycarbonyl-hydrazino)-5-(3,3-dimethyl-but-1-ynyl)-thiophene-2-carboxylic acid methyl ester (2.6 g, 7.4 mmol).

3-(N-tert-Butoxycarbonyl-hydrazino)-5-(3,3-dimethyl-but-1-ynyl)-thiophene-2-carboxylic acid methyl ester (2.6 g, 7.4 mmol) in $Et_2O$ (37 mL) was cooled to 0° C. and treated with trifluoroacetic anhydride (1.9 g, 8.9 mmol) for 1 h. The reaction was concentrated, dissolved with neat TFA (4.3 g, 37 mmol) and heated to 60° C. After 15 min, the reaction was cooled to rt, diluted with toluene (30 mL) and concentrated, this step was repeated three times, to give crystalline 5-(3,3-Dimethyl-but-1-ynyl)-3-[N'-(2,2,2-trifluoro-acetyl)-hydrazino]-thiophene-2-carboxylic acid methyl ester (2.1 g, 6.0 mmol).

A mixture of 5-(3,3-dimethyl-but-1-ynyl)-3-[N'-(2,2,2-trifluoro-acetyl)-hydrazino]-thiophene-2-carboxylic acid methyl ester (2.1 g, 6.0 mmol), 4-methyl-cyclohexanecarbonyl chloride (1.45 g, 9 mmol), DMAP (1.1 g, 9 mmol) and DCE (20 mL) was heated to 40° C. for 16 h. After cooling, the mixture was concentrated and the product was purified by silica gel chromatography 0-30% EtOAc/hexanes to give 5-(3,3-dimethyl-but-1-ynyl)-3-[N-(4-methyl-cyclohexanecarbonyl)-N'-(2,2,2-trifluoro-acetyl)-hydrazino]-thiophene-2-carboxylic acid methyl ester (2.74 g, 5.8 mmol).

To a solution of 5-(3,3-dimethyl-but-1-ynyl)-3-[N-(4-methyl-cyclohexanecarbonyl)-N'-(2,2,2-trifluoro-acetyl)-hydrazino]-thiophene-2-carboxylic acid methyl ester (1.6 g, 3.4 mmol) in THF (17 mL) was added K-OtBu (4.1 mmol, 1.0 M in THF), followed by MeI (1.0 g, 6.8 mmol). After stirring at rt for 16 h the reaction was diluted with EtOAc washed once with 20 mL of brine and purified by silica gel chromatography 0-20% EtOAc/hexanes to give 5-(3,3-dimethyl-but-1-ynyl)-3-[N'-methyl-N-(4-methyl-cyclohexanecarbonyl)-N'-(2,2,2-trifluoro-acetyl)-hydrazino]-thiophene-2-carboxylic acid methyl ester. This was then diluted with EtOAc (20 mL) and treated with NaOH (6.8 mL of 2M aq solution) to give 5-(3,3-Dimethyl-but-1-ynyl)-3-[N'-methyl-N-(4-methyl-cyclohexanecarbonyl)-hydrazino]-thiophene-2-carboxylic acid.

A mixture of 5-(3,3-Dimethyl-but-1-ynyl)-3-[N'-methyl-N-(4-methyl-cyclohexanecarbonyl)-hydrazino]-thiophene-2-carboxylic acid (300 mg, 0.8 mmol), 1,4-cyclohexadione-mono-ethylene ketal (149 mg, 1 mmol), AcOH (300 mg, 5 mmol) in DCE (2 mL) was treated with $NaBH(OAc)_3$ (430 mg, 2 mmol) for 16 h. The reaction was quenched with water (10 mL) and extracted with EtOAc. A portion of this material was then purified by HPLC (Gemini column, 35% acetonitrile:water, 2 min, 35-50% acetonitrile:water, 2 min, 50-100% acetonitrile: water 13 min, both solvents containing 0.1% trifluoroacetic acid) giving 5-(3,3-dimethyl-but-1-ynyl)-3-[N'-(1,4-dioxa-spiro[4.5]dec-8-yl)-N'-methyl-N-(4-methyl-cyclohexanecarbonyl)-hydrazino]-thiophene-2-carboxylic acid as its TFA salt: MS (m/z): 517.1 [M–H]+; HPLC retention time: 4.73 min (2-98% acetonitrile:water with 0.05% trifluoroacetic acid).

Example 123 (Compound 123) and 124 (Compound 124)

Synthesis of 3-(2-(4-hydroxycyclohexyl)-2-methyl-1-(4-methylcyclohexanecarbonyl)hydrazinyl)-5-(3,3-dimethylbut-1-ynyl)thiophene-2-carboxylic acid (123) and 3-(2-(4-hydroxycyclohexyl)-2-methyl-1-(4-methylcyclohexanecarbonyl)hydrazinyl)-5-(3,3-dimethylbut-1-ynyl)thiophene-2-carboxylic acid (124)

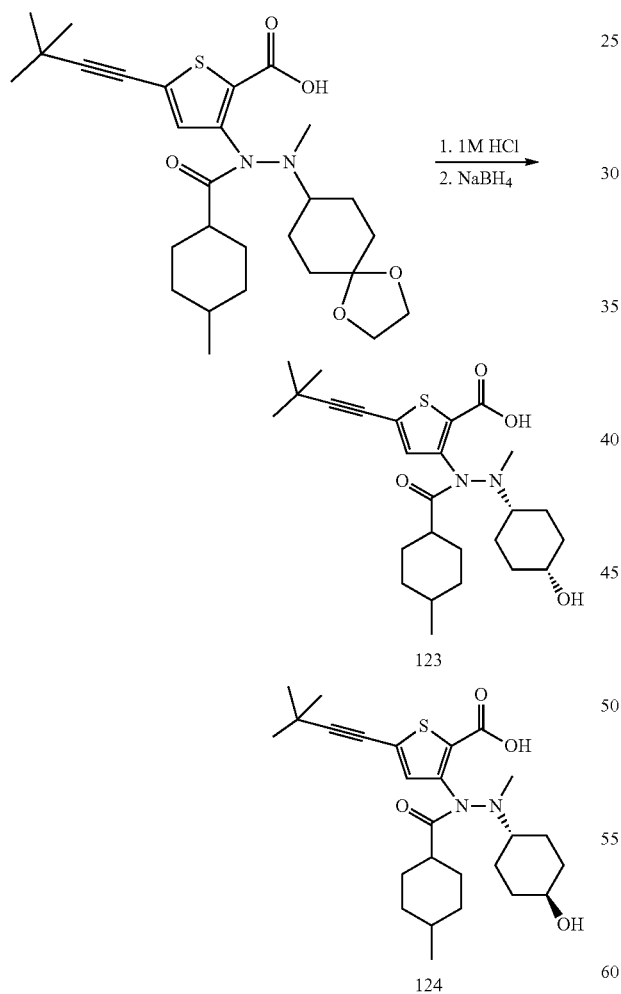

A mixture of 5-(3,3-dimethyl-but-1-ynyl)-3-[N'-(1,4-dioxa-spiro[4.5]dec-8-yl)-N'-methyl-N-(4-methyl-cyclohexanecarbonyl)-hydrazino]-thiophene-2-carboxylic (500 mg, 1 mmol) in a 1:1 mixture of THF and MeOH (2.5 mL) was treated with 1 M HCl (2.5 mL) and heated for 3 h at 60° C. The reaction mixture was cooled to room temperature, diluted with EtOAc (10 mL), neutralized with sat. NaHCO₃, washed once with brine (10 mL), dried over Na₂SO₄, and concentrated. The crude material was dissolved in wet THF (5 mL) and treated with NaBH₄ (38 mg, 1.1 mmol) at 0° C. for 30 min. A portion of 5-(3,3-dimethyl-but-1-ynyl)-3-[N'-(4-hydroxy-cyclohexyl)-N'-methyl-N-(4-methyl-cyclohexanecarbonyl)-hydrazino]-thiophene-2-carboxylic acid was purified by HPLC (Gemini column, 35% acetonitrile:water, 2 min, 35-50% acetonitrile:water, 2 min, 50-100% acetonitrile: water 13 min, both solvents containing 0.1% trifluoroacetic acid) to give 20 mg as its TFA salt: MS (m/z): 475.7 [M–H]+; HPLC retention time: 4.33 min (2-98% acetonitrile:water with 0.05% trifluoroacetic acid).

Additional HPLC purification separated Example 123 (retention time: 27.89 min) from Example 124 (retention time 27.89).

Example 125 and 126

Synthesis of 5-(3,3-dimethylbut-1-ynyl)-3-(2-methyl-1-(4-methylcyclohexanecarbonyl)-2-(4-(pyridin-3-yloxy)cyclohexyl)hydrazinyl)thiophene-2-carboxylic acid (Compound 125) and 5-(3,3-dimethylbut-1-ynyl)-3-(2-methyl-1-(4-methylcyclohexanecarbonyl)-2-(4-(pyridin-3-yloxy)cyclohexyl)hydrazinyl)thiophene-2-carboxylic acid (Compound 126)

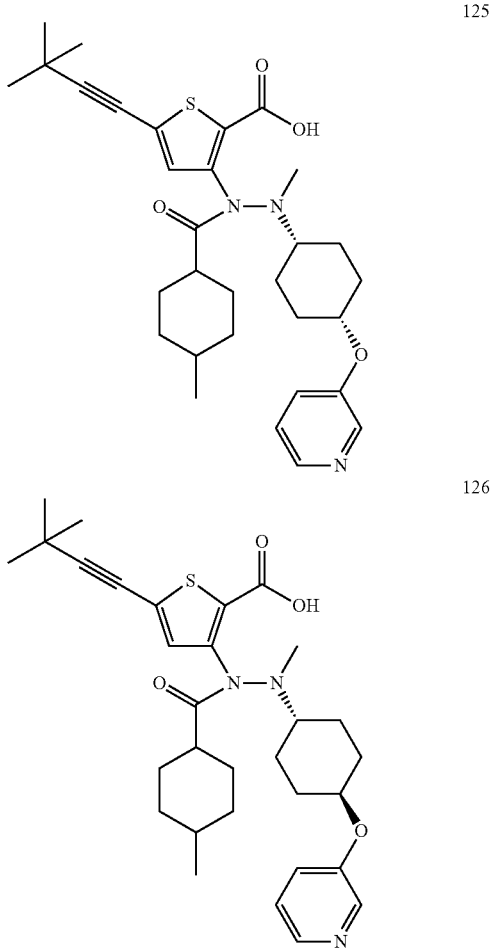

A mixture of 5-(3,3-dimethyl-but-1-ynyl)-3-[N'-(4-hydroxy-cyclohexyl)-N'-methyl-N-(4-methyl-cyclohexanecarbonyl)-hydrazino]-thiophene-2-carboxylic acid (100 mg, 0.2 mmol) and 3-fluoro-pyridine (97 µL, 1 mmol) in DMF (0.6 mL) was treated with sodium hydride (40 mg, 1 mmol, 60% oil dispersion) in two or three portions. The mixture was stirred until the bubbling slowed, and was sealed and heated at 100 deg C. for 8 h. After cooling, ethyl acetate (2-3 mL) was added and the mixture was carefully quenched with citric acid (10% aqueous solution, 2-3 mL). Water was added and the mixture was extracted with ethyl acetate (2×30 mL). The combined organic layers were dried over sodium sulfate, filtered and concentrated. The residue was purified by HPLC (Gemini column, 35% acetonitrile:water, 2 min, 35-50% acetonitrile:water, 2 min, 50-95% acetonitrile: water 13 min, both solvents containing 0.1% trifluoroacetic acid). This resulted in 37 mg of the title compound as a white powder (bis-TFA salt): MS (m/z): 552.1 [M−H]$^+$; HPLC retention time: 3.50 min (2-98% acetonitrile:water with 0.05% trifluoroacetic acid).

Additional HPLC purification separated Example 125 (retention time: 22.46 min) from Example 126 (retention time 22.62).

Example 127

Compound 127—Synthesis of 4-[(N'-[2-carboxy-5-(3,3-dimethyl-but-1-ynyl)-thiophen-3-yl]-N-methyl-N'-(4-methyl-cyclohexanecarbonyl)-hydrazino]-piperidine-1-carboxylic acid tert-butyl ester

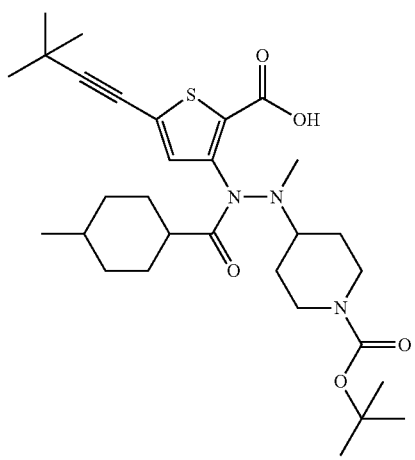

127

The title compound was synthesized in a manner analogous to Example 122, using 1-N-Boc-4-piperidone in place of 1,4-cyclohexadione-mono-ethylene ketal: MS (m/z): 560.1 [M−H]$^+$; HPLC retention time: 5.10 min (2-98% acetonitrile: water with 0.05% trifluoroacetic acid).

Example 128

Compound 128—Synthesis of 5-(3,3-dimethyl-but-1-ynyl)-3-[N'-methyl-N-(4-methyl-cyclohexanecarbonyl)-N'-piperidin-4-yl-hydrazino]-thiophene-2-carboxylic acid

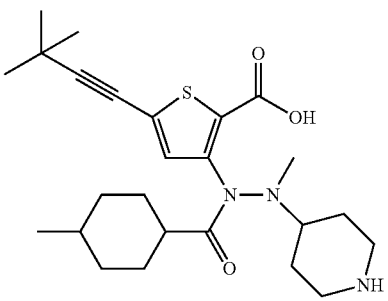

128

Crude 4-[N'-[2-carboxy-5-(3,3-dimethyl-but-1-ynyl)-thiophen-3-yl]-N-methyl-N'-(4-methyl-cyclohexanecarbonyl)-hydrazino]-piperidine-1-carboxylic acid tert-butyl ester (220 mg, 500 mmol) (Example 127) was treated with TFA (3 mL, 4.6 mmol) at 60° C. for 10 min. After cooling, toluene (2-3 mL) was added and the mixture was concentrated, this was repeated several times, and a portion of this crude material was purified by HPLC (Gemini column, 35% acetonitrile: water, 2 min, 35-50% acetonitrile:water, 2 min, 50-95% acetonitrile: water 13 min, both solvents containing 0.1% trifluoroacetic acid). This resulted in 20 mg of the title compound as a white powder (bis-TFA salt): MS (m/z): 460.2 [M−H]$^+$; HPLC retention time: 3.15 min (2-98% acetonitrile: water with 0.05% trifluoroacetic acid).

Example 129

Compound 129—Synthesis of 5-(3,3-dimethyl-but-1-ynyl)-3-[N'-methyl-N-(4-methyl-cyclohexanecarbonyl)-N'-(1-methyl-piperidin-4-yl)-hydrazino]-thiophene-2-carboxylic acid

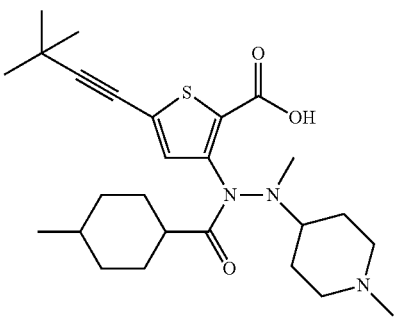

129

A mixture of 5-(3,3-dimethyl-but-1-ynyl)-3-[N'-methyl-N-(4-methyl-cyclo-hexanecarbonyl)-N'-piperidin-4-yl-hydrazino]-thiophene-2-carboxylic acid (100 mg, 225 mmol) (Example 128), formaldehyde (1.12 mmol), acetic acid (0.5 mL, 8 mmol) in DCE (3 mL) was treated with NaBH(OAc)$_3$ (36 mg, 168 mmol) for 16 h. The reaction was quenched with water (10 mL) and extracted with EtOAc. The crude material was then purified by HPLC (Gemini column, 35% acetonitrile:water, 2 min, 35-50% acetonitrile:water, 2 min, 50-100% acetonitrile: water 13 min, both solvents containing 0.1% trifluoroacetic acid) giving 5-(3,3-dimethyl-but-1-ynyl)-3-[N'-methyl-N-(4-methyl-cyclohexanecarbonyl)-N'-(1-methyl-piperidin-4-yl)-hydrazino]-thiophene-2-carboxylic acid as its bis-TFA salt: MS (m/z): 474.2 [M−H]$^+$; HPLC retention time: 3.17 min (2-98% acetonitrile:water with 0.05% trifluoroacetic acid).

Example 130

Compound 130—Synthesis of 5-(3,3-dimethyl-but-1-ynyl)-3-{N'-methyl-N-(4-methyl-cyclohexanecarbonyl)-N'-[2-(pyridin-3-yloxy)-ethyl]-hydrazino}-thiophene-2-carboxylic acid

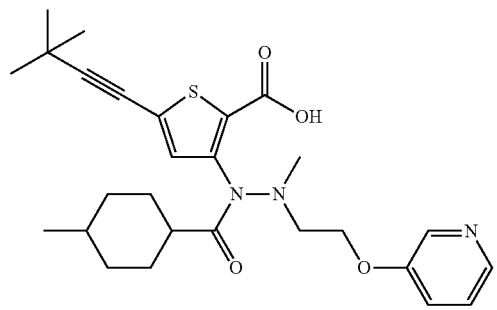

130

The title compound was synthesized in a manner analogous to Example 122, using (pyridin-3-yloxy)-acetaldehyde in place of 1,4-cyclohexadione-mono-ethylene ketal: MS (m/z): 498.1 [M−H]$^+$; HPLC retention time: 3.31 min (2-98% acetonitrile:water with 0.05% trifluoroacetic acid).

Example 131

Compound 131—Synthesis of 5-(3,3-dimethyl-but-1-ynyl)-3-[N'-methyl-N-(4-methyl-cyclohexanecarbonyl)-N'-(tetrahydro-pyran-4-ylmethyl)-hydrazino]-thiophene-2-carboxylic acid

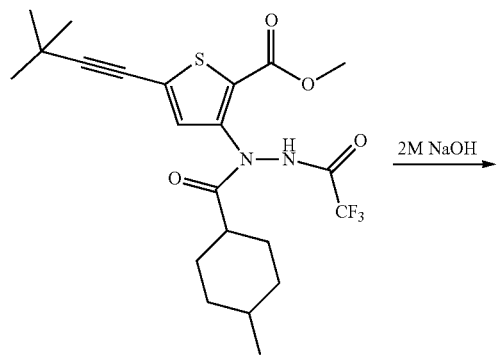

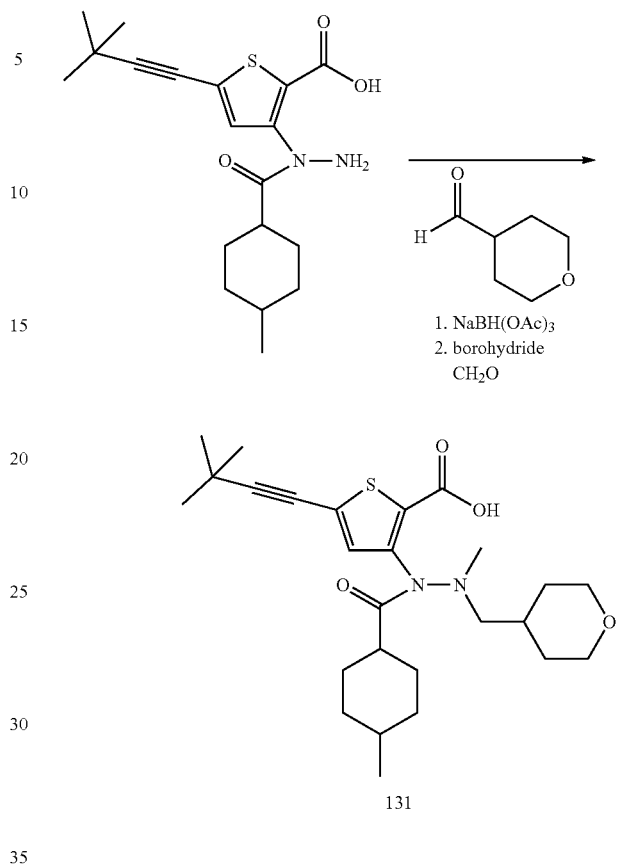

131

To a solution of 5-(3,3-dimethyl-but-1-ynyl)-3-[N-(4-methyl-cyclohexanecarbonyl)-N'-(2,2,2-trifluoro-acetyl)-hydrazino]-thiophene-2-carboxylic acid methyl ester (1.6 g, 3.4 mmol) in EtOAc (20 mL) was added NaOH (6.8 mL of 2M aq solution). After 2 h stirring at rt, the reaction was neutralized with 1M HCl aq, extracted with EtOAc, dried over Na$_2$SO$_4$, and concentrated to give 5-(3,3-dimethyl-but-1-ynyl)-3-[N-(4-methyl-cyclohexanecarbonyl)-hydrazino]-thiophene-2-carboxylic acid (1.1 g, 3 mmol) as an off white solid.

A mixture of 5-(3,3-dimethyl-but-1-ynyl)-3-[N-(4-methyl-cyclohexanecarbonyl)-hydrazino]-thiophene-2-carboxylic acid (50 mg, 0.132 mmol), tetrahydro-pyran-4-carbaldehyde (19 mg, 0.172 mmol), AcOH (24 mg, 0.4 mmol) in DCE (2 mL) was treated with NaBH(OAc)$_3$ (42 mg, 0.2 mmol) for 16 h. The reaction was quenched with water (10 mL), extracted with EtOAc and concentrated. A mixture of the crude material, AcOH (47 mg, 2.37 mmol), dissolved in iPrOH (3 mL) was treated with NaCNBH$_3$ (13 mg, 0.198 mmol) then heated to 50° C. for 16 h. The product was then purified by HPLC (Gemini column, 35% acetonitrile:water, 2 min, 35-50% acetonitrile:water, 2 min, 50-100% acetonitrile: water 13 min, both solvents containing 0.1% trifluoroacetic acid) giving 5-(3,3-dimethyl-but-1-ynyl)-3-[N'-methyl-N-(4-methyl-cyclohexanecarbonyl)-N'-(tetrahydro-pyran-4-ylmethyl)-hydrazino]-thiophene-2-carboxylic acid as its TFA salt: MS (m/z): 475.1 [M−H]$^+$; HPLC retention time: 4.62 min (2-98% acetonitrile:water with 0.05% trifluoroacetic acid).

Example 132

Compound 132—Synthesis of 5-(3,3-dimethyl-but-1-ynyl)-3-{N'-methyl-N-(4-methyl-cyclohexanecarbonyl)-N'-[2-(pyridin-2-yloxy)-ethyl]-hydrazino}-thiophene-2-carboxylic acid

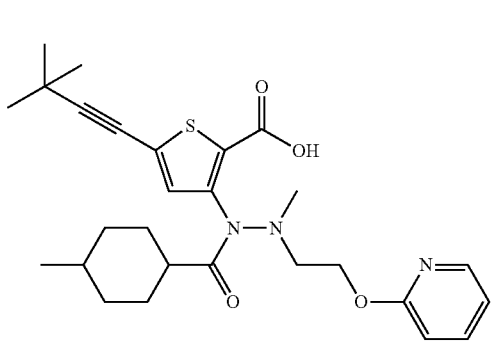

The title compound was synthesized in a manner analogous to Example 131, using (pyridin-2-yloxy)-acetaldehyde in place of tetrahydro-pyran-4-carbaldehyde: MS (m/z): 498.1 [M−H]$^+$; HPLC retention time: 29.8 min (2-98% acetonitrile:water with 0.05% trifluoroacetic acid) 30 min run.

Example 133

Compound 133—Synthesis of 5-(3,3-dimethyl-but-1-ynyl)-3-{N-(4-methyl-cyclohexanecarbonyl)-N'-[2-(pyridin-3-yloxy)-ethyl]-hydrazino}-thiophene-2-carboxylic acid

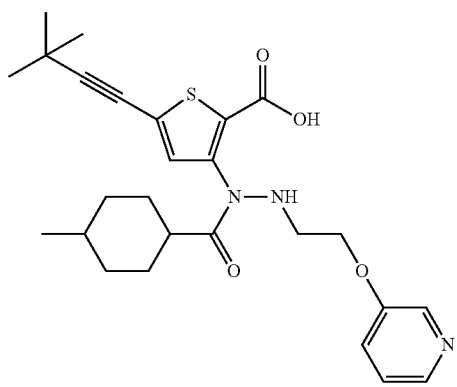

The title compound was synthesized from 5-(3,3-dimethyl-but-1-ynyl)-3-[N-(4-methyl-cyclohexanecarbonyl)-hydrazino]-thiophene-2-carboxylic acid and (pyridin-3-yloxy)-acetaldehyde in a manner similar to that of Example 131. MS (m/z): 484.0 [M−H]$^+$; HPLC retention time: 3.44 min (2-98% acetonitrile:water with 0.05% trifluoroacetic acid).

Example 134

Compound 134—Synthesis of 5-(3,3-dimethyl-but-1-ynyl)-3-[N'-(2-hydroxy-ethyl)-N-(4-methyl-cyclohexanecarbonyl)-N'-oxetan-3-yl-hydrazino]-thiophene-2-carboxylic acid

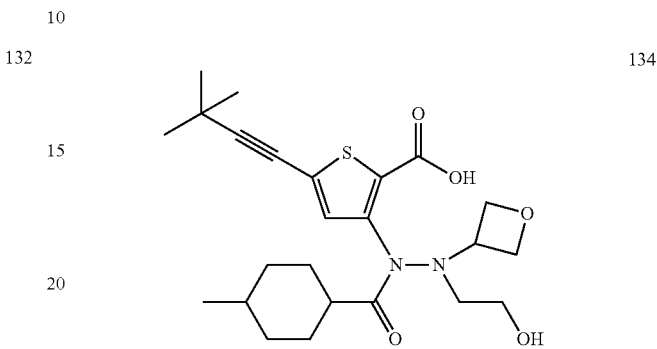

The title compound was synthesized in a manner analogous to Example 131, using 3-(tert-butyl-dimethyl-silanyloxy)-acetaldehyde in place of tetrahydro-pyran-4-carbaldehyde, treating the crude with TBAF (1 mmol, 0.1 M in THF) prior to the second reductive amination in which formaldehyde is replaced with oxetan-3-one: MS (m/z): 461.2 [M−H]$^-$; HPLC retention time: 4.38 min (2-98% acetonitrile:water with 0.05% trifluoroacetic acid).

Example 135

Compound 135—Synthesis of 5-(3,3-dimethyl-but-1-ynyl)-3-[N'-(2-hydroxy-ethyl)-N'-methyl-N-(4-methyl-cyclohexanecarbonyl)-hydrazino]-thiophene-2-carboxylic acid

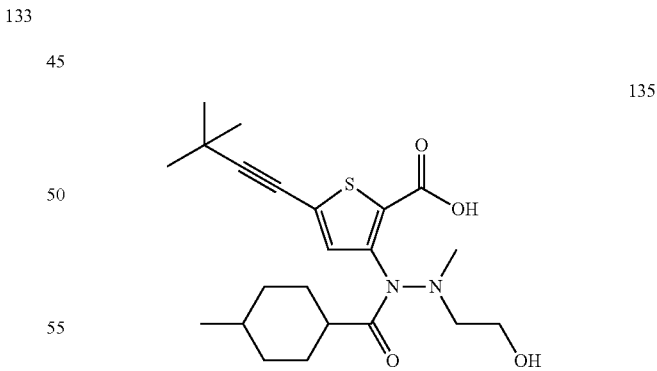

The title compound was synthesized in a manner analogous to Example 131, using 3-(tert-butyl-dimethyl-silanyloxy)-acetaldehyde in place of tetrahydro-pyran-4-carbaldehyde and treating the crude with TBAF (1 mmol, 0.1 M in THF) prior to the second reductive amination with formaldehyde: MS (m/z): 422.1 [M−H]$^+$; HPLC retention time: 4.06 min (2-98% acetonitrile:water with 0.05% trifluoroacetic acid).

Example 136

Compound 136—Synthesis of 5-(3,3-dimethyl-but-1-ynyl)-3-[N'-dimethyl-N-(4-methyl-cyclohexanecarbonyl)-hydrazino]-thiophene-2-carboxylic acid

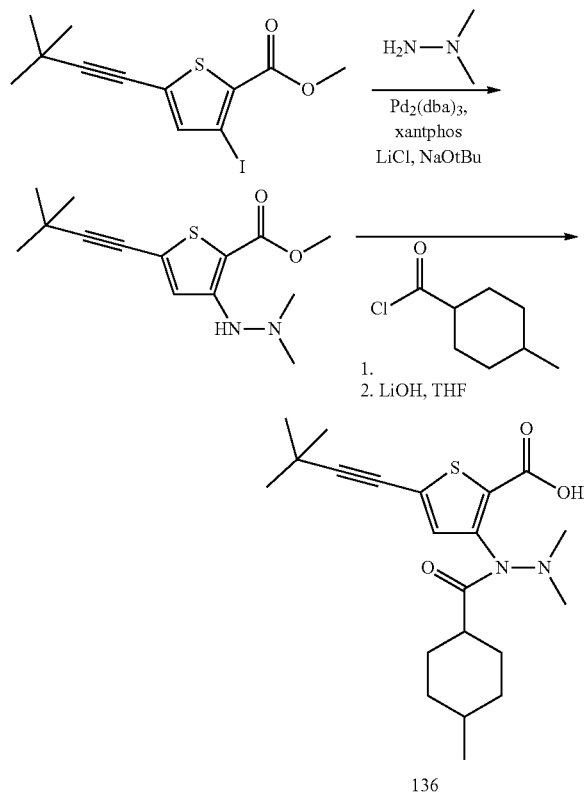

A mixture of 5-(3,3-dimethyl-but-1-ynyl)-3-iodo-thiophene-2-carboxylic acid methyl ester (0.200 g, 0.574 mmol), LiCl (0.048, 1.14 mmol), N,N-dimethylhydrazine (0.043 mL, 0.57 mmol), Pd$_2$(dba)$_3$ (0.003 g, 0.005 mmol), xantphos (0.008 g, 0.005 mmol), and NaOtBu (0.037 g, 0.394 mmol) in toluene (3 mL) was heated to 80° C. for 16 h. The reaction was diluted with ethyl acetate filtered through a Celite pad and concentrated the crude material was purified by silica gel chromatography (0-15% EtOAc/hexane) to give 5-(3,3-dimethyl-but-1-ynyl)-3-(N'-dimethyl-hydrazino)-thiophene-2-carboxylic acid methyl ester in 63% yield. This was then dissolved in pyridine (5 mL) and treated with neat trans-4-methyl-cyclohexanecarbonyl chloride (0.132 g, 0.825 mmol). The reaction was heated for 16 h at 85° C. and quenched with saturated ammonium chloride solution. The reaction mixture was diluted with EtOAc, washed with water, brine, dried over sodium sulfate, filtered and concentrated. The crude material was then dissolved in a 3:2:1 mixture of THF:MeOH:water (5 mL), treated with lithium hydroxide monohydrate (0.69 g, 1.65 mmol) and heated to 60° C. for 1 hour. The organic volatiles were evaporated under reduced pressure and the crude material was purified by HPLC to afford the title compound. MS (m/z): 456.0 [M+H]$^-$; HPLC retention time: 3.91 min (2-98% acetonitrile:water with 0.05% trifluoroacetic acid).

Example 137

Compound 137—Synthesis of 5-(3,3-dimethyl-but-1-ynyl)-3-[N'-methyl-N-(4-methyl-cyclohexanecarbonyl)-N'-pyridin-2-yl-hydrazino]-thiophene-2-carboxylic acid

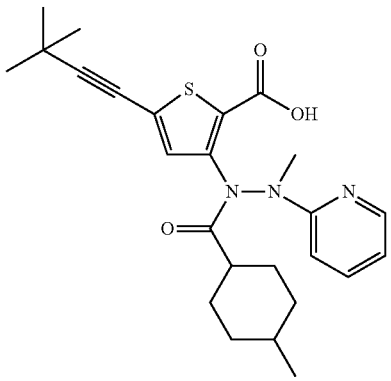

A mixture of 5-(3,3-dimethyl-but-1-ynyl)-3-iodo-thiophene-2-carboxylic acid methyl ester (0.100 g, 0.28 mmol), N,N-diethylenediamine (9 μL, 0.086 mmol), N-methyl-N-pyridin-2-yl-hydrazine (0.105 g, 0.86 mmol), CuI (0.01 g, 0.057 mmol), 4 Å ms (0.114 mg) and K$_2$CO$_3$ (0.118 g, 0.861 mmol) in DMF (3 mL) was heated to 80° C. for 16 h. The reaction was diluted with ethyl acetate, washed twice with 5% LiCl, concentrated and the crude material was purified by silica gel chromatography (0-20% EtOH in DCM) to give 5-(3,3-dimethyl-but-1-ynyl)-3-(N'-methyl-N'-pyridin-2-yl-hydrazino)-thiophene-2-carboxylic acid methyl ester in 50% yield. This was then dissolved in pyridine (5 mL) and treated with neat trans-4-methyl-cyclohexanecarbonyl chloride (0.132 g, 0.825 mmol). The reaction was heated for 16 h at 85° C. and quenched with saturated ammonium chloride solution. The reaction mixture was diluted with EtOAc, washed with water, brine, dried over sodium sulfate, filtered and concentrated. The crude material was then dissolved in a 3:2:1 mixture of THF:MeOH:water (5 mL), treated with lithium hydroxide monohydrate (0.69 g, 1.65 mmol) and heated to 60° C. for 1 hour. The organic volatiles were evaporated under reduced pressure and the crude material was purified by HPLC to afford the title compound. MS (m/z): 454.1 [M+H]$^-$; HPLC retention time: 3.95 min (2-98% acetonitrile:water with 0.05% trifluoroacetic acid).

Example 140

Compound 140—Synthesis of 5-(3,3-dimethyl-but-1-ynyl)-3-{(4-methyl-cyclohexanecarbonyl)-[1-(pyridine-3-carbonyl)-piperidin-4-yl]-amino}-thiophene-2-carboxylic acid

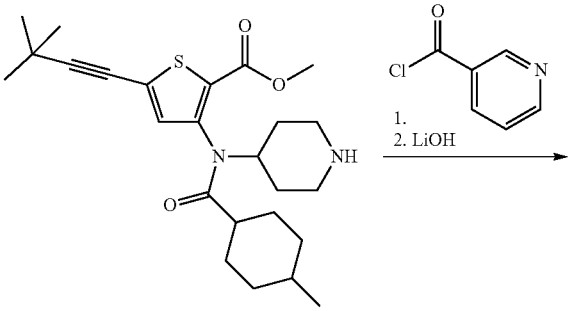

-continued

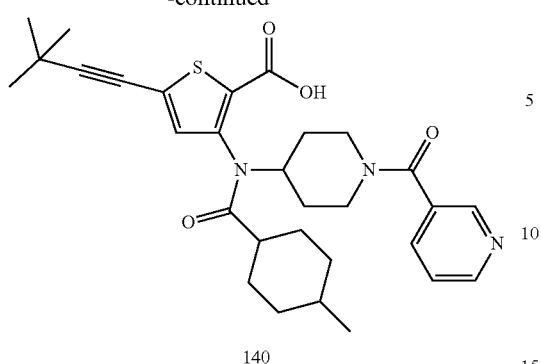

140

A mixture of 5-(3,3-Dimethyl-but-1-ynyl)-3-[(4-methyl-cyclohexanecarbonyl)-piperidin-4-yl-amino]-thiophene-2-carboxylic acid methyl ester (63 mg, 0.141 mmol) and pyridine-2-carbonyl chloride HCl salt (33 mg, 0.184 mmol) in DCM (2 mL) was treated with DIEA (124 μL, 0.7 mmol). After 30 min, NaHCO₃ (saturated aqueous solution, 4-8 mL) was added to the mixture, followed by brine (20 mL), and the crude product was extracted with ethyl acetate (2×20 mL). The combined organic layers were concentrated and the crude material was dissolved in a 3:2:1 mixture of THF:MeOH:water (5 mL), treated with lithium hydroxide (42 mg, 1 mmol,) and heated to 60 deg C. for 2 hours. The residue was purified by HPLC (Gemini column, 35% acetonitrile:water, 2 min, 35-50% acetonitrile:water, 2 min, 50-100% acetonitrile:water 13 min, both solvents containing 0.1% trifluoroacetic acid). This resulted in 40 mg of the title compound as its TFA salt: MS (m/z): 536.9 [M–H]⁺; HPLC retention time: 4.17 min (2-98% acetonitrile:water with 0.05% trifluoroacetic acid).

Example 141

Compound 141—Synthesis of 5-(3,3-dimethyl-but-1-ynyl)-3-{(4-methyl-cyclohexanecarbonyl)-[1-(pyrazine-2-carbonyl)-piperidin-4-yl]-amino}-thiophene-2-carboxylic acid

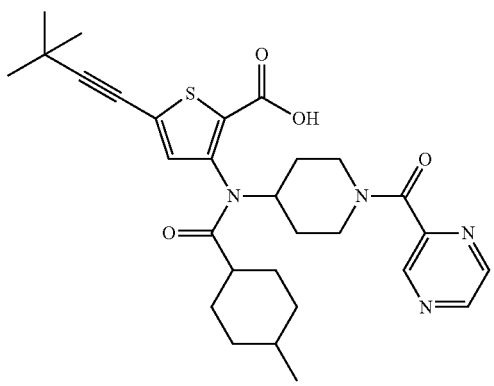

141

The title compound was synthesized in a manner analogous to Example 140, using pyrazine-2-carbonyl chloride in place of pyridine-2-carbonyl chloride HCl salt: MS (m/z): 538.0 [M–H]⁺; HPLC retention time: 3.52 min (2-98% acetonitrile:water with 0.05% trifluoroacetic acid) 30 min run.

Example 142

Compound 142—Synthesis of 5-(3,3-Dimethyl-but-1-ynyl)-3-{(4-methyl-cyclohexanecarbonyl)-[1-(pyridine-3-carbonyl)-pyrrolidin-3-yl]-amino}-thiophene-2-carboxylic acid

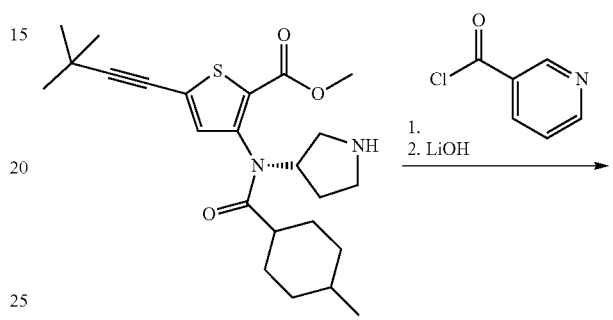

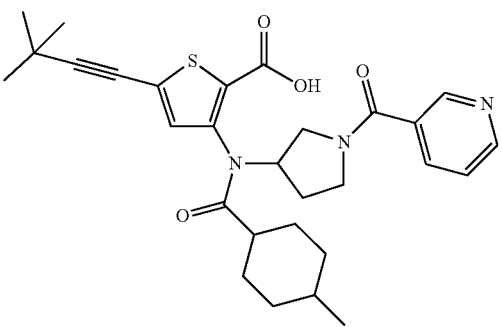

142

A mixture of 5-(3,3-Dimethyl-but-1-ynyl)-3-[(4-methyl-cyclohexanecarbonyl)-pyrrolidin-3-yl-amino]-thiophene-2-carboxylic acid methyl ester (74 mg, 0.158 mmol) and pyridine-2-carbonyl chloride HCl salt (56 mg, 0.31 mmol) in DCM (2 mL) was treated with DIEA (124 μL, 0.8 mmol). After 30 min, NaHCO₃ (saturated aqueous solution, 4-8 mL) was added to the mixture, followed by brine (20 mL), and the crude product was extracted with ethyl acetate (2×20 mL). The combined organic layers were concentrated and the crude material was dissolved in a 3:2:1 mixture of THF:MeOH:water (5 mL), treated with lithium hydroxide (42 mg, 1 mmol,) and heated to 60 deg C. for 2 hours. The residue was purified by HPLC (Gemini column, 35% acetonitrile:water, 2 min, 35-50% acetonitrile:water, 2 min, 50-100% acetonitrile:water 13 min, both solvents containing 0.1% trifluoroacetic acid). This resulted in 37 mg of the title compound as its TFA salt: MS (m/z): 522.0 [M–H]⁺; HPLC retention time: 3.58 min (2-98% acetonitrile:water with 0.05% trifluoroacetic acid).

Example 164

Compound 164—Synthesis of 5-(3,3-dimethyl-but-1-ynyl)-3-((4-trans-methyl-cyclohexanecarbonyl)-{4-trans-[methyl-(pyridine-3-sulfonyl)-amino]-cyclohexyl}-amino)-thiophene-2-carboxylic acid

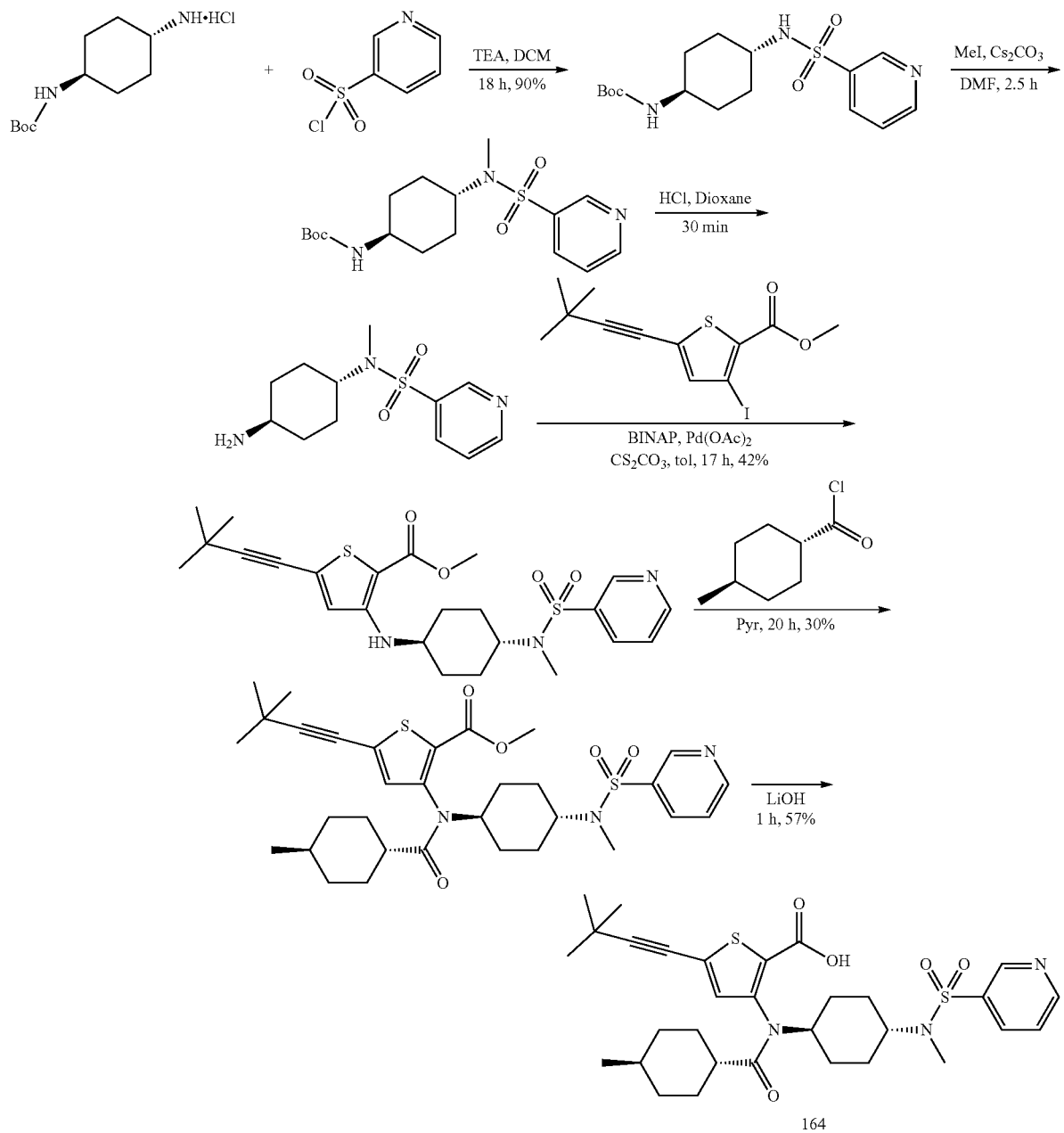

164

(4-trans-Amino-cyclohexyl)-carbamic acid tert-butyl ester (705 mg, 2.8 mmol) and triethyamine were dissolved in DCM (30 mL) under an atmosphere of nitrogen and cooled to 0° C. After 10 minutes, pyridine-3-sulfonyl chloride (1.00 g, 5.6 mmol) was added. The reaction was allowed to warm to room temperature and was stirred for 18 h. The reaction was found complete by LC/MS. The reaction was washed with water (2×10 mL). The organic layer was dried with sodium sulfate and filtered. [4-trans-(pyridine-3-sulfonylamino)-cyclohexyl]-carbamic acid tert-butyl ester (927 mg, 90%) was purified by precipitation into a white solid. LC/MS=300 (M$^+$-55)

[4-trans-(Pyridine-3-sulfonylamino)-cyclohexyl]-carbamic acid tert-butyl ester (1.08 g, 3.04 mmol) was dissolved in DMF (30 mL) under an atmosphere of nitrogen. The solution was cooled to 0° C. and Cs$_2$CO$_3$ (2.97 g, 9.12 mmol) was added. After 10 minutes, iodomethane (947 µL, 15.19 mmol) was added. After 10 minutes, the reaction was allowed to warm to room temperature. The reaction was stirred for 2.5 h until found complete by LC/MS. The reaction was quenched with water and extracted with ethyl acetate (2×30 mL). The combined organics were washed with a 5% LiCl solution in water, dried with sodium sulfate, filtered and concentrated. {4-trans-[methyl-(pyridine-3-sulfonyl)-amino]-cyclohexyl}-carbamic acid tert-butyl ester (741 mg, 66%) was purified by silica gel chromatography to afford a white solid. LC/MS=314 (M$^+$−55)

{4-trans-[Methyl-(pyridine-3-sulfonyl)-amino]-cyclohexyl}-carbamic acid tert-butyl ester (741 mg, 2.01 mmol) was dissolved in a 4N solution of HCl in dioxane (2.0 mL, 8.00 mmol). The reaction was allowed to stir for 30 min until complete by LC/MS. The reaction was concentrated and used without purification. LC/MS=269 (M$^+$)

5-(3,3-Dimethyl-but-1-ynyl)-3-iodo-thiophene-2-carboxylic acid methyl ester (469 mg, 1.35 mmol), BINAP (126 mg, 0.2 mmol), Pd(OAc)$_2$ (55 mg, 0.2 mmol) and Cs$_2$CO$_3$ (2.20 g, 6.75 mmol) were combined in degassed toluene (15 mL) under an atmosphere of argon. To the reaction was added the HCl salt of pyridine-3-sulfonic acid (4-trans-amino-cyclohexyl)-methyl-amide (crude, 2.01 mmol max). After 15 minutes, the reaction was heated to 100° C. After 17 h, the reaction was complete by LC/MS. The reaction was cooled to room temperature and was filtered. The reaction was concentrated. 5-(3,3-dmethyl-but-1-ynyl)-3-{4-trans-[methyl-(pyridine-3-sulfonyl)-amino]-cyclohexylamino}-thiophene-2-carboxylic acid methyl ester (281 mg, 42%) was purified by silica gel chromatography to afford a yellow solid. LC/MS=490 (M$^+$+1)

5-(3,3-Dimethyl-but-1-ynyl)-3-{4-trans-[methyl-(pyridine-3-sulfonyl)-amino]-cyclohexylamino}-thiophene-2-carboxylic acid methyl ester (281 mg, 0.57 mmol) was dissolved in pyridine (5 mL) under an atmosphere of nitrogen. To the reaction was added 4-trans-methyl-cyclohexanecarbonyl chloride (138 mg, 0.86 mmol). The reaction was heated to 90° C. for 20 h. The reaction was cooled to room temperature and was diluted with EtOAc. The reaction was washed with water (2×5 mL). The organic layer was dried with sodium sulfate, filtered and was concentrated. 5-(3,3-dimethyl-but-1-ynyl)-3-((4-trans-methyl-cyclohexanecarbonyl)-{4-trans-[methyl-(pyridine-3-sulfonyl)-amino]-cyclohexyl}-amino)-thiophene-2-carboxylic acid methyl ester (105 mg, 30%) was purified by silica gel chromatography to afford a yellow solid. LC/MS=613 (M$^+$)

5-(3,3-Dimethyl-but-1-ynyl)-3-((4-trans-methyl-cyclohexanecarbonyl)-{4-trans-[methyl-(pyridine-3-sulfonyl)-amino]-cyclohexyl}-amino)-thiophene-2-carboxylic acid methyl ester (105 mg, 0.18 mmol) was dissolved in THF (1 mL) and MeOH (0.5 mL). To the reaction was added a solution of LION (20 mg, 0.88 mmol) in water (1 mL). The reaction was stirred for 1 h. The reaction was neutralized with 0.88 mL of 1N HCl in water. The solution was concentrated. 5-(3,3-dimethyl-but-1-ynyl)-3-((4-trans-methyl-cyclohexanecarbonyl)-{4-trans-[methyl-(pyridine-3-sulfonyl)-amino]-cyclohexyl}-amino)-thiophene-2-carboxylic acid (62 mg, 57) was purified by HPLC to afford a white powder.

LC/MS=597 (M$^+$-2) Neg ionization

Retention time: 2.62 min

LC: Thermo Electron Surveyor HPLC

MS: Finnigan LCQ Advantage MAX Mass Spectrometer

Column: Phenomenex Polar RP 30 mm×4.6 mm

Solvents: Acetonitrile with 0.1% formic acid, Water with 0.1% formic acid

Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN.

Example 165

Compound 165—Synthesis of 5-(3,3-dimethyl-but-1-ynyl)-3-{(4-trans-methyl-cyclohexanecarbonyl)-[4-(pyridine-3-sulfonylamino)-cyclohexyl]-amino}-thiophene-2-carboxylic acid

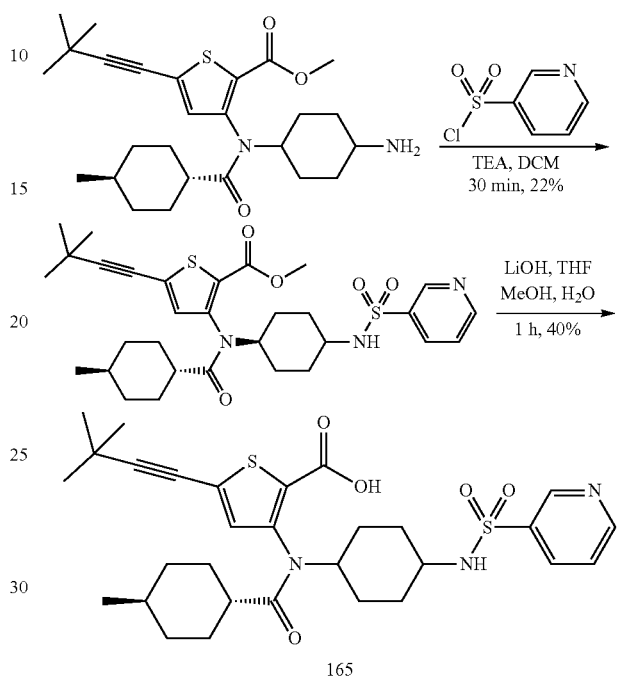

165

3-[(4-Amino-cyclohexyl)-(4-trans-methyl-cyclohexanecarbonyl)-amino]-5-(3,3-dimethyl-but-1-ynyl)-thiophene-2-carboxylic acid methyl ester (200 mg, 0.44 mmol) and TEA (245 μL, 1.76 mmol) were dissolved in DCM (3 mL) under an atmosphere of nitrogen and cooled to 0° C. To the reaction was added pridine-3-sulfonyl chloride (155 mg, 0.88 mmol). The reaction was allowed to warm to room temperature and was stirred for 30 minutes. The reaction was concentrated. 5-(3,3-dimethyl-but-1-ynyl)-3-{(4-trans-methyl-cyclohexanecarbonyl)-[4-(pyridine-3-sulfonylamino)-cyclohexyl]-amino}-thiophene-2-carboxylic acid methyl ester (50 mg, 22%) was purified by silica gel chromatography to afford a yellow solid. LC/MS=600 (M$^+$+1)

5-(3,3-Dimethyl-but-1-ynyl)-3-{(4-trans-methyl-cyclohexanecarbonyl)-[4-(pyridine-3-sulfonylamino)-cyclohexyl]-amino}-thiophene-2-carboxylic acid methyl ester (50 mg, 0.1 mmol) was dissolved in a THF (1 mL) and MeOH (1 mL). To the reaction was added a solution of LiOH (12 mg, 0.5 mmol.) in water (1 mL). The reaction was stirred for 1 hour. The reaction was quenched with 1N HCl in water (0.5 m L). 5-(3,3-Dimethyl-but-1-ynyl)-3-{(4-trans-methyl-cyclohexanecarbonyl)-[4-(pyridine-3-sulfonylamino)-cyclohexyl]-amino}-thiophene-2-carboxylic acid (23 mg, 40%) was purified by HPLC to afford a white powder.

LC/MS=584 (M$^+$-1) Neg ionization

Retention time: 2.52 min

LC: Thermo Electron Surveyor HPLC

MS: Finnigan LCQ Advantage MAX Mass Spectrometer

Column: Phenomenex Polar RP 30 mm×4.6 mm

Solvents: Acetonitrile with 0.1% formic acid, Water with 0.1% formic acid

Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN.

Example 186

Compound 186—Synthesis of 3-{4-[[2-carboxy-5-(3,3-dimethyl-but-1-ynyl)-thiophen-3-yl]-(4-methyl-cyclohexanecarbonyl)-amino]-cyclohexylcarbamoyloxy}-azetidine-1-carboxylic acid tert-butyl ester

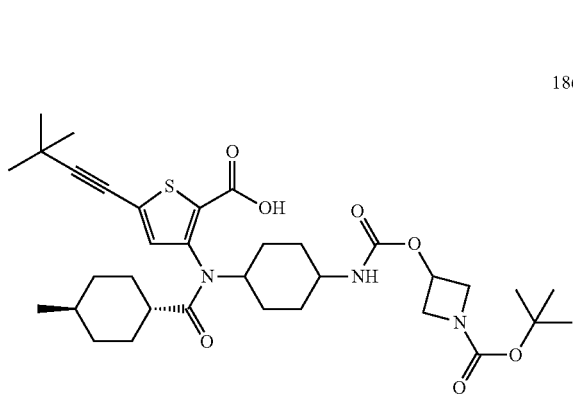 [SMILES: CC(C)(C)C#Cc1cc(N(C(=O)[C@H]2CC[C@H](C)CC2)C2CCC(NC(=O)OC3CN(C(=O)OC(C)(C)C)C3)CC2)c(C(=O)O)s1]

3-{4-[[2-Carboxy-5-(3,3-dimethyl-but-1-ynyl)-thiophen-3-yl]-(4-methyl-cyclohexanecarbonyl)-amino]-cyclohexylcarbamoyloxy}-azetidine-1-carboxylic acid tert-butyl ester was prepared in a similar fashion to 4-[[2-carboxy-5-(3,3-dimethyl-but-1-ynyl)-thiophen-3-yl]-(4-trans-methyl-cyclohexanecarbonyl)-amino]-piperidine-1-carboxylic acid piperidin-4-yl ester using method A except that the HCl salt of 3-[(4-amino-cyclohexyl)-(4-trans-methyl-cyclohexanecarbonyl)-amino]-5-(3,3-dimethyl-but-1-ynyl)-thiophene-2-carboxylic acid was used instead of the HCl salt of 5-(3,3-dimethyl-but-1-ynyl)-3-[(4-trans-methyl-cyclohexanecarbonyl)-piperidin-4-yl-amino]-thiophene-2-carboxylic acid and 3-hydroxy-azetidine-1-carboxylic acid tert-butyl ester was used instead of 4-hydroxy-piperidine-1-carboxylic acid tert-butyl ester.

LC/MS (m/z): 544 [M−99]
Retention time: 2.52 min
LC: Thermo Electron Surveyor HPLC
MS: Finnigan LCQ Advantage MAX Mass Spectrometer
Column: Phenomenex Polar RP 30 mm×4.6 mm
Solvents: Acetonitrile with 0.1% formic acid, Water with 0.1% formic acid
Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN.

Example 217

Compound 217—Synthesis of 5-(3,3-dimethyl-but-1-ynyl)-3-((4-methyl-cyclohexanecarbonyl)-{4-[N'-methyl-N'-(tetrahydro-pyran-4-yloxycarbonyl)-hydrazino]-cyclohexyl}-amino)-thiophene-2-carboxylic acid

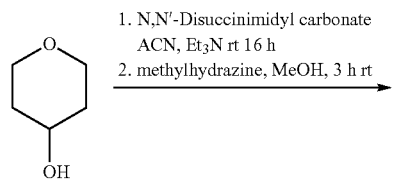
1. N,N'-Disuccinimidyl carbonate ACN, Et₃N rt 16 h
2. methylhydrazine, MeOH, 3 h rt

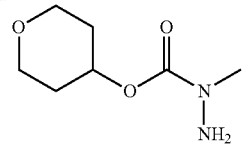

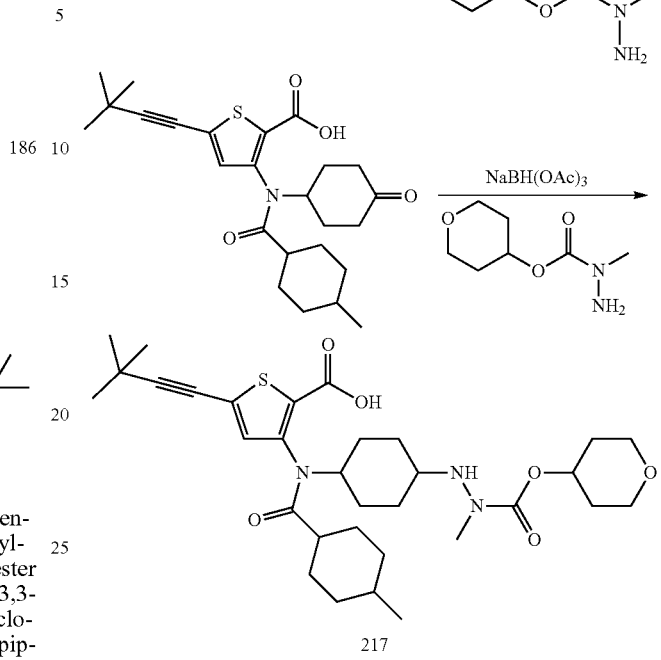

To a solution of tetrahydro-pyran-4-ol (0.215 mL, 2.27 mmol) and N,N'-disuccimidyl carbonate (0.87 g, 3.4 mmol) in ACN (7 mL) was added triethylamine (1 mL, 6.81 mmol). After 16 h stirring at rt, the reaction was quenched with LiCl solution (5% in water, 10 mL) and diluted with EtOAc (20 mL). The crude product was washed 2×10 mL with 5% LiCl solution, dried over Na₂SO₄ and concentrated. The crude material was used as is for the next step.

A mixture of 5-(3,3-dimethyl-but-1-ynyl)-3-[(4-methyl-cyclohexanecarbonyl)-(4-oxo-cyclohexyl)-amino]-thiophene-2-carboxylic acid (100 mg, 0.23 mmol), N-methyl-hydrazinecarboxylic acid tetrahydro-pyran-4-yl ester (70 mg, ~0.4 mmol), acetic acid (3 drops) in DCE (3 mL) was treated with NaBH(OAc)₃ (12 mg, 56 mmol) for 16 h. The reaction was quenched with water (10 mL) and extracted with EtOAc. The crude material was then purified by HPLC (Gemini column, 35% acetonitrile:water, 2 min, 35-50% acetonitrile:water, 2 min, 50-100% acetonitrile: water 13 min, both solvents containing 0.1% trifluoroacetic acid) giving the title compound as a TFA salt: MS (m/z): 603.1 [M−H]⁺; HPLC retention time: 27.4 min (2-98% acetonitrile: water with 0.05% trifluoroacetic acid) 30 min run.

Example 218

Compound 218—Synthesis of 5-(3,3-dimethyl-but-1-ynyl)-3-((4-methyl-cyclohexanecarbonyl)-{4-[N-methyl-N'-(pyridin-2-yloxycarbonyl)-hydrazino]-cyclohexyl}-amino)-thiophene-2-carboxylic acid

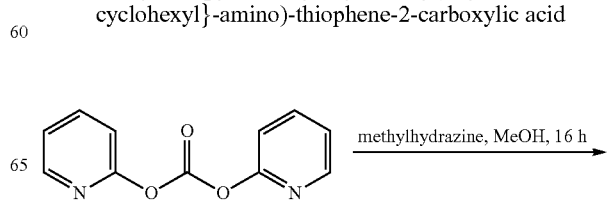
methylhydrazine, MeOH, 16 h

-continued

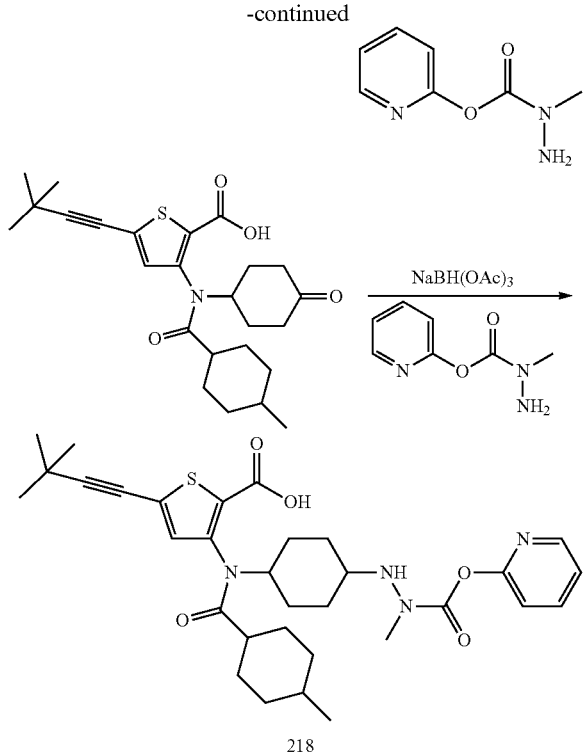

218

To a solution of carbonic acid di-2-pyridyl ester (300 mg, 1.38 mmol) in MeOH (10 mL) was added methylhydrazine (94 uL, 1.8 mmol). After 16 h stirring at rt, the reaction was concentrated and the crude material was used as is for the next step.

A mixture of 5-(3,3-dimethyl-but-1-ynyl)-3-[(4-methyl-cyclohexanecarbonyl)-(4-oxo-cyclohexyl)-amino]-thiophene-2-carboxylic acid (100 mg, 0.23 mmol), N-methyl-hydrazinecarboxylic acid pyridin-2-yl ester (67 mg, ~0.4 mmol), acetic acid (3 drops) in DCE (3 mL) was treated with NaBH(OAc)$_3$ (12 mg, 56 mmol) for 16 h. The reaction was quenched with water (10 mL) and extracted with EtOAc. The crude material was then purified by HPLC (Gemini column, 35% acetonitrile:water, 2 min, 35-50% acetonitrile:water, 2 min, 50-100% acetonitrile: water 13 min, both solvents containing 0.1% trifluoroacetic acid) giving the title compound as a TFA salt: MS (m/z): 595.1 [M–H]$^+$; HPLC retention time: 28.9 min (2-98% acetonitrile:water with 0.05% trifluoroacetic acid) 30 min run.

Biological Examples

Antiviral Activity

Another aspect of the invention relates to methods of inhibiting viral infections, comprising the step of treating a sample or subject suspected of needing such inhibition with a composition of the invention.

Within the context of the invention samples suspected of containing a virus include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which induces a viral infection, frequently a pathogenic organism such as a tumor virus. Samples can be contained in any medium including water and organic solvent\water mixtures. Samples include living organisms such as humans, and man made materials such as cell cultures.

If desired, the anti-virus activity of a compound of the invention after application of the composition can be observed by any method including direct and indirect methods of detecting such activity. Quantitative, qualitative, and semiquantitative methods of determining such activity are all contemplated. Typically one of the screening methods described above are applied, however, any other method such as observation of the physiological properties of a living organism are also applicable.

The antiviral activity of a compound of the invention can be measured using standard screening protocols that are known. For example, the antiviral activity of a compound can be measured using the following general protocols.

Cell-Based Flavivirus Immunodetection assay

BHK21 or A549 cells are trypsinized, counted and diluted to $2\times10^5$ cells/mL in Hams F-12 media (A549 cells) or RPMI-1640 media (BHK21 cells) supplemented with 2% fetal bovine serum (FBS) and 1% penicillin/streptomycin. $2\times10^4$ cells are dispensed in a clear 96-well tissue culture plates per well and placed at 37° C., 5% $CO_2$ overnight. On the next day, the cells are infected with viruses at multiplicity of infection (MOI) of 0.3 in the presence of varied concentrations of test compounds for 1 hour at 37° C. and 5% $CO_2$ for another 48 hours. The cells are washed once with PBS and fixed with cold methanol for 10 min. After washing twice with PBS, the fixed cells are blocked with PBS containing 1% FBS and 0.05% Tween-20 for 1 hour at room temperature. The primary antibody solution (4G2) is then added at a concentration of 1:20 to 1:100 in PBS containing 1% FBS and 0.05% Tween-20 for 3 hours. The cells are then washed three times with PBS followed by one hour incubation with horseradish peroxidase (HRP)-conjugated anti-mouse IgG (Sigma, 1:2000 dilution). After washing three times with PBS, 50 microliters of 3,3',5,5'-tetramethylbenzidine (TMB) substrate solution (Sigma) is added to each well for two minutes. The reaction is stopped by addition of 0.5 M sulfuric acid. The plates are read at 450 nm absorbance for viral load quantification. After measurement, the cells are washed three times with PBS followed by incubation with propidium iodide for 5 min. The plate is read in a Tecan Safire™ reader (excitation 537 nm, emission 617 nm) for cell number quantification. Dose response curves are plotted from the mean absorbance versus the log of the concentration of test compounds. The $EC_{50}$ is calculated by non-linear regression analysis. A positive control such as N-nonyl-deoxynojirimycin may be used.

Cell-Based Flavivirus Cytopathic Effect Assay

For testing against West Nile virus or Japanese encephalitis virus, BHK21 cells are trypsinized and diluted to a concentration of $4\times10^5$ cells/mL in RPMI-1640 media supplemented with 2% FBS and 1% penicillin/streptomycin. For testing against dengue virus, Huh7 cells are trypsinized and diluted to a concentration of $4\times10^5$ cells/mL in DMEM media supplemented with 5% FBS and 1% penicillin/streptomycin. A 50 microliter of cell suspension ($2\times10^4$ cells) is dispensed per well in a 96-well optical bottom PIT polymer-based plates (Nunc). Cells are grown overnight in culture medium at 37° C., 5% $CO_2$, and then infected with West Nile virus (e.g. B956 strain) or Japanese encephalitis virus (e.g. Nakayama strain) at MOI=0.3, or with dengue virus (e.g. DEN-2 NGC strain) at MOI=1, in the presence of different concentrations of test compounds. The plates containing the virus and the compounds are further incubated at 37° C., 5% $CO_2$ for 72 hours. At the end of incubation, 100 microliters of CellTiter-Glo™ reagent is added into each well. Contents are mixed for 2 minutes on an orbital shaker to induce cell lysis. The plates are incubated at room temperature for 10 minutes to stabilize luminescent signal. Luminescence reading is recorded using a plate reader. A positive control such as N-nonyl-deoxynojirimycin may be used.

Antiviral Activity in a Mouse Model of Dengue Infection.

Compounds are tested in vivo in a mouse model of dengue virus infection (Schul et al. J. Infectious Dis. 2007; 195:665-74). Six to ten week old AG129 mice (B&K Universal Ltd, HII, UK) are housed in individually ventilated cages. Mice are injected intraperitoneally with 0.4 mL TSV01 dengue virus 2 suspension. Blood samples are taken by retro orbital puncture under isoflurane anaesthesia. Blood samples are collected in tubes containing sodium citrate to a final concentration of 0.4%, and immediately centrifuged for 3 minutes at 6000 g to obtain plasma. Plasma (20 microliters) is diluted in 780 microliters RPMI-1640 medium and snap frozen in liquid nitrogen for plaque assay analysis. The remaining plasma is reserved for cytokine and NS1 protein level determination. Mice develop dengue viremia rising over several days, peaking on day 3 post-infection.

For testing of antiviral activity, a compound of the invention is dissolved in vehicle fluid, e.g. 10% ethanol, 30% PEG 300 and 60% D5W (5% dextrose in water; or 6N HCl (1.5 eq):1N NaOH (pH adjusted to 3.5): 100 mM citrate buffer pH 3.5 (0.9% v/v:2.5% v/v:96.6% v/v). Thirty six 6-10 week old AG129 mice are divided into six groups of six mice each. All mice are infected with dengue virus as described above (day 0). Group 1 is dosed by oral gavage of 200 mL/mouse with 0.2 mg/kg of a compound of the invention twice a day (once early in the morning and once late in the afternoon) for three consecutive days starting on day 0 (first dose just before dengue infection). Groups 2, 3 and 4 are dosed the same way with 1 mg/kg, 5 mg/kg and 25 mg/kg of the compound, respectively. A positive control may be used, such as (2R,3R,4R,5R)-2-(2-amino-6-hydroxy-purin-9-yl)-5-hydroxymethyl-3-methyl-tetrahydro-furan-3,4-diol, dosed by oral gavage of 200 microliters/mouse the same way as the previous groups. A further group is treated with only vehicle fluid.

On day 3 post-infection approximately 100 microliter blood samples (anti-coagulated with sodium citrate) are taken from the mice by retro-orbital puncture under isoflurane anaesthesia. Plasma is obtained from each blood sample by centrifugation and snap frozen in liquid nitrogen for plague assay analysis. The collected plasma samples are analyzed by plague assay as described in Schul at al. Cytokines are also analysed as described by Schul. NS1 protein levels are analysed using a Platelia™ kit (BioRad Laboratories). An antiviral effect is indicated by a reduction in cytokine levels and/or NS1 protein levels.

Typically, reductions in viremia of about 5-100 fold, more typically 10-60 fold, most typically 20-30 fold, are obtained with 5-50 mg/kg bid dosages of the compounds of the invention.

HCV Assay Protocol

The anti-HCV activity of the compounds of this invention was tested in a human hepatoma Huh-7 cell line harboring a HCV replicon. The assay comprised the following steps:

Step 1: Compound Preparation and Serial Dilution.

Serial dilution was performed in 100% DMSO in a 384-well plate. A solution containing a compound at 225-fold concentration of the starting final serial dilution concentration was prepared in 100% DMSO and 15 uL added to the pre-specified wells in column 3 or 13 of a polypropylene 384-well plate. The rest of the 384-well plate was filled with 10 uL 100% DMSO except for columns 23 and 24, where 10 uL of 500 uM a HCV protease inhibitor (ITMN-191) in 100% DMSO was added. The HCV protease inhibitor was used a control of 100% inhibition of HCV replication. The plate was then placed on a Biomek FX Workstation to start the serial dilution. The serial dilution was performed for ten cycles of 3-fold dilution from column 3 to 12 or from column 13 to 22.

Step 2: Cell Culture Plate Preparation and Compound Addition

To each well of a black polypropylene 384-well plate, 90 μL of cell media containing 1600 suspended Huh-7 HCV replicon cells was added with a Biotek uFlow Workstation. A volume of 0.4 μL of the compound solution was transferred from the serial dilution plate to the cell culture plate on a Biomek FX Workstation. The DMSO concentration in the final assay condition was 0.44%. The plates were incubated for 3 days at 37° C. with 5% $CO_2$ and 85% humidity.

Step 3: Detection of Cytotoxicity and Inhibition of Viral Replication a) Assessment of cytotoxicity: The media in the 384-well cell culture plate was aspirated with a Biotek EL405 plate-washer. A volume of 50 μL of a solution containing 400 nM Calcein AM in 100% PBS was added to each well of the plate with a Biotek uFlow Workstation. The plate was incubated for 30 minutes at room temperature before the fluorescence signal (emission 490 nm, exitation 520 nm) was measured with a Perkin Elmer Envision Plate Reader.

b) Assessment of inhibition of viral replication: The calcein-PBS solution in the 384-well cell culture plate was aspirated with a Biotek EL405 plate-washer. A volume of 20 μL of Dual-Glo luciferase buffer (Promega, Dual-Glo Luciferase Assay Reagent, cat. #E298B) was added to each well of the plate with a Biotek uFlow Workstation. The plate was incubated for 10 minutes at room temperature. A volume of 20 μL of a solution containing 1:100 mixture of Dual-Glo Stop & Glo substrate (Promega, Dual-Glo Luciferase Assay Reagent, cat. #E313B) and Dual-Glo Stop & Glo buffer (Promega, Dual-Glo Luciferase Assay Reagent, cat. #E314B) was then added to each well of the plate with a Biotek uFlow Workstation. The plate was incubated at room temperature for 10 minutes before the luminescence signal was measured with a Perkin Elmer Envision Plate Reader.

Step 4: Calculation

The percent cytotoxicity was determined by calcein AM conversion to fluorescent product. The average fluorescent signal from the DMSO control wells were defined as 100% nontoxic. The individual fluorescent signal from testing compound treated well was divided by the average signal from DMSO control wells and then multiplied by 100% to get the percent viability. The percent anti-HCV replication activity was determined by the luminescence signal from the testing well compared to DMSO controls wells. The background signal was determined by the average luminescence signal from the HCV protease inhibitor treated wells and was subtracted from the signal from the testing wells as well as the DMSO control wells. Following 3-fold serial dilutions, the $EC_{50}$ and $CC_{50}$ values were calculated by fitting % inhibition at each concentration to the following equation:

$$\% \text{ inhibition} = 100\%/[(EC_{50}/[I])^b + 1]$$

Where b is Hill's coefficient. See, for reference, Hill, A. V., *The Possible Effects of the Aggregation of the Molecules of Hemoglobin on its Dissociation Curves*, J. Physiol. 40: iv-vii. (1910).

% inhibition values at a specific concentration, for example 2 μM, can also be derived from the formula above.

When tested, certain compounds of this invention were found to inhibit viral replication as listed in Table 1:

TABLE 1

| Compound | % inhibition at 2 μM |
|---|---|
| 31 | 93.1 |
| 32 | 100 |
| 33 | 96.2 |
| 34 | 97.8 |
| 35 | 99.8 |
| 36 | 100 |
| 37 | 99.6 |
| 38 | 99.6 |
| 39 | 98.8 |
| 40 | 98.6 |
| 41 | 99.9 |
| 42 | 99.9 |
| 43 | 96.2 |
| 44 | 100 |
| 45 | 100 |
| 46 | 97.0 |
| 47 | 99.9 |
| 48 | 100 |
| 49 | 99.2 |
| 50 | 99.9 |
| 51 | 85.5 |
| 52 | 93.5 |
| 53 | 99.9 |
| 54 | 99.8 |
| 55 | 87.9 |
| 56 | 92.8 |
| 57 | 78.2 |
| 64 | 100 |
| 65 | 99.9 |
| 66 | 99.9 |
| 67 | 99.0 |
| 68 | 98.5 |
| 69 | 99.5 |
| 70 | 99.1 |
| 71 | 95.1 |
| 72 | 99.7 |
| 73 | 93.1 |
| 74 | 99.7 |
| 75 | 97.5 |
| 76 | 99.4 |
| 77 | 99.9 |
| 79 | 100 |
| 80 | 99.8 |
| 81 | 100 |
| 82 | 100 |
| 83 | 99.9 |
| 112 | 99.9 |
| 113 | 98.1 |
| 114 | 100 |
| 115 | 99.8 |
| 116 | 99.9 |
| 117 | 99.9 |
| 118 | 100 |
| 119 | 97.1 |
| 120 | 99.9 |
| 121 | 99.9 |
| 122 | 99.7 |
| 123 | 99.9 |
| 124 | 99.9 |
| 125 | 99.7 |
| 126 | 98.9 |
| 127 | 98.3 |
| 128 | 99.8 |
| 129 | 100 |
| 130 | 98.7 |
| 131 | 99.9 |
| 132 | 77.4 |
| 133 | 96.7 |
| 134 | 99.0 |
| 135 | 99.8 |
| 136 | 98.9 |
| 137 | 100 |

TABLE 1-continued

| Compound | % inhibition at 2 μM |
|---|---|
| 140 | 99.9 |
| 141 | 99.9 |
| 142 | 99.6 |
| 164 | 98.9 |
| 165 | 95.7 |
| 186 | 98.9 |
| 217 | 100 |
| 218 | 100 |

Preferred compounds according to Table 1 include Examples 32, 36, 38, 41, 48, 50, 64, 65, 66, 77, 79, 80, 81, 82, 83, 112, 114, 118, 129, 217, and 218.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:

1. A compound of Formula I:

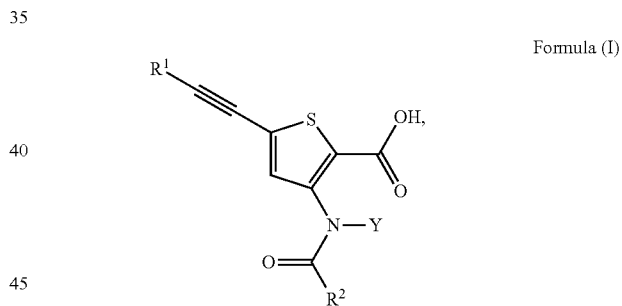

Formula (I)

or a pharmaceutically acceptable salt thereof, wherein:
R$^1$ is selected from the group consisting of optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{6-14}$ aryl, optionally substituted 3-14 membered heteroaryl, optionally substituted 3-12 membered heterocyclyl, optionally substituted 3-18 membered heteroarylalkyl, optionally substituted 3-18 membered heterocyclylalkyl and optionally substituted C$_{6-18}$ arylalkyl, wherein, each substituted R$^1$ is substituted with one or more Q$^1$;

each Q$^1$ is independently selected from the group consisting of halogen, oxo, oxide, —NO$_2$, —N(═O), —SR$^{10}$, —S(O)R$^{10}$, —S(O)$_2$R$^{10}$, —S(O)$_2$NR$^{10}$R$^{11}$, —NR$^{10}$C(O)R$^{11}$, —NR$^{10}$C(O)NR$^{11}$R$^{12}$, —NR$^{10}$S(O)R$^{11}$, —NR$^{10}$S(O)$_2$R$^{11}$, —OP(O)R$^{11}$R$^{12}$, —P(O)R$^{11}$R$^{12}$, —P(O)OR$^{11}$R$^{12}$, —P(O)(OR$^{11}$)OR$^{12}$, —C(O)NR$^{11}$R$^{12}$, optionally substituted C$_{1-6}$ alkyl, optionally substituted C$_{2-6}$ alkenyl, optionally substituted $C_{2-6}$ alkynyl, optionally substituted $C_{3-6}$ cycloalkyl, optionally substituted $C_{6-12}$ arylalkyl, optionally substituted $C_{6-12}$ aryl, optionally substituted 3-14 membered heteroaryl, optionally substituted $C_{1-6}$ alkyloxy, optionally substituted $C_{2-6}$ alkenyloxy, optionally substituted $C_{2-6}$ alkynyloxy, optionally substituted $C_{3-6}$ cycloalkyloxy, optionally substituted $C_{6-12}$ aryloxy, optionally substituted 3-14 membered heteroaryloxy, optionally substituted 4-12 membered heterocycyloxy, optionally substituted —C(O)$C_{1-6}$ alkyl, optionally substituted —C(O)$C_{2-6}$ alkenyl, optionally substituted —C(O)$C_{2-6}$ alkynyl, optionally substituted —C(O)$C_{3-6}$ cycloalkyl, optionally substituted —C(O)$C_{6-12}$ aryl, optionally substituted —C(O)-3-14 membered heteroaryl, optionally substituted —C(O)$C_{6-12}$ arylalkyl, optionally substituted -3-10 membered heterocyclyl, —OH, —NR$^{11}$R$^{12}$, —C(O)OR$^{10}$, —CN, —N$_3$, —C(=NR$^{13}$)NR$^{11}$R$^{12}$, —C(=NR$^{13}$)OR$^{10}$, —NR$^{10}$C(=NR$^{13}$)NR$^{11}$R$^{12}$, —NR$^{11}$C(O)OR$^{10}$, and —OC(O)NR$^{11}$R$^{12}$;

each R$^{10}$, R$^{11}$, and R$^{12}$, independently, is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, and optionally substituted $C_{6-18}$ arylalkyl;

or R$^{11}$ and R$^{12}$ taken together with the atoms to which they are attached form a 3 to 10 membered heterocyclyl;

each R$^{13}$, independently, is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, optionally substituted $C_{6-18}$ arylalkyl, —CN, —C(O)R$^{14}$, —CHO and —S(O)$_2$R$^{14}$;

each R$^{14}$, independently, is optionally substituted $C_{1-12}$ alkyl;

wherein, each substituted Q$^1$, substituted R$^{10}$, substituted R$^{11}$, substituted R$^{12}$, substituted R$^{13}$, or substituted R$^{14}$ is independently substituted with one or more Q$^6$;

R$^2$ is selected from the group consisting of optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, and optionally substituted $C_{6-18}$ arylalkyl;

wherein, each substituted R$^2$ is substituted with one or more Q$^2$;

each Q$^2$, independently, is selected from the group consisting of halogen, oxo, oxide, —NO$_2$, —N(=O), —SR$^{20}$, —S(O)R$^{20}$, —S(O)$_2$R$^{20}$, —S(O)$_2$NR$^{20}$R$^{21}$, —NR$^{20}$C(O)R$^{21}$, —NR$^{20}$C(O)NR$^{21}$R$^{22}$, —NR$^{20}$S(O)R$^{21}$, —NR$^{20}$S(O)$_2$R$^{21}$, —OP(O)R$^{21}$R$^{22}$, —P(O)R$^{21}$R$^{22}$, —P(O)OR$^{21}$R$^{22}$, —P(O)(OR$^{21}$)OR$^{22}$, —C(O)NR$^{21}$R$^{22}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{6-12}$ arylalkyl, optionally substituted $C_{6-12}$ aryl, optionally substituted 3-14 membered heteroaryl, optionally substituted $C_{1-6}$ alkyloxy, optionally substituted $C_{2-6}$ alkenyloxy, optionally substituted $C_{2-6}$ alkynyloxy, optionally substituted $C_{3-6}$ cycloalkyloxy, optionally substituted $C_{6-12}$ aryloxy, optionally substituted 3-14 membered heteroaryloxy, optionally substituted 4-12 membered heterocyclyloxy, optionally substituted —C(O)$C_{1-6}$ alkyl, optionally substituted —C(O)$C_{2-6}$ alkenyl, optionally substituted —C(O)$C_{2-6}$ alkynyl, optionally substituted —C(O)$C_{3-6}$ cycloalkyl, optionally substituted —C(O)$C_{6-12}$ aryl, optionally substituted —C(O)-3-14 membered heteroaryl, optionally substituted —C(O)$C_{6-12}$ arylalkyl, optionally substituted 3-10 membered heterocyclyl, —OH, —NR$^{21}$R$^{22}$, —C(O)OR$^{20}$, —CN, —N$_3$, —C(=NR$^{23}$)NR$^{21}$R$^{22}$, —C(=NR$^{23}$)OR$^{20}$, —NR$^{20}$C(=NR$^{23}$)NR$^{21}$R$^{22}$, NR$^{21}$C(O)OR$^{20}$, and —OC(O)NR$^{21}$R$^{22}$;

each R$^{20}$, R$^{21}$, and R$^{22}$, independently, is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, and optionally substituted $C_{6-18}$ arylalkyl;

or R$^{21}$ and R$^{22}$ taken together with the atoms to which they are attached form a 3 to 10 membered heterocyclyl;

each R$^{23}$, independently, is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, optionally substituted $C_{6-18}$ arylalkyl, —CN, —C(O)R$^{24}$, —CHO and —S(O)$_2$R$^{24}$;

each R$^{24}$ individually is optionally substituted $C_{1-12}$ alkyl;

wherein, each substituted Q$^2$, substituted R$^{20}$, substituted R$^{21}$, substituted R$^{22}$, substituted R$^{23}$, or substituted R$^{24}$ is independently substituted with one or more Q$^6$;

Y is —R$^3$-L-Het, —N(R$^4$)(R$^5$) or —R$^6$=NOR$^7$;

R$^3$ is selected from the group consisting of optionally substituted $C_{1-12}$ alkylene, $C_{2-12}$ alkenylene, substituted $C_{2-12}$ alkenylene, $C_{2-12}$ alkynylene, substituted $C_{2-12}$ alkynylene, $C_{3-12}$ cycloalkylene, substituted $C_{3-12}$ cycloalkylene, $C_{3-12}$ cycloalkylalkylene, substituted $C_{3-12}$ cycloalkylalkylene, optionally substituted $C_{6-14}$ arylene, optionally substituted 3-14 membered heteroarylene, optionally substituted 3-12 membered heterocyclylene, optionally substituted 3-18 membered heteroarylalkylene, and optionally substituted $C_{6-18}$ arylalkylene;

wherein each substituted R$^3$ is substituted with one or more Q$^3$;

each Q$^3$, independently, is selected from the group consisting of halogen, oxo, oxide, —NO$_2$, —N(=O), —SR$^{30}$, —S(O)R$^{30}$, —S(O)$_2$R$^{30}$, —S(O)$_2$NR$^{30}$R$^{31}$, —NR$^{30}$C(O)R$^{31}$, —NR$^{30}$C(O)NR$^{31}$R$^{32}$, —NR$^{30}$S(O)R$^{31}$, —NR$^{30}$S(O)$_2$ $R^{31}$, —OP(O)$R^{31}R^{32}$, —P(O)$R^{31}R^{32}$, —P(O)O$R^{31}R^{32}$, —P(O)(O$R^{31}$)O$R^{32}$, —C(O)N$R^{31}R^{32}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{6-12}$ arylalkyl, optionally substituted $C_{6-12}$ aryl, optionally substituted 3-14 membered heteroaryl, optionally substituted $C_{1-6}$ alkyloxy, optionally substituted $C_{2-6}$ alkenyloxy, optionally substituted $C_{2-6}$ alkynyloxy, optionally substituted $C_{3-6}$ cycloalkyloxy, optionally substituted $C_{6-12}$ aryloxy, optionally substituted 3-14 membered heteroaryloxy, optionally substituted 4-12 membered heterocyclyloxy, optionally substituted —C(O)$C_{1-6}$ alkyl, optionally substituted —C(O)$C_{2-6}$ alkenyl, optionally substituted —C(O)$C_{2-6}$ alkynyl, optionally substituted —C(O)$C_{3-6}$ cycloalkyl, optionally substituted —C(O)$C_{6-12}$ aryl, optionally substituted —C(O)-3-14 membered heteroaryl, optionally substituted —C(O)$C_{6-12}$ arylalkyl, optionally substituted 3-10 membered heterocyclyl, —OH, —N$R^{31}R^{32}$, —C(O)O$R^{30}$, —CN, —$N_3$, —C(=N$R^{33}$)N$R^{31}R^{32}$, —C(=N$R^{33}$)O$R^{30}$, —N$R^{30}$C(=N$R^{33}$)N$R^{31}R^{32}$, —N$R^{31}$C(O)O$R^{30}$, and —OC(O)N$R^{31}R^{32}$;

each $R^{30}$, $R^{31}$, and $R^{32}$, independently is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, and optionally substituted $C_{6-18}$ arylalkyl;

or $R^{31}$ and $R^{32}$ taken together with the atoms to which they are attached form a 3 to 10 membered heterocyclyl;

each $R^{33}$ independently is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, optionally substituted $C_{6-18}$ arylalkyl, —CN, —C(O)$R^{34}$, —CHO and —S(O)$_2R^{34}$;

each $R^{34}$ individually is optionally substituted $C_{1-12}$ alkyl;

wherein, each substituted $Q^3$, substituted $R^{30}$, substituted $R^{31}$, substituted $R^{32}$, substituted $R^{33}$, or substituted $R^{34}$ is independently substituted with one or more $Q^6$;

L is selected from the group consisting of —OC(O)N($R^4$)—, —N($R^4$)C(O)O—, —N($R^4$)S(O)$_2$—, —N($R^4$)C(O)—, —C(O)—, —C(O)O—, —OC(O)—, —N($R^4$)N($R^4$)C(O)O—, and —N($R^4$)N($R^4$)—;

Het is an optionally substituted 3-12 membered heterocyclyl or optionally substituted 3-14 membered heteroaryl;

wherein, each substituted Het is substituted with one or more $Q^4$;

each $Q^4$, independently, is selected from the group consisting of halogen, oxo, oxide, —NO$_2$, —N(=O), —SR$^{40}$, —S(O)$R^{40}$, —S(O)$_2R^{40}$, —S(O)$_2$N$R^{40}R^{41}$, —N$R^{40}$C(O)$R^{41}$, —N$R^{40}$C(O)N$R^{41}R^{42}$, —N$R^{40}$S(O)$R^{41}$, —N$R^{40}$S(O)$_2R^{41}$, —OP(O)$R^{41}R^{42}$, —P(O)$R^{41}R^{42}$, —P(O)O$R^{41}R^{42}$, —P(O)(O$R^{41}$)O$R^{42}$, —C(O)N$R^{41}R^{42}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{6-12}$ arylalkyl, optionally substituted $C_{6-12}$ aryl, optionally substituted 3-14 membered heteroaryl, optionally substituted $C_{1-6}$ alkyloxy, optionally substituted $C_{2-6}$ alkenyloxy, optionally substituted $C_{2-6}$ alkynyloxy, optionally substituted $C_{3-6}$ cycloalkyloxy, optionally substituted $C_{6-12}$ aryloxy, optionally substituted 3-14 membered heteroaryloxy, optionally substituted 4-12 membered heterocyclyloxy, optionally substituted —C(O)$C_{1-6}$ alkyl, optionally substituted —C(O)$C_{2-6}$ alkenyl, optionally substituted —C(O)$C_{2-6}$ alkynyl, optionally substituted —C(O)$C_{3-6}$ cycloalkyl, optionally substituted —C(O)$C_{6-12}$ aryl, optionally substituted —C(O)-3-14 membered heteroaryl, optionally substituted —C(O)$C_{6-12}$ arylalkyl, optionally substituted 3-10 membered heterocyclyl, —OH, —N$R^{41}R^{42}$, —C(O)O$R^{40}$, —CN, —$N_3$, —C(=N$R^{43}$)N$R^{41}R^{42}$, —C(=N$R^{43}$)O$R^{40}$, —N$R^{40}$C(=N$R^{43}$)N$R^{41}R^{42}$, —N$R^{41}$C(O)O$R^{40}$, and —OC(O)N$R^{41}R^{42}$;

each $R^{40}$, $R^{41}$, and $R^{42}$, independently is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, and optionally substituted $C_{6-18}$ arylalkyl;

or $R^{41}$ and $R^{42}$ taken together with the atoms to which they are attached form a 3 to 10 membered heterocyclyl;

each $R^{43}$, independently, is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, optionally substituted $C_{6-18}$ arylalkyl, —CN, —C(O)$R^{44}$, —CHO and —S(O)$_2R^{44}$;

each $R^{44}$ individually is optionally substituted $C_{1-12}$ alkyl;

wherein, each substituted $Q^4$, substituted $R^{40}$, substituted $R^{41}$, substituted $R^{42}$, substituted $R^{43}$, or substituted $R^{44}$ is independently substituted with one or more $Q^5$;

each $Q^5$, individually, is selected from the group consisting of halogen, oxo, oxide, —NO$_2$, —N(=O), —SR$^{50}$, —S(O)$R^{50}$, —S(O)$_2R^{50}$, —S(O)$_2$N$R^{50}R^{51}$, —N$R^{50}$C(O)$R^{51}$, —N$R^{50}$C(O)N$R^{51}R^{52}$, —N$R^{50}$S(O)$R^{51}$, —N$R^{50}$S(O)$_2R^{51}$, —OP(O)$R^{51}R^{52}$, —P(O)$R^{51}R^{52}$, —P(O)O$R^{51}R^{52}$, —P(O)(O$R^{51}$)O$R^{52}$, —C(O)N$R^{51}R^{52}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{6-12}$ arylalkyl, optionally substituted $C_{6-12}$ aryl, optionally substituted 3-14 membered heteroaryl, optionally substituted $C_{1-6}$ alkyloxy, optionally substituted $C_{2-6}$ alkenyloxy, optionally substituted $C_{2-6}$ alkynyloxy, optionally substituted $C_{3-6}$ cycloalkyloxy, optionally substituted $C_{6-12}$ aryloxy, optionally substituted 3-14 membered heteroaryloxy, optionally substituted 4-12 membered heterocyclyloxy, optionally substituted —C(O)C$_{1-6}$ alkyl, optionally substituted —C(O)C$_{2-6}$ alkenyl, optionally substituted —C(O)C$_{2-6}$ alkynyl, optionally substituted —C(O)C$_{3-6}$ cycloalkyl, optionally substituted —C(O)C$_{6-12}$ aryl, optionally substituted —C(O)-3-14 membered heteroaryl, optionally substituted —C(O)C$_{6-12}$ arylalkyl, optionally substituted 3-10 membered heterocyclyl, —OH, —NR$^{51}$R$^{52}$, —C(O)OR$^{50}$, —CN, —N$_3$, —C(═NR$^{53}$)NR$^{51}$R$^{52}$, —C(═NR$^{53}$)OR$^{50}$, —NR$^{50}$C(═NR$^{53}$)NR$^{51}$R$^{52}$, —NR$^{51}$C(O)OR$^{50}$, and —OC(O)NR$^{51}$R$^{52}$;

each R$^{50}$, R$^{51}$, and R$^{52}$, independently is selected from the group consisting of H, optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{6-14}$ aryl, optionally substituted 3-14 membered heteroaryl, optionally substituted 3-12 membered heterocyclyl, optionally substituted 3-18 membered heteroarylalkyl, and optionally substituted C$_{6-18}$ arylalkyl;

or R$^{51}$ and R$^{52}$ taken together with the atoms to which they are attached form a 3 to 10 membered heterocyclyl;

each R$^{53}$, independently, is selected from the group consisting of H, optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{6-14}$ aryl, optionally substituted 3-14 membered heteroaryl, optionally substituted 3-12 membered heterocyclyl, optionally substituted 3-18 membered heteroarylalkyl, optionally substituted C$_{6-18}$ arylalkyl, —CN, —C(O)R$^{54}$, —CHO and —S(O)$_2$R$^{54}$;

each R$^{54}$, independently, is optionally substituted C$_{1-12}$ alkyl;

wherein, each substituted Q$^5$, substituted R$^{50}$, substituted R$^{51}$, substituted R$^{52}$, substituted R$^{53}$, or substituted R$^{54}$ is independently substituted with one or more Q$^6$;

each Q$^6$, independently, is selected from the group consisting of halogen, oxo, oxide, —NO$_2$, —N(═O), —SR$^{60}$, —S(O)R$^{60}$, —S(O)$_2$R$^{60}$, —S(O)$_2$NR$^{60}$R$^{61}$, —NR$^{60}$C(O)R$^{61}$, —NR$^{60}$C(O)NR$^{61}$R$^{62}$, —NR$^{60}$S(O)R$^{61}$, —NR$^{60}$S(O)$_2$R$^{61}$, —OP(O)R$^{61}$R$^{62}$, —P(O)R$^{61}$R$^{62}$, —P(O)OR$^{61}$R$^{62}$, —P(O)(OR$^{61}$)OR$^{62}$, —C(O)NR$^{61}$R$^{62}$, C$_{1-6}$ alkyl, C$_{2-6}$ alkenyl, C$_{2-6}$ alkynyl, C$_{3-6}$ cycloalkyl, C$_{6-12}$ arylalkyl, C$_{6-12}$ aryl, 3-14 membered heteroaryl, C$_{1-6}$ alkyloxy, C$_{2-6}$ alkenyloxy, C$_{2-6}$ alkynyloxy, C$_{3-6}$ cycloalkyloxy, C$_{6-12}$ aryloxy, 3-14 membered heteroaryloxy, 4-12 membered heterocyclyloxy, —C(O)C$_{1-6}$ alkyl, —C(O)C$_{2-6}$ alkenyl, —C(O)C$_{2-6}$ alkynyl, —C(O)C$_{3-6}$ cycloalkyl, —C(O)C$_{1-6}$ haloalkyl, —C(O)C$_{6-12}$ aryl, —C(O)-3-14 membered heteroaryl, —C(O)C$_{6-12}$ arylalkyl, 3-10 membered heterocyclyl, —OH, —NR$^{61}$R$^{62}$, —C(O)OR$^{60}$, —CN, —N$_3$, —C(═NR$^{63}$)NR$^{61}$R$^{62}$, —C(═NR$^{63}$)OR$^{60}$, —NR$^{60}$C(═NR$^{63}$)NR$^{61}$R$^{62}$, —NR$^{61}$C(O)OR$^{60}$, and —OC(O)NR$^{61}$R$^{62}$;

each R$^{60}$, R$^{61}$, and R$^{62}$, independently, is selected from the group consisting of H, C$_{1-12}$ alkyl, C$_{2-12}$ alkenyl, C$_{2-12}$ alkynyl, C$_{3-12}$ cycloalkyl, C$_{1-12}$ haloalkyl, C$_{6-14}$ aryl, 3-14 membered heteroaryl, 3-12 membered heterocyclyl, 3-18 membered heteroarylalkyl, and C$_{6-18}$ arylalkyl;

or R$^{61}$ and R$^{62}$ taken together with the atoms to which they are attached form a 3 to 10 membered heterocyclyl;

each R$^{63}$ independently is selected from the group consisting of H, C$_{1-12}$ alkyl, C$_{2-12}$ alkenyl, C$_{2-12}$ alkynyl, C$_{3-12}$ cycloalkyl, C$_{6-14}$ aryl, 3-14 membered heteroaryl, 3-12 membered heterocyclyl, 3-18 membered heteroarylalkyl, C$_{6-18}$ arylalkyl, —CN, —C(O)R$^{64}$, —CHO and —S(O)$_2$R$^{64}$;

each R$^{64}$ individually is C$_{1-12}$ alkyl;

each R$^4$ is independently H, C$_1$-C$_{12}$ alkyl, C$_3$-C$_{12}$ cycloalkyl, 3-14 membered heteroaryl or 3-12 membered heterocyclyl wherein each C$_1$-C$_{12}$ alkyl, C$_3$-C$_{12}$ cycloalkyl, 3-14 membered heteroaryl or 3-12 membered heterocyclyl is optionally substituted with one or more Q$^1$;

each R$^5$ is independently C$_1$-C$_{12}$ alkyl, C$_3$-C$_{12}$ cycloalkyl, 3-14 membered heteroaryl or 3-12 membered heterocyclyl wherein each C$_1$-C$_{12}$ alkyl, C$_3$-C$_{12}$ cycloalkyl, 3-14 membered heteroaryl or 3-12 membered heterocyclyl is optionally substituted with one or more Q$^1$;

R$^6$ is C$_1$-C$_{12}$ alkylyne, C$_3$-C$_{12}$ cycloalkylyne, or 3-12 membered heterocyclylyne wherein each C$_1$-C$_{12}$ alkylyne, C$_3$-C$_{12}$ cycloalkylyne, or 3-12 membered heterocyclylyne is optionally substituted with one or more Q$^1$; and R$^7$ is selected from the group consisting of optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{6-14}$ aryl, optionally substituted 3-14 membered heteroaryl, optionally substituted 3-12 membered heterocyclyl, optionally substituted 3-18 membered heteroarylalkyl, optionally substituted 3-18 membered heterocyclylalkyl and optionally substituted C$_{6-18}$ arylalkyl;

wherein, each substituted R$^7$ is substituted with one or more Q$^2$.

2. The compound of claim 1, wherein R$^1$ is optionally substituted C$_{1-12}$ alkyl, optionally substituted C$_{2-12}$ alkenyl, optionally substituted C$_{2-12}$ alkynyl, or optionally substituted C$_{3-12}$ cycloalkyl.

3. The compound of claim 2, wherein R$^2$ is optionally substituted methylcyclohexyl or optionally substituted methylcyclohexenyl.

4. The compound of claim 3, wherein Y is —R$^3$-L-Het.

5. The compound of claim 4, wherein R$^3$ is optionally substituted C$_{1-12}$ alkylene, C$_{3-12}$ cycloalkylene, substituted C$_{3-12}$ cycloalkylene, C$_{3-12}$ cycloalkylalkylene, substituted C$_{3-12}$ cycloalkylalkylene, optionally substituted C$_{6-14}$ arylene, or optionally substituted 3-12 membered heterocyclylene.

6. The compound of claim 5, wherein R$^3$ is optionally substituted C$_{1-6}$ alkylene, C$_{4-6}$ cycloalkylene, substituted C$_{4-6}$ cycloalkylene or optionally substituted 5-6 membered heterocyclylene.

7. The compound of claim 6, wherein Het is an optionally substituted 3-12 membered heterocyclyl or optionally substituted 3-14 membered heteroaryl wherein said optionally substituted 3-12 membered heterocyclyl or optionally substituted 3-14 membered heteroaryl comprises one to four heteroatoms selected from O, S, or N.

8. The compound of claim 7, wherein Het is optionally substituted pyridinyl, optionally substituted pyridazinyl, optionally substituted tetrahydro-2H-pyranyl, optionally substituted piperidinyl, optionally substituted pyrrolidinyl, optionally substituted tetrahydrothiophenyl, optionally substituted pyrazinyl, optionally substituted 1H-tetrazolyl, optionally substituted azetidinyl, optionally substituted tetrahydrofuranyl, optionally substituted tetrahydro-2H-furo[2,3-b]furanyl, optionally substituted thiazoyl, optionally substituted 1H-imidazolyl, optionally substituted 4H-1,2,4-triazolyl, optionally substituted 1H-pyrazolyl, optionally substituted 1,3,4-thiadiazolyl, optionally substituted quinolinyl, optionally substituted [1,2,4]triazolo[4,3-a]pyridinyl, optionally substituted thiophenyl, optionally substituted 1,2,4-thiadiazolyl, optionally substituted pyrimidinyl, optionally substituted 1H-1,2,3-triazolyl, optionally substituted 1,3,4-oxadiazolyl, or optionally substituted imidazo[1,2-b]pyridazinyl.

9. The compound of claim 3, wherein Y is —N(R$^4$)(R$^5$).

10. The compound of claim 9 wherein R$^4$ is H or optionally substituted $C_1$-$C_6$ alkyl and R$^5$ is $C_1$-$C_6$ alkyl, $C_5$-$C_6$ cycloalkyl, 5-10 membered heteroaryl or 4-10 membered heterocyclyl wherein each $C_1$-$C_6$ alkyl, $C_5$-$C_6$ cycloalkyl, 5-10 membered heteroaryl or 4-10 membered heterocyclyl is optionally substituted with one or more Q$^1$.

11. The compound of claim 3, wherein Y is —R$^6$=NOR$^7$.

12. The compound of claim 11, wherein R$^6$ is $C_5$-$C_6$ cycloalkylyne or 4-6 membered heterocyclylyne wherein each $C_5$-$C_6$ cycloalkylyne or 4-6 membered heterocyclylyne is optionally substituted with one or more Q$^1$.

13. The compound of claim 12, wherein R$^6$ is cyclohexylyne.

14. The compound of claim 13, wherein R$^7$ is optionally substituted $C_1$-$C_6$ alkyl, optionally substituted $C_7$-$C_{11}$ arylalkyl, optionally substituted 6-11 membered heteroarylalkyl, or optionally substituted 6-11 membered heterocyclylalkyl.

15. The compound of claim 3 represented by Formula II:

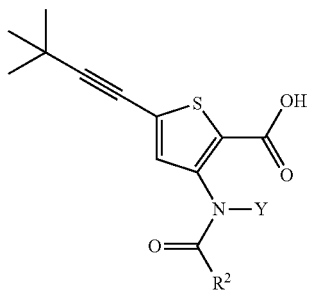

Formula (II)

or pharmaceutically acceptable salts or esters thereof, wherein
R$^2$ is optionally substituted 4-methylcyclohexyl or optionally substituted 4-methylcyclohexenyl.

16. The compound of claim 1 selected from

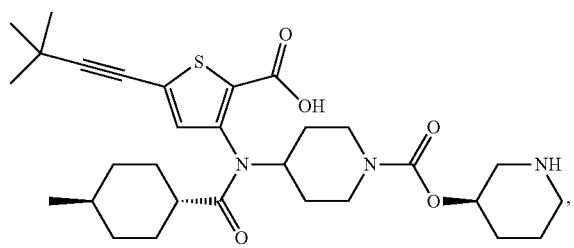

-continued

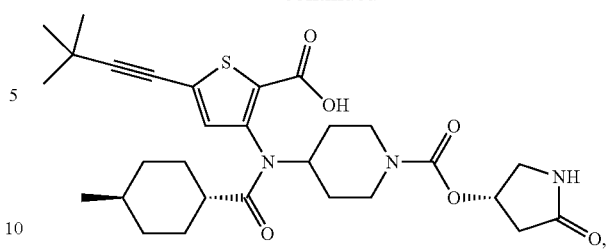

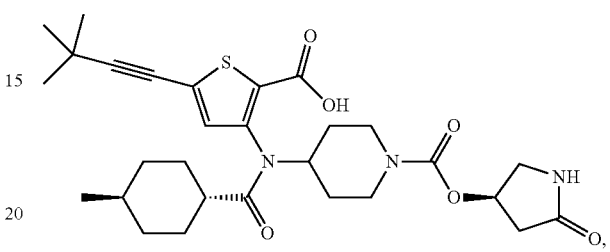

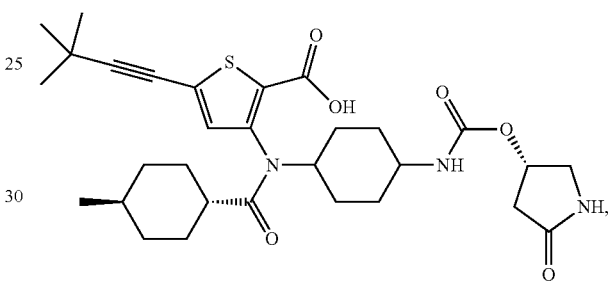

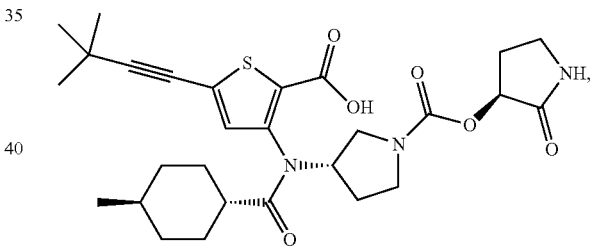

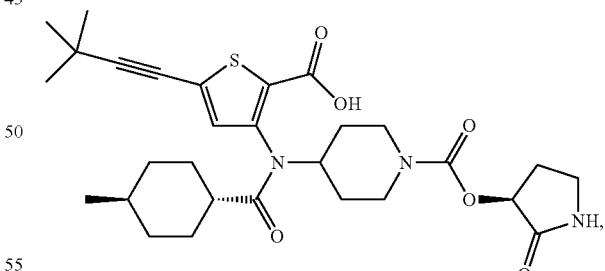

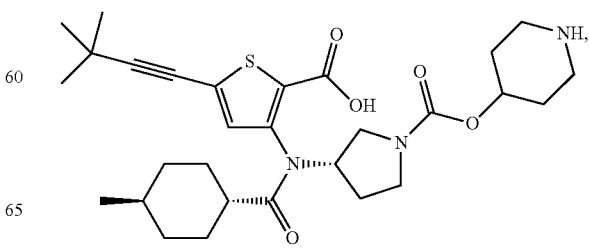

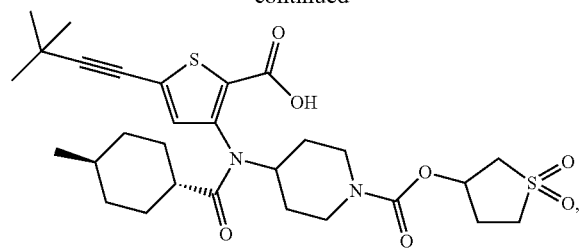
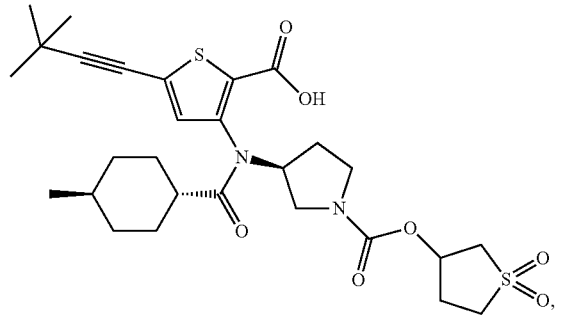
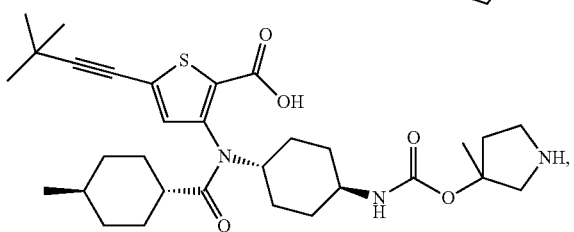
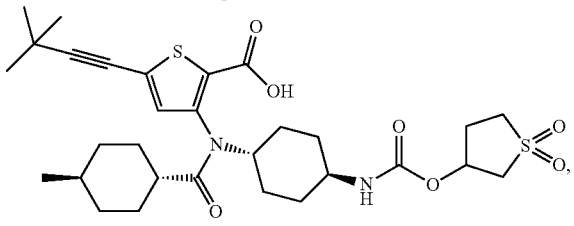
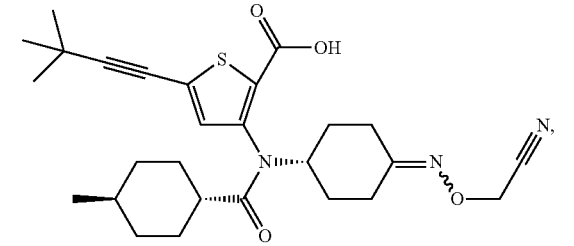
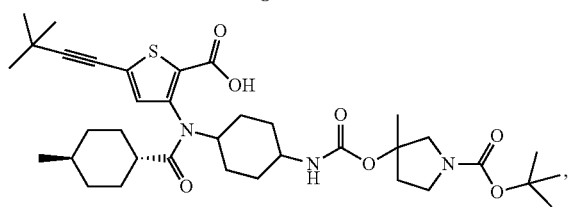
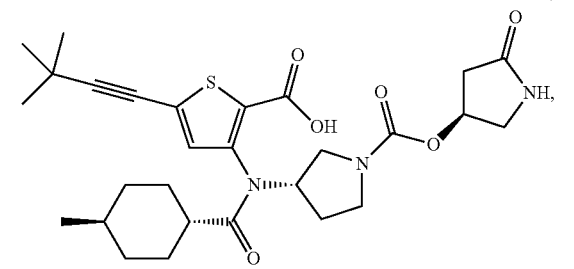
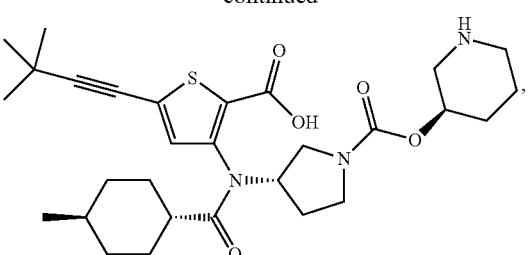
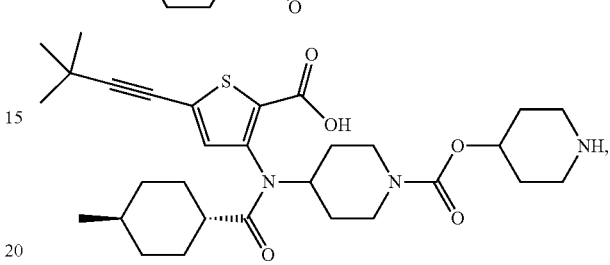
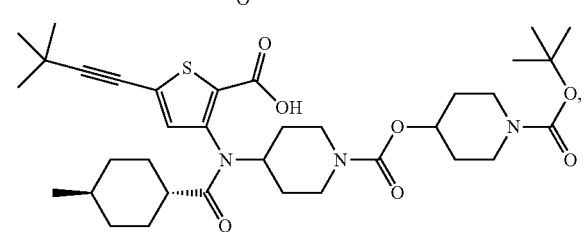
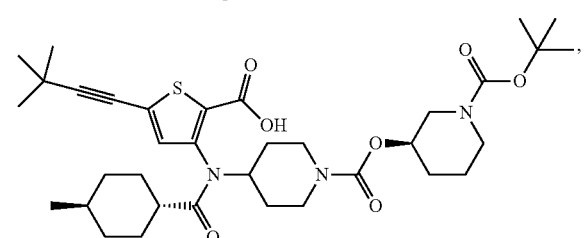
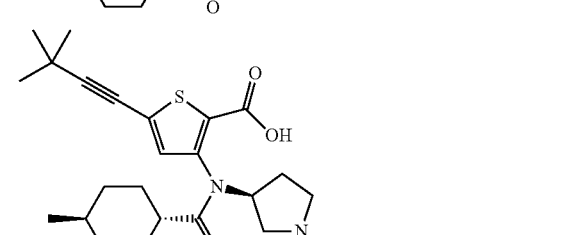
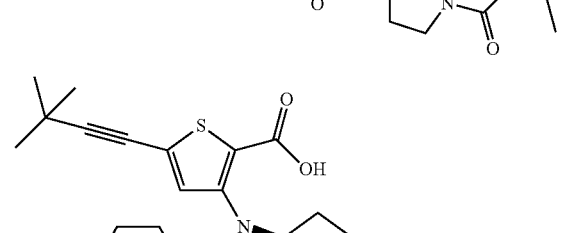
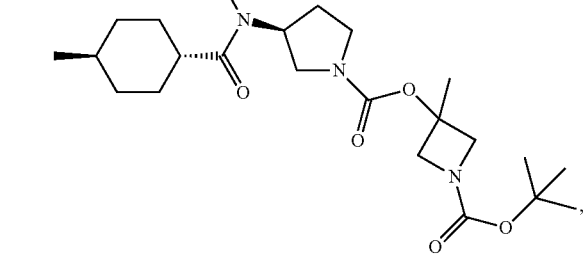

145
-continued
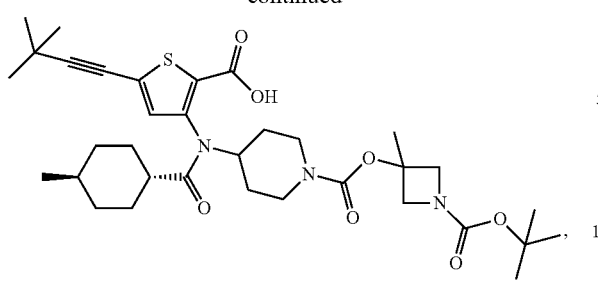
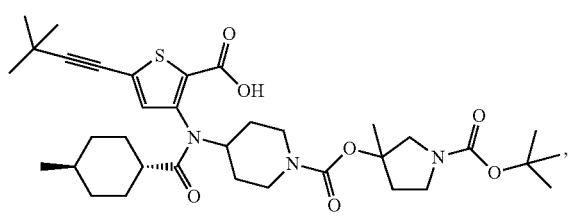
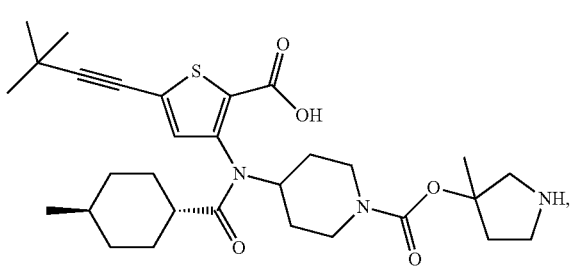
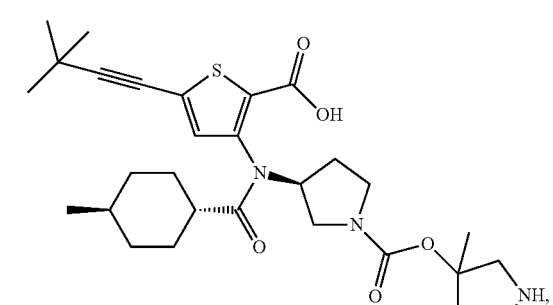
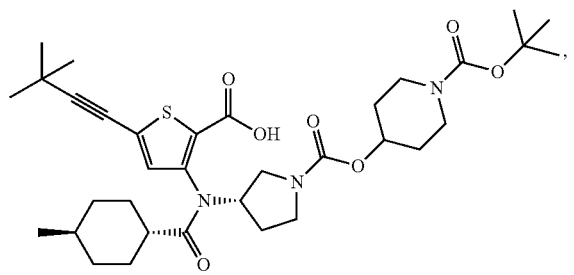
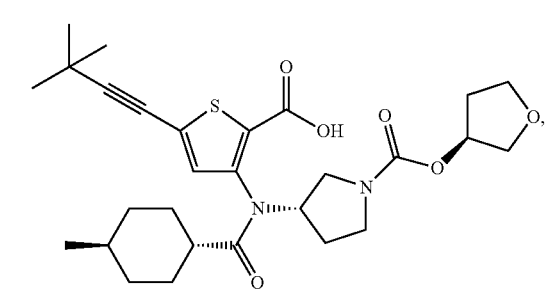
146
-continued
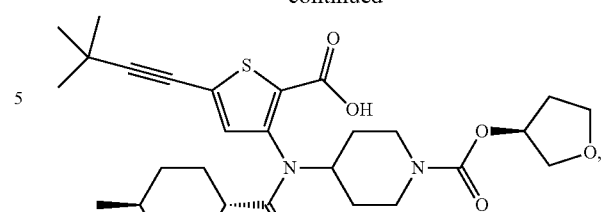
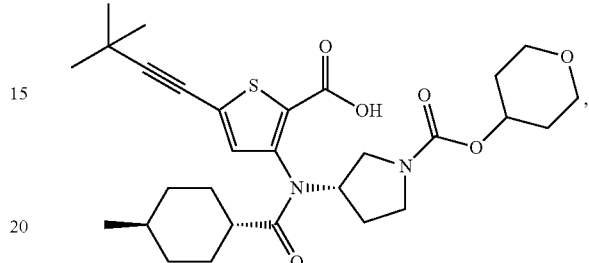
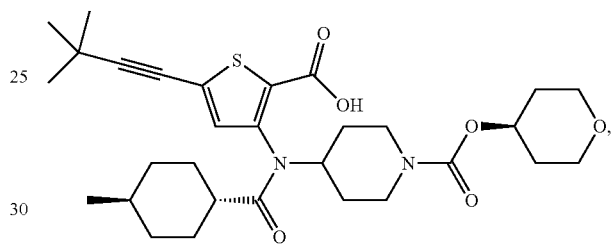
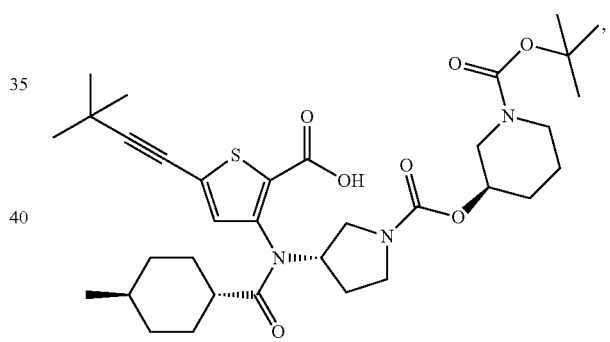
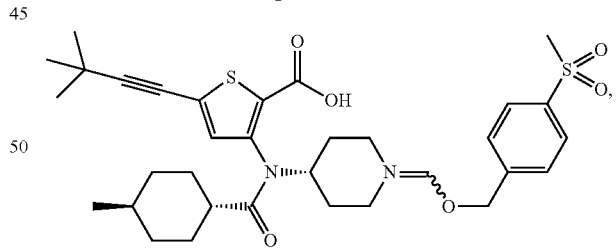
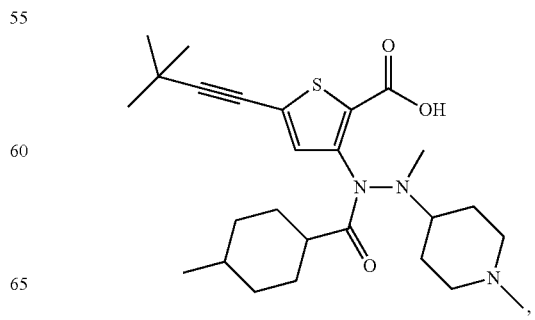

147
-continued
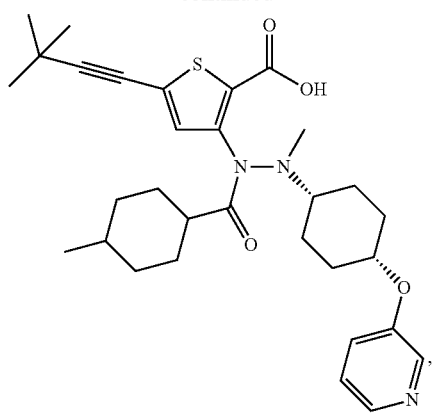
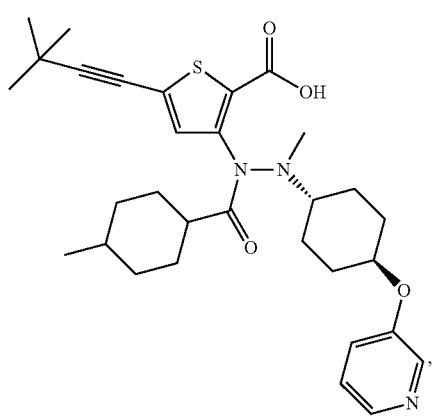
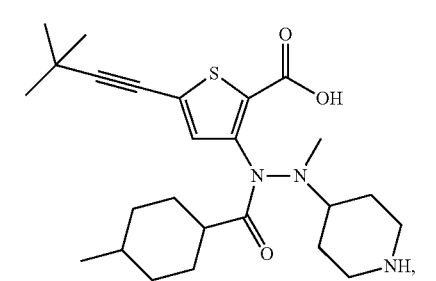
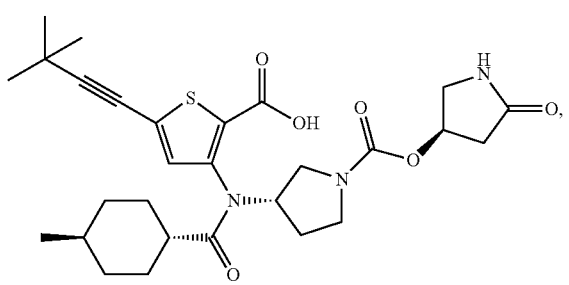
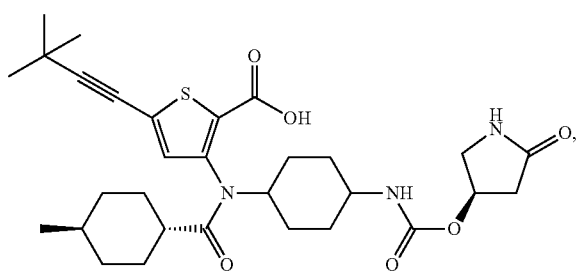
148
-continued
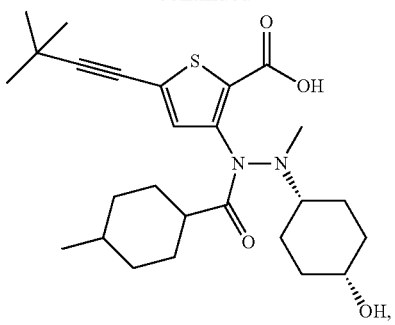
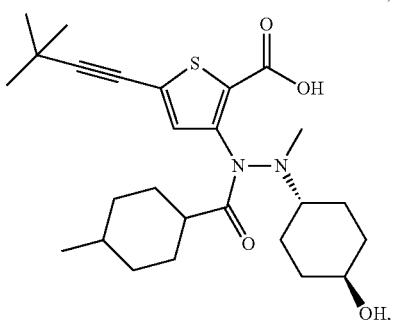
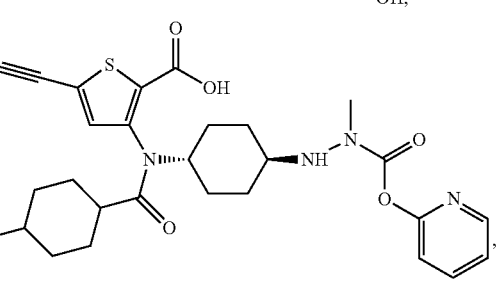
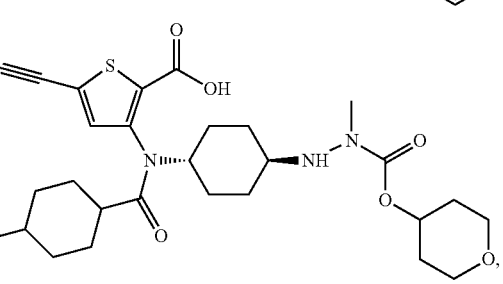
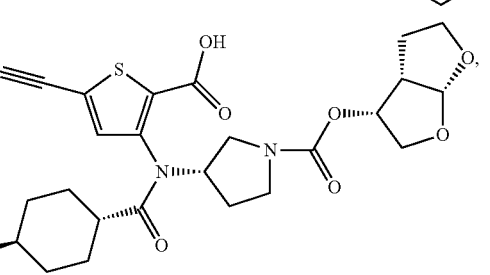
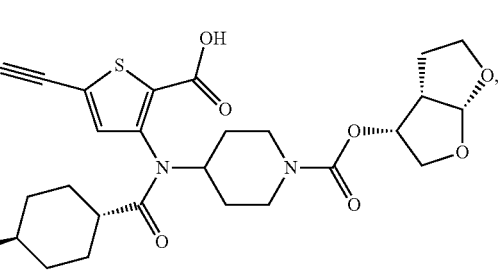

149
-continued
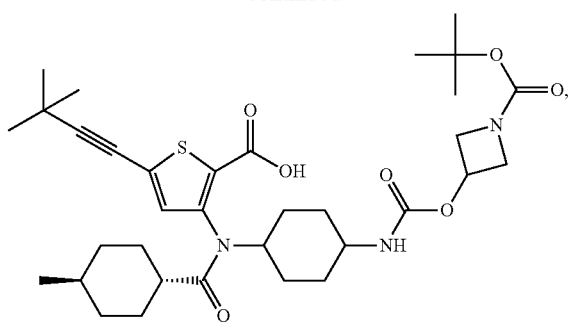
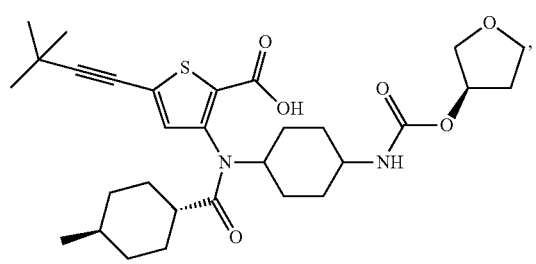
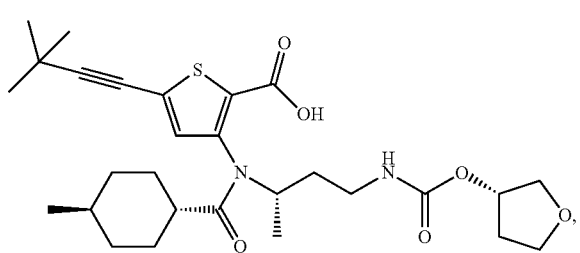
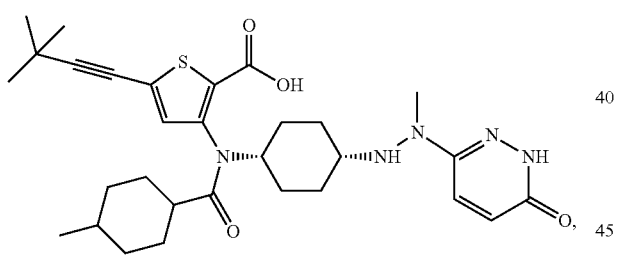
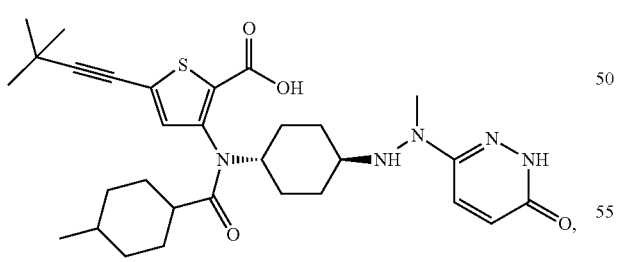
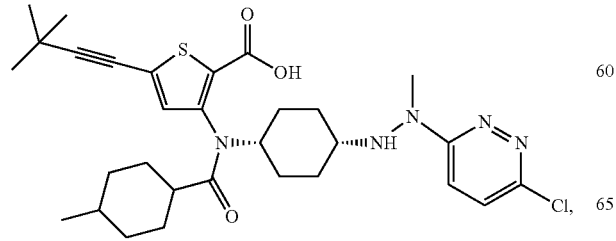
150
-continued
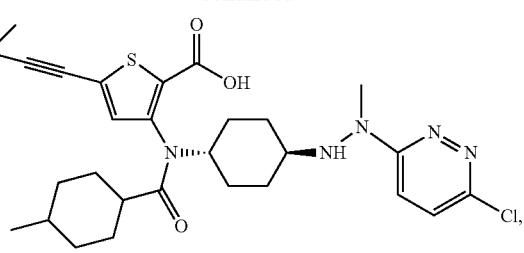
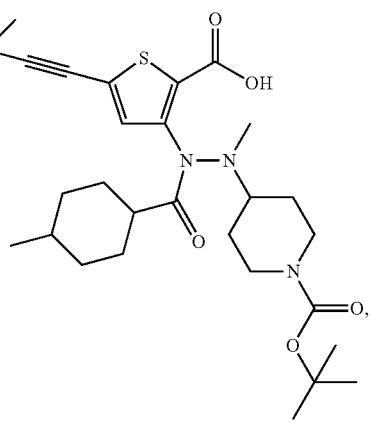
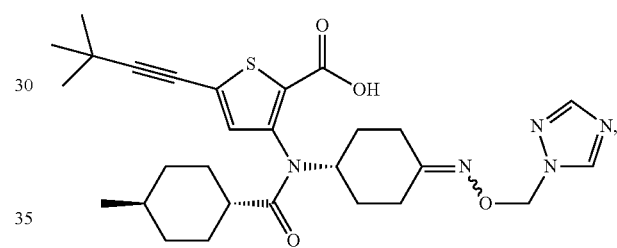
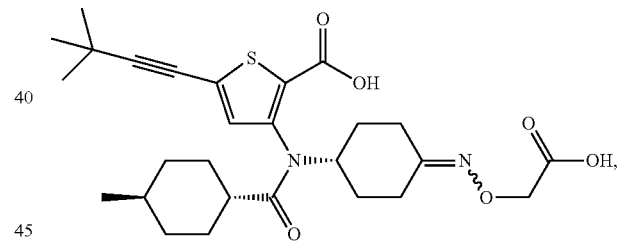
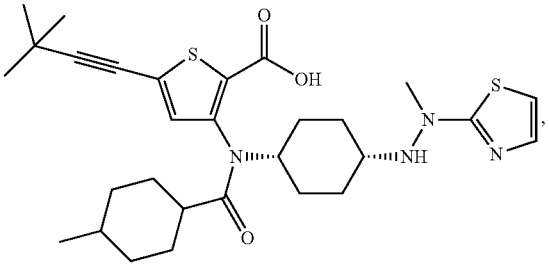
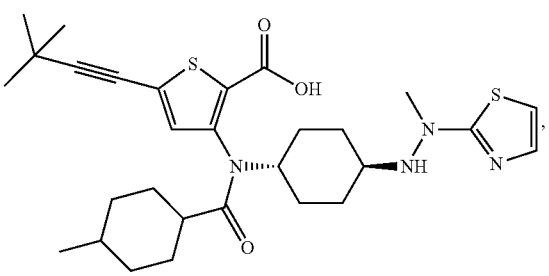

151
-continued
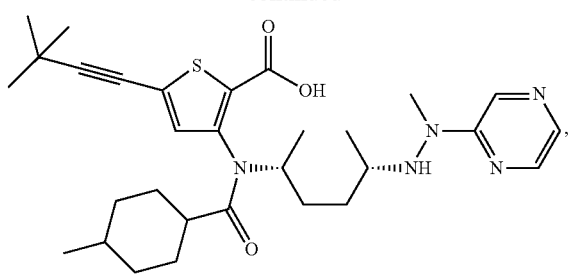
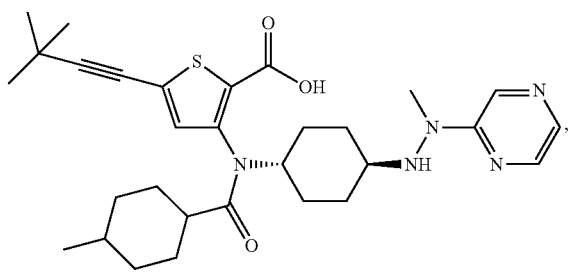
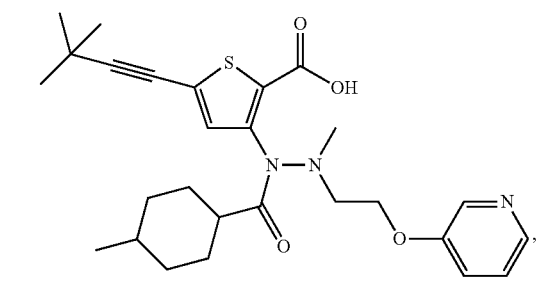
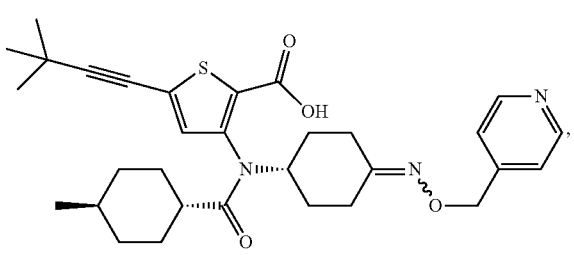
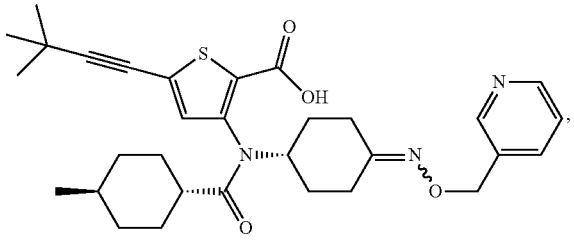
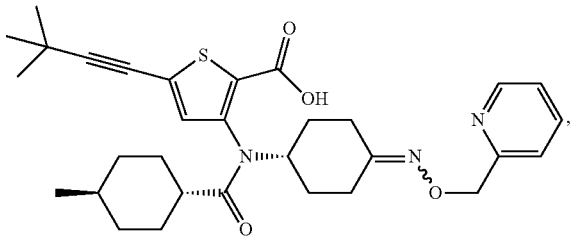
152
-continued
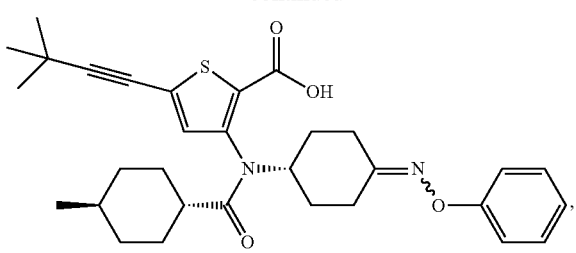
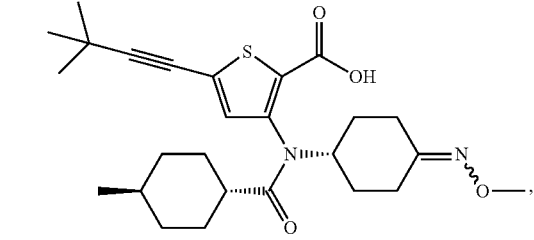
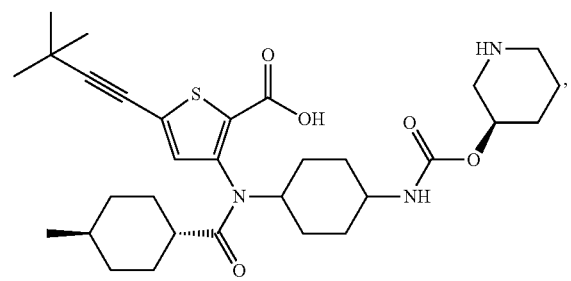
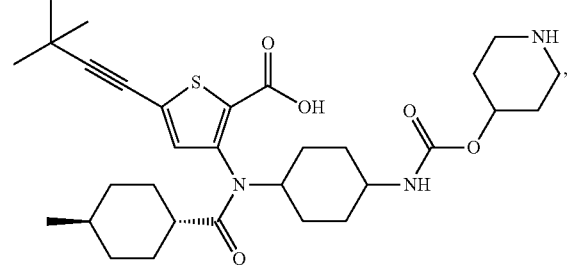
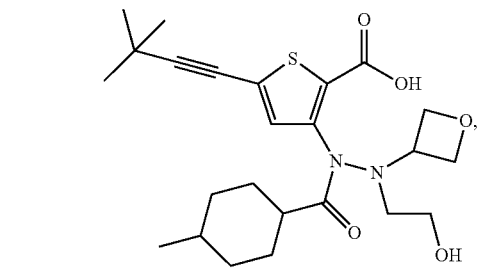
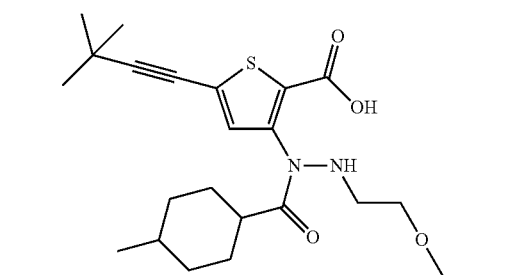

153
-continued
154
-continued
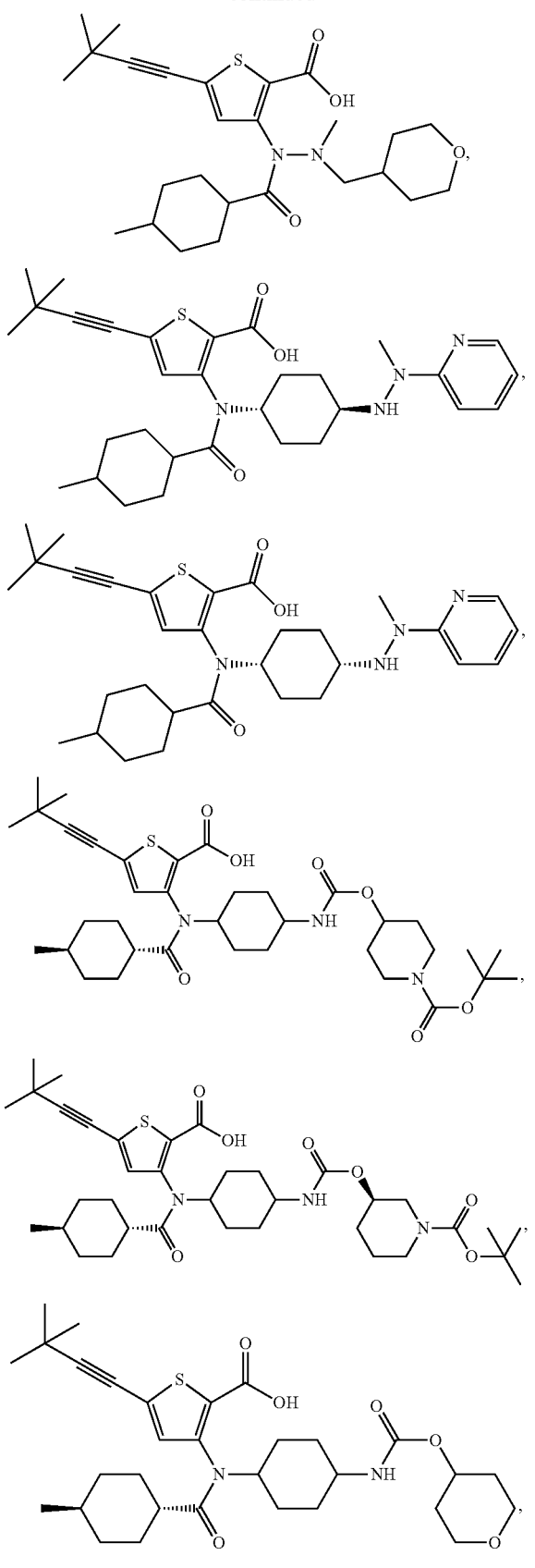
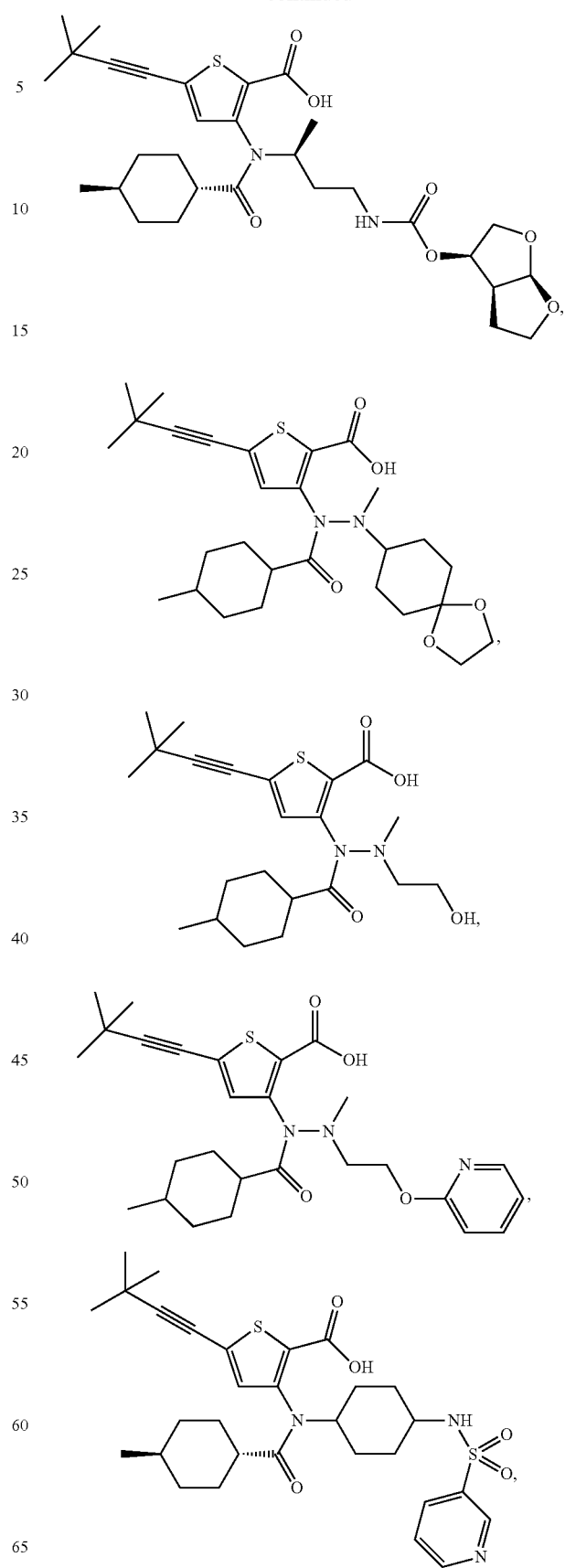

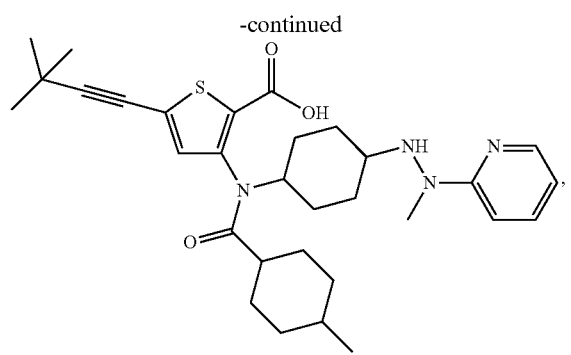

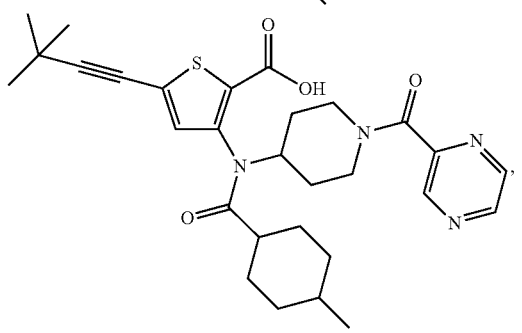

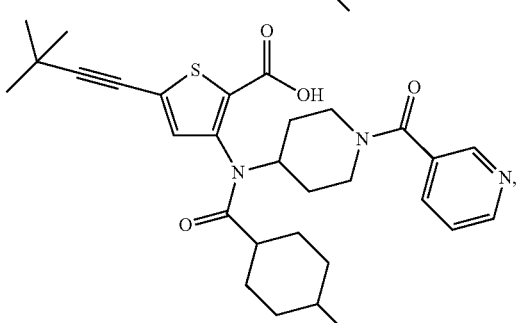

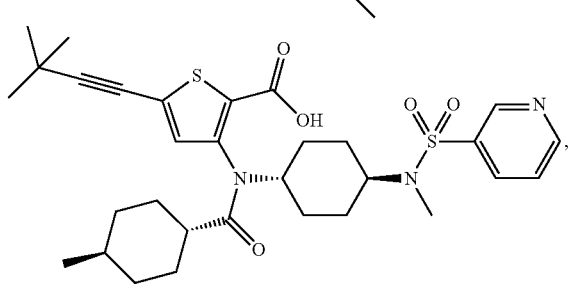

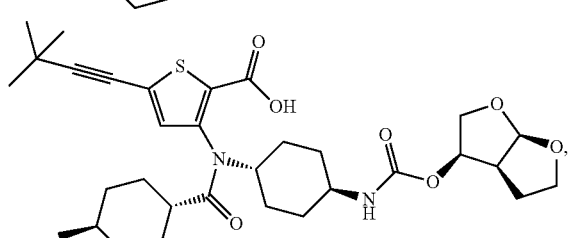

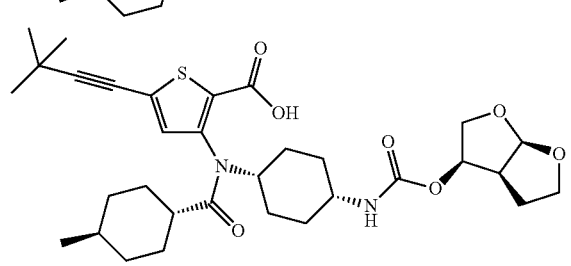

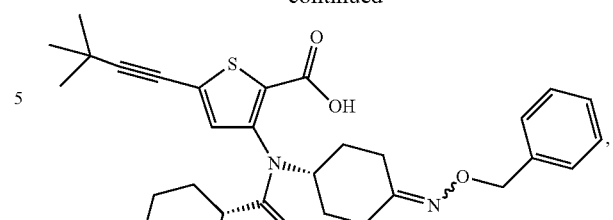

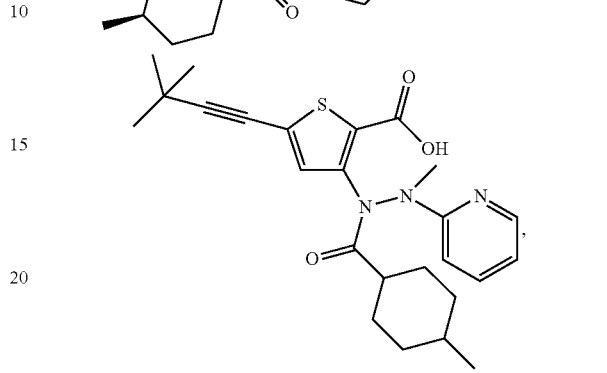

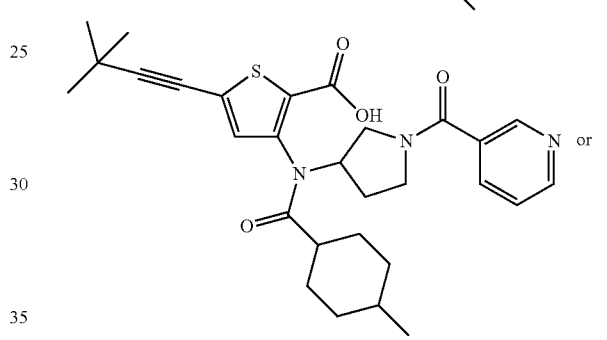

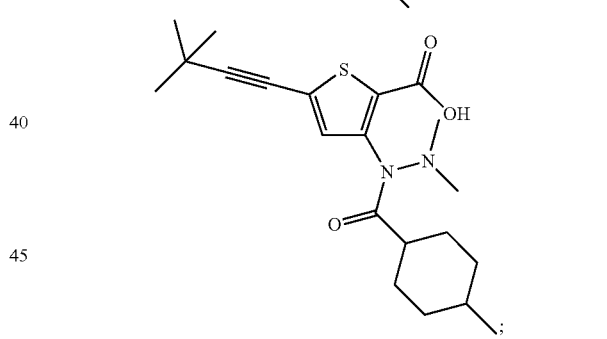

or a pharmaceutically acceptable salt or ester thereof.

17. A pharmaceutical composition comprising a therapeutically effective amount of a compound of claim 1 and a pharmaceutically acceptable carrier or excipient.

18. The pharmaceutical composition of claim 17 further comprising at least one additional therapeutic agent selected from the group consisting of interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers and other drugs for treating HCV; or mixtures thereof.

19. A method of treating Hepatitis C virus comprising administering to a mammal in need thereof a therapeutically effective amount of a compound or pharmaceutical composition of claim 1.

20. The method of claim 19 further comprising administering at least one additional therapeutic agent selected from the group consisting of interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers and other drugs for treating HCV; or mixtures thereof.

* * * * *

UNITED STATES PATENT AND TRADEMARK OFFICE
CERTIFICATE OF CORRECTION

PATENT NO. : 8,524,764 B2  
APPLICATION NO. : 13/006761  
DATED : September 3, 2013  
INVENTOR(S) : Canales et al.

Page 1 of 3

It is certified that error appears in the above-identified patent and that said Letters Patent is hereby corrected as shown below:

In the Claims:

In column 142, claim 16, lines 25-30, please delete the following compound

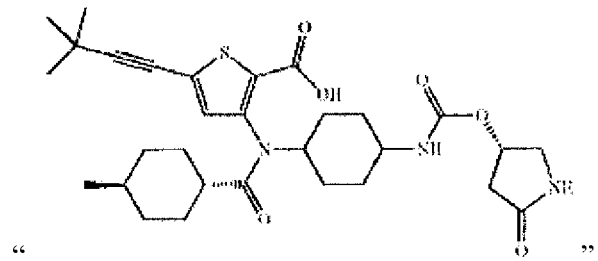

and replace with the following compound:

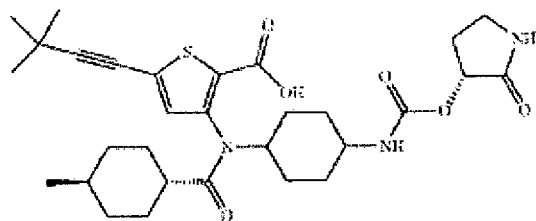

In column 145, claim 16, lines 60-65, please delete the following compound

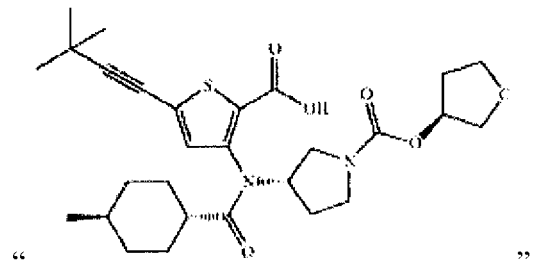

Signed and Sealed this  
Sixth Day of May, 2014

Michelle K. Lee  
*Deputy Director of the United States Patent and Trademark Office* and replace with the following compound:
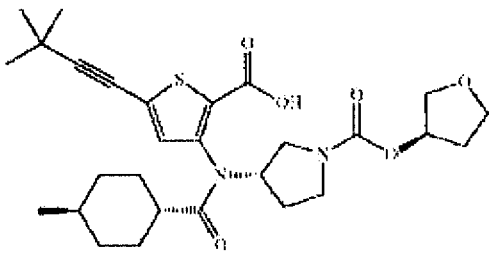
In column 146, claim 16, lines 5-10, please delete the following compound
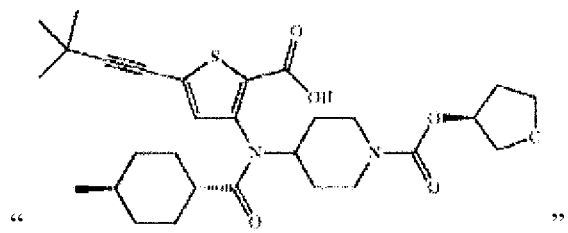
" "
and replace with the following compound:
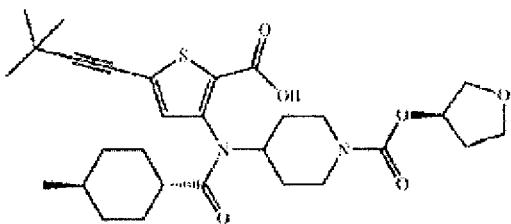
In column 146, claim 16, lines 25-30, please delete the following compound
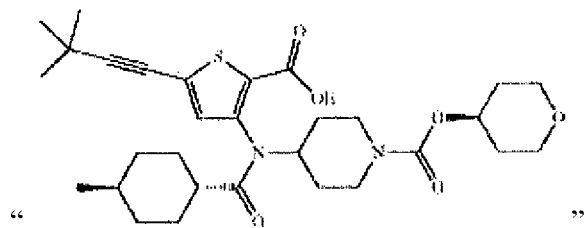
" "
and replace with the following compound:
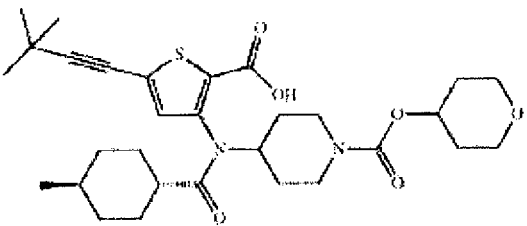

CERTIFICATE OF CORRECTION (continued)

In column 149, claim 16, lines 30-35, please delete the following compound

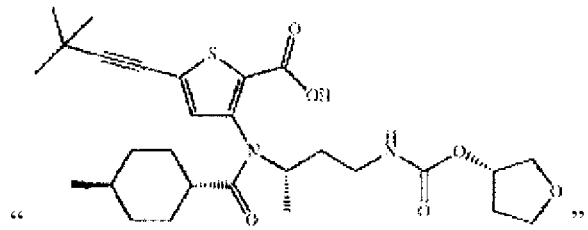

and replace with the following compound:

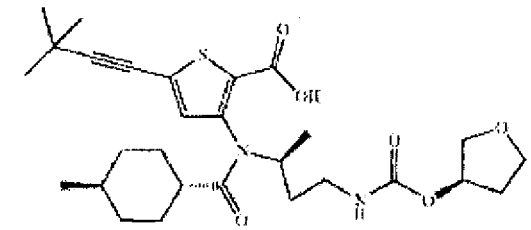

In column 156, claim 16, line 51, please delete "or ester".